US011001576B2

(12) United States Patent
Dobelmann-Mara et al.

(10) Patent No.: US 11,001,576 B2
(45) Date of Patent: May 11, 2021

(54) COMPOUNDS FOR OPTICALLY ACTIVE DEVICES

(71) Applicant: Merck Patent GmbH, Darmstadt (DE)

(72) Inventors: Lars Dobelmann-Mara, Darmstadt (DE); Stefan Riedmueller, Frankfurt Am Main (DE); Martin Schraub, Alsbach-Haehnlein (DE)

(73) Assignee: Merck Patent GmbH, Darmstadt (DE)

( * ) Notice: Subject to any disclaimer, the term of this patent is extended or adjusted under 35 U.S.C. 154(b) by 14 days.

(21) Appl. No.: 16/485,847

(22) PCT Filed: Feb. 14, 2018

(86) PCT No.: PCT/EP2018/053621
§ 371 (c)(1),
(2) Date: Aug. 14, 2019

(87) PCT Pub. No.: WO2018/149850
PCT Pub. Date: Aug. 23, 2018

(65) Prior Publication Data
US 2020/0062739 A1 Feb. 27, 2020

(30) Foreign Application Priority Data

Feb. 15, 2017 (EP) ..................... 17156327

(51) Int. Cl.
| C07D 407/12 | (2006.01) |
| A61F 2/16 | (2006.01) |
| C07D 401/12 | (2006.01) |
| C07D 409/12 | (2006.01) |
| C08F 124/00 | (2006.01) |
| C08F 126/06 | (2006.01) |
| C08F 128/06 | (2006.01) |

(52) U.S. Cl.
CPC .............. *C07D 407/12* (2013.01); *A61F 2/16* (2013.01); *C07D 401/12* (2013.01); *C07D 409/12* (2013.01); *C08F 124/00* (2013.01); *C08F 126/06* (2013.01); *C08F 128/06* (2013.01)

(58) Field of Classification Search
CPC .................................................. C07D 407/12
See application file for complete search history.

(56) References Cited

U.S. PATENT DOCUMENTS

| 5,290,892 A | 3/1994 | Namdaran et al. |
| 5,331,073 A | 7/1994 | Weinschenk et al. |
| 5,693,095 A | 12/1997 | Freeman et al. |
| 6,887,269 B1* | 5/2005 | Hampp ................ A61K 9/0051 623/6.16 |
| 8,109,999 B2 | 2/2012 | Hampp |
| 10,457,658 B2 | 10/2019 | Dobelmann-Mara |
| 2010/0160482 A1* | 6/2010 | Nachbaur ............. C08F 220/34 523/106 |
| 2010/0324165 A1* | 12/2010 | Ritter ....................... A61F 2/14 523/106 |
| 2011/0092612 A1 | 4/2011 | Miki |

FOREIGN PATENT DOCUMENTS

| WO | 07033831 A1 | 3/2007 |
| WO | 09074520 A2 | 6/2009 |
| WO | 09074521 A1 | 6/2009 |

OTHER PUBLICATIONS

M. Schraub et al., European Polymer Journal, vol. 51, 2014, pp. 21-27.
C.H. Krauch et al., Chemische Berichte Jahrg, vol. 99, 1966, pp. 1723.
A. Bouquet et al., Tetrahedron, vol. 37, 1981, pp. 75-81.
David L. Oldroyd et al., Tetrahedron Letters, vol. 34, No. 7, 1993, pp. 1087-1090.
Schmidt et al., Pure Appl. Chem. 1971, 27, 647-678.
International Search Report PCT/EP2018/053621 dated Apr. 12, 2018.(pp. 1-3).
Nasu et al.; J. Mater. Chem., 2010, 20, 6688-6695.
N. K. Sangwan et al., Indian Journal of Chemistry, 1990, vol. 29B, pp. 294-296.
Search report in corresponding Indian application Application No. 201937036658 dated Mar. 23, 2021 (pp. 1-5).

\* cited by examiner

*Primary Examiner* — Michael F Pepitone
(74) *Attorney, Agent, or Firm* — Millen White Zelano & Branigan, PC; Brion P. Heaney

(57) ABSTRACT

The present invention relates to novel compounds, particularly to compounds comprising a photoactive unit, said novel compounds being particularly suitable for compositions and ophthalmic devices as well as to compositions and ophthalmic devices comprising such compounds.

17 Claims, 1 Drawing Sheet

COMPOUNDS FOR OPTICALLY ACTIVE DEVICES

FIELD OF THE INVENTION

The present invention relates to novel compounds, particularly to compounds comprising a photoactive unit, said novel compounds being particularly suitable for compositions and ophthalmic devices as well as to compositions and ophthalmic devices comprising such compounds.

BACKGROUND OF THE INVENTION

Cataract is a general term for an affection of the eye that leads to a loss of vision and in the extreme to blindness by clouding of the normally clear lens of the eye. It is the major cause of blindness in the world, affecting more than 100 million people. Due to the fact that its major cause is age and the population's average age is increasing, it is expected that the number of cataracts will continue to increase substantially in the future.

Effective treatment of cataract is only possible by surgical intervention, whereby the natural lens of the eye is removed through an incision in the cornea and replaced with an artificial lens, often also referred to as "intraocular lens". In preparation of surgery current state-of-the-art surgical methods employ eye mapping so as to approximate the refractive power best suited to the respective patient.

Even though cataract surgery is one of the most widely used and safest surgical procedures it is not without specific post-surgery problems. It frequently happens that the refractive power of the implanted intraocular lens (IOL) is insufficient for restoring good vision. Such problems may, for example, be caused by changes in eye geometry as consequence of the surgery as well as irregular wound healing and positioning errors that result in the artificial lens not having the optimal optical properties. As a result the patient will still require corrective vision aids, e.g. glasses, to be able to see correctly. In some cases the resulting refractive power of the implanted artificial lens is so far removed from the required refractive power that further surgery will be required. Particularly for aged persons this is not desirable because the body's capability for healing is reduced with increasing age. Furthermore, there is the risk of attracting endophthalmitis, an inflammation of the eye, which can even lead to a complete loss of vision or worse, loss of the eye.

There is therefore a need in the health sector for optically active devices, and particularly for artificial intraocular lenses, that would allow for non-invasive adjustment of refractive power after implantation of the lens, thereby preferably further reducing the need for post-surgery vision aids.

Some developments in this sense have already been made, as for example evidenced by WO 2007/033831 A1, WO 2009/074520 A2 or US 2010/0324165 A1.

M. Schraub et al, European Polymer Journal 51 (2014) 21-27 describes the photochemistry of 3-phenyl-coumarin containing polymethacrylates.

C. H. Krauch et al, Chemische Berichte Jahrg. 99, 1966, 1723 describe photochemical reactions on coumaron.

A. Bouquet et al, Tetrahedron, 1981, vol. 37, 75 to 81 describe the photochemical behavior of several benzo[b]thiophenes in neutral solutions or in the presence of primary and tertiary amines.

David L. Oldroyd et al, Tetrahedron Letters, 1993, vol. 34, no. 7, 1087-1090 describe photochemical dimerization reactions of N-acylindoles.

4-Alkyl-3-phenyl-2H-1-benzopyran-2-ones and related compounds as potential pesticides are described in Sangwan et al, Indian Journal of Chemistry, 1990, 29B, 294-296.

In order to change the optical properties and particularly the refractive power of the intraocular lens it is exposed to irradiation. The irradiation induces a photochemical reaction, converting unsaturated coumarin moieties to cyclobutane dimers as shown in FIG. 1.

The Schmidt criterion for topochemical reactions states that only neighbouring double bonds separated by translation axis in the order of 4 Å can undergo cyclodimerization (Pure Appl. Chem. 1971, 27, 647-678).

Therefore the molecular arrangement plays an important role for photodimerizations of coumarins to occur.

A molecular design which forces non-substituted coumarin derivatives to aggregate into a short-distance packing (4.2-3.5 Å) enhances the speed and yield of coumarin photodimerization (J. Mater. Chem., 2010, 20, 6688-6695).

However, the compounds disclosed so far suffer from having no optimized short-distance packing and/or being too stiff and too brittle so that they can't be rolled or folded and are thus not fit to be implanted by state of the art cataract surgical methods, particularly by state of the art micro-incision cataract surgical methods.

Consequently, it is an objective of the present application to provide for novel compounds suitable for ophthalmic devices.

It is also an objective of the present application to provide for compounds, the optical properties of which may be changed, preferably by non-invasive techniques.

It is a further objective of the present application to provide for novel compounds having advantages over currently known compounds, preferably in combination with being suitable for ophthalmic devices.

Advantages such as better flexibility or enhanced efficiency of the necessary photoreaction and objectives of the compounds of the present application will be evident to the skilled person from the following detailed description as well as from the examples.

SUMMARY OF THE INVENTION

The present inventors have now found that the above objects may be attained either individually or in any combination by the compounds and ophthalmic devices of the present application.

The invention relates to compounds of formula (I)

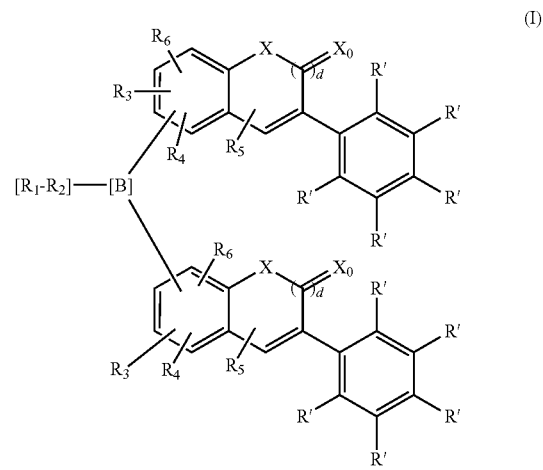

wherein
X is O, S or NR$_0$,
X$_0$ is O or S,
d is 0 or 1,

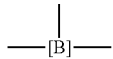

is selected from the group consisting of

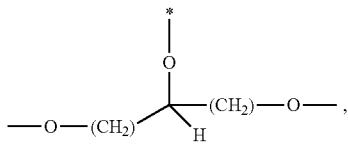

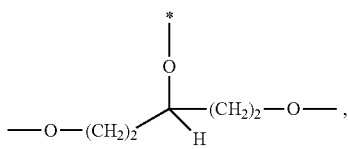

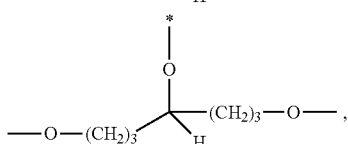

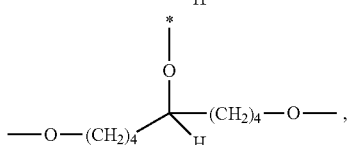

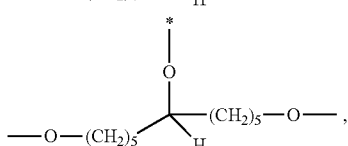

and

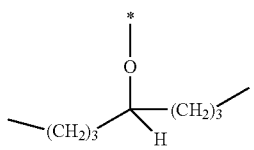

and the asterisk "*" denotes a linkage to the linker [—R$_2$—R$_1$],
R is at each occurrence independently selected from the group consisting of H, F, OH, a linear or branched alkyl group having 1 to 4 C atoms, a linear or branched hydroxyalkyl group having 1 to 4 C atoms or a linear or branched partially or fully fluorinated alkyl group having 1 to 4 C atoms,
R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms,
R$_0$ is at each occurrence independently selected from the group consisting of a linear or branched alkyl group having 1 to 10 C atoms or a cycloalkyl group having 3 to 6 C atoms,
R$_1$ is a polymerizable group selected from the group consisting of
an alkenyl group of formula (1),

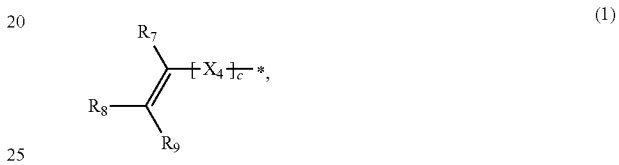

wherein
X$_4$ is selected from the group consisting of O, S, C(=O), C(=O)O,
R$_7$, R$_8$, R$_9$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and silyl groups of formula (2), (3) or (4),

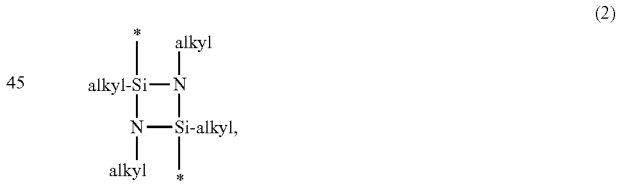

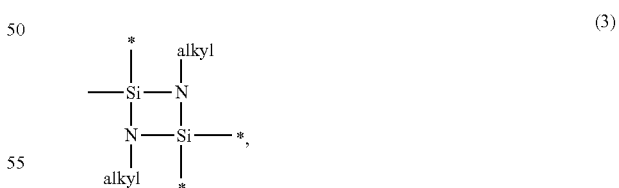

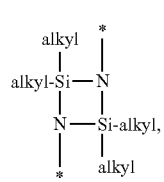

where alkyl means at each occurrence independently of each other a linear or branched alkyl group having 1 to 6 C atoms and the asterisk "*" denotes at each occurrence independently of each other a linkage to the linker [—$R_2$—], $R_2$— is —$(C(R)_2)_o$—, —$(C(R)_2)_p$—$X_1$—$(C(R)_2)_q$—$(X_2)_s$—$(C(R)_2)_r$—$(X_3)_t$—$(C(R)_2)_u$—, or a cycloalkylene group having 5 or 6 C atoms substituted with at least one R which is different from H, o is selected from the group consisting of 1 to 20, $X_1$, $X_2$, $X_3$ are at each occurrence independently O, S or $NR_0$, s, t is 0 or 1, p, q are at each occurrence independently selected from the group consisting of 1 to 10 and r, u are at each occurrence independently selected from the group consisting of 0 to 10, wherein the overall number of atoms for —$(C(R)_2)_p$—$X_1$—$(C(R)_2)_q$—$(X_2)_s$—$(C(R)_2)_r$—$(X_3)_t$—$(C(R)_2)_u$— is up to 20 atoms, $R_3$, $R_4$, $R_5$, $R_6$ are at each occurrence independently R'.

The invention relates further to compositions comprising at least one of said compounds of formula (I) and/or their polymerized forms as well as to articles comprising at least one polymerized compound of formula (I).

In addition, the invention relates to a process for forming such article, said process comprising the steps of
  providing a composition comprising at least one compound of formula (I) and/or an oligomer or polymer as described before;
  subsequently forming the article of said composition.

Furthermore, the invention relates to a process for changing the optical properties of an article according to the invention, said process comprising the steps of
  providing an article comprising at least one polymerized compound of formula (I), and
  subsequently exposing said article to irradiation having a wavelength of at least 200 nm and at most 1500 nm.

DETAILED DESCRIPTION OF THE INVENTION

The compounds of formula (I) and all preferred embodiments of compounds of formula (I) according to the present invention include all stereoisomers or racemic mixtures.

The compounds of formula (I) provide several advantages over prior art materials
  by having two chromophores within the compounds of formula (I) e.g. two coumarin chromophores they have an optimized short-distance packing and controlled arrangement thus showing a faster and more efficient photoreaction,
  by adding a linker —[$R_2$]— and a specific substitution pattern represented by the substituents R' their melting point or glass transition temperature will decrease, thus being better foldable or bendable.

In comparison to known coumarin-type photoactive chromophores, the coumarin groups in the dendritic arrangement of the compounds according to the invention show faster and/or more efficient photodimerization than those from coumarin derivatives on separate entities as shown in FIG. 2.

Polymers that are foldable at room temperature generally exhibit glass transition temperatures ($T_g$) lower than room temperature (ca. 21° C.). They are easily deformable at this temperature without causing physical damage to the polymer, for example by inducing creep, stress or fissures. For polymers in intraocular lenses, $T_g$s of less than or equal to 15° C. are preferred.

Polymers used in intraocular lens manufacturing have preferably relative high refractive indices, which enable the fabrication of thinner intraocular lenses. Preferably, the polymer used in an intraocular lens will have a refractive index greater than about 1.5 and presently most preferably greater than about 1.55.

In case an asterisk ("*") is used within the description of the present invention, it denotes a linkage to an adjacent unit or group or, in case of a polymer, to an adjacent repeating unit or any other group.

A linear or branched alkyl group having 1 to 10 C atoms denotes an alkyl group having 1, 2, 3, 4, 5, 6, 7, 8, 9 or 10 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl or n-decyl. A linear or branched alkyl group having 1 to 20 C atoms include all examples for a linear or branched alkyl group having 1 to 10 C atoms including any alkyl group having 11, 12, 13, 14, 15, 16, 17, 18, 19 and 20 C atoms such as n-undecyl, n-dodecyl, n-tridecyl, n-tetradecyl, n-pentadecyl, n-hexadecyl, n-heptadecyl, n-octadecyl, n-nonadecyl and n-eicosyl.

The term partially halogenated alkyl group denotes that at least one H atom of the alkyl group is replaced by F, Cl, Br or I. Preferably, the alkyl group is partially fluorinated meaning that at least one H atom of the alkyl group is replaced by F.

The term completely halogenated alkyl group denotes that all H atoms of the alkyl group are replaced by F, Cl, Br and/or I. Preferably, the alkyl group is completely fluorinated meaning that all H atoms of the alkyl group are replaced by F. A preferred completely fluorinated alkyl group is trifluoromethyl.

The term halogenated or preferably fluorinated corresponds additionally to other groups such as a halogenated cycloalkyl group, a halogenated alkoxy group or a halogenated thioalkyl group.

A linear or branched hydroxyalkyl group having 1 to 20 C atoms denotes an alkyl group having 1, 2, 3, 4, 5, 6, 7, 8, 9, 10, 11, 12, 13, 14, 15, 16, 17, 18, 19 or 20 C atoms wherein at least one H atom is replaced by a hydroxyl group (—OH). The hydroxyl group is preferably replaced on the last C atom of the alkyl group, for example hydroxymethyl, 2-hydroxyethyl, 3-hydroxy-propyl, 4-hydroxy-butyl, 5-hydroxy-pentyl, 4-hydroxy-1-, -2- or -3-methylbutyl, 3-hydroxy-1,1-, -1,2- or -2,2-dimethylpropyl, 3-hydroxy-1-ethylpropyl, 6-hydroxy-hexyl, 7-hydroxy-heptyl, 8-hydroxy-octyl, 6-hydroxy-1-ethylhexyl, 9-hydroxy-nonyl, 10-hydroxy-decyl, 11-hydroxy-undecyl, 12-hydroxy-dodecyl, 13-hydroxy-tridecyl, 14-hydroxy-tetradecyl, 15-hydroxy-pentadecyl, 16-hydroxy-hexadecyl, 17-hydroxy-heptadecyl, 18-hydroxy-octadecyl, 19-hydroxy-nonadecyl and 20-hydroxy-eicosyl. A preferred hydroxyalkyl group is 3-hydroxy-propyl.

A cycloalkyl group having 3 to 6 C atoms includes cyclopropyl, cyclobutyl, cyclopentyl and cyclohexyl which may be partially or completely halogenated or fluorinated as explained before.

A linear or branched alkoxy group having 1 to 20 C atoms denotes an O-alkyl group having 1, 2, 3, 4, 5, 6, 7, 8, 9, 10, 11, 12, 13, 14, 15, 16, 17, 18, 19 or 20 C atoms, for example methoxy, ethoxy, iso-propoxy, n-propoxy, iso-butoxy, n-butoxy, tert-butoxy, n-pentyloxy, 1-, 2- or 3-methylbutyloxy, 1,1-, 1,2- or 2,2-dimethylpropoxy, 1-ethylpropoxy, n-hexyloxy, n-heptyloxy, n-octyloxy, ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy and n-eicosyloxy which may be partially or completely halogenated or preferably may be partially or completely fluorinated. A preferred completely fluorinated alkoxy group is trifluoromethoxy.

A linear or branched thioalkyl group having 1 to 20 C atoms denotes a S-alkyl group having 1, 2, 3, 4, 5, 6, 7, 8, 9, 10, 11, 12, 13, 14, 15, 16, 17, 18, 19 or 20 C atoms, for example thiomethyl, 1-thioethyl, 1-thio-iso-propyl, 1-thio-n-propoyl, 1-thio-iso-butyl, 1-thio-n-butyl, 1-thio-tert-butyl, 1-thio-n-pentyl, 1-thio-1-, -2- or -3-methylbutyl, 1-thio-1,1-, -1,2- or -2,2-dimethylpropyl, 1-thio-1-ethylpropyl, 1-thio-n-hexyl, 1-thio-n-heptyl, 1-thio-n-octyl, 1-thio-ethylhexyl, 1-thio-n-nonyl, 1-thio-n-decyl, 1-thio-n-undecyl, 1-thio-n-dodecyl, 1-thio-n-tridecyl, 1-thio-n-tetradecyl, 1-thio-n-pentadecyl, 1-thio-n-hexadecyl, 1-thio-n-heptadecyl, 1-thio-n-octadecyl, 1-thio-n-nonadecyl and 1-thio-n-eicosyl which may be partially or completely halogenated or preferably may be partially or completely fluorinated. A preferred completely fluorinated thioether group is trifluoromethyl thioether.

Preferred alkyl and alkoxy radicals have 1, 2, 3, 4, 5, 6, 7, 8, 9 or 10 C atoms.

A polymerizable group is a group which can be subject to or can undergo polymerization thus forming an oligomer or a polymer.

Polymerization is the process of taking individual monomers and chaining them together to make longer units. These longer units are called polymers. The compounds of formula (I) as described before and preferably described below are suitable monomers.

Within the gist of the invention, the polymerizable group $R_1$ once oligomerized or polymerized thus forms or is part of the backbone of the oligomer or polymer comprising polymerized compounds of formula (I). Suitable polymerizable groups contain at least one double bond or at least one triple bond thus forming polymers where the linking is formed via carbon-carbon bonds. Alternatively, a suitable polymerizable group may contain silicon thus forming polysiloxanes or polysilazanes.

The suitable polymerizable groups are selected from the group consisting of
an alkenyl group of formula (1),

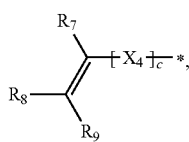

(1)

wherein
$X_4$ is selected from the group consisting of O, S, C(=O), C(=O)O,
$R_7$, $R_8$, $R_9$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and
silyl groups of formula (2), (3) or (4),

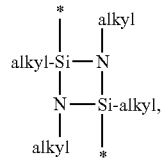

(2)

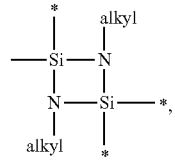

(3)

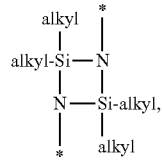

(4)

where alkyl means at each occurrence independently of each other a linear or branched alkyl group having 1 to 6 C atoms and the asterisk "*" denotes at each occurrence independently of each other a linkage to the linker [—$R_2$—] as described before or preferably described before.

A preferred polymerizable group is selected from the group consisting of trimethoxysilyl, triethoxysilyl, diethoxymethylsilyl and the alkenyl group of formula (1) as described before and preferably described below.

Aryl with 6 to 14 C atoms is an aryl group preferably selected from the group consisting of phenyl, naphthyl or anthryl, particularly preferably phenyl.

The linker

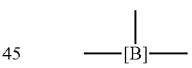

is selected from the group of

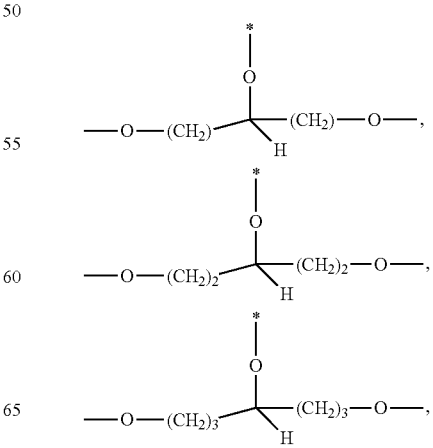

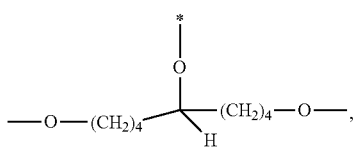

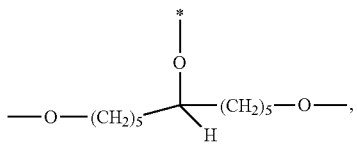

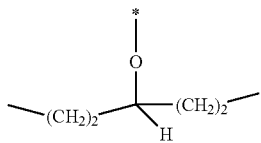

and

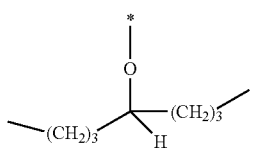

where the asterisk "*" denotes a linkage to the linker [—R₂—R₁] as described before or preferably described below.

The linker

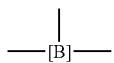

is alternatively selected from the group of

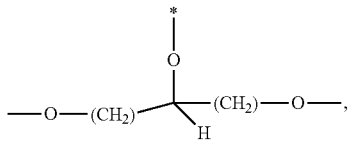

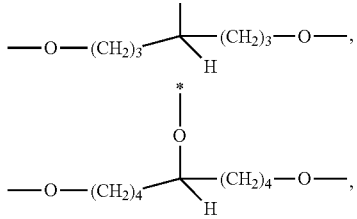

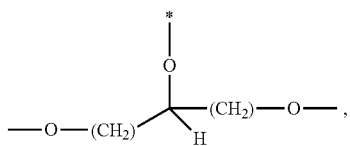

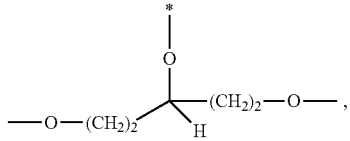

where the asterisk "*" denotes a linkage to the linker [—R₂—R₁] as described before or preferably described below.

The linker

—[B]— is preferably selected from the group of

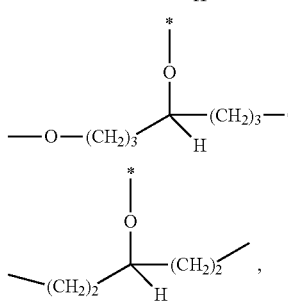

 and where the asterisk "*" denotes a linkage to the linker [—R₂—R₁] as described before or preferably described below.

The linker

—[B]— is preferably selected from the group of

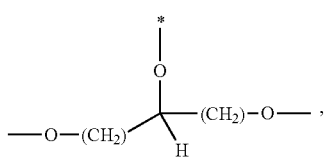

-continued

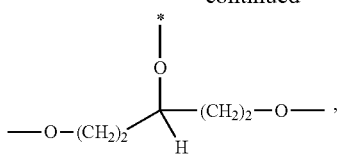

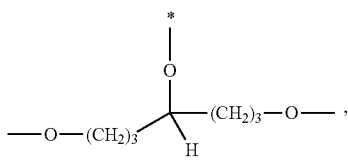

where the asterisk "*" denotes a linkage to the linker [—$R_2$—$R_1$] as described before or preferably described below.

The linker

is particularly preferably

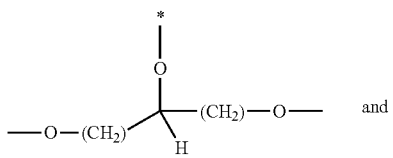 and
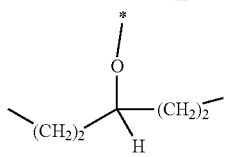

where the asterisk "*" denotes a linkage to the linker [—$R_2$—$R_1$] as described before or preferably described below.

The linker

is particularly preferably

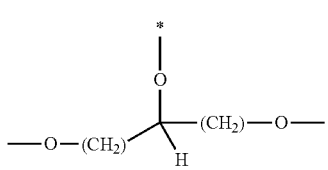

where the asterisk "*" denotes a linkage to the linker [—$R_2$—$R_1$] as described before or preferably described below.

The invention therefore relates additionally to compounds of formula (I) as described before wherein

corresponds to.

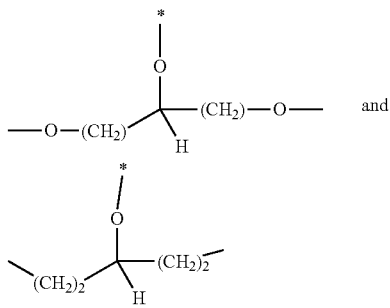

where the asterisk "*" denotes a linkage to the linker [—$R_2$—$R_1$] as described before or preferably described below.

The invention therefore relates additionally to compounds of formula (I) as described before wherein

corresponds to.

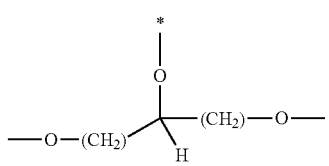

where the asterisk "*" denotes a linkage to the linker [—$R_2$—$R_1$] as described before or preferably described below.

Preferably, the substituent [$R_1$—$R_2$] is bonded to the O atom which is bonded to the CH group which can be visualized through formulae (5), (6), (7), (8), (9), (10) and (11):

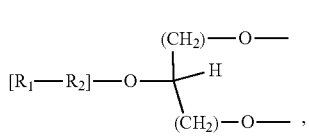 (5)

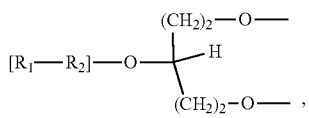 (6)

-continued

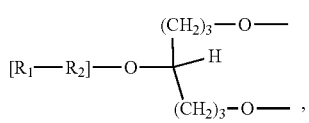
(7)

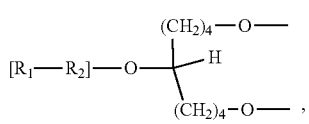
(8)

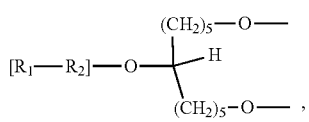
(9)

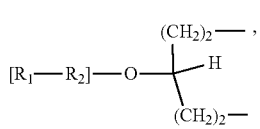
(10)

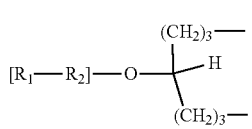
(11)

where $R_1$ and $R_2$ have a meaning as described before or preferably described below.

Compounds of formula (I) as described before are particularly preferred where $[R_1-R_2]$ is bonded to the O atom of the linker

which is bonded to the CH group corresponding to formulae (5), (6), (7), and (10) as described before.

Compounds of formula (I) as described before are particularly preferred where $[R_1-R_2]$ is bonded to the O atom of the linker

which is bonded to the CH group corresponding to formulae (5), (6), and (7) as described before.

The invention therefore relates additionally to compounds of formula (I) as described before where $[R_1-R_2]$ is bonded to the O atom of the linker

which is bonded to the CH group corresponding to formulae (5), (6), (7) and (10) as described before.

Compounds of formula (I) with linkers

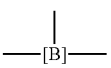

as defined before or preferably defined before are based on a 1-benzopyran-2-one ring system (coumarin or chromene-2-one) in case both X and $X_0$ are O and d is 1 as represented through formula (I-1),

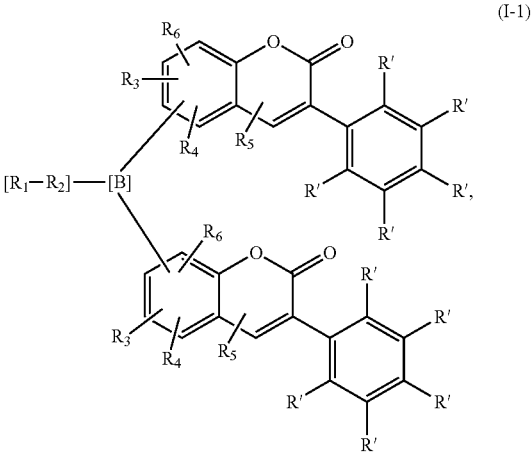
(I-1)

where $R_1$, $-R_2-$, $R_3$, $R_4$, $R_5$, $R_6$ and R' have a meaning as described before or preferably described below. Preferably, the linker

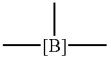

is bonded in position 7 or 6 of the 1-benzopyran-2-one ring systems.

Particularly preferably, the linker

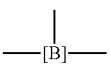

is bonded in position 7 of the 1-benzopyran-2-one ring systems.

Compounds of formula (I) with linkers

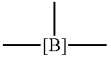

as defined before or preferably defined before are based on a 1-benzopyran-2-thione ring system (thiocoumarin or chromene-2-thione) in case X is O, $X_0$ is S and d is 1 as represented through formula (I-2),

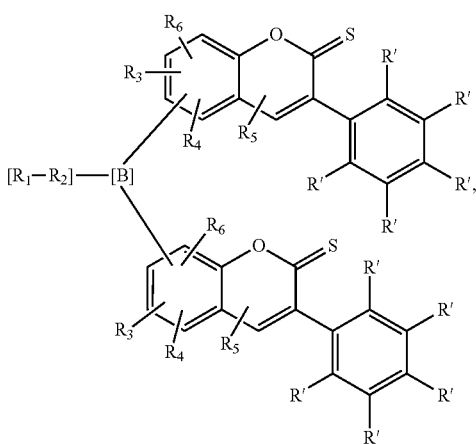
(I-2)

where $R_1$, —$R_2$—, $R_3$, $R_4$, $R_5$, $R_6$ and R' have a meaning as described before or preferably described below. Preferably, the linker

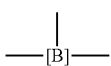

is bonded in position 7 or 6 of the 1-benzopyran-2-thione ring systems.

Particularly preferably, the linker

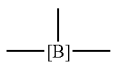

is bonded in position 7 of the 1-benzopyran-2-thione ring systems.

Compounds of formula (I) with linkers

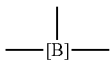

as defined before or preferably defined before are based on a thiochromene-2-one ring system in case X is S, $X_0$ is O and d is 1 as represented through formula (I-3),

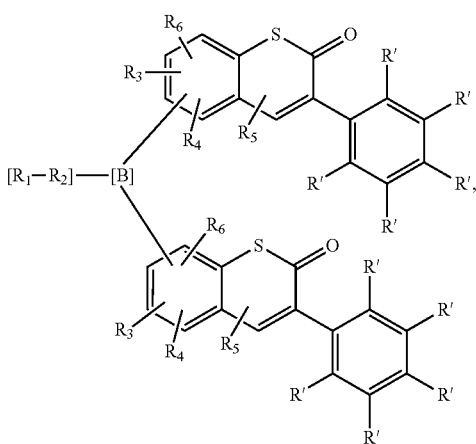
(I-3)

where $R_1$, —$R_2$—, $R_3$, $R_4$, $R_5$, $R_6$ and R' have a meaning as described before or preferably described below. Preferably, the linker

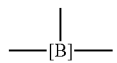

is bonded in position 7 or 6 of the thiochromene-2-one ring systems.

Particularly preferably, the linker

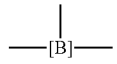

is bonded in position 7 of the thiochromene-2-one ring systems.

Compounds of formula (I) with linkers

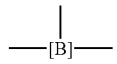

as defined before or preferably defined before are based on a thiochromene-2-thione ring system in case both X and $X_0$ are S and d is 1 as represented through formula (I-4),

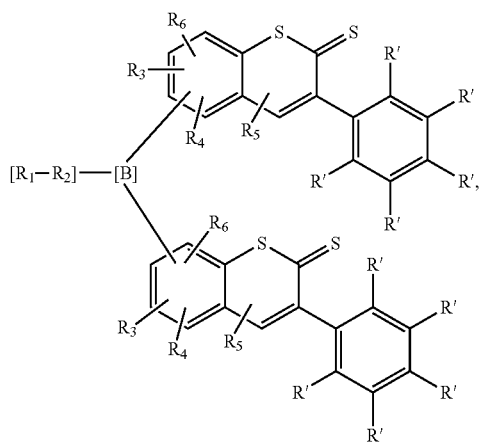
(I-4)

where $R_1$, —$R_2$—, $R_3$, $R_4$, $R_5$, $R_6$ and R' have a meaning as described before or preferably described below. Preferably, the linker

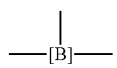

is bonded in position 7 or 6 of the thiochromene-2-thione ring systems.

Particularly preferably, the linker

is bonded in position 7 of the thiochromene-2-thione ring systems.

Compounds of formula (I) with linkers

as defined before or preferably defined before are based on a quinoline-2-one ring system in case X is $NR_0$, $X_0$ is O and d is 1 as represented through formula (I-5),

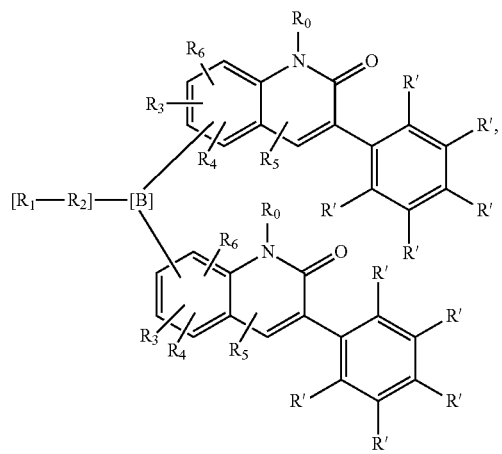

(I-5)

where $R_1$, —$R_2$—, $R_3$, $R_4$, $R_5$, $R_6$, $R_0$ and R' have a meaning as described before or preferably described below. Preferably, the linker

is bonded in position 7 or 6 of the quinoline-2-one ring systems.

Particularly preferably, the linker

is bonded in position 7 of the quinoline-2-one ring systems.

Compounds of formula (I) with linkers

as defined before or preferably defined before are based on a quinoline-2-thione ring system in case X is $NR_0$, $X_0$ is S and d is 1 as represented through formula (I-6),

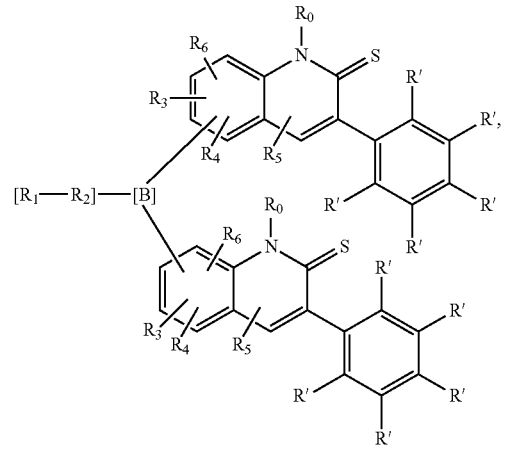

(I-6)

where $R_1$, —$R_2$—, $R_3$, $R_4$, $R_5$, $R_6$, $R_0$ and R' have a meaning as described before or preferably described below. Preferably, the linker

is bonded in position 7 or 6 of the quinoline-2-thione ring systems.

Particularly preferably, the linker

is bonded in position 7 of the quinoline-2-thione ring systems.

Compounds of formula (I) with linkers

as defined before or preferably defined before are based on a benzo[b]furan ring system in case X is O and d is 0 as represented through formula (I-7)

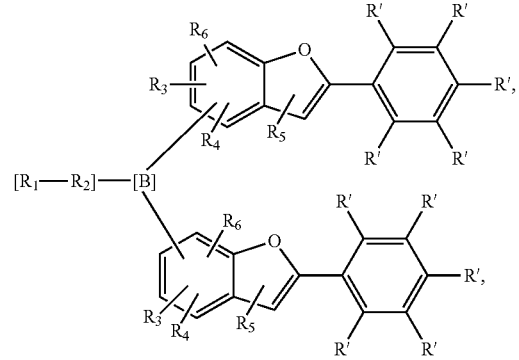

(I-7)

where $R_1$, —$R_2$—, $R_3$, $R_4$, $R_5$, $R_6$ and R' have a meaning as described before or preferably described below. Preferably, the linker

is bonded in position 6 or 5 of the benzo[b]furan ring systems.

Particularly preferably, the linker

is bonded in position 6 of the benzo[b]furan ring systems.

Compounds of formula (I) with linkers

as defined before or preferably defined before are based on a benzo[b]thiophene ring system in case X is S and d is 0 as represented through formula (I-8)

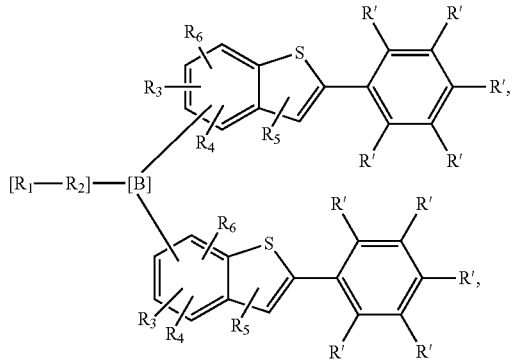

(I-8)

where $R_1$, —$R_2$—, $R_3$, $R_4$, $R_5$, $R_6$ and R' have a meaning as described before or preferably described below. Preferably, the linker

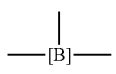

is bonded in position 6 or 5 of the benzo[b]thiophene ring systems.

Particularly preferably, the linker

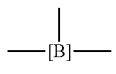

is bonded in position 6 of the benzo[b]thiophene ring systems.

Compounds of formula (I) with linkers

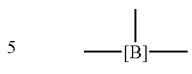

as defined before or preferably defined before are based on a benzo[b]pyrrol ring system in case d is 0 and X is $NR_0$ as represented through formula (I-9)

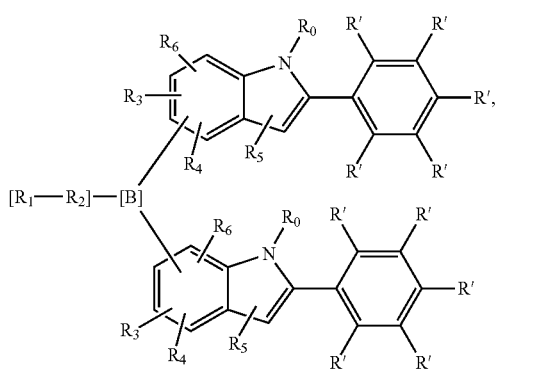

(I-9)

where $R_1$, —$R_2$—, $R_3$, $R_4$, $R_5$, $R_6$, $R_0$ and R' have a meaning as described before or preferably described below. Preferably, the linker

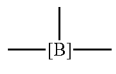

is bonded in position 6 or 5 of the benzo[b]pyrrol ring systems.

Particularly preferably, the linker

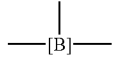

is bonded in position 6 of the benzo[b]pyrrol ring systems.

$R_0$ is at each occurrence independently preferably methyl, ethyl, iso-propyl, 2-methyl-propyl, n-butyl, n-pentyl, 4-methyl-pentyl or cyclopropyl.

In case X is $NR_0$, $R_0$ is particularly preferably ethyl, iso-propyl, 2-methyl-propyl, n-pentyl or 4-methyl-pentyl.

Compounds of formula (I) with linkers

as defined before or preferably defined before are preferred when d is 1 resulting in compounds of formulae (I-1), (I-2), (I-3), (I-4), (I-5) and (I-6), where $R_1$, —$R_2$—, $R_3$, $R_4$, $R_5$, $R_6$, $R_0$ and R' have a meaning as described before or preferably described below.

The invention is therefore additionally directed to compounds of formula (I) wherein d is 1.

Compounds of formula (I) with linkers

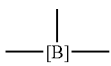

as defined before or preferably defined before are particularly preferred when d is 1 and X and $X_0$ are O as represented through formula (I-1), where $R_1$, —$R_2$—, $R_3$, $R_4$, $R_5$, $R_6$ and R' have a meaning as described before or preferably described below.

The invention is therefore additionally directed to compounds of formula (I) wherein d is 1 and X and $X_0$ are O.

R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms.

It is preferred that at least one R' in the compounds according to the invention as described before or preferably described before is different from H and is selected from the group consisting of F, a linear or branched, non-halogenated, partially or completely halogenated alkyl group having 1 to 20 C atoms, a non-halogenated, a linear or branched hydroxyalkyl group having 1 to 20 C atoms, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is particularly preferred that at least two or at least four R' are different from H and are independently selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms With regard to said substituent R', R' is at each occurrence independently preferably selected from the group consisting of H, F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is preferred that at least one R' in the compounds according to the invention as described before or preferably described before is different from H and is selected from the group consisting of F, a linear or branched, non-halogenated, partially or completely halogenated alkyl group having 1 to 10 C atoms, a linear or branched, non-halogenated and a partially or completely halogenated alkoxy group having 1 to 10 C atoms.

It is particularly preferred that at least two or at least four R' are different from H and are independently selected from the group consisting of F, a linear or branched, non-halogenated, partially or completely halogenated alkyl group having 1 to 10 C atoms, a linear or branched, non-halogenated and a partially or completely halogenated alkoxy group having 1 to 10 C atoms.

R' is at each occurrence independently particularly preferably selected from the group consisting of H, F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluormethoxy, pentafluorethoxy, 2-hydroxy-ethyl, 3-hydroxy-propyl, 4-hydroxy-butyl and 5-hydroxy-pentyl.

R' is at each occurrence independently very particularly preferably selected from the group consisting of H, F, ethyl, n-pentyl, trifluoromethyl, methoxy and trifluoromethoxy.

Compounds of formula (I), (I-1), (1-2), (1-3), (1-4), (1-5), (1-6), (1-7), (1-8) and (I-9) with linkers

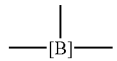

as defined before or preferably defined before are further preferred through their substitution pattern built through the selection of the substituents R' which are independent at each occurrence.

Therefore, the invention is further directed to compounds of formula (I) as described before or preferably described before and wherein at least one R' is not H.

Therefore, the invention is further directed to compounds of formula (I) as described before, or preferably described in formulae (I-1) to (I-9) before,
where [$R_1$—$R_2$] is bonded to the O atom of the linker

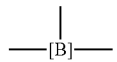

which is bonded to the CH group corresponding to formulae (5) to (11) as described before, wherein at least one R' is not H.

In another embodiment of the invention, compounds of formula (I) as described before are preferred wherein at least two R' are not H.

Therefore, the invention is further directed to compounds of formula (I) as described before or preferably described before wherein at least two R' are not H.

Therefore, the invention is further directed to compounds of formula (I) as described before, or preferably described in formulae (I-1) to (I-9) before,
where [$R_1$—$R_2$] is bonded to the O atom of the linker

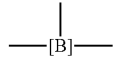

which is bonded to the CH group corresponding to formulae (5) to (11) as described before, wherein at least two R' are not H.

In another embodiment of the invention, compounds of formula (I) as described before are preferred wherein at least four R' are not H.

Therefore, the invention is further directed to compounds of formula (I) as described before or preferably described before wherein at least four R' are not H.

Therefore, the invention is further directed to compounds of formula (I) as described before, or preferably described in formulae (I-1) to (I-9) before, where [R$_1$—R$_2$] is bonded to the O atom of the linker

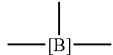

which is bonded to the CH group corresponding to formulae (5) to (11) as described before, wherein at least four R' are not H.

In all cases when R' is preferably not H, it is selected from the preferred group consisting of F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluoromethoxy, pentafluoroethoxy, 2-hydroxyethyl, 3-hydroxy-propyl, 4-hydroxy-butyl and 5-hydroxypentyl or from the particular preferred group consisting of F, ethyl, n-pentyl, trifluoromethyl, methoxy and trifluoromethoxy.

As described before, the substituents R$_3$, R$_4$, R$_5$ and R$_6$ are at each occurrence independently R' where R' has a meaning or a preferred or particularly preferred meaning as described before. It is preferred that the substituents R$_3$, R$_4$, R$_5$ and R$_6$ are at each occurrence identical.

Therefore, the invention is further directed to compounds of formula (I) as described before or preferably described in formulae (I-1) to (I-9) before, wherein the substituents R$_3$, R$_4$, R$_5$ and R$_6$ are at each occurrence identical.

R$_3$, R$_4$, R$_5$ and R$_6$ are preferably H or F. R$_3$, R$_4$, R$_5$ and R$_6$ are particularly preferably H.

Compounds of formula (I), (I-1) to (I-9) with a linker

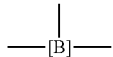

and substituents as described before or preferably described before have a polymerizable group as described before or preferably described before or below and have at least one linking element [—R$_2$—].

The linking element —R$_2$— is selected from the group consisting of —(C(R)$_2$)$_o$—, —(C(R)$_2$)$_p$—X$_1$—(C(R)$_2$)$_q$—(X$_2$)$_s$—(C(R)$_2$)$_r$—(X$_3$)$_t$—(C(R)$_2$)$_u$— and or a cycloalkylene group having 5 or 6 C atoms which is substituted with at least one R which is different from H, wherein o is selected from the group consisting of 1 to 20, X$_1$, X$_2$ and X$_3$ are at each occurrence O, S or NR$_0$, s and t are 0 or 1, p and q are at each occurrence independently selected from the group consisting of 1 to 10, r and u are at each occurrence independently selected from the group consisting of 0 to 10, wherein the overall number of atoms for —(C(R)$_2$)$_p$—X$_1$—(C(R)$_2$)$_q$—(X$_2$)$_s$—(C(R)$_2$)$_r$—(X$_3$)$_t$—(C(R)$_2$)$_u$— is up to 20 atoms.

R is at each occurrence independently selected from the group consisting of H, F, OH, a linear or branched alkyl group having 1 to 4 C atoms, a linear or branched hydroxyalkyl group having 1 to 4 C atoms or a linear or branched partially or fully fluorinated alkyl group having 1 to 4 C atoms.

R is preferably at each occurrence independently H, F, OH, methyl, ethyl, n-propyl, isopropyl, n-butyl, n-pentyl, isobutyl, ethylhexyl, hydroxymethyl, 2-hydroxy-ethyl, 3-hydroxypropyl and 4-hydroxybutyl, 2,2,2-trifluoroethyl, 3,3,3-trifluoropropyl, 2,2,3,3,3-pentafluoropropyl, trifluoromethyl, pentafluoroethyl, heptafluoropropyl and nonafluorobutyl.

R is particularly preferably H, OH, hydroxymethyl, F, methyl, 2,2,2-trifluoroethyl or trifluoromethyl.

R is very particularly preferably H.

Suitable examples for —R$_2$— are —(CH$_2$)—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—, —(CHCH$_3$)—, —(CHCH$_3$)$_2$—, —(CHCH$_3$)$_3$—, —(CHCH$_3$)$_4$—, —(CHCH$_3$)$_5$—, —(CHCH$_3$)$_6$—, —(CHCH$_3$)$_7$—, —(CHCH$_3$)$_8$—, —(CHCH$_3$)$_9$—, —(CHCH$_3$)$_{10}$—, —(CHCH$_3$)$_{11}$—, —(CHCH$_3$)$_{12}$—, —(CHCH$_3$)$_{13}$—, —(CHCH$_3$)$_{14}$—, —(CHCH$_3$)$_{15}$—, —(CHCH$_3$)$_{16}$—, —(CHCH$_3$)$_{17}$—, —(CHCH$_3$)$_{18}$—, —(CHCH$_3$)$_{19}$—, —(CHCH$_3$)$_{20}$—, —(C(CH$_3$)$_2$)—, —(C(CH$_3$)$_2$)$_2$—, —(C(CH$_3$)$_2$)$_3$—, —(C(CH$_3$)$_2$)$_4$—, —(C(CH$_3$)$_2$)$_5$—, —(C(CH$_3$)$_2$)$_6$—, —(C(CH$_3$)$_2$)$_7$—, —(C(CH$_3$)$_2$)$_8$—, —(C(CH$_3$)$_2$)$_9$—, —(C(CH$_3$)$_2$)$_{10}$—, —(C(CH$_3$)$_2$)$_{11}$—, —(C(CH$_3$)$_2$)$_{12}$—, —(C(CH$_3$)$_2$)$_{13}$—, —(C(CH$_3$)$_2$)$_{14}$—, —(C(CH$_3$)$_2$)$_{15}$—, —(C(CH$_3$)$_2$)$_{16}$—, —(C(CH$_3$)$_2$)$_{17}$—, —(C(CH$_3$)$_2$)$_{18}$—, —(C(CH$_3$)$_2$)$_{19}$—, —(C(CH$_3$)$_2$)$_{20}$—, —(CHC$_2$H$_5$)—, —(CHC$_2$H$_5$)$_2$—, —(CHC$_2$H$_5$)$_3$—, —(CHC$_2$H$_5$)$_4$—, —(CHC$_2$H$_5$)$_5$—, —(CHC$_2$H$_5$)$_6$—, —(CHC$_2$H$_5$)$_7$—, —(CHC$_2$H$_5$)$_8$—, —(CHC$_2$H$_5$)$_9$—, —(CHC$_2$H$_5$)$_{10}$—, —(CHC$_2$H$_5$)$_{11}$—, —(CHC$_2$H$_5$)$_{12}$—, —(CHC$_2$H$_5$)$_{13}$—, —(CHC$_2$H$_5$)$_{14}$—, —(CHC$_2$H$_5$)$_{15}$—, —(CHC$_2$H$_5$)$_{16}$—, —(CHC$_2$H$_5$)$_{17}$—, —(CHC$_2$H$_5$)$_{18}$—, —(CHC$_2$H$_5$)$_{19}$—, —(CHC$_2$H$_5$)$_{20}$—, —(CH$_2$)—(CHCH$_3$)—(CH$_2$)—, —(CH$_2$)—(CHCH$_3$)—(CH$_2$)$_2$—, —(CH$_2$)—(CHCH$_3$)—(CH$_2$)$_3$—, —(CH$_2$)—(CHCH$_3$)—(CH$_2$)$_{11}$—, —(CH$_2$)$_2$—(CHCH$_3$)—(CH$_2$)—, —(CH$_2$)$_3$—(CHCH$_3$)—(CH$_2$)—, —(CH$_2$)$_{11}$—(CHCH$_3$)—(CH$_2$)—, —(CH$_2$)$_2$—O—(CH$_2$)$_2$—, —(CH$_2$)$_3$—O—(CH$_2$)$_3$—, —(CH$_2$)$_2$—O—(CH$_2$)$_2$—O—(CH$_2$)$_2$—, —(CH$_2$)$_3$—O—(CH$_2$)$_3$—O—(CH$_2$)$_3$—, —(CH$_2$)$_2$—O—(CH$_2$)$_2$—O—(CH$_2$)$_6$—, —(CH$_2$)$_6$—O—(CH$_2$)$_2$—O—(CH$_2$)$_2$—, —(CH$_2$)$_2$—O—(CH$_2$)$_2$—O—(CH$_2$)$_8$—, —(CH$_2$)$_8$—O—(CH$_2$)$_2$—O—(CH$_2$)$_2$—, —(CH$_2$)$_2$—S—(CH$_2$)$_2$—, —(CH$_2$)$_3$—S—(CH$_2$)$_3$—, —(CH$_2$)$_2$—S—(CH$_2$)$_2$—S—(CH$_2$)$_2$—, —(CH$_2$)$_3$—S—(CH$_2$)$_3$—S—(CH$_2$)$_3$—, —(CH$_2$)$_2$—S—(CH$_2$)$_2$—S—(CH$_2$)$_6$—, —(CH$_2$)$_6$—S—(CH$_2$)$_2$—S—(CH$_2$)$_2$—, —(CH$_2$)$_2$—S—(CH$_2$)$_2$—S—(CH$_2$)$_8$—, —(CH$_2$)$_8$—S—(CH$_2$)$_2$—S—(CH$_2$)$_2$—, —(CH$_2$)$_2$—(NCH$_3$)—(CH$_2$)$_2$—, —(CH$_2$)$_3$—(NCH$_3$)—(CH$_2$)$_3$—, —(CH$_2$)$_2$—(NCH$_3$)—(CH$_2$)$_2$—(NCH$_3$)—(CH$_2$)$_2$—, —(CH$_2$)$_3$—(NCH$_3$)—(CH$_2$)$_3$—(NCH$_3$)—(CH$_2$)$_3$—, —(CH$_2$)$_2$—(NCH$_3$)—(CH$_2$)$_2$—(NCH$_3$)—(CH$_2$)$_6$—, —(CH$_2$)$_6$—(NCH$_3$)—(CH$_2$)$_2$—(NCH$_3$)—(CH$_2$)$_2$—, —(CH$_2$)$_2$—(NCH$_3$)—(CH$_2$)$_2$—(NCH$_3$)—(CH$_2$)$_8$— and —(CH$_2$)$_8$—(NCH$_3$)—(CH$_2$)$_2$—(NCH$_3$)—(CH$_2$)$_2$—, —(CHOH)—(CH$_2$)—, —(CH$_2$)—(CHOH)—, —(CH$_2$)—(CHOH)—(CH$_2$)—, —(CH$_2$)—(CHOH)—(CH$_2$)$_2$—, —(CH$_2$)—(CHOH)—(CH$_2$)$_3$—, —(CH$_2$)—(CHOH)—(CH$_2$)$_4$—, —(CH$_2$)—(CHOH)—(CH$_2$)$_5$—, —(CH$_2$)—(CHOH)—(CH$_2$)$_6$—, —(CH$_2$)—(CHOH)—(CH$_2$)$_7$—, —(CH$_2$)—(CHOH)—(CH$_2$)$_8$—, —(CH$_2$)$_2$—(CHOH)—(CH$_2$)—, —(CH$_2$)$_3$—(CHOH)—(CH$_2$)—, —(CH$_2$)$_4$—(CHOH)—(CH$_2$)—, —(CH$_2$)$_5$—(CHOH)—(CH$_2$)—, —(CH$_2$)$_6$—(CHOH)—(CH$_2$)—, —(CH$_2$)$_7$—(CHOH)—(CH$_2$)—, —(CH$_2$)$_8$—(CHOH)—(CH$_2$)—, —(CH$_2$)$_2$—(CHOH)—(CH$_2$)$_2$—, —(CH$_2$)$_3$—(CHOH)—(CH$_2$)$_3$—, —(CH$_2$)$_4$—(CHOH)—(CH$_2$)$_4$—, —(CH$_2$)$_5$—(CHOH)—(CH$_2$)$_5$—, —[CH(CH$_2$OH)]—(CH$_2$)—, —(CH₂)—[CH(CH₂OH)]—, —(CH₂)—[CH(CH₂OH)]—(CH₂)—, —(CH₂)—[CH(CH₂OH)]—(CH₂)₂—, —(CH₂)—[CH(CH₂OH)]—(CH₂)₃—, —(CH₂)—[CH(CH₂OH)]—(CH₂)₄—, —(CH₂)—[CH(CH₂OH)]—(CH₂)₅—, —(CH₂)—[CH(CH₂OH)]—(CH₂)₆—, —(CH₂)—[CH(CH₂OH)]—(CH₂)₇—, —(CH₂)—[CH(CH₂OH)]—(CH₂)₈—, —(CH₂)₂—[CH(CH₂OH)]—(CH₂)—, —(CH₂)₃—[CH(CH₂OH)]—(CH₂)—, —(CH₂)₄—[CH(CH₂OH)]—(CH₂)—, —(CH₂)₅—[CH(CH₂OH)]—(CH₂)—, —(CH₂)₆—[CH(CH₂OH)]—(CH₂)—, —(CH₂)₇—[CH(CH₂OH)]—(CH₂)—, —(CH₂)₈—[CH(CH₂OH)]—(CH₂)—, —(CH₂)₂—[CH(CH₂OH)]—(CH₂)₂—, —(CH₂)₃—[CH(CH₂OH)]—(CH₂)₃—, —(CH₂)₄—[CH(CH₂OH)]—(CH₂)₄—, —(CH₂)₅—[CH(CH₂OH)]—(CH₂)₅—, —(CH₂)—(CHOH)—(CHOH)—(CH₂)—, —(CH₂)₂—(CHOH)—(CHOH)—(CH₂)₂—, —(CH₂)₃—(CHOH)—(CHOH)—(CH₂)₃—, —(CH₂)₄—(CHOH)—(CHOH)—(CH₂)₄—, —(CH₂)—(CHOH)—(CHOH)—(CH₂)₃—, —(CH₂)—(CHOH)—(CHOH)—(CH₂)₄—, —(CH₂)—(CHOH)—(CHOH)—(CH₂)₅—, —(CH₂)—(CHOH)—(CHOH)—(CH₂)₆—, —(CH₂)—(CHOH)—(CHOH)—(CH₂)₇—, —(CH₂)₃—(CHOH)—(CHOH)—(CH₂)—, —(CH₂)₄—(CHOH)—(CHOH)—(CH₂)—, —(CH₂)₅—(CHOH)—(CHOH)—(CH₂)—, —(CH₂)₆—(CHOH)—(CHOH)—(CH₂)—, —(CH₂)₇—(CHOH)—(CHOH)—(CH₂)—, —(CH₂)₂—(CHOH)—(CHOH)—(CH₂)₃—, —(CH₂)₂—(CHOH)—(CHOH)—(CH₂)₄—, —(CH₂)₂—(CHOH)—(CHOH)—(CH₂)₅—, —(CH₂)₂—(CHOH)—(CHOH)—(CH₂)₆—, —(CH₂)₃—(CHOH)—(CHOH)—(CH₂)₂—, —(CH₂)₄—(CHOH)—(CHOH)—(CH₂)₂—, —(CH₂)₅—(CHOH)—(CHOH)—(CH₂)₂—, —(CH₂)₆—(CHOH)—(CHOH)—(CH₂)₂—, —(CH₂)₃—(CHOH)—(CHOH)—(CH₂)₂—, —(CH₂)₄—(CHOH)—(CHOH)—(CH₂)₃—, —(CH₂)₃—(CHOH)—(CHOH)—(CH₂)₅—, —(CH₂)₅—(CHOH)—(CHOH)—(CH₂)₃—, —(CH₂)—(CHOH)—(CH₂)—, —(CH₂)—(CHOH)—(CH₂)₂—, —(CH₂)—(CHOH)—(CH₂)₃—, —(CH₂)—(CHOH)—(CH₂)₄—, —(CH₂)—(CHOH)—(CH₂)₃—, —(CH₂)—(CHOH)—(CH₂)₄—, —(CH₂)—(CHOH)—(CH₂)₅—, —(CH₂)—(CHOH)—(CH₂)₆—, —(CH₂)—(CHOH)—(CH₂)₇—, —(CH₂)—(CHOH)—(CH₂)—, —(CH₂)—(CHOH)—(CH₂)—, —(CH₂)—(CHOH)—(CH₂)—, —(CH₂)—(CHOH)—(CH₂)—, —(CH₂)—(CHOH)—(CH₂)—, —(CH₂)—(CHOH)—(CH₂)₃—, —(CH₂)—(CHOH)—(CH₂)₄—, —(CH₂)—(CHOH)—(CH₂)₅—, —(CH₂)—(CHOH)—(CH₂)₆—, —(CH₂)—(CHOH)—(CH₂)₂—, —(CH₂)—(CHOH)—(CH₂)₂—, —(CH₂)—(CHOH)—(CH₂)₂—, —(CH₂)—(CHOH)—(CH₂)₂—, —(CH₂)—(CHOH)—(CH₂)₄—, —(CH₂)—(CHOH)—(CH₂)₃—, —(CH₂)₂—(CHOH)—(CH₂)—, —(CH₂)₂—(CHOH)—(CH₂)₂—, —(CH₂)₂—(CHOH)—(CH₂)₃—, —(CH₂)₂—(CHOH)—(CH₂)₄—, —(CH₂)₂—(CHOH)—(CH₂)₃—, —(CH₂)₂—(CHOH)—(CH₂)₄—, —(CH₂)₂—(CHOH)—(CH₂)₅—, —(CH₂)₂—(CHOH)—(CH₂)₆—, —(CH₂)₂—(CHOH)—(CH₂)₇—, —(CH₂)₂—(CHOH)—(CH₂)—, —(CH₂)₂—(CHOH)—(CH₂)—, —(CH₂)₂—(CHOH)—(CH₂)—, —(CH₂)₂—(CHOH)—(CH₂)—, —(CH₂)₂—(CHOH)—(CH₂)—, —(CH₂)₂—(CHOH)—(CH₂)—, —(CH₂)₂—(CHOH)—(CH₂)—, —(CH₂)₂—(CHOH)—(CH₂)₃—, —(CH₂)₂—(CHOH)—(CH₂)₄—, —(CH₂)₂—(CHOH)—(CH₂)₅—, —(CH₂)₂—(CHOH)—(CH₂)₆—, —(CH₂)₂—(CHOH)—(CH₂)₂—, —(CH₂)₂—(CHOH)—(CH₂)₂—, —(CH₂)₂—(CHOH)—(CH₂)₂—, —(CH₂)₂—(CHOH)—(CH₂)₂—, —(CH₂)₂—(CHOH)—(CH₂)₄—, —(CH₂)₂—(CHOH)—(CH₂)₃—, —(CH₂)—[CH(CH₂OH)]—(CH₂)—, —(CH₂)—[CH(CH₂OH)]—(CH₂)₂—, —(CH₂)—[CH(CH₂OH)]—(CH₂)₃—(CH₂)₄—(CHOH)—, —(CH₂)—[CH(CH₂OH)]—(CH₂)₄—, —(CH₂)—[CH(CH₂OH)]—(CH₂)₃—, —(CH₂)—[CH(CH₂OH)]—(CH₂)₄—, —(CH₂)—[CH(CH₂OH)]—(CH₂)₅—, —(CH₂)—[CH(CH₂OH)]—(CH₂)₆—, —(CH₂)—[CH(CH₂OH)]—(CH₂)₇—, —(CH₂)—[CH(CH₂OH)]—(CH₂)—, —(CH₂)—[CH(CH₂OH)]—(CH₂)—, —(CH₂)—[CH(CH₂OH)]—(CH₂)—, —(CH₂)—[CH(CH₂OH)]—(CH₂)—, —(CH₂)—[CH(CH₂OH)]—(CH₂)—, —(CH₂)—[CH(CH₂OH)]—(CH₂)—, —(CH₂)—[CH(CH₂OH)]—(CH₂)₃—, —(CH₂)—[CH(CH₂OH)]—(CH₂)₄—, —(CH₂)—[CH(CH₂OH)]—(CH₂)₅—, —(CH₂)—[CH(CH₂OH)]—(CH₂)₆—, —(CH₂)—[CH(CH₂OH)]—(CH₂)₂—, —(CH₂)—[CH(CH₂OH)]—(CH₂)₂—, —(CH₂)—[CH(CH₂OH)]—(CH₂)₂—, —(CH₂)—[CH(CH₂OH)]—(CH₂)₂—, —(CH₂)—[CH(CH₂OH)]—(CH₂)₄—(CH₂)₄—(CHOH)—, —(CH₂)—[CH(CH₂OH)]—(CH₂)₃—, —(CH₂)—(CHOH)—, —(CH₂)₂—[CH(CH₂OH)]—(CH₂)—, —(CH₂)₂—(CHOH)—, —(CH₂)₂—[CH(CH₂OH)]—(CH₂)₂—, —(CH₂)₃—(CHOH)—(CH₂)₂—[CH(CH₂OH)]—(CH₂)₃—, —(CH₂)₄—(CHOH)—(CH₂)₂—[CH(CH₂OH)]—(CH₂)₄—, —(CH₂)—(CHOH)—(CH₂)₂—[CH(CH₂OH)]—(CH₂)₃—, —(CH₂)—(CHOH)—(CH₂)₂—[CH(CH₂OH)]—(CH₂)₄—, —(CH₂)—(CHOH)—(CH₂)₂—[CH(CH₂OH)]—(CH₂)₅—, —(CH₂)—(CHOH)—(CH₂)₂—[CH(CH₂OH)]—(CH₂)₆—, —(CH₂)—(CHOH)—(CH₂)₂—[CH(CH₂OH)]—(CH₂)₇—, —(CH₂)₃—(CHOH)—(CH₂)₂—[CH(CH₂OH)]—(CH₂)—, —(CH₂)₄—(CHOH)—(CH₂)₂—[CH(CH₂OH)]—(CH₂)—, —(CH₂)₅—(CHOH)—(CH₂)₂—[CH(CH₂OH)]—(CH₂)—, —(CH₂)₆—(CHOH)—(CH₂)₂—[CH(CH₂OH)]—(CH₂)—, —(CH₂)₇—(CHOH)—(CH₂)₂—[CH(CH₂OH)]—(CH₂)—, —(CH₂)₂—(CHOH)—(CH₂)₂—[CH(CH₂OH)]—(CH₂)₃—, —(CH₂)₂—(CHOH)—(CH₂)₂—[CH(CH₂OH)]—(CH₂)₄—, —(CH₂)₂—(CHOH)—(CH₂)₂—[CH(CH₂OH)]—(CH₂)₅—, —(CH₂)₂—(CHOH)—(CH₂)₂—[CH(CH₂OH)]—(CH₂)₆—, —(CH₂)₃—(CHOH)—(CH₂)₂—[CH(CH₂OH)]—(CH₂)₂—, —(CH₂)₄—(CHOH)—(CH₂)₂—[CH(CH₂OH)]—(CH₂)₂—, —(CH₂)₅—(CHOH)—(CH₂)₂—[CH(CH₂OH)]—(CH₂)₂—, —(CH₂)₆—(CHOH)—(CH₂)₂—[CH(CH₂OH)]—(CH₂)₂—, —(CH₂)₂—[CH(CH₂OH)]—(CH₂)₂—, —(CH₂)₃—(CHOH)—(CH₂)₂—[CH(CH₂OH)]—(CH₂)₄—, —(CH₂)₄—(CHOH)—(CH₂)₂—[CH(CH₂OH)]—

—(CH₂)₃—, —(CH₂)—[CH(CH₂OH)]—(CH₂)₂—(CHOH)—(CH₂)—, —(CH₂)₂—[CH(CH₂OH)]—(CH₂)₂—(CHOH)—(CH₂)₂—, —(CH₂)₃—[CH(CH₂OH)]—(CH₂)₂—(CHOH)—(CH₂)₃—, —(CH₂)₄—[CH(CH₂OH)]—(CH₂)₂—(CHOH)—(CH₂)₄—, —(CH₂)₅—[CH(CH₂OH)]—(CH₂)₂—(CHOH)—(CH₂)₃—, —(CH₂)₅—[CH(CH₂OH)]—(CH₂)₂—(CHOH)—(CH₂)₄—, —(CH₂)₆—[CH(CH₂OH)]—(CH₂)₂—(CHOH)—(CH₂)₅—, —(CH₂)₇—[CH(CH₂OH)]—(CH₂)₂—(CHOH)—(CH₂)₆—, —(CH₂)₇—[CH(CH₂OH)]—(CH₂)₂—(CHOH)—(CH₂)₇—, —(CH₂)₃—[CH(CH₂OH)]—(CH₂)₂—(CHOH)—(CH₂)—, —(CH₂)₄—[CH(CH₂OH)]—(CH₂)₂—(CHOH)—(CH₂)—, —(CH₂)₅—[CH(CH₂OH)]—(CH₂)₂—(CHOH)—(CH₂)—, —(CH₂)₆—[CH(CH₂OH)]—(CH₂)₂—(CHOH)—(CH₂)—, —(CH₂)₇—[CH(CH₂OH)]—(CH₂)₂—(CHOH)—(CH₂)—, —(CH₂)₂—[CH(CH₂OH)]—(H₂)₂—(CHOH)—(H₂)₃—(CH₂)₂—[CH(CH₂OH)]—(CH₂)₂—(CHOH)—(CH₂)₄—, —(CH₂)₂—[CH(CH₂OH)]—(CH₂)₂—(CHOH)—(CH₂)₅—, —(CH₂)₂—[CH(CH₂OH)]—(CH₂)₂—(CHOH)—(CH₂)₆—, —(CH₂)₃—[CH(CH₂OH)]—(CH₂)₂—(CHOH)—(CH₂)₂—, —(CH₂)₄—[CH(CH₂OH)]—(CH₂)₂—(CHOH)—(CH₂)₂—, —(CH₂)₅—[CH(CH₂OH)]—(CH₂)₂—(CHOH)—(CH₂)₂—, —(CH₂)₆—[CH(CH₂OH)]—(CH₂)₂—(CHOH)—(CH₂)₂—, —(CH₂)₃—[CH(CH₂OH)]—(CH₂)₂—(CHOH)—(CH₂)₄—, —(CH₂)₄—[CH(CH₂OH)]—(CH₂)₂—(CHOH)—(CH₂)₃—, —(CH₂)—[CH(CH₂OH)]—(CH₂)—(CHOH)—(CH₂)—, —(CH₂)₂—[CH(CH₂OH)]—(CH₂)—(CHOH)—(CH₂)₂—, —(CH₂)₃—[CH(CH₂OH)]—(CH₂)—(CHOH)—(CH₂)₃—, —(CH₂)₄—[CH(CH₂OH)]—(CH₂)—(CHOH)—(CH₂)₄—, —(CH₂)₄—[CH(CH₂OH)]—(CH₂)—(CHOH)—(CH₂)₃—, —(CH₂)₅—[CH(CH₂OH)]—(CH₂)—(CHOH)—(CH₂)₄—, —(CH₂)₅—[CH(CH₂OH)]—(CH₂)—(CHOH)—(CH₂)₅—, —(CH₂)₆—[CH(CH₂OH)]—(CH₂)—(CHOH)—(CH₂)₆—, —(CH₂)₃—[CH(CH₂OH)]—(CH₂)—(CHOH)—(CH₂)₇—, —(CH₂)₄—[CH(CH₂OH)]—(CH₂)—(CHOH)—(CH₂)—, —(CH₂)₅—[CH(CH₂OH)]—(CH₂)—(CHOH)—(CH₂)—, —(CH₂)₆—[CH(CH₂OH)]—(H₂)—(CH₂OH)—(CH₂)—, —(CH₂)₇—[CH(CH₂OH)]—(CH₂)—(CHOH)—(CH₂)—, —(CH₂)₂—[CH(CH₂OH)]—(CH₂)—(CHOH)—(CH₂)₃—, —(CH₂)₂—[CH(CH₂OH)]—(CH₂)—(CHOH)—(CH₂)₄—, —(CH₂)₂—[CH(CH₂OH)]—(CH₂)—(CHOH)—(CH₂)₅—, —(CH₂)₂—[CH(CH₂OH)]—(CH₂)—(CHOH)—(CH₂)₆—, —(CH₂)₃—[CH(CH₂OH)]—(CH₂)—(CHOH)—(CH₂)₂—, —(CH₂)₄—[CH(CH₂OH)]—(CH₂)—(CHOH)—(CH₂)₂—, —(CH₂)₅—[CH(CH₂OH)]—(H₂)—(CHOH)—(CH₂)₂—, —(CH₂)₆—[CH(CH₂OH)]—(CH₂)—(CHOH)—(CH₂)₂—, —(CH₂)₃—[CH(CH₂OH)]—(CH₂)—(CHOH)—(CH₂)₄—, —(CH₂)₄—[CH(CH₂OH)]—(H₂)—(CHOH)—(CH₂)₃—, —(CH₂)—(CHOH)—(CHOH)—(CH₂)—(CHOH)—(CHOH)—(CH₂)—, —(CH₂)₂—(CHOH)—(CHOH)—(CH₂)—(CHOH)—(CHOH)—(CH₂)₂—, —(CH₂)₃—(CHOH)—(CHOH)—(CH₂)—(CHOH)—(CHOH)—(CH₂)₃—, —(CH₂)₄—(CHOH)—(CH₂)—(CHOH)—(CHOH)—(CH₂)₄—, —(CH₂)—(CHOH)—(CHOH)—(CH₂)—(CHOH)—(CHOH)—(CH₂)₃—, —(CH₂)—(CHOH)—(CHOH)—(CH₂)—(CHOH)—(CHOH)—(CH₂)₄—, —(CH₂)—(CHOH)—(CHOH)—(CH₂)—(CHOH)—(CHOH)—(CH₂)₅—, —(CH₂)—(CHOH)—(CHOH)—(CH₂)—(CHOH)—(CHOH)—(CH₂)₆—, —(CH₂)—(CHOH)—(CHOH)—(CH₂)—(CHOH)—(CHOH)—(CH₂)₇—, —(CH₂)₃—(CHOH)—(CHOH)—(CH₂)—(CHOH)—(CHOH)—(CH₂)—, —(CH₂)₄—(CHOH)—(CHOH)—(CH₂)—(CHOH)—(CHOH)—(CH₂)—, —(CH₂)₅—(CHOH)—(CHOH)—(CH₂)—(CHOH)—(CHOH)—(CH₂)—, —(CH₂)₆—(CHOH)—(CHOH)—(CH₂)—(CHOH)—(CHOH)—(CH₂)—, —(CH₂)₇—(CHOH)—(CHOH)—(CH₂)—(CHOH)—(CHOH)—(CH₂)—, —(CH₂)₂—(CHOH)—(CHOH)—(CH₂)—(CHOH)—(CHOH)—(CH₂)₃—, —(CH₂)₂—(CHOH)—(CHOH)—(CH₂)—(CHOH)—(CHOH)—(CH₂)₄—, —(CH₂)₂—(CHOH)—(CHOH)—(CH₂)—(CHOH)—(CHOH)—(CH₂)₅—, —(CH₂)₂—(CHOH)—(CHOH)—(CH₂)—(CHOH)—(CHOH)—(CH₂)₆—, —(CH₂)₃—(CHOH)—(CHOH)—(CH₂)—(CHOH)—(CHOH)—(CH₂)₂—, —(CH₂)₄—(CHOH)—(CHOH)—(CH₂)—(CHOH)—(CHOH)—(CH₂)₂—, —(CH₂)₅—(CHOH)—(CHOH)—(CH₂)—(CHOH)—(CHOH)—(CH₂)₂—, —(CH₂)₆—(CHOH)—(CHOH)—(CH₂)—(CHOH)—(CHOH)—(CH₂)₂—, —(CH₂)₃—(CHOH)—(CHOH)—(CH₂)—(CHOH)—(CHOH)—(CH₂)₄—, —(CH₂)₄—(CHOH)—(CHOH)—(CH₂)—(CHOH)—(CHOH)—(CH₂)₃—, —(CH₂)—(CHOH)—(CHOH)—(CH₂)—(CHOH)—(CHOH)—(CH₂)—O—(CH₂)₂—O—(CH₂)—(CHOH)—(CH₂)—, —(CH₂)₂—(CHOH)—(CH₂)—O—(CH₂)₂—O—(CH₂)—(CHOH)—(CH₂)₂—, —(CH₂)₃—(CHOH)—(CH₂)—O—(CH₂)₂—O—(CH₂)—(CHOH)—(CH₂)₃—, —(CH₂)₄—(CHOH)—(CH₂)—O—(CH₂)₂—O—(CH₂)—(CHOH)—(CH₂)₄—, —(CH₂)—(CHOH)—(CH₂)—O—(CH₂)₂—O—(CH₂)—(CHOH)—(CH₂)₃—, —(CH₂)—(CHOH)—(CH₂)—O—(CH₂)₂—O—(CH₂)—(CHOH)—(CH₂)₄—, —(CH₂)—(CHOH)—(CH₂)—O—(CH₂)₂—O—(CH₂)—(CHOH)—(CH₂)₅—, —(CH₂)—(CHOH)—(CH₂)—O—(CH₂)₂—O—(CH₂)—(CHOH)—(CH₂)₆—, —(CH₂)—(CHOH)—(CH₂)—O—(CH₂)₂—O—(CH₂)—(CHOH)—(CH₂)₇—, —(CH₂)₃—(CHOH)—(CH₂)—O—(CH₂)₂—O—(CH₂)—(CHOH)—(CH₂)—, —(CH₂)₄—(CHOH)—(CH₂)—O—(CH₂)₂—O—(CH₂)—(CHOH)—(CH₂)—, —(CH₂)₅—(CHOH)—(CH₂)—O—(CH₂)₂—O—(CH₂)—(CHOH)—(CH₂)—, —(CH₂)₆—(CHOH)—(CH₂)—O—(CH₂)₂—O—(CH₂)—(CHOH)—(CH₂)—, —(CH₂)₇—(CHOH)—(CH₂)—O—(CH₂)₂—O—(CH₂)—(CHOH)—(CH₂)—, —(CH₂)₂—(CHOH)—(CH₂)—O—(CH₂)₂—O—(CH₂)—(CHOH)—(CH₂)₃—, —(CH₂)₂—(CHOH)—(CH₂)—O—(CH₂)₂—O—(CH₂)—(CHOH)—(CH₂)₄—, —(CH₂)₂—(CHOH)—(CH₂)—O—(CH₂)₂—O—(CH₂)—(CHOH)—(CH₂)₅—, —(CH₂)₂—(CHOH)—(CH₂)—O—(CH₂)₂—O—(CH₂)—(CHOH)—(CH₂)₆—, —(CH₂)₃—(CHOH)—(CH₂)—O—(CH₂)₂—O—(CH₂)—(CHOH)—(CH₂)₂—, —(CH₂)₄—(CHOH)—(CH₂)—O—(CH₂)₂—O—(CH₂)—(CHOH)—(CH₂)₂—, —(CH₂)₅—(CHOH)—(CH₂)—O—(CH₂)₂—O—(CH₂)—(CHOH)—(CH₂)₂—, —(CH₂)₆—(CHOH)—(CH₂)—O—(CH₂)₂—O—(CH₂)—(CHOH)—(CH₂)₂—, —(CH₂)₃—(CHOH)—(CH₂)—O—(CH₂)₂—O—(CH₂)—(CHOH)—(CH₂)₄—, —(CH₂)₄—(CHOH)—(CH₂)—O—(CH₂)₂—O—(CH₂)—(CHOH)—(CH₂)₃—, —(CH₂)₃—(CHOH)—(CH₂)—O—(CH₂)₃—O—(CH₂)—(CHOH)—(CH₂)—, —(CH₂)₂—(CHOH)—(CH₂)—O—(CH₂)₃—O—(CH₂)—(CHOH)—(CH₂)₂—, —(CH₂)₃—(CHOH)—(CH₂)—O—(CH₂)₃—O—(CH₂)—(CHOH)—(CH₂)₃—, —(CH₂)₄—(CHOH)—(CH₂)—O—(CH₂)₃—O—(CH₂)—(CHOH)—(CH₂)₄—, —(CH₂)—(CHOH)—(CH₂)—O—(CH₂)₃—O—(CH₂)—(CHOH)—(CH₂)₃—, —(CH₂)—(CHOH)—(CH₂)—O—(CH₂)₃—O—(CH₂)—(CHOH)—(CH₂)₄—, —(CH₂)—(CHOH)—(CH₂)—O—(CH₂)₃—O—(CH₂)—(CHOH)—(CH₂)₅—, —(CH₂)—(CHOH)—(CH₂)—O—(CH₂)₃—O—(CH₂)

—(CHOH)—(CH₂)₆—, —(CH₂)—(CHOH)—(CH₂)—O—(CH₂)₃—O—(CH₂)—(CHOH)—(CH₂)₇—, —(CH₂)₃—(CHOH)—(CH₂)—O—(CH₂)₃—O—(CH₂)—(CHOH)—(CH₂)—, —(CH₂)₄—(CHOH)—(CH₂)—O—(CH₂)₃—O—(CH₂)—(CHOH)—(CH₂)—, —(CH₂)₅—(CHOH)—(CH₂)—O—(CH₂)₃—O—(CH₂)—(CHOH)—(CH₂)—, —(CH₂)₆—(CHOH)—(CH₂)—O—(CH₂)₃—O—(CH₂)—(CHOH)—(CH₂)—, —(CH₂)₇—(CHOH)—(CH₂)—O—(CH₂)₃—O—(CH₂)—(CHOH)—(CH₂)—, —(CH₂)₂—(CHOH)—(CH₂)—O—(CH₂)₃—O—(CH₂)—(CHOH)—(CH₂)₃—, —(CH₂)₂—(CHOH)—(CH₂)—O—(CH₂)₃—O—(CH₂)—(CHOH)—(CH₂)₄—, —(CH₂)₂—(CHOH)—(CH₂)—O—(CH₂)₃—O—(CH₂)—(CHOH)—(CH₂)₅—, —(CH₂)₂—(CHOH)—(CH₂)—O—(CH₂)₃—O—(CH₂)—(CHOH)—(CH₂)₆—, —(CH₂)₃—(CHOH)—(CH₂)—O—(CH₂)₃—O—(CH₂)—(CHOH)—(CH₂)₂—, —(CH₂)₄—(CHOH)—(CH₂)—O—(CH₂)₃—O—(CH₂)—(CHOH)—(CH₂)₂—, —(CH₂)₅—(CHOH)—(CH₂)—O—(CH₂)₃—O—(CH₂)—(CHOH)—(CH₂)₂—, —(CH₂)₆—(CHOH)—(CH₂)—O—(CH₂)₃—O—(CH₂)—(CHOH)—(CH₂)₂—, —(CH₂)₃—(CHOH)—(CH₂)—O—(CH₂)₃—O—(CH₂)—(CHOH)—(CH₂)₄—, —(CH₂)₄—(CHOH)—(CH₂)—O—(CH₂)₃—O—(CH₂)—(CHOH)—(CH₂)₃—, —(CH₂)₃—(CHOH)—(CH₂)—O—(CH₂)₃—O—(CH₂)—(CHOH)—(CH₂)₅—, —(CH₂)₅—(CHOH)—(CH₂)—O—(CH₂)₃—O—(CH₂)—(CHOH)—(CH₂)₃—, —(CH₂)—(CHOH)—(CH₂)—O—(CH₂)₄—O—(CH₂)—(CHOH)—(CH₂)—, —(CH₂)₂—(CHOH)—(CH₂)—O—(CH₂)₄—O—(CH₂)—(CHOH)—(CH₂)₂—, —(CH₂)₃—(CHOH)—(CH₂)—O—(CH₂)₄—O—(CH₂)—(CHOH)—(CH₂)₃—, —(CH₂)₄—(CHOH)—(CH₂)—O—(CH₂)₄—O—(CH₂)—(CHOH)—(CH₂)₄—, —(CH₂)—(CHOH)—(CH₂)—O—(CH₂)₄—O—(CH₂)—(CHOH)—(CH₂)₃—, —(CH₂)—(CHOH)—(CH₂)—O—(CH₂)₄—O—(CH₂)—(CHOH)—(CH₂)₄—, —(CH₂)—(CHOH)—(CH₂)—O—(CH₂)₄—O—(CH₂)—(CHOH)—(CH₂)₅—, —(CH₂)—(CHOH)—(CH₂)—O—(CH₂)₄—O—(CH₂)—(CHOH)—(CH₂)₆—, —(CH₂)—(CHOH)—(CH₂)—O—(CH₂)₄—O—(CH₂)—(CHOH)—(CH₂)₇—, —(CH₂)₃—(CHOH)—(CH₂)—O—(CH₂)₄—O—(CH₂)—(CHOH)—(CH₂)—, —(CH₂)₄—(CHOH)—(CH₂)—O—(CH₂)₄—O—(CH₂)—(CHOH)—(CH₂)—, —(CH₂)₅—(CHOH)—(CH₂)—O—(CH₂)₄—O—(CH₂)—(CHOH)—(CH₂)—, —(CH₂)₆—(CHOH)—(CH₂)—O—(CH₂)₄—O—(CH₂)—(CHOH)—(CH₂)—, —(CH₂)₇—(CHOH)—(CH₂)—O—(CH₂)₄—O—(CH₂)—(CHOH)—(CH₂)—, —(CH₂)₂—(CHOH)—(CH₂)—O—(CH₂)₄—O—(CH₂)—(CHOH)—(CH₂)₃—, —(CH₂)₂—(CHOH)—(CH₂)—O—(CH₂)₄—O—(CH₂)—(CHOH)—(CH₂)₄—, —(CH₂)₂—(CHOH)—(CH₂)—O—(CH₂)₄—O—(CH₂)—(CHOH)—(CH₂)₅—, —(CH₂)₂—(CHOH)—(CH₂)—O—(CH₂)₄—O—(CH₂)—(CHOH)—(CH₂)₆—, —(CH₂)₃—(CHOH)—(CH₂)—O—(CH₂)₄—O—(CH₂)—(CHOH)—(CH₂)₂—, —(CH₂)₄—(CHOH)—(CH₂)—O—(CH₂)₄—O—(CH₂)—(CHOH)—(CH₂)₂—, —(CH₂)₅—(CHOH)—(CH₂)—O—(CH₂)₄—O—(CH₂)—(CHOH)—(CH₂)₃—, —(CH₂)₄—(CHOH)—(CH₂)—O—(CH₂)₄—O—(CH₂)—(CHOH)—(CH₂)₃—, —(CH₂)₃—(CHOH)—(CH₂)—O—(CH₂)₄—O—(CH₂)—(CHOH)—(CH₂)₅—, —(CH₂)₅—(CHOH)—(CH₂)—O—(CH₂)₄—O—(CH₂)—(CHOH)—(CH₂)₃—, —(CH₂)—(CHOH)—(CH₂)—O—(CH₂)₅—O—(CH₂)—(CHOH)—(CH₂)—, —(CH₂)₂—(CHOH)—(CH₂)—O—(CH₂)₅—O—(CH₂)—(CHOH)—(CH₂)₂—, —(CH₂)₃—(CHOH)—(CH₂)—O—(CH₂)₅—O—(CH₂)—(CHOH)—(CH₂)₃—, —(CH₂)—(CHOH)—(CH₂)—O—(CH₂)₅—O—(CH₂)—(CHOH)—(CH₂)₄—, —(CH₂)—(CHOH)—(CH₂)—O—(CH₂)₅—O—(CH₂)—(CHOH)—(CH₂)₅—, —(CH₂)—(CHOH)—(CH₂)—O—(CH₂)₅—O—(CH₂)—(CHOH)—(CH₂)₆—, —(CH₂)—(CHOH)—(CH₂)—O—(CH₂)₅—O—(CH₂)—(CHOH)—(CH₂)₇—, —(CH₂)₃—(CHOH)—(CH₂)—O—(CH₂)₅—O—(CH₂)—(CHOH)—(CH₂)—, —(CH₂)₄—(CHOH)—(CH₂)—O—(CH₂)₅—O—(CH₂)—(CHOH)—(CH₂)—, —(CH₂)₅—(CHOH)—(CH₂)—O—(CH₂)₅—O—(CH₂)—(CHOH)—(CH₂)—, —(CH₂)₆—(CHOH)—(CH₂)—O—(CH₂)₅—O—(CH₂)—(CHOH)—(CH₂)—, —(CH₂)₇—(CHOH)—(CH₂)—O—(CH₂)₅—O—(CH₂)—(CHOH)—(CH₂)—, —(CH₂)₂—(CHOH)—(CH₂)—O—(CH₂)₅—O—(CH₂)—(CHOH)—(CH₂)₃—, —(CH₂)₂—(CHOH)—(CH₂)—O—(CH₂)₅—O—(CH₂)—(CHOH)—(CH₂)₄—, —(CH₂)₂—(CHOH)—(CH₂)—O—(CH₂)₅—O—(CH₂)—(CHOH)—(CH₂)₅—, —(CH₂)₂—(CHOH)—(CH₂)—O—(CH₂)₅—O—(CH₂)—(CHOH)—(CH₂)₆—, —(CH₂)₃—(CHOH)—(CH₂)—O—(CH₂)₅—O—(CH₂)—(CHOH)—(CH₂)₂—, —(CH₂)₄—(CHOH)—(CH₂)—O—(CH₂)₅—O—(CH₂)—(CHOH)—(CH₂)₂—, —(CH₂)₅—(CHOH)—(CH₂)—O—(CH₂)₅—O—(CH₂)—(CHOH)—(CH₂)₂—, —(CH₂)₆—(CHOH)—(CH₂)—O—(CH₂)₅—O—(CH₂)—(CHOH)—(CH₂)₂—, —(CH₂)₃—(CHOH)—(CH₂)—O—(CH₂)₅—O—(CH₂)—(CHOH)—(CH₂)₄—, —(CH₂)₄—(CHOH)—(CH₂)—O—(CH₂)₅—O—(CH₂)—(CHOH)—(CH₂)₃—, —(CH₂)₃—(CHOH)—(CH₂)—O—(CH₂)₅—O—(CH₂)—(CHOH)—(CH₂)₅—, —(CH₂)₅—(CHOH)—(CH₂)—O—(CH₂)₅—O—(CH₂)—(CHOH)—(CH₂)₃—, —(CH₂)—(CHOH)—(CH₂)—O—(CH₂)₆—O—(CH₂)—(CHOH)—(CH₂)—, —(CH₂)₂—(CHOH)—(CH₂)—O—(CH₂)₆—O—(CH₂)—(CHOH)—(CH₂)₂—, —(CH₂)₃—(CHOH)—(CH₂)—O—(CH₂)₆—O—(CH₂)—(CHOH)—(CH₂)₃—, —(CH₂)₄—(CHOH)—(CH₂)—O—(CH₂)₆—O—(CH₂)—(CHOH)—(CH₂)₄—, —(CH₂)—(CHOH)—(CH₂)—O—(CH₂)₆—O—(CH₂)—(CHOH)—(CH₂)₃—, —(CH₂)—(CHOH)—(CH₂)—O—(CH₂)₆—O—(CH₂)—(CHOH)—(CH₂)₄—, —(CH₂)—(CHOH)—(CH₂)—O—(CH₂)₆—O—(CH₂)—(CHOH)—(CH₂)₅—, —(CH₂)—(CHOH)—(CH₂)—O—(CH₂)₆—O—(CH₂)—(CHOH)—(CH₂)₆—, —(CH₂)—(CHOH)—(CH₂)—O—(CH₂)₆—O—(CH₂)—(CHOH)—(CH₂)₇—, —(CH₂)₃—(CHOH)—(CH₂)—O—(CH₂)₆—O—(CH₂)—(CHOH)—(CH₂)—, —(CH₂)₄—(CHOH)—(CH₂)—O—(CH₂)₆—O—(CH₂)—(CHOH)—(CH₂)—, —(CH₂)₅—(CHOH)—(CH₂)—O—(CH₂)₆—O—(CH₂)—(CHOH)—(CH₂)—, —(CH₂)₆—(CHOH)—(CH₂)—O—(CH₂)₆—O—(CH₂)—(CHOH)—(CH₂)—, —(CH₂)₇—(CHOH)—(CH₂)—O—(CH₂)₆—O—(CH₂)—(CHOH)—(CH₂)—, —(CH₂)₂—(CHOH)—(CH₂)—O—(CH₂)₆—O—(CH₂)—(CHOH)—(CH₂)₃—, —(CH₂)₂—(CHOH)—(CH₂)—O—(CH₂)₆—O—(CH₂)—(CHOH)—(CH₂)₄—, —(CH₂)₂—(CHOH)—(CH₂)—O—(CH₂)₆—O—(CH₂)—(CHOH)—(CH₂)₅—, —(CH₂)₂—(CHOH)—(CH₂)—O—(CH₂)₆—O—(CH₂)—(CHOH)—(CH₂)₆—, —(CH₂)₃—(CHOH)—(CH₂)—O—(CH₂)₆—O—(CH₂)—(CHOH)—(CH₂)₂—, —(CH₂)₄—(CHOH)—(CH₂)—O—(CH₂)₆—O—(CH₂)—(CHOH)—(CH₂)₂—, —(CH₂)₅—(CHOH)—(CH₂)—O—(CH₂)₆—O—(CH₂)—(CHOH)—(CH₂)₂—, —(CH₂)₆—(CHOH)—(CH₂)—O—(CH₂)₆—O—(CH₂)—(CHOH)—(CH₂)₂—, —(CH₂)₃—(CHOH)—(CH₂)—O—(CH₂)₆—O—(CH₂)—(CHOH)—(CH₂)₄—, —(CH₂)₄—(CHOH)—(CH₂)—O—(CH₂)₆—O—(CH₂)—(CHOH)—(CH₂)₃—, —(CH₂)₃—(CHOH)—(CH₂)—O—(CH₂)₆—O—(CH₂)—(CHOH)—(CH₂)₅— and —(CH₂)₅—(CHOH)—(CH₂)—

O—(CH$_2$)$_6$—O—(CH$_2$)—(CHOH)—(CH$_2$)$_3$—, —(CF$_2$)—(CH$_2$)—, —(CH$_2$)—(CF$_2$)—, —(CH$_2$)—(CF$_2$)—(CH$_2$)—, —(CH$_2$)—(CF$_2$)—(CH$_2$)$_2$—, —(CH$_2$)—(CF$_2$)—(CH$_2$)$_3$—, —(CH$_2$)—(CF$_2$)—(CH$_2$)$_4$—, —(CH$_2$)—(CF$_2$)—(CH$_2$)$_5$—, —(CH$_2$)—(CF$_2$)—(CH$_2$)$_6$—, —(CH$_2$)—(CF$_2$)—(CH$_2$)$_7$—, —(CH$_2$)—(CF$_2$)—(CH$_2$)$_8$—, —(CH$_2$)—(CF$_2$)—(CH$_2$)$_9$—, —(CH$_2$)—(CF$_2$)—(CH$_2$)$_{10}$—, —(CH$_2$)$_2$—(CF$_2$)—(CH$_2$)—, —(CH$_2$)$_3$—(CF$_2$)—(CH$_2$)—, —(CH$_2$)$_4$—(CF$_2$)—(CH$_2$)—, —(CH$_2$)$_5$—(CF$_2$)—(CH$_2$)—, —(CH$_2$)$_6$—(CF$_2$)—(CH$_2$)—, —(CH$_2$)$_7$—(CF$_2$)—(CH$_2$)—, —(CH$_2$)$_8$—(CF$_2$)—(CH$_2$)—, —(CH$_2$)$_9$—(CF$_2$)—(CH$_2$)—, —(CH$_2$)$_{10}$—(CF$_2$)—(CH$_2$)—, —(CH$_2$)$_2$—(CF$_2$)—(CH$_2$)$_2$—, —(CH$_2$)$_3$—(CF$_2$)—(CH$_2$)$_3$—, —(CH$_2$)$_4$—(CF$_2$)—(CH$_2$)$_4$—, (CH$_2$)$_5$—(CF$_2$)—(CH$_2$)$_5$—, —(CH$_2$)$_2$—(CF$_2$)—(CH$_2$)—, —(CH$_2$)$_2$—(CF$_2$)—(CH$_2$)$_3$—, —(CH$_2$)$_2$—(CF$_2$)—(CH$_2$)$_4$—, —(CH$_2$)$_2$—(CF$_2$)—(CH$_2$)$_5$—, —(CH$_2$)$_2$—(CF$_2$)—(CH$_2$)$_6$—, —(CH$_2$)$_2$—(CF$_2$)—(CH$_2$)$_7$—, —(CH$_2$)$_2$—(CF$_2$)—(CH$_2$)$_8$—, —(CH$_2$)$_2$—(CF$_2$)—(CH$_2$)$_9$—, —(CH$_2$)$_3$—(CF$_2$)—(CH$_2$)—, —(CH$_2$)$_3$—(CF$_2$)—(CH$_2$)$_2$—, —(CH$_2$)$_3$—(CF$_2$)—(CH$_2$)$_4$—, —(CH$_2$)$_3$—(CF$_2$)—(CH$_2$)$_5$—, —(CH$_2$)$_3$—(CF$_2$)—(CH$_2$)$_6$—, —(CH$_2$)$_3$—(CF$_2$)—(CH$_2$)$_7$—, —(CH$_2$)$_3$—(CF$_2$)—(CH$_2$)$_8$—, —(CH$_2$)$_4$—(CF$_2$)—(CH$_2$)—, —(CH$_2$)$_4$—(CF$_2$)—(CH$_2$)$_2$—, —(CH$_2$)$_4$—(CF$_2$)—(CH$_2$)$_3$—, —(CH$_2$)$_4$—(CF$_2$)—(CH$_2$)$_5$—, —(CH$_2$)$_4$—(CF$_2$)—(CH$_2$)$_6$—, —(CH$_2$)$_4$—(CF$_2$)—(CH$_2$)$_7$—, —(CH$_2$)$_5$—(CF$_2$)—(CH$_2$)—, —(CH$_2$)$_5$—(CF$_2$)—(CH$_2$)$_2$—, —(CH$_2$)$_5$—(CF$_2$)—(CH$_2$)$_3$—, —(CH$_2$)$_5$—(CF$_2$)—(CH$_2$)$_4$—, —(CH$_2$)$_5$—(CF$_2$)—(CH$_2$)$_6$—, —(CH$_2$)$_6$—(CF$_2$)—(CH$_2$)—, —(CH$_2$)$_6$—(CF$_2$)—(CH$_2$)$_2$—, —(CH$_2$)$_6$—(CF$_2$)—(CH$_2$)$_3$—, —(CH$_2$)$_6$—(CF$_2$)—(CH$_2$)$_4$—, —(CH$_2$)$_6$—(CF$_2$)—(CH$_2$)$_5$—, —(CF$_2$)$_2$—(CH$_2$)—, —(CH$_2$)—(CF$_2$)$_2$—(CH$_2$)—, —(CH$_2$)—(CF$_2$)$_2$—(CH$_2$)$_2$—, —(CH$_2$)—(CF$_2$)$_2$—(CH$_2$)$_3$—, —(CH$_2$)—(CF$_2$)$_2$—(CH$_2$)$_4$—, —(CH$_2$)—(CF$_2$)$_2$—(CH$_2$)$_5$—, —(CH$_2$)—(CF$_2$)$_2$—(CH$_2$)$_6$—, —(CH$_2$)—(CF$_2$)$_2$—(CH$_2$)$_7$—, —(CH$_2$)—(CF$_2$)$_2$—(CH$_2$)$_8$—, —(CH$_2$)—(CF$_2$)$_2$—(CH$_2$)$_9$—, —(CH$_2$)$_2$—(CF$_2$)$_2$—(CH$_2$)—, —(CH$_2$)$_3$—(CF$_2$)$_2$—(CH$_2$)—, —(CH$_2$)$_4$—(CF$_2$)$_2$—(CH$_2$)—, —(CH$_2$)$_5$—(CF$_2$)$_2$—(CH$_2$)—, —(CH$_2$)$_6$—(CF$_2$)$_2$—(CH$_2$)—, —(CH$_2$)$_7$—(CF$_2$)$_2$—(CH$_2$)—, —(CH$_2$)$_8$—(CF$_2$)$_2$—(CH$_2$)—, —(CH$_2$)$_9$—(CF$_2$)$_2$—(CH$_2$)—, —(CH$_2$)$_2$—(CF$_2$)$_2$—(CH$_2$)$_2$—, —(CH$_2$)$_3$—(CF$_2$)$_2$—(CH$_2$)$_3$—, —(CH$_2$)$_4$—(CF$_2$)$_2$—(CH$_2$)$_4$—, —(CH$_2$)$_5$—(CF$_2$)$_2$—(CH$_2$)$_5$—, —(CH$_2$)$_2$—(CF$_2$)$_2$—(CH$_2$)$_3$—, —(CH$_2$)$_2$—(CF$_2$)$_2$—(CH$_2$)$_4$—, —(CH$_2$)$_2$—(CF$_2$)$_2$—(CH$_2$)$_5$—, (CH$_2$)$_2$—(CF$_2$)$_2$—(CH$_2$)$_6$—, —(CH$_2$)$_2$—(CF$_2$)$_2$—(CH$_2$)$_7$—, —(CH$_2$)$_2$—(CF$_2$)$_2$—(CH$_2$)$_8$—, —(CH$_2$)$_3$—(CF$_2$)$_2$—(CH$_2$)—, —(CH$_2$)$_3$—(CF$_2$)$_2$—(CH$_2$)$_2$—, —(CH$_2$)$_3$—(CF$_2$)$_2$—(CH$_2$)$_4$—, —(CH$_2$)$_3$—(CF$_2$)$_2$—(CH$_2$)$_5$—, —(CH$_2$)$_3$—(CF$_2$)$_2$—(CH$_2$)$_6$—, —(CH$_2$)$_3$—(CF$_2$)$_2$—(CH$_2$)$_7$—, —(CH$_2$)$_4$—(CF$_2$)$_2$—(CH$_2$)—, —(CH$_2$)$_4$—(CF$_2$)$_2$—(CH$_2$)$_2$—, —(CH$_2$)$_4$—(CF$_2$)$_2$—(CH$_2$)$_3$—, —(CH$_2$)$_4$—(CF$_2$)$_2$—(CH$_2$)$_5$—, —(CH$_2$)$_4$—(CF$_2$)$_2$—(CH$_2$)$_6$—, —(CH$_2$)$_5$—(CF$_2$)$_2$—(CH$_2$)—, —(CH$_2$)$_5$—(CF$_2$)$_2$—(CH$_2$)$_2$—, —(CH$_2$)$_5$—(CF$_2$)$_2$—(CH$_2$)$_3$—, —(CH$_2$)$_5$—(CF$_2$)$_2$—(CH$_2$)$_4$—, —(CH$_2$)$_6$—(CF$_2$)$_2$—(CH$_2$)—, —(CH$_2$)$_6$—(CF$_2$)$_2$—(CH$_2$)$_2$—, —(CH$_2$)$_6$—(CF$_2$)$_2$—(CH$_2$)$_3$—, —(CF$_2$)$_3$—(CH$_2$)—, —(CH$_2$)—(CF$_2$)$_3$—(CH$_2$)—, —(CH$_2$)—(CF$_2$)$_3$—(CH$_2$)$_2$—, —(CH$_2$)—(CF$_2$)$_3$—(CH$_2$)$_3$—,

—(CH$_2$)$_2$—(CF$_2$)$_3$—(CH$_2$)—, —(CH$_2$)$_3$—(CF$_2$)$_3$—(CH$_2$)—, —(CH$_2$)$_4$—(CF$_2$)$_3$—(CH$_2$)—, —(CH$_2$)$_5$—(CF$_2$)$_3$—(CH$_2$)—, —(CH$_2$)$_6$—(CF$_2$)$_3$—(CH$_2$)—, —(CH$_2$)$_7$—(CF$_2$)$_3$—(CH$_2$)—, —(CH$_2$)$_8$—(CF$_2$)$_3$—(CH$_2$)—, —(CH$_2$)—(CF$_2$)$_3$—(CH$_2$)$_2$—, —(CH$_2$)$_2$—(CF$_2$)$_3$—(CH$_2$)$_2$—, —(CH$_2$)$_3$—(CF$_2$)$_3$—(CH$_2$)$_3$—, —(CH$_2$)$_4$—(CF$_2$)$_3$—(CH$_2$)$_4$—, —(CH$_2$)$_2$—(CF$_2$)$_3$—(CH$_2$)—, —(CH$_2$)$_2$—(CF$_2$)$_3$—(CH$_2$)$_3$—, —(CH$_2$)$_2$—(CF$_2$)$_3$—(CH$_2$)$_4$—, —(CH$_2$)$_2$—(CF$_2$)$_3$—(CH$_2$)$_5$—, —(CH$_2$)$_2$—(CF$_2$)$_3$—(CH$_2$)$_6$—, —(CH$_2$)$_2$—(CF$_2$)$_3$—(CH$_2$)$_7$—, —(CH$_2$)$_3$—(CF$_2$)$_3$—(CH$_2$)$_2$—, —(CH$_2$)$_3$—(CF$_2$)$_3$—(CH$_2$)$_4$—, —(CH$_2$)$_3$—(CF$_2$)$_3$—(CH$_2$)$_5$—, —(CH$_2$)$_3$—(CF$_2$)$_3$—(CH$_2$)$_6$—, —(CH$_2$)$_4$—(CF$_2$)$_3$—(CH$_2$)—, —(CH$_2$)$_4$—(CF$_2$)$_3$—(CH$_2$)$_2$—, —(CH$_2$)$_4$—(CF$_2$)$_3$—(CH$_2$)$_3$—, —(CH$_2$)$_4$—(CF$_2$)$_3$—(CH$_2$)$_5$—, —(CH$_2$)$_5$—(CF$_2$)$_3$—(CH$_2$)—, —(CH$_2$)$_5$—(CF$_2$)$_3$—(CH$_2$)$_2$—, —(CH$_2$)$_5$—(CF$_2$)$_3$—(CH$_2$)$_3$—, —(CH$_2$)$_5$—(CF$_2$)$_3$—(CH$_2$)$_4$—, —(CH$_2$)$_6$—(CF$_2$)$_3$—(CH$_2$)—, —(CH$_2$)$_6$—(CF$_2$)$_3$—(CH$_2$)$_2$—, —(CH$_2$)$_6$—(CF$_2$)$_3$—(CH$_2$)$_3$—, —(CF$_2$)$_4$—(CH$_2$)—, —(CH$_2$)—(CF$_2$)$_4$—, —(CH$_2$)—(CF$_2$)$_4$—(CH$_2$)—, —(CH$_2$)—(CF$_2$)$_4$—(CH$_2$)$_2$—, —(CH$_2$)—(CF$_2$)$_4$—(CH$_2$)$_3$—, —(CH$_2$)—(CF$_2$)$_4$—(CH$_2$)$_4$—, —(CH$_2$)—(CF$_2$)$_4$—(CH$_2$)$_5$—, —(CH$_2$)—(CF$_2$)$_4$—(CH$_2$)$_6$—, —(CH$_2$)—(CF$_2$)$_4$—(CH$_2$)$_7$—, —(CH$_2$)—(CF$_2$)$_4$—(CH$_2$)$_8$—, —(CH$_2$)—(CF$_2$)$_4$—(CH$_2$)$_9$—, —(CH$_2$)—(CF$_2$)$_4$—(CH$_2$)$_{10}$—, —(CH$_2$)$_2$—(CF$_2$)$_4$—(CH$_2$)—, —(CH$_2$)$_3$—(CF$_2$)$_4$—(CH$_2$)—, —(CH$_2$)$_4$—(CF$_2$)$_4$—(CH$_2$)—, —(CH$_2$)$_5$—(CF$_2$)$_4$—(CH$_2$)—, —(CH$_2$)$_6$—(CF$_2$)$_4$—(CH$_2$)—, —(CH$_2$)$_7$—(CF$_2$)$_4$—(CH$_2$)—, —(CH$_2$)$_2$—(CF$_2$)$_4$—(CH$_2$)$_2$—, —(CH$_2$)$_3$—(CF$_2$)$_4$—(CH$_2$)$_3$—, —(CH$_2$)$_4$—(CF$_2$)$_4$—(CH$_2$)$_4$—, —(CH$_2$)$_5$—(CF$_2$)$_4$—(CH$_2$)$_5$—, —(CH$_2$)$_2$—(CF$_2$)$_4$—(CH$_2$)$_3$—, —(CH$_2$)$_2$—(CF$_2$)$_4$—(CH$_2$)$_4$—, —(CH$_2$)$_2$—(CF$_2$)$_4$—(CH$_2$)$_5$—, —(CH$_2$)$_2$—(CF$_2$)$_4$—(CH$_2$)$_6$—, —(CH$_2$)$_3$—(CF$_2$)$_4$—(CH$_2$)$_2$—, —(CH$_2$)$_3$—(CF$_2$)$_4$—(CH$_2$)$_4$—, —(CH$_2$)$_4$—(CF$_2$)$_4$—(CH$_2$)$_2$—, —(CH$_2$)$_4$—(CF$_2$)$_4$—(CH$_2$)$_3$—, —(CH$_2$)$_4$—(CF$_2$)$_4$—(CH$_2$)$_5$—, —(CH$_2$)$_5$—(CF$_2$)$_4$—(CH$_2$)$_2$—, —(CH$_2$)$_5$—(CF$_2$)$_4$—(CH$_2$)$_3$—, —(CH$_2$)$_6$—(CF$_2$)$_4$—(CH$_2$)$_2$—, —(CF$_2$)$_5$—(CH$_2$)—, —(CH$_2$)—(CF$_2$)$_5$—, —(CH$_2$)—(CF$_2$)$_5$—(CH$_2$)—, —(CH$_2$)—(CF$_2$)$_5$—(CH$_2$)$_2$—, —(CH$_2$)—(CF$_2$)$_5$—(CH$_2$)$_3$—, —(CH$_2$)—(CF$_2$)$_5$—(CH$_2$)$_4$—, —(CH$_2$)—(CF$_2$)$_5$—(CH$_2$)$_5$—, —(CH$_2$)—(CF$_2$)$_5$—(CH$_2$)$_6$—, —(CH$_2$)$_2$—(CF$_2$)$_5$—(CH$_2$)—, —(CH$_2$)$_3$—(CF$_2$)$_5$—(CH$_2$)—, —(CH$_2$)$_4$—(CF$_2$)$_5$—(CH$_2$)—, —(CH$_2$)$_5$—(CF$_2$)$_5$—(CH$_2$)—, —(CH$_2$)$_6$—(CF$_2$)$_5$—(CH$_2$)—, —(CH$_2$)$_2$—(CF$_2$)$_5$—(CH$_2$)$_2$—, —(CH$_2$)$_3$—(CF$_2$)$_5$—(CH$_2$)$_3$—, —(CH$_2$)$_4$—(CF$_2$)$_5$—(CH$_2$)$_4$—, —(CH$_2$)$_5$—(CF$_2$)$_5$—(CH$_2$)$_3$—, —(CH$_2$)$_2$—(CF$_2$)$_5$—(CH$_2$)$_4$—, —(CH$_2$)$_2$—(CF$_2$)$_5$—(CH$_2$)$_5$—, —(CH$_2$)$_2$—(CF$_2$)$_5$—(CH$_2$)$_6$—, —(CH$_2$)$_3$—(CF$_2$)$_5$—(CH$_2$)$_2$—, —(CH$_2$)$_3$—(CF$_2$)$_5$—(CH$_2$)$_4$—, —(CH$_2$)$_4$—(CF$_2$)$_5$—(CH$_2$)$_2$—, —(CH$_2$)$_4$—(CF$_2$)$_5$—(CH$_2$)$_3$—, —(CH$_2$)$_5$—(CF$_2$)$_5$—(CH$_2$)$_2$—, —(CHCF$_3$)—(CH$_2$)—, —(CH$_2$)—(CHCF$_3$)—, —(CH$_2$)—(CHCF$_3$)—(CH$_2$)—, —(CH$_2$)—(CHCF$_3$)—(CH$_2$)$_2$—, —(CH$_2$)—(CHCF$_3$)—(CH$_2$)$_3$—, —(CH$_2$)—(CHCF$_3$)—(CH$_2$)$_4$—, —(CH$_2$)—(CHCF$_3$)—(CH$_2$)$_5$—, —(CH$_2$)—(CHCF$_3$)—(CH$_2$)$_6$—, —(CH$_2$)—(CHCF$_3$)—(CH$_2$)$_7$—, —(CH$_2$)—(CHCF$_3$)—(CH$_2$)$_8$—, —(CH$_2$)—(CHCF$_3$)—(CH$_2$)$_9$—, —(CH$_2$)—(CHCF$_3$)—(CH$_2$)$_{10}$—, —(CH$_2$)$_2$—(CHCF$_3$)—(CH$_2$)—, —(CH$_2$)$_3$—(CHCF$_3$)—(CH$_2$)—, —(CH$_2$)$_4$—(CHCF$_3$)—(CH$_2$)—, —(CH$_2$)$_5$—(CHCF$_3$)—(CH$_2$)—, —(CH$_2$)$_6$—(CHCF$_3$)—(CH$_2$)—, —(CH$_2$)$_7$—(CHCF$_3$)—(CH$_2$)—, —(CH$_2$)$_8$—(CHCF$_3$)—(CH$_2$)—, —(CH$_2$)$_9$—(CHCF$_3$)—(CH$_2$)—, —(CH$_2$)$_{10}$—(CHCF$_3$)—(CH$_2$)—, —(CH$_2$)$_2$—(CHCF$_3$)—(CH$_2$)$_2$—, —(CH$_2$)$_3$—(CHCF$_3$)—(CH$_2$)$_3$—, —(CH$_2$)$_4$—(CHCF$_3$)—

—(CH$_2$)$_4$—, —(CH$_2$)$_5$—(CHCF$_3$)—(CH$_2$)$_5$—, —(CH$_2$)$_2$—(CHCF$_3$)—(CH$_2$)$_3$—, —(CH$_2$)$_2$—(CHCF$_3$)—(CH$_2$)$_4$—, —(CH$_2$)$_2$—(CHCF$_3$)—(CH$_2$)$_5$—, —(CH$_2$)$_2$—(CHCF$_3$)—(CH$_2$)$_6$—, —(CH$_2$)$_2$—(CHCF$_3$)—(CH$_2$)$_7$—, —(CH$_2$)$_2$—(CHCF$_3$)—(CH$_2$)$_8$—, —(CH$_2$)$_2$—(CHCF$_3$)—(CH$_2$)$_9$—, —(CH$_2$)$_3$—(CHCF$_3$)—(CH$_2$)$_2$—, —(CH$_2$)$_3$—(CHCF$_3$)—(CH$_2$)$_4$—, —(CH$_2$)$_3$—(CHCF$_3$)—(CH$_2$)$_5$—, —(CH$_2$)$_3$—(CHCF$_3$)—(CH$_2$)$_6$—, —(CH$_2$)$_3$—(CHCF$_3$)—(CH$_2$)$_7$—, —(CH$_2$)$_3$—(CHCF$_3$)—(CH$_2$)$_8$—, —(CH$_2$)$_4$—(CHCF$_3$)—(CH$_2$)$_2$—, —(CH$_2$)$_4$—(CHCF$_3$)—(CH$_2$)$_3$—, —(CH$_2$)$_4$—(CHCF$_3$)—(CH$_2$)$_5$—, —(CH$_2$)$_4$—(CHCF$_3$)—(CH$_2$)$_6$—, —(CH$_2$)$_4$—(CHCF$_3$)—(CH$_2$)$_7$—, —(CH$_2$)$_5$—(CHCF$_3$)—(CH$_2$)$_2$—, —(CH$_2$)$_5$—(CHCF$_3$)—(CH$_2$)$_3$—, —(CH$_2$)$_5$—(CHCF$_3$)—(CH$_2$)$_4$—, —(CH$_2$)$_5$—(CHCF$_3$)—(CH$_2$)$_6$—, —(CH$_2$)$_6$—(CHCF$_3$)—(CH$_2$)$_2$—, —(CH$_2$)$_6$—(CHCF$_3$)—(CH$_2$)$_3$—, —(CH$_2$)$_6$—(CHCF$_3$)—(CH$_2$)$_4$—, —(CH$_2$)$_6$—(CHCF$_3$)—(CH$_2$)$_5$—, —(CHCF$_3$)$_2$—(CH$_2$)—, —(CH$_2$)—(CHCF$_3$)$_2$—, —(CH$_2$)—(CHCF$_3$)$_2$—(CH$_2$)—, —(CH$_2$)—(CHCF$_3$)$_2$—(CH$_2$)$_2$—, —(CH$_2$)—(CHCF$_3$)$_2$—(CH$_2$)$_3$—, —(CH$_2$)—(CHCF$_3$)$_2$—(CH$_2$)$_4$—, —(CH$_2$)—(CHCF$_3$)$_2$—(CH$_2$)$_5$—, —(CH$_2$)—(CHCF$_3$)$_2$—(CH$_2$)$_6$—, —(CH$_2$)—(CHCF$_3$)$_2$—(CH$_2$)$_7$—, —(CH$_2$)—(CHCF$_3$)$_2$—(CH$_2$)$_8$—, —(CH$_2$)—(CHCF$_3$)$_2$—(CH$_2$)$_9$—, —(CH$_2$)$_2$—(CHCF$_3$)$_2$—(CH$_2$)—, —(CH$_2$)$_3$—(CHCF$_3$)$_2$—(CH$_2$)—, —(CH$_2$)$_4$—(CHCF$_3$)$_2$—(CH$_2$)—, —(CH$_2$)$_5$—(CHCF$_3$)$_2$—(CH$_2$)—, —(CH$_2$)$_6$—(CHCF$_3$)$_2$—(CH$_2$)—, —(CH$_2$)$_7$—(CHCF$_3$)$_2$—(CH$_2$)—, —(CH$_2$)$_8$—(CHCF$_3$)$_2$—(CH$_2$)—, —(CH$_2$)$_9$—(CHCF$_3$)$_2$—(CH$_2$)—, —(CH$_2$)$_2$—(CHCF$_3$)$_2$—(CH$_2$)$_2$—, —(CH$_2$)$_3$—(CHCF$_3$)$_2$—(CH$_2$)$_3$—, —(CH$_2$)$_4$—(CHCF$_3$)$_2$—(CH$_2$)$_4$—, —(CH$_2$)$_5$—(CHCF$_3$)$_2$—(CH$_2$)$_5$—, —(CH$_2$)$_2$—(CHCF$_3$)$_2$—(CH$_2$)$_3$—, —(CH$_2$)$_2$—(CHCF$_3$)$_2$—(CH$_2$)$_4$—, —(CH$_2$)$_2$—(CHCF$_3$)$_2$—(CH$_2$)$_5$—, —(CH$_2$)$_2$—(CHCF$_3$)$_2$—(CH$_2$)$_6$—, —(CH$_2$)$_2$—(CHCF$_3$)$_2$—(CH$_2$)$_7$—, —(CH$_2$)$_2$—(CHCF$_3$)$_2$—(CH$_2$)$_8$—, —(CH$_2$)$_3$—(CHCF$_3$)$_2$—(CH$_2$)$_2$—, —(CH$_2$)$_3$—(CHCF$_3$)$_2$—(CH$_2$)$_4$—, —(CH$_2$)$_3$—(CHCF$_3$)$_2$—(CH$_2$)$_5$—, —(CH$_2$)$_3$—(CHCF$_3$)$_2$—(CH$_2$)$_6$—, —(CH$_2$)$_4$—(CHCF$_3$)$_2$—(CH$_2$)$_2$—, —(CH$_2$)$_4$—(CHCF$_3$)$_2$—(CH$_2$)$_3$—, —(CH$_2$)$_4$—(CHCF$_3$)$_2$—(CH$_2$)$_5$—, —(CH$_2$)$_4$—(CHCF$_3$)$_2$—(CH$_2$)$_6$—, —(CH$_2$)$_5$—(CHCF$_3$)$_2$—(CH$_2$)$_2$—, —(CH$_2$)$_5$—(CHCF$_3$)$_2$—(CH$_2$)$_3$—, —(CH$_2$)$_5$—(CHCF$_3$)$_2$—(CH$_2$)$_4$—, —(CH$_2$)$_6$—(CHCF$_3$)$_2$—(CH$_2$)$_2$—, —(CH$_2$)$_6$—(CHCF$_3$)$_2$—(CH$_2$)$_3$—, —(CH$_2$)$_6$—(CHCF$_3$)$_2$—(CH$_2$)$_4$—, —(CHCF$_3$)$_3$—(CH$_2$)—, —(CH$_2$)—(CHCF$_3$)$_3$—, —(CH$_2$)—(CHCF$_3$)$_3$—(CH$_2$)—, —(CH$_2$)—(CHCF$_3$)$_3$—(CH$_2$)$_2$—, —(CH$_2$)—(CHCF$_3$)$_3$—(CH$_2$)$_3$—, —(CH$_2$)—(CHCF$_3$)$_3$—(CH$_2$)$_4$—, —(CH$_2$)—(CHCF$_3$)$_3$—(CH$_2$)$_5$—, —(CH$_2$)—(CHCF$_3$)$_3$—(CH$_2$)$_6$—, —(CH$_2$)—(CHCF$_3$)$_3$—(CH$_2$)$_7$—, —(CH$_2$)—(CHCF$_3$)$_3$—(CH$_2$)$_8$—, —(CH$_2$)$_2$—(CHCF$_3$)$_3$—(CH$_2$)—, —(CH$_2$)$_3$—(CHCF$_3$)$_3$—(CH$_2$)—, —(CH$_2$)$_4$—(CHCF$_3$)$_3$—(CH$_2$)—, —(CH$_2$)$_5$—(CHCF$_3$)$_3$—(CH$_2$)—, —(CH$_2$)$_6$—(CHCF$_3$)$_3$—(CH$_2$)—, —(CH$_2$)$_7$—(CHCF$_3$)$_3$—(CH$_2$)—, —(CH$_2$)$_8$—(CHCF$_3$)$_3$—(CH$_2$)—, —(CH$_2$)$_2$—(CHCF$_3$)$_3$—(CH$_2$)$_2$—, —(CH$_2$)$_3$—(CHCF$_3$)$_3$—(CH$_2$)$_3$—, —(CH$_2$)$_4$—(CHCF$_3$)$_3$—(CH$_2$)$_4$—, —(CH$_2$)$_2$—(CHCF$_3$)$_3$—(CH$_2$)$_3$—, —(CH$_2$)$_2$—(CHCF$_3$)$_3$—(CH$_2$)$_4$—, —(CH$_2$)$_2$—(CHCF$_3$)$_3$—(CH$_2$)$_5$—, —(CH$_2$)$_2$—(CHCF$_3$)$_3$—(CH$_2$)$_6$—, —(CH$_2$)$_2$—(CHCF$_3$)$_3$—(CH$_2$)$_7$—, —(CH$_2$)$_3$—(CHCF$_3$)$_3$—(CH$_2$)$_2$—, —(CH$_2$)$_3$—(CHCF$_3$)$_3$—(CH$_2$)$_4$—, —(CH$_2$)$_3$—(CHCF$_3$)$_3$—(CH$_2$)$_5$—, —(CH$_2$)$_3$—(CHCF$_3$)$_3$—(CH$_2$)$_6$—, —(CH$_2$)$_4$—(CHCF$_3$)$_3$—(CH$_2$)$_2$—, —(CHCF$_3$)$_4$—(CH$_2$)—, —(CH$_2$)—(CHCF$_3$)$_4$—, —(CH$_2$)—(CHCF$_3$)$_4$—(CH$_2$)—, —(CH$_2$)—(CHCF$_3$)$_4$—(CH$_2$)$_2$—, —(CH$_2$)—(CHCF$_3$)$_4$—(CH$_2$)$_3$—, —(CH$_2$)—(CHCF$_3$)$_4$—(CH$_2$)$_4$—, —(CH$_2$)—(CHCF$_3$)$_4$—(CH$_2$)$_5$—, —(CH$_2$)—(CHCF$_3$)$_4$—(CH$_2$)$_6$—, —(CH$_2$)—(CHCF$_3$)$_4$—(CH$_2$)$_7$—, —(CH$_2$)—(CHCF$_3$)$_4$—(CH$_2$)$_8$—, —(CH$_2$)—(CHCF$_3$)$_4$—(CH$_2$)$_9$—, —(CH$_2$)—(CHCF$_3$)$_4$—(CH$_2$)$_{10}$—, —(CH$_2$)$_2$—(CHCF$_3$)$_4$—(CH$_2$)—, —(CH$_2$)$_3$—(CHCF$_3$)$_4$—(CH$_2$)—, —(CH$_2$)$_4$—(CHCF$_3$)$_4$—(CH$_2$)—, —(CH$_2$)$_5$—(CHCF$_3$)$_4$—(CH$_2$)—, —(CH$_2$)$_6$—(CHCF$_3$)$_4$—(CH$_2$)—, —(CH$_2$)$_7$—(CHCF$_3$)$_4$—(CH$_2$)—, —(CH$_2$)$_2$—(CHCF$_3$)$_4$—(CH$_2$)$_2$—, —(CH$_2$)$_3$—(CHCF$_3$)$_4$—(CH$_2$)$_3$—, —(CH$_2$)$_4$—(CHCF$_3$)$_4$—(CH$_2$)$_4$—, —(CH$_2$)$_5$—(CHCF$_3$)$_4$—(CH$_2$)$_5$—, —(CH$_2$)$_2$—(CHCF$_3$)$_4$—(CH$_2$)$_3$—, —(CH$_2$)$_2$—(CHCF$_3$)$_4$—(CH$_2$)$_4$—, —(CH$_2$)$_2$—(CHCF$_3$)$_4$—(CH$_2$)$_5$—, —(CH$_2$)$_2$—(CHCF$_3$)$_4$—(CH$_2$)$_6$—, —(CH$_2$)$_3$—(CHCF$_3$)$_4$—(CH$_2$)$_2$—, —(CH$_2$)$_3$—(CHCF$_3$)$_4$—(CH$_2$)$_4$—, —(CH$_2$)$_4$—(CHCF$_3$)$_4$—(CH$_2$)$_2$—, —(CH$_2$)$_4$—(CHCF$_3$)$_4$—(CH$_2$)$_3$—, —(CH$_2$)$_4$—(CHCF$_3$)$_4$—(CH$_2$)$_5$—, —(CH$_2$)$_5$—(CHCF$_3$)$_4$—(CH$_2$)$_2$—, —(CH$_2$)$_5$—(CHCF$_3$)$_4$—(CH$_2$)$_3$—, —(CH$_2$)$_6$—(CHCF$_3$)$_4$—(CH$_2$)$_2$—, —(CHCF$_3$)$_5$—(CH$_2$)—, —(CH$_2$)—(CHCF$_3$)$_5$—, —(CH$_2$)—(CHCF$_3$)$_5$—(CH$_2$)—, —(CH$_2$)—(CHCF$_3$)$_5$—(CH$_2$)$_2$—, —(CH$_2$)—(CHCF$_3$)$_5$—(CH$_2$)$_3$—, —(CH$_2$)—(CHCF$_3$)$_5$—(CH$_2$)$_4$—, —(CH$_2$)—(CHCF$_3$)$_5$—(CH$_2$)$_5$—, —(CH$_2$)—(CHCF$_3$)$_5$—(CH$_2$)$_6$—, —(CH$_2$)$_2$—(CHCF$_3$)$_5$—(CH$_2$)—, —(CH$_2$)$_3$—(CHCF$_3$)$_5$—(CH$_2$)—, —(CH$_2$)$_4$—(CHCF$_3$)$_5$—(CH$_2$)—, —(CH$_2$)$_5$—(CHCF$_3$)$_5$—(CH$_2$)—, —(CH$_2$)$_6$—(CHCF$_3$)$_5$—(CH$_2$)—, —(CH$_2$)$_2$—(CHCF$_3$)$_5$—(CH$_2$)$_2$—, —(CH$_2$)$_3$—(CHCF$_3$)$_5$—(CH$_2$)$_3$—, —(CH$_2$)$_4$—(CHCF$_3$)$_5$—(CH$_2$)$_4$—, —(CH$_2$)$_2$—(CHCF$_3$)$_5$—(CH$_2$)$_3$—, —(CH$_2$)$_2$—(CHCF$_3$)$_5$—(CH$_2$)$_4$—, —(CH$_2$)$_2$—(CHCF$_3$)$_5$—(CH$_2$)$_5$—, —(CH$_2$)$_2$—(CHCF$_3$)$_5$—(CH$_2$)$_6$—, —(CH$_2$)$_3$—(CHCF$_3$)$_5$—(CH$_2$)$_2$—, —(CH$_2$)$_3$—(CHCF$_3$)$_5$—(CH$_2$)$_4$—, —(CH$_2$)$_4$—(CHCF$_3$)$_5$—(CH$_2$)$_2$—, —(CH$_2$)$_4$—(CHCF$_3$)$_5$—(CH$_2$)$_3$—, —(CH$_2$)$_5$—(CHCF$_3$)$_5$—(CH$_2$)$_2$—, —[C(CH$_3$)CF$_3$]—(CH$_2$)—, —(CH$_2$)—[C(CH$_3$)CF$_3$]—, —(CH$_2$)—[C(CH$_3$)CF$_3$]—(CH$_2$)—, —(CH$_2$)—[C(CH$_3$)CF$_3$]—(CH$_2$)$_2$—, —(CH$_2$)—[C(CH$_3$)CF$_3$]—(CH$_2$)$_3$—, —(CH$_2$)—[C(CH$_3$)CF$_3$]—(CH$_2$)$_4$—, —(CH$_2$)—[C(CH$_3$)CF$_3$]—(CH$_2$)$_5$—, —(CH$_2$)—[C(CH$_3$)CF$_3$]—(CH$_2$)$_6$—, —(CH$_2$)—[C(CH$_3$)CF$_3$]—(CH$_2$)$_7$—, —(CH$_2$)—[C(CH$_3$)CF$_3$]—(CH$_2$)$_8$—, —(CH$_2$)—[C(CH$_3$)CF$_3$]—(CH$_2$)$_9$—, —(CH$_2$)—[C(CH$_3$)CF$_3$]—(CH$_2$)$_{10}$—, —(CH$_2$)$_2$—[C(CH$_3$)CF$_3$]—(CH$_2$)—, —(CH$_2$)$_3$—[C(CH$_3$)CF$_3$]—(CH$_2$)—, —(CH$_2$)$_4$—[C(CH$_3$)CF$_3$]—(CH$_2$)—, —(CH$_2$)$_5$—[C(CH$_3$)CF$_3$]—(CH$_2$)—, —(CH$_2$)$_6$—[C(CH$_3$)CF$_3$]—(CH$_2$)—, —(CH$_2$)$_7$—[C(CH$_3$)CF$_3$]—(CH$_2$)—, —(CH$_2$)$_8$—[C(CH$_3$)CF$_3$]—(CH$_2$)—, —(CH$_2$)$_9$—[C(CH$_3$)CF$_3$]—(CH$_2$)—, —(CH$_2$)$_{10}$—[C(CH$_3$)CF$_3$]—(CH$_2$)—, —(CH$_2$)$_2$—[C(CH$_3$)CF$_3$]—(CH$_2$)$_2$—, —(CH$_2$)$_3$—[C(CH$_3$)CF$_3$]—(CH$_2$)$_3$—, —(CH$_2$)$_4$—[C(CH$_3$)CF$_3$]—(CH$_2$)$_4$—, —(CH$_2$)$_5$—[C(CH$_3$)CF$_3$]—(CH$_2$)$_5$—, —(CH$_2$)$_2$—[C(CH$_3$)CF$_3$]—(CH$_2$)$_3$—, —(CH$_2$)$_2$—[C(CH$_3$)CF$_3$]—(CH$_2$)$_4$—, —(CH$_2$)$_2$—[C(CH$_3$)CF$_3$]—(CH$_2$)$_5$—, —(CH$_2$)$_2$—[C(CH$_3$)CF$_3$]—(CH$_2$)$_6$—, —(CH$_2$)$_2$—[C(CH$_3$)CF$_3$]—(CH$_2$)$_7$—, —(CH$_2$)$_2$—[C(CH$_3$)CF$_3$]—(CH$_2$)$_8$—, —(CH$_2$)$_2$—[C(CH$_3$)CF$_3$]—(CH$_2$)$_9$—, —(CH$_2$)$_3$—[C(CH$_3$)CF$_3$]—(CH$_2$)$_2$—, —(CH$_2$)$_3$—[C(CH$_3$)CF$_3$]—(CH$_2$)$_4$—, —(CH$_2$)$_3$—[C(CH$_3$)CF$_3$]—(CH$_2$)$_5$—, —(CH$_2$)$_3$—[C(CH$_3$)CF$_3$]—(CH$_2$)$_6$—, —(CH$_2$)$_3$—[C(CH$_3$)CF$_3$]—(CH$_2$)$_7$—, —(CH$_2$)$_3$—[C(CH$_3$)CF$_3$]—(CH$_2$)$_8$—, —(CH$_2$)$_4$—[C(CH$_3$)CF$_3$]—(CH$_2$)$_2$—, —(CH$_2$)$_4$—[C(CH$_3$)CF$_3$]—(CH$_2$)$_3$—, —(CH$_2$)$_4$—[C(CH$_3$)CF$_3$]—(CH$_2$)$_5$—, —(CH$_2$)$_4$—[C(CH$_3$)CF$_3$]—(CH$_2$)$_6$—, —(CH$_2$)$_4$—[C(CH$_3$)CF$_3$]—(CH$_2$)$_7$—, —(CH$_2$)$_5$—[C(CH$_3$)CF$_3$]—(CH$_2$)$_2$—, —(CH$_2$)$_5$—[C(CH$_3$)CF$_3$]—(CH$_2$)$_3$—, —(CH$_2$)$_5$—[C(CH$_3$)CF$_3$]—(CH$_2$)$_4$—, —(CH$_2$)$_5$—[C(CH$_3$)CF$_3$]—(CH$_2$)$_6$—,

—(CH$_2$)$_6$—[C(CH$_3$)CF$_3$]—(CH$_2$)$_2$—, —(CH$_2$)$_6$—[C(CH$_3$)CF$_3$]—(CH$_2$)$_3$—, —(CH$_2$)$_6$—[C(CH$_3$)CF$_3$]—(CH$_2$)$_4$—, —(CH$_2$)$_6$—[C(CH$_3$)CF$_3$]—(CH$_2$)$_5$—, —[C(CH$_3$)CF$_3$]$_2$—(CH$_2$)—, —(CH$_2$)—[C(CH$_3$)CF$_3$]$_2$—, —(CH$_2$)—[C(CH$_3$)CF$_3$]$_2$—(CH$_2$)—, —(CH$_2$)—[C(CH$_3$)CF$_3$]$_2$—(CH$_2$)$_2$—, —(CH$_2$)—[C(CH$_3$)CF$_3$]$_2$—(CH$_2$)$_3$—, —(CH$_2$)—[C(CH$_3$)CF$_3$]$_2$—(CH$_2$)$_4$—, —(CH$_2$)—[C(CH$_3$)CF$_3$]$_2$—(CH$_2$)$_5$—, —(CH$_2$)—[C(CH$_3$)CF$_3$]$_2$—(CH$_2$)$_6$—, —(CH$_2$)—[C(CH$_3$)CF$_3$]$_2$—(CH$_2$)$_7$—, —(CH$_2$)—[C(CH$_3$)CF$_3$]$_2$—(CH$_2$)$_8$—, —(CH$_2$)—[C(CH$_3$)CF$_3$]$_2$—(CH$_2$)$_9$—, —(CH$_2$)$_2$—[C(CH$_3$)CF$_3$]$_2$—(CH$_2$)—, —(CH$_2$)$_3$—[C(CH$_3$)CF$_3$]$_2$—(CH$_2$)—, —(CH$_2$)$_4$—[C(CH$_3$)CF$_3$]$_2$—(CH$_2$)—, —(CH$_2$)$_5$—[C(CH$_3$)CF$_3$]$_2$—(CH$_2$)—, —(CH$_2$)$_6$—[C(CH$_3$)CF$_3$]$_2$—(CH$_2$)—, —(CH$_2$)$_7$—[C(CH$_3$)CF$_3$]$_2$—(CH$_2$)—, —(CH$_2$)$_8$—[C(CH$_3$)CF$_3$]$_2$—(CH$_2$)—, —(CH$_2$)$_9$—[C(CH$_3$)CF$_3$]$_2$—(CH$_2$)—, —(CH$_2$)$_2$—[C(CH$_3$)CF$_3$]$_2$—(CH$_2$)$_2$—, —(CH$_2$)$_3$—[C(CH$_3$)CF$_3$]$_2$—(CH$_2$)$_3$—, —(CH$_2$)$_4$—[C(CH$_3$)CF$_3$]$_2$—(CH$_2$)$_4$—, —(CH$_2$)$_5$—[C(CH$_3$)CF$_3$]$_2$—(CH$_2$)$_5$—, —(CH$_2$)$_2$—[C(CH$_3$)CF$_3$]$_2$—(CH$_2$)$_3$—, —(CH$_2$)$_2$—[C(CH$_3$)CF$_3$]$_2$—(CH$_2$)$_4$—, —(CH$_2$)$_2$—[C(CH$_3$)CF$_3$]$_2$—(CH$_2$)$_5$—, —(CH$_2$)$_2$—[C(CH$_3$)CF$_3$]$_2$—(CH$_2$)$_6$—, —(CH$_2$)$_2$—[C(CH$_3$)CF$_3$]$_2$—(CH$_2$)$_7$—, —(CH$_2$)$_2$—[C(CH$_3$)CF$_3$]$_2$—(CH$_2$)$_8$—, —(CH$_2$)$_3$—[C(CH$_3$)CF$_3$]$_2$—(CH$_2$)$_2$—, —(CH$_2$)$_3$—[C(CH$_3$)CF$_3$]$_2$—(CH$_2$)$_4$—, —(CH$_2$)$_3$—[C(CH$_3$)CF$_3$]$_2$—(CH$_2$)$_5$—, —(CH$_2$)$_3$—[C(CH$_3$)CF$_3$]$_2$—(CH$_2$)$_6$—, —(CH$_2$)$_3$—[C(CH$_3$)CF$_3$]$_2$—(CH$_2$)$_7$—, —(CH$_2$)$_4$—[C(CH$_3$)CF$_3$]$_2$—(CH$_2$)$_2$—, —(CH$_2$)$_4$—[C(CH$_3$)CF$_3$]$_2$—(CH$_2$)$_3$—, —(CH$_2$)$_4$—[C(CH$_3$)CF$_3$]$_2$—(CH$_2$)$_5$—, —(CH$_2$)$_4$—[C(CH$_3$)CF$_3$]$_2$—(CH$_2$)$_6$—, —(CH$_2$)$_5$—[C(CH$_3$)CF$_3$]$_2$—(CH$_2$)$_2$—, —(CH$_2$)$_5$—[C(CH$_3$)CF$_3$]$_2$—(CH$_2$)$_3$—, —(CH$_2$)$_5$—[C(CH$_3$)CF$_3$]$_2$—(CH$_2$)$_4$—, —(CH$_2$)$_6$—[C(CH$_3$)CF$_3$]$_2$—(CH$_2$)$_2$—, —(CH$_2$)$_6$—[C(CH$_3$)CF$_3$]$_2$—(CH$_2$)$_3$—, —(CH$_2$)$_6$—[C(CH$_3$)CF$_3$]$_2$—(CH$_2$)$_4$—, —[C(CH$_3$)CF$_3$]$_3$—(CH$_2$)—, —(CH$_2$)—[C(CH$_3$)CF$_3$]$_3$—, —(CH$_2$)—[C(CH$_3$)CF$_3$]$_3$—(CH$_2$)—, —(CH$_2$)—[C(CH$_3$)CF$_3$]$_3$—(CH$_2$)$_2$—, —(CH$_2$)—[C(CH$_3$)CF$_3$]$_3$—(CH$_2$)$_3$—, —(CH$_2$)—[C(CH$_3$)CF$_3$]$_3$—(CH$_2$)$_4$—, —(CH$_2$)—[C(CH$_3$)CF$_3$]$_3$—(CH$_2$)$_5$—, —(CH$_2$)—[C(CH$_3$)CF$_3$]$_3$—(CH$_2$)$_6$—, —(CH$_2$)—[C(CH$_3$)CF$_3$]$_3$—(CH$_2$)$_7$—, —(CH$_2$)—[C(CH$_3$)CF$_3$]$_3$—(CH$_2$)$_8$—, —(CH$_2$)$_2$—[C(CH$_3$)CF$_3$]$_3$—(CH$_2$)—, —(CH$_2$)$_3$—[C(CH$_3$)CF$_3$]$_3$—(CH$_2$)—, —(CH$_2$)$_4$—[C(CH$_3$)CF$_3$]$_3$—(CH$_2$)—, —(CH$_2$)$_5$—[C(CH$_3$)CF$_3$]$_3$—(CH$_2$)—, —(CH$_2$)$_6$—[C(CH$_3$)CF$_3$]$_3$—(CH$_2$)—, —(CH$_2$)$_7$—[C(CH$_3$)CF$_3$]$_3$—(CH$_2$)—, —(CH$_2$)$_8$—[C(CH$_3$)CF$_3$]$_3$—(CH$_2$)—, —(CH$_2$)$_2$—[C(CH$_3$)CF$_3$]$_3$—(CH$_2$)$_2$—, —(CH$_2$)$_3$—[C(CH$_3$)CF$_3$]$_3$—(CH$_2$)$_3$—, —(CH$_2$)$_4$—[C(CH$_3$)CF$_3$]$_3$—(CH$_2$)$_4$—, —(CH$_2$)$_2$—[C(CH$_3$)CF$_3$]$_3$—(CH$_2$)$_3$—, —(CH$_2$)$_2$—[C(CH$_3$)CF$_3$]$_3$—(CH$_2$)$_4$—, —(CH$_2$)$_2$—[C(CH$_3$)CF$_3$]$_3$—(CH$_2$)$_5$—, —(CH$_2$)$_2$—[C(CH$_3$)CF$_3$]$_3$—(CH$_2$)$_6$—, —(CH$_2$)$_2$—[C(CH$_3$)CF$_3$]$_3$—(CH$_2$)$_7$—, —(CH$_2$)$_3$—[C(CH$_3$)CF$_3$]$_3$—(CH$_2$)$_2$—, —(CH$_2$)$_3$—[C(CH$_3$)CF$_3$]$_3$—(CH$_2$)$_4$—, —(CH$_2$)$_3$—[C(CH$_3$)CF$_3$]$_3$—(CH$_2$)$_5$—, —(CH$_2$)$_3$—[C(CH$_3$)CF$_3$]$_3$—(CH$_2$)$_6$—, —(CH$_2$)$_4$—[C(CH$_3$)CF$_3$]$_3$—(CH$_2$)$_2$—, —(CH$_2$)$_4$—[C(CH$_3$)CF$_3$]$_3$—(CH$_2$)$_3$—, —(CH$_2$)$_4$—[C(CH$_3$)CF$_3$]$_3$—(CH$_2$)$_5$—, —(CH$_2$)$_5$—[C(CH$_3$)CF$_3$]$_3$—(CH$_2$)$_2$—, —(CH$_2$)$_5$—[C(CH$_3$)CF$_3$]$_3$—(CH$_2$)$_3$—, —(CH$_2$)$_5$—[C(CH$_3$)CF$_3$]$_3$—(CH$_2$)$_4$—, —(CH$_2$)$_6$—[C(CH$_3$)CF$_3$]$_3$—(CH$_2$)$_2$—, —(CH$_2$)$_6$—[C(CH$_3$)CF$_3$]$_3$—(CH$_2$)$_3$—, —[C(CH$_3$)CF$_3$]$_4$—(CH$_2$)—, —(CH$_2$)—[C(CH$_3$)CF$_3$]$_4$—, —(CH$_2$)—[C(CH$_3$)CF$_3$]$_4$—(CH$_2$)—, —(CH$_2$)—[C(CH$_3$)CF$_3$]$_4$—(CH$_2$)$_2$—, —(CH$_2$)—[C(CH$_3$)CF$_3$]$_4$—(CH$_2$)$_3$—, —(CH$_2$)—[C(CH$_3$)CF$_3$]$_4$—(CH$_2$)$_4$—, —(CH$_2$)—[C(CH$_3$)CF$_3$]$_4$—(CH$_2$)$_5$—, —(CH$_2$)—[C(CH$_3$)CF$_3$]$_4$—(CH$_2$)$_6$—, —(CH$_2$)—[C(CH$_3$)CF$_3$]$_4$—(CH$_2$)$_7$—, —(CH$_2$)—[C(CH$_3$)CF$_3$]$_4$—(CH$_2$)$_8$—, —(CH$_2$)—[C(CH$_3$)CF$_3$]$_4$—(CH$_2$)$_9$—, —(CH$_2$)—[C(CH$_3$)CF$_3$]$_4$—(CH$_2$)$_{10}$—, —(CH$_2$)$_2$—[C(CH$_3$)CF$_3$]$_4$—(CH$_2$)—, —(CH$_2$)$_3$—[C(CH$_3$)CF$_3$]$_4$—(CH$_2$)—, —(CH$_2$)$_4$—[C(CH$_3$)CF$_3$]$_4$—(CH$_2$)—, —(CH$_2$)$_5$—[C(CH$_3$)CF$_3$]$_4$—(CH$_2$)—, —(CH$_2$)$_6$—[C(CH$_3$)CF$_3$]$_4$—(CH$_2$)—, —(CH$_2$)$_7$—[C(CH$_3$)CF$_3$]$_4$—(CH$_2$)—, —(CH$_2$)$_2$—[C(CH$_3$)CF$_3$]$_4$—(CH$_2$)$_2$—, —(CH$_2$)$_3$—[C(CH$_3$)CF$_3$]$_4$—(CH$_2$)$_3$—, —(CH$_2$)$_4$—[C(CH$_3$)CF$_3$]$_4$—(CH$_2$)$_4$—, —(CH$_2$)$_5$—[C(CH$_3$)CF$_3$]$_4$—(CH$_2$)$_5$—, —(CH$_2$)$_2$—[C(CH$_3$)CF$_3$]$_4$—(CH$_2$)$_3$—, —(CH$_2$)$_2$—[C(CH$_3$)CF$_3$]$_4$—(CH$_2$)$_4$—, —(CH$_2$)$_2$—[C(CH$_3$)CF$_3$]$_4$—(CH$_2$)$_5$—, —(CH$_2$)$_2$—[C(CH$_3$)CF$_3$]$_4$—(CH$_2$)$_6$—, —(CH$_2$)$_3$—[C(CH$_3$)CF$_3$]$_4$—(CH$_2$)$_2$—, —(CH$_2$)$_3$—[C(CH$_3$)CF$_3$]$_4$—(CH$_2$)$_4$—, —(CH$_2$)$_4$—[C(CH$_3$)CF$_3$]$_4$—(CH$_2$)$_2$—, —(CH$_2$)$_4$—[C(CH$_3$)CF$_3$]$_4$—(CH$_2$)$_3$—, —(CH$_2$)$_5$—[C(CH$_3$)CF$_3$]$_4$—(CH$_2$)$_2$—, —(CH$_2$)$_5$—[C(CH$_3$)CF$_3$]$_4$—(CH$_2$)$_3$—, —(CH$_2$)$_6$—[C(CH$_3$)CF$_3$]$_4$—(CH$_2$)$_2$—, —[C(CH$_3$)CF$_3$]$_5$—(CH$_2$)—, —(CH$_2$)—[C(CH$_3$)CF$_3$]$_5$—, —(CH$_2$)—[C(CH$_3$)CF$_3$]$_5$—(CH$_2$)—, —(CH$_2$)—[C(CH$_3$)CF$_3$]$_5$—(CH$_2$)$_2$—, —(CH$_2$)—[C(CH$_3$)CF$_3$]$_5$—(CH$_2$)$_3$—, —(CH$_2$)—[C(CH$_3$)CF$_3$]$_5$—(CH$_2$)$_4$—, —(CH$_2$)—[C(CH$_3$)CF$_3$]$_5$—(CH$_2$)$_5$—, —(CH$_2$)—[C(CH$_3$)CF$_3$]$_5$—(CH$_2$)$_6$—, —(CH$_2$)$_2$—[C(CH$_3$)CF$_3$]$_5$—(CH$_2$)—, —(CH$_2$)$_3$—[C(CH$_3$)CF$_3$]$_5$—(CH$_2$)—, —(CH$_2$)$_4$—[C(CH$_3$)CF$_3$]$_5$—(CH$_2$)—, —(CH$_2$)$_5$—[C(CH$_3$)CF$_3$]$_5$—(CH$_2$)—, —(CH$_2$)$_6$—[C(CH$_3$)CF$_3$]$_5$—(CH$_2$)—, —(CH$_2$)$_2$—[C(CH$_3$)CF$_3$]$_5$—(CH$_2$)$_2$—, —(CH$_2$)$_3$—[C(CH$_3$)CF$_3$]$_5$—(CH$_2$)$_3$—, —(CH$_2$)$_4$—[C(CH$_3$)CF$_3$]$_5$—(CH$_2$)$_4$—, —(CH$_2$)$_2$—[C(CH$_3$)CF$_3$]$_5$—(CH$_2$)$_3$—, —(CH$_2$)$_2$—[C(CH$_3$)CF$_3$]$_5$—(CH$_2$)$_4$—, —(CH$_2$)$_2$—[C(CH$_3$)CF$_3$]$_5$—(CH$_2$)$_5$—, —(CH$_2$)$_2$—[C(CH$_3$)CF$_3$]$_5$—(CH$_2$)$_6$—, —(CH$_2$)$_3$—[C(CH$_3$)CF$_3$]$_5$—(CH$_2$)$_2$—, —(CH$_2$)$_3$—[C(CH$_3$)CF$_3$]$_5$—(CH$_2$)$_4$—, —(CH$_2$)$_4$—[C(CH$_3$)CF$_3$]$_5$—(CH$_2$)$_2$—, —(CH$_2$)$_4$—[C(CH$_3$)CF$_3$]$_5$—(CH$_2$)$_3$—, —(CH$_2$)$_5$—[C(CH$_3$)CF$_3$]$_5$—(CH$_2$)$_2$—, —[CH(CH$_2$CF$_3$)]—(CH$_2$)—, —(CH$_2$)—[CH(CH$_2$CF$_3$)]—, —(CH$_2$)—[CH(CH$_2$CF$_3$)]—(CH$_2$)—, —(CH$_2$)—[CH(CH$_2$CF$_3$)]—(CH$_2$)$_2$—, —(CH$_2$)—[CH(CH$_2$CF$_3$)]—(CH$_2$)$_3$—, —(CH$_2$)—[CH(CH$_2$CF$_3$)]—(CH$_2$)$_4$—, —(CH$_2$)—[CH(CH$_2$CF$_3$)]—(CH$_2$)$_5$—, —(CH$_2$)—[CH(CH$_2$CF$_3$)]—(CH$_2$)$_6$—, —(CH$_2$)—[CH(CH$_2$CF$_3$)]—(CH$_2$)$_7$—, —(CH$_2$)—[CH(CH$_2$CF$_3$)]—(CH$_2$)$_8$—, —(CH$_2$)—[CH(CH$_2$CF$_3$)]—(CH$_2$)$_9$—, —(CH$_2$)—[CH(CH$_2$CF$_3$)]—(CH$_2$)$_{10}$—, —(CH$_2$)$_2$—[CH(CH$_2$CF$_3$)]—(CH$_2$)—, —(CH$_2$)$_3$—[CH(CH$_2$CF$_3$)]—(CH$_2$)—, —(CH$_2$)$_4$—[CH(CH$_2$CF$_3$)]—(CH$_2$)—, —(CH$_2$)$_5$—[CH(CH$_2$CF$_3$)]—(CH$_2$)—, —(CH$_2$)$_6$—[CH(CH$_2$CF$_3$)]—(CH$_2$)—, —(CH$_2$)$_7$—[CH(CH$_2$CF$_3$)]—(CH$_2$)—, —(CH$_2$)$_8$—[CH(CH$_2$CF$_3$)]—(CH$_2$)—, —(CH$_2$)$_9$—[CH(CH$_2$CF$_3$)]—(CH$_2$)—, —(CH$_2$)$_{10}$—[CH(CH$_2$CF$_3$)]—(CH$_2$)—, —(CH$_2$)$_2$—[CH(CH$_2$CF$_3$)]—(CH$_2$)$_2$—, —(CH$_2$)$_3$—[CH(CH$_2$CF$_3$)]—(CH$_2$)$_3$—, —(CH$_2$)$_4$—[CH(CH$_2$CF$_3$)]—(CH$_2$)$_4$—, —(CH$_2$)$_5$—[CH(CH$_2$CF$_3$)]—(CH$_2$)$_5$—, —(CH$_2$)$_2$—[CH(CH$_2$CF$_3$)]—(CH$_2$)$_3$—, —(CH$_2$)$_2$—[CH(CH$_2$CF$_3$)]—(CH$_2$)$_4$—, —(CH$_2$)$_2$—[CH(CH$_2$CF$_3$)]—(CH$_2$)$_5$—, —(CH$_2$)$_2$—[CH(CH$_2$CF$_3$)]—(CH$_2$)$_6$—, —(CH$_2$)$_2$—[CH(CH$_2$CF$_3$)]—(CH$_2$)$_7$—, —(CH$_2$)$_2$—[CH(CH$_2$CF$_3$)]—(CH$_2$)$_8$—, —(CH$_2$)$_2$—[CH(CH$_2$CF$_3$)]—(CH$_2$)$_9$—, —(CH$_2$)$_3$—[CH(CH$_2$CF$_3$)]—(CH$_2$)$_2$—, —(CH$_2$)$_3$—[CH(CH$_2$CF$_3$)]—(CH$_2$)$_4$—, —(CH$_2$)$_3$—[CH(CH$_2$CF$_3$)]—(CH$_2$)$_5$—, —(CH$_2$)$_3$—[CH(CH$_2$CF$_3$)]—(CH$_2$)$_6$—, —(CH$_2$)$_3$—[CH(CH$_2$CF$_3$)]—(CH$_2$)$_7$—, —(CH$_2$)$_3$—[CH(CH$_2$CF$_3$)]—(CH$_2$)$_8$—, —(CH$_2$)$_4$—[CH(CH$_2$CF$_3$)]—(CH$_2$)$_2$—, —(CH$_2$)$_4$—[CH(CH$_2$CF$_3$)]—(CH$_2$)$_3$—, —(CH$_2$)$_4$—[CH(CH$_2$CF$_3$)]—(CH$_2$)$_5$—, —(CH$_2$)$_4$—[CH(CH$_2$CF$_3$)]—(CH$_2$)$_6$—, —(CH$_2$)$_4$—[CH(CH$_2$CF$_3$)]—(CH$_2$)$_7$—, —(CH$_2$)$_5$—[CH(CH$_2$CF$_3$)]—(CH$_2$)$_2$—, —(CH$_2$)$_5$—[CH(CH$_2$CF$_3$)]—(CH$_2$)$_3$—, —(CH$_2$)$_5$—[CH(CH$_2$CF$_3$)]—(CH$_2$)$_4$—,

—(CH$_2$)$_5$—[CH(CH$_2$CF$_3$)]—(CH$_2$)$_6$—, —(CH$_2$)$_6$—[CH(CH$_2$CF$_3$)]—(CH$_2$)$_2$—, —(CH$_2$)$_6$—[CH(CH$_2$CF$_3$)]—(CH$_2$)$_3$—, —(CH$_2$)$_6$—[CH(CH$_2$CF$_3$)]—(CH$_2$)$_4$—, —(CH$_2$)$_6$—[CH(CH$_2$CF$_3$)]—(CH$_2$)$_5$—, —(CH$_2$)$_6$—[CH(CH$_2$CF$_3$)]$_2$—(CH$_2$)—, —(CH$_2$)—[CH(CH$_2$CF$_3$)]2-, —(CH$_2$)—[CH(CH$_2$CF$_3$)]2-(CH$_2$)—, —(CH$_2$)—[CH(CH$_2$CF$_3$)]$_2$—(CH$_2$)$_2$—, —(CH$_2$)—[CH(CH$_2$CF$_3$)]$_2$—(CH$_2$)$_3$—, —(CH$_2$)—[CH(CH$_2$CF$_3$)]$_2$—(CH$_2$)$_4$—, —(CH$_2$)—[CH(CH$_2$CF$_3$)]$_2$—(CH$_2$)$_5$—, —(CH$_2$)—[CH(CH$_2$CF$_3$)]$_2$—(CH$_2$)$_6$—, —(CH$_2$)—[CH(CH$_2$CF$_3$)]$_2$—(CH$_2$)$_7$—, —(CH$_2$)—[CH(CH$_2$CF$_3$)]$_2$—(CH$_2$)$_8$—, —(CH$_2$)—[CH(CH$_2$CF$_3$)]$_2$—(CH$_2$)$_9$—, —(CH$_2$)$_2$—[CH(CH$_2$CF$_3$)]$_2$—(CH$_2$)—, —(CH$_2$)$_3$—[CH(CH$_2$CF$_3$)]$_2$—(CH$_2$)—, —(CH$_2$)$_4$—[CH(CH$_2$CF$_3$)]$_2$—(CH$_2$)—, —(CH$_2$)$_5$—[CH(CH$_2$CF$_3$)]$_2$—(CH$_2$)—, —(CH$_2$)$_6$—[CH(CH$_2$CF$_3$)]$_2$—(CH$_2$)—, —(CH$_2$)$_7$—[CH(CH$_2$CF$_3$)]$_2$—(CH$_2$)—, —(CH$_2$)$_8$—[CH(CH$_2$CF$_3$)]$_2$—(CH$_2$)—, —(CH$_2$)$_9$—[CH(CH$_2$CF$_3$)]$_2$—(CH$_2$)—, —(CH$_2$)$_2$—[CH(CH$_2$CF$_3$)]$_2$—(CH$_2$)$_2$—, —(CH$_2$)$_3$—[CH(CH$_2$CF$_3$)]$_2$—(CH$_2$)$_3$—, —(CH$_2$)$_4$—[CH(CH$_2$CF$_3$)]$_2$—(CH$_2$)$_4$—, —(CH$_2$)$_5$—[CH(CH$_2$CF$_3$)]$_2$—(CH$_2$)$_5$—, —(CH$_2$)$_2$—[CH(CH$_2$CF$_3$)]$_2$—(CH$_2$)$_3$—, —(CH$_2$)$_2$—[CH(CH$_2$CF$_3$)]$_2$—(CH$_2$)$_4$—, —(CH$_2$)$_2$—[CH(CH$_2$CF$_3$)]$_2$—(CH$_2$)$_5$—, —(CH$_2$)$_2$—[CH(CH$_2$CF$_3$)]$_2$—(CH$_2$)$_6$—, —(CH$_2$)$_2$—[CH(CH$_2$CF$_3$)]$_2$—(CH$_2$)$_7$—, —(CH$_2$)$_2$—[CH(CH$_2$CF$_3$)]$_2$—(CH$_2$)$_8$—, —(CH$_2$)$_3$—[CH(CH$_2$CF$_3$)]$_2$—(CH$_2$)$_2$—, —(CH$_2$)$_3$—[CH(CH$_2$CF$_3$)]$_2$—(CH$_2$)$_4$—, —(CH$_2$)$_3$—[CH(CH$_2$CF$_3$)]$_2$—(CH$_2$)$_5$—, —(CH$_2$)$_3$—[CH(CH$_2$CF$_3$)]$_2$—(CH$_2$)$_6$—, —(CH$_2$)$_3$—[CH(CH$_2$CF$_3$)]$_2$—(CH$_2$)$_7$—, —(CH$_2$)$_4$—[CH(CH$_2$CF$_3$)]$_2$—(CH$_2$)$_2$—, —(CH$_2$)$_4$—[CH(CH$_2$CF$_3$)]$_2$—(CH$_2$)$_3$—, —(CH$_2$)$_4$—[CH(CH$_2$CF$_3$)]$_2$—(CH$_2$)$_5$—, —(CH$_2$)$_4$—[CH(CH$_2$CF$_3$)]$_2$—(CH$_2$)$_6$—, —(CH$_2$)$_5$—[CH(CH$_2$CF$_3$)]$_2$—(CH$_2$)$_2$—, —(CH$_2$)$_5$—[CH(CH$_2$CF$_3$)]$_2$-(0H$_2$)$_3$—, —(CH$_2$)$_5$—[CH(CH$_2$CF$_3$)]$_2$-(0H$_2$)$_4$—, —(CH$_2$)$_6$—[CH(CH$_2$CF$_3$)]$_2$—(CH$_2$)$_2$—, —(CH$_2$)$_6$—[CH(CH$_2$CF$_3$)]$_2$—(CH$_2$)$_3$—, —(CH$_2$)$_6$—[CH(CH$_2$CF$_3$)]$_2$—(CH$_2$)$_4$—, —[CH(CH$_2$CF$_3$)]$_3$—(CH$_2$)—, —(CH$_2$)—[CH(CH$_2$CF$_3$)]$_3$—, —(CH$_2$)—[CH(CH$_2$CF$_3$)]3-(CH$_2$)—, —(CH$_2$)—[CH(CH$_2$CF$_3$)]$_3$—(CH$_2$)$_2$—, —(CH$_2$)—[CH(CH$_2$CF$_3$)]$_3$—(CH$_2$)$_3$—, —(CH$_2$)—[CH(CH$_2$CF$_3$)]$_3$—(CH$_2$)$_4$—, —(CH$_2$)—[CH(CH$_2$CF$_3$)]$_3$—(CH$_2$)$_5$—, —(CH$_2$)—[CH(CH$_2$CF$_3$)]$_3$—(CH$_2$)$_6$—, —(CH$_2$)—[CH(CH$_2$CF$_3$)]$_3$—(CH$_2$)$_7$—, —(CH$_2$)—[CH(CH$_2$CF$_3$)]$_3$—(CH$_2$)$_8$—, —(CH$_2$)$_2$—[CH(CH$_2$CF$_3$)]$_3$—(CH$_2$)—, —(CH$_2$)$_3$—[CH(CH$_2$CF$_3$)]$_3$—(CH$_2$)—, —(CH$_2$)$_4$—[CH(CH$_2$CF$_3$)]$_3$—(CH$_2$)—, —(CH$_2$)$_5$—[CH(CH$_2$CF$_3$)]$_3$—(CH$_2$)—, —(CH$_2$)$_6$—[CH(CH$_2$CF$_3$)]$_3$—(CH$_2$)—, —(CH$_2$)$_7$—[CH(CH$_2$CF$_3$)]$_3$—(CH$_2$)—, —(CH$_2$)$_8$—[CH(CH$_2$CF$_3$)]$_3$—(CH$_2$)—, —(CH$_2$)$_2$—[CH(CH$_2$CF$_3$)]$_3$—(CH$_2$)$_2$—, —(CH$_2$)$_3$—[CH(CH$_2$CF$_3$)]$_3$—(CH$_2$)$_3$—, —(CH$_2$)$_4$—[CH(CH$_2$CF$_3$)]$_3$—(CH$_2$)$_4$—, —(CH$_2$)$_2$—[CH(CH$_2$CF$_3$)]$_3$—(CH$_2$)$_3$—, —(CH$_2$)$_2$—[CH(CH$_2$CF$_3$)]$_3$—(CH$_2$)$_4$—, —(CH$_2$)$_2$—[CH(CH$_2$CF$_3$)]$_3$—(CH$_2$)$_5$—, —(CH$_2$)$_2$—[CH(CH$_2$CF$_3$)]$_3$—(CH$_2$)$_6$—, —(CH$_2$)$_2$—[CH(CH$_2$CF$_3$)]$_3$—(CH$_2$)$_7$—, —(CH$_2$)$_3$—[CH(CH$_2$CF$_3$)]$_3$—(CH$_2$)$_2$—, —(CH$_2$)$_3$—[CH(CH$_2$CF$_3$)]$_3$—(CH$_2$)$_4$—, —(CH$_2$)$_3$—[CH(CH$_2$CF$_3$)]$_3$—(CH$_2$)$_5$—, —(CH$_2$)$_3$—[CH(CH$_2$CF$_3$)]$_3$—(CH$_2$)$_6$—, —(CH$_2$)$_4$—[CH(CH$_2$CF$_3$)]$_3$—(CH$_2$)$_2$—, —(CH$_2$)$_4$—[CH(CH$_2$CF$_3$)]$_3$—(CH$_2$)$_3$—, —(CH$_2$)$_4$—[CH(CH$_2$CF$_3$)]$_3$—(CH$_2$)$_5$—, —(CH$_2$)$_5$—[CH(CH$_2$CF$_3$)]$_3$—(CH$_2$)$_2$—, —(CH$_2$)$_5$—[CH(CH$_2$CF$_3$)]$_3$—(CH$_2$)$_3$—, —(CH$_2$)$_5$—[CH(CH$_2$CF$_3$)]$_3$—(CH$_2$)$_4$—, —(CH$_2$)$_6$—[CH(CH$_2$CF$_3$)]$_3$—(CH$_2$)$_2$—, —(CH$_2$)$_6$—[CH(CH$_2$CF$_3$)]$_3$—(CH$_2$)$_3$—, —[CH(CH$_2$CF$_3$)]$_4$—(CH$_2$)—, —(CH$_2$)—[CH(CH$_2$CF$_3$)]4-, —(CH$_2$)—[CH(CH$_2$CF$_3$)]4-(CH$_2$)—, —(CH$_2$)—[CH(CH$_2$CF$_3$)]$_4$—(CH$_2$)$_2$—, —(CH$_2$)—[CH(CH$_2$CF$_3$)]$_4$—(CH$_2$)$_3$—, —(CH$_2$)—[CH(CH$_2$CF$_3$)]$_4$—(CH$_2$)$_4$—, —(CH$_2$)—[CH(CH$_2$CF$_3$)]$_4$—(CH$_2$)$_5$—, —(CH$_2$)—[CH(CH$_2$CF$_3$)]$_4$—(CH$_2$)$_6$—, —(CH$_2$)—[CH(CH$_2$CF$_3$)]$_4$—(CH$_2$)$_7$—, —(CH$_2$)—[CH(CH$_2$CF$_3$)]$_4$—(CH$_2$)$_8$—, —(CH$_2$)—[CH(CH$_2$CF$_3$)]$_4$—(CH$_2$)$_9$—, —(CH$_2$)—[CH(CH$_2$CF$_3$)]$_4$—(CH$_2$)$_{10}$—, —(CH$_2$)$_2$—[CH(CH$_2$CF$_3$)]$_4$—(CH$_2$)—, —(CH$_2$)$_3$—[CH(CH$_2$CF$_3$)]$_4$—(CH$_2$)—, —(CH$_2$)$_4$—[CH(CH$_2$CF$_3$)]$_4$—(CH$_2$)—, —(CH$_2$)$_5$—[CH(CH$_2$CF$_3$)]$_4$—(CH$_2$)—, —(CH$_2$)$_6$—[CH(CH$_2$CF$_3$)]$_4$—(CH$_2$)—, —(CH$_2$)$_7$—[CH(CH$_2$CF$_3$)]$_4$—(CH$_2$)—, —(CH$_2$)$_2$—[CH(CH$_2$CF$_3$)]$_4$—(CH$_2$)$_2$—, —(CH$_2$)$_3$—[CH(CH$_2$CF$_3$)]$_4$—(CH$_2$)$_3$—, —(CH$_2$)$_4$—[CH(CH$_2$CF$_3$)]$_4$—(CH$_2$)$_4$—, —(CH$_2$)$_5$—[CH(CH$_2$CF$_3$)]$_4$—(CH$_2$)$_5$—, —(CH$_2$)$_2$—[CH(CH$_2$CF$_3$)]$_4$—(CH$_2$)$_3$—, —(CH$_2$)$_2$—[CH(CH$_2$CF$_3$)]$_4$—(CH$_2$)$_4$—, —(CH$_2$)$_2$—[CH(CH$_2$CF$_3$)]$_4$—(CH$_2$)$_5$—, —(CH$_2$)$_2$—[CH(CH$_2$CF$_3$)]$_4$—(CH$_2$)$_6$—, —(CH$_2$)$_3$—[CH(CH$_2$CF$_3$)]$_4$—(CH$_2$)$_2$—, —(CH$_2$)$_3$—[CH(CH$_2$CF$_3$)]$_4$—(CH$_2$)$_4$—, —(CH$_2$)$_4$—[CH(CH$_2$CF$_3$)]$_4$—(CH$_2$)$_2$—, —(CH$_2$)$_4$—[CH(CH$_2$CF$_3$)]$_4$—(CH$_2$)$_3$—, —(CH$_2$)$_5$—[CH(CH$_2$CF$_3$)]$_4$—(CH$_2$)$_2$—, —(CH$_2$)$_5$—[CH(CH$_2$CF$_3$)]$_4$—(CH$_2$)$_3$—, —(CH$_2$)$_6$—[CH(CH$_2$CF$_3$)]$_4$—(CH$_2$)$_2$—, —[CH(CH$_2$CF$_3$)]$_5$—(CH$_2$)—, —(CH$_2$)—[CH(CH$_2$CF$_3$)]$_5$—, —(CH$_2$)—[CH(CH$_2$CF$_3$)]$_5$—(CH$_2$)—, —(CH$_2$)—[CH(CH$_2$CF$_3$)]$_5$—(CH$_2$)$_2$—, —(CH$_2$)—[CH(CH$_2$CF$_3$)]$_5$—(CH$_2$)$_3$—, —(CH$_2$)—[CH(CH$_2$CF$_3$)]$_5$—(CH$_2$)$_4$—, —(CH$_2$)—[CH(CH$_2$CF$_3$)]$_5$—(CH$_2$)$_5$—, —(CH$_2$)—[CH(CH$_2$CF$_3$)]$_5$—(CH$_2$)$_6$—, —(CH$_2$)$_2$—[CH(CH$_2$CF$_3$)]$_5$—(CH$_2$)—, —(CH$_2$)$_3$—[CH(CH$_2$CF$_3$)]$_5$—(CH$_2$)—, —(CH$_2$)$_4$—[CH(CH$_2$CF$_3$)]$_5$—(CH$_2$)—, —(CH$_2$)$_5$—[CH(CH$_2$CF$_3$)]$_5$—(CH$_2$)—, —(CH$_2$)$_6$—[CH(CH$_2$CF$_3$)]$_5$—(CH$_2$)—, —(CH$_2$)$_2$—[CH(CH$_2$CF$_3$)]$_5$—(CH$_2$)$_2$—, —(CH$_2$)$_3$—[CH(CH$_2$CF$_3$)]$_5$—(CH$_2$)$_3$—, —(CH$_2$)$_4$—[CH(CH$_2$CF$_3$)]$_5$—(CH$_2$)$_4$—, —(CH$_2$)$_2$—[CH(CH$_2$CF$_3$)]$_5$—(CH$_2$)$_3$—, —(CH$_2$)$_2$—[CH(CH$_2$CF$_3$)]$_5$—(CH$_2$)$_4$—, —(CH$_2$)$_2$—[CH(CH$_2$CF$_3$)]$_5$—(CH$_2$)$_5$—, —(CH$_2$)$_2$—[CH(CH$_2$CF$_3$)]$_5$—(CH$_2$)$_6$—, —(CH$_2$)$_3$—[CH(CH$_2$CF$_3$)]$_5$—(CH$_2$)$_2$—, —(CH$_2$)$_3$—[CH(CH$_2$CF$_3$)]$_5$—(CH$_2$)$_4$—, —(CH$_2$)$_4$—[CH(CH$_2$CF$_3$)]$_5$—(CH$_2$)$_2$—, —(CH$_2$)$_4$—[CH(CH$_2$CF$_3$)]$_5$—(CH$_2$)$_3$—, —(CH$_2$)$_5$—[CH(CH$_2$CF$_3$)]$_5$—(CH$_2$)$_2$—, —[C(CH$_3$)(CH$_2$CF$_3$)]—(CH$_2$)—, —(CH$_2$)—[C(CH$_3$)(CH$_2$CF$_3$)]—, —(CH$_2$)—[C(CH$_3$)(CH$_2$CF$_3$)]—(CH$_2$)—, —(CH$_2$)—[C(CH$_3$)(CH$_2$CF$_3$)]—(CH$_2$)$_2$—, —(CH$_2$)—[C(CH$_3$)(CH$_2$CF$_3$)]—(CH$_2$)$_3$—, —(CH$_2$)—[C(CH$_3$)(CH$_2$CF$_3$)]—(CH$_2$)$_4$—, —(CH$_2$)—[C(CH$_3$)(CH$_2$CF$_3$)]—(CH$_2$)$_5$—, —(CH$_2$)—[C(CH$_3$)(CH$_2$CF$_3$)]—(CH$_2$)$_6$—, —(CH$_2$)—[C(CH$_3$)(CH$_2$CF$_3$)]—(CH$_2$)$_7$—, —(CH$_2$)—[C(CH$_3$)(CH$_2$CF$_3$)]—(CH$_2$)$_8$—, —(CH$_2$)—[C(CH$_3$)(CH$_2$CF$_3$)]—(CH$_2$)$_9$—, —(CH$_2$)—[C(CH$_3$)(CH$_2$CF$_3$)]—(CH$_2$)$_{10}$—, —(CH$_2$)$_2$—[C(CH$_3$)(CH$_2$CF$_3$)]—(CH$_2$)—, —(CH$_2$)$_3$—[C(CH$_3$)(CH$_2$CF$_3$)]—(CH$_2$)—, —(CH$_2$)$_4$—[C(CH$_3$)(CH$_2$CF$_3$)]—(CH$_2$)—, —(CH$_2$)$_5$—[C(CH$_3$)(CH$_2$CF$_3$)]—(CH$_2$)—, —(CH$_2$)$_6$—[C(CH$_3$)(CH$_2$CF$_3$)]—(CH$_2$)—, —(CH$_2$)$_7$—[C(CH$_3$)(CH$_2$CF$_3$)]—(CH$_2$)—, —(CH$_2$)$_8$—[C(CH$_3$)(CH$_2$CF$_3$)]—(CH$_2$)—, —(CH$_2$)$_9$—[C(CH$_3$)(CH$_2$CF$_3$)]—(CH$_2$)—, —(CH$_2$)$_{10}$—[C(CH$_3$)(CH$_2$CF$_3$)]—(CH$_2$)—, —(CH$_2$)$_2$—[C(CH$_3$)(CH$_2$CF$_3$)]—(CH$_2$)$_2$—, —(CH$_2$)$_3$—[C(CH$_3$)(CH$_2$CF$_3$)]—(CH$_2$)$_3$—, —(CH$_2$)$_4$—[C(CH$_3$)(CH$_2$CF$_3$)]—(CH$_2$)$_4$—, —(CH$_2$)$_5$—[C(CH$_3$)(CH$_2$CF$_3$)]—(CH$_2$)$_5$—, —(CH$_2$)$_2$—[C(CH$_3$)(CH$_2$CF$_3$)]—(CH$_2$)$_3$—, —(CH$_2$)$_2$—[C(CH$_3$)(CH$_2$CF$_3$)]—(CH$_2$)$_4$—, —(CH$_2$)$_2$—[C(CH$_3$)(CH$_2$CF$_3$)]—(CH$_2$)$_5$—, —(CH$_2$)$_2$—[C(CH$_3$)(CH$_2$CF$_3$)]—(CH$_2$)$_6$—, —(CH$_2$)$_2$—[C(CH$_3$)(CH$_2$CF$_3$)]—(CH$_2$)$_7$—, —(CH$_2$)$_2$—[C(CH$_3$)(CH$_2$CF$_3$)]—(CH$_2$)$_8$—, —(CH$_2$)$_2$—[C(CH$_3$)(CH$_2$CF$_3$)]—(CH$_2$)$_9$—, —(CH$_2$)$_3$—[C(CH$_3$)(CH$_2$CF$_3$)]—(CH$_2$)$_2$—, —(CH$_2$)$_3$—[C(CH$_3$)(CH$_2$CF$_3$)]—(CH$_2$)$_4$—, —(CH$_2$)$_3$—[C(CH$_3$)(CH$_2$CF$_3$)]—(CH$_2$)$_5$—,

—(CH₂)₃—[C(CH₃)(CH₂CF₃)]—(CH₂)₆—, —(CH₂)₃—[C(CH₃)(CH₂CF₃)]—(CH₂)₇—, —(CH₂)₃—[C(CH₃)(CH₂CF₃)]—(CH₂)₈—, —(CH₂)₄—[C(CH₃)(CH₂CF₃)]—(CH₂)₂—, —(CH₂)₄—[C(CH₃)(CH₂CF₃)]—(CH₂)₃—, —(CH₂)₄—[C(CH₃)(CH₂CF₃)]—(CH₂)₅—, —(CH₂)₄—[C(CH₃)(CH₂CF₃)]—(CH₂)₆—, —(CH₂)₄—[C(CH₃)(CH₂CF₃)]—(CH₂)₇—, —(CH₂)₅—[C(CH₃)(CH₂CF₃)]—(CH₂)₂—, —(CH₂)₅—[C(CH₃)(CH₂CF₃)]—(CH₂)₃—, —(CH₂)₅—[C(CH₃)(CH₂CF₃)]—(CH₂)₄—, —(CH₂)₅—[C(CH₃)(CH₂CF₃)]—(CH₂)₆—, —(CH₂)₆—[C(CH₃)(CH₂CF₃)]—(CH₂)₂—, —(CH₂)₆—[C(CH₃)(CH₂CF₃)]—(CH₂)₃—, —(CH₂)₆—[C(CH₃)(CH₂CF₃)]—(CH₂)₄—, —(CH₂)₆—[C(CH₃)(CH₂CF₃)]—(CH₂)₅—, —[C(CH₃)(CH₂CF₃)]₂—(CH₂)—, —(CH₂)—[C(CH₃)(CH₂CF₃)]2-, —(CH₂)—[C(CH₃)(CH₂CF₃)]₂—(CH₂)—, —(CH₂)—[C(CH₃)(CH₂CF₃)]₂—(CH₂)₂—, —(CH₂)—[C(CH₃)(CH₂CF₃)]₂—(CH₂)₃—, —(CH₂)—[C(CH₃)(CH₂CF₃)]₂—(CH₂)₄—, —(CH₂)—[C(CH₃)(CH₂CF₃)]₂—(CH₂)₅—, —(CH₂)—[C(CH₃)(CH₂CF₃)]₂—(CH₂)₆—, —(CH₂)—[C(CH₃)(CH₂CF₃)]₂—(CH₂)₇—, —(CH₂)—[C(CH₃)(CH₂CF₃)]₂—(CH₂)₈—, —(CH₂)—[C(CH₃)(CH₂CF₃)]₂—(CH₂)₉—, —(CH₂)₂—[C(CH₃)(CH₂CF₃)]₂—(CH₂)—, —(CH₂)₃—[C(CH₃)(CH₂CF₃)]₂—(CH₂)—, —(CH₂)₄—[C(CH₃)(CH₂CF₃)]₂—(CH₂)—, —(CH₂)₅—[C(CH₃)(CH₂CF₃)]₂—(CH₂)—, —(CH₂)₆—[C(CH₃)(CH₂CF₃)]₂—(CH₂)—, —(CH₂)₇—[C(CH₃)(CH₂CF₃)]₂—(CH₂)—, —(CH₂)₈—[C(CH₃)(CH₂CF₃)]₂—(CH₂)—, —(CH₂)₉—[C(CH₃)(CH₂CF₃)]₂—(CH₂)—, —(CH₂)₂—[C(CH₃)(CH₂CF₃)]₂—(CH₂)₂—, —(CH₂)₃—[C(CH₃)(CH₂CF₃)]₂—(CH₂)₃—, —(CH₂)₄—[C(CH₃)(CH₂CF₃)]₂—(CH₂)₄—, —(CH₂)₅—[C(CH₃)(CH₂CF₃)]₂—(CH₂)₅—, —(CH₂)₂—[C(CH₃)(CH₂CF₃)]₂—(CH₂)₃—, —(CH₂)₂—[C(CH₃)(CH₂CF₃)]₂—(CH₂)₄—, —(CH₂)₂—[C(CH₃)(CH₂CF₃)]₂—(CH₂)₅—, —(CH₂)₂—[C(CH₃)(CH₂CF₃)]₂—(CH₂)₆—, —(CH₂)₂—[C(CH₃)(CH₂CF₃)]₂—(CH₂)₇—, —(CH₂)₂—[C(CH₃)(CH₂CF₃)]₂—(CH₂)₈—, —(CH₂)₃—[C(CH₃)(CH₂CF₃)]₂—(CH₂)₂—, —(CH₂)₃—[C(CH₃)(CH₂CF₃)]₂—(CH₂)₄—, —(CH₂)₃—[C(CH₃)(CH₂CF₃)]₂—(CH₂)₅—, —(CH₂)₃—[C(CH₃)(CH₂CF₃)]₂—(CH₂)₆—, —(CH₂)₃—[C(CH₃)(CH₂CF₃)]₂—(CH₂)₇—, —(CH₂)₄—[C(CH₃)(CH₂CF₃)]₂—(CH₂)₂—, —(CH₂)₄—[C(CH₃)(CH₂CF₃)]₂—(CH₂)₃—, —(CH₂)₄—[C(CH₃)(CH₂CF₃)]₂—(CH₂)₅—, —(CH₂)₄—[C(CH₃)(CH₂CF₃)]₂—(CH₂)₆—, —(CH₂)₅—[C(CH₃)(CH₂CF₃)]₂—(CH₂)₂—, —(CH₂)₅—[C(CH₃)(CH₂CF₃)]₂—(CH₂)₃—, —(CH₂)₅—[C(CH₃)(CH₂CF₃)]₂—(CH₂)₄—, —(CH₂)₆—[C(CH₃)(CH₂CF₃)]₂—(CH₂)₂—, —(CH₂)₆—[C(CH₃)(CH₂CF₃)]₂—(CH₂)₃—, —(CH₂)₆—[C(CH₃)(CH₂CF₃)]₂—(CH₂)₄—, —[C(CH₃)(CH₂CF₃)]₃—(CH₂)—, —(CH₂)—[C(CH₃)(CH₂CF₃)]₃—, —(CH₂)—[C(CH₃)(CH₂CF₃)]₃—(CH₂)—, —(CH₂)—[C(CH₃)(CH₂CF₃)]₃—(CH₂)₂—, —(CH₂)—[C(CH₃)(CH₂CF₃)]₃—(CH₂)₃—, —(CH₂)—[C(CH₃)(CH₂CF₃)]₃—(CH₂)₄—, —(CH₂)—[C(CH₃)(CH₂CF₃)]₃—(CH₂)₅—, —(CH₂)—[C(CH₃)(CH₂CF₃)]₃—(CH₂)₆—, —(CH₂)—[C(CH₃)(CH₂CF₃)]₃—(CH₂)₇—, —(CH₂)—[C(CH₃)(CH₂CF₃)]₃—(CH₂)₈—, —(CH₂)₂—[C(CH₃)(CH₂CF₃)]₃—(CH₂)—, —(CH₂)₃—[C(CH₃)(CH₂CF₃)]₃—(CH₂)—, —(CH₂)₄—[C(CH₃)(CH₂CF₃)]₃—(CH₂)—, —(CH₂)₅—[C(CH₃)(CH₂CF₃)]₃—(CH₂)—, —(CH₂)₆—[C(CH₃)(CH₂CF₃)]₃—(CH₂)—, —(CH₂)₇—[C(CH₃)(CH₂CF₃)]₃—(CH₂)—, —(CH₂)₈—[C(CH₃)(CH₂CF₃)]₃—(CH₂)—, —(CH₂)₂—[C(CH₃)(CH₂CF₃)]₃—(CH₂)₂—, —(CH₂)₃—[C(CH₃)(CH₂CF₃)]₃—(CH₂)₃—, —(CH₂)₄—[C(CH₃)(CH₂CF₃)]₃—(CH₂)₄—, —(CH₂)₂—[C(CH₃)(CH₂CF₃)]₃—(CH₂)₅—, —(CH₂)₂—[C(CH₃)(CH₂CF₃)]₃—(CH₂)₆—, —(CH₂)₂—[C(CH₃)(CH₂CF₃)]₃—(CH₂)₇—, —(CH₂)₃—[C(CH₃)(CH₂CF₃)]₃—(CH₂)₂—, —(CH₂)₃—[C(CH₃)(CH₂CF₃)]₃—(CH₂)₄—, —(CH₂)₃—[C(CH₃)(CH₂CF₃)]₃—(CH₂)₅—, —(CH₂)₃—[C(CH₃)(CH₂CF₃)]₃—(CH₂)₆—, —(CH₂)₄—[C(CH₃)(CH₂CF₃)]₃—(CH₂)₂—, —(CH₂)₄—[C(CH₃)(CH₂CF₃)]₃—(CH₂)₃—, —(CH₂)₄—[C(CH₃)(CH₂CF₃)]₃—(CH₂)₅—, —(CH₂)₅—[C(CH₃)(CH₂CF₃)]₃—(CH₂)₂—, —(CH₂)₅—[C(CH₃)(CH₂CF₃)]₃—(CH₂)₃—, —(CH₂)₅—[C(CH₃)(CH₂CF₃)]₃—(CH₂)₄—, —(CH₂)₆—[C(CH₃)(CH₂CF₃)]₃—(CH₂)₂—, —(CH₂)₆—[C(CH₃)(CH₂CF₃)]₃—(CH₂)₃—, —[C(CH₃)(CH₂CF₃)]₄—(CH₂)—, —(CH₂)—[C(CH₃)(CH₂CF₃)]4-, —(CH₂)—[C(CH₃)(CH₂CF₃)]₄—(CH₂)—, —(CH₂)—[C(CH₃)(CH₂CF₃)]₄—(CH₂)₂—, —(CH₂)—[C(CH₃)(CH₂CF₃)]₄—(CH₂)₃—, —(CH₂)—[C(CH₃)(CH₂CF₃)]₄—(CH₂)₄—, —(CH₂)—[C(CH₃)(CH₂CF₃)]₄—(CH₂)₅—, —(CH₂)—[C(CH₃)(CH₂CF₃)]₄—(CH₂)₆—, —(CH₂)—[C(CH₃)(CH₂CF₃)]₄—(CH₂)₇—, —(CH₂)—[C(CH₃)(CH₂CF₃)]₄—(CH₂)₈—, —(CH₂)—[C(CH₃)(CH₂CF₃)]₄—(CH₂)₉—, —(CH₂)—[C(CH₃)(CH₂CF₃)]₄—(CH₂)₁₀—, —(CH₂)₂—[C(CH₃)(CH₂CF₃)]₄—(CH₂)—, —(CH₂)₃—[C(CH₃)(CH₂CF₃)]₄—(CH₂)—, —(CH₂)₄—[C(CH₃)(CH₂CF₃)]₄—(CH₂)—, —(CH₂)₅—[C(CH₃)(CH₂CF₃)]₄—(CH₂)—, —(CH₂)₆—[C(CH₃)(CH₂CF₃)]₄—(CH₂)—, —(CH₂)₇—[C(CH₃)(CH₂CF₃)]₄—(CH₂)₂—, —(CH₂)₂—[C(CH₃)(CH₂CF₃)]₄—(CH₂)₂—, —(CH₂)₃—[C(CH₃)(CH₂CF₃)]₄—(CH₂)₃—, —(CH₂)₄—[C(CH₃)(CH₂CF₃)]₄—(CH₂)₄—, —(CH₂)₅—[C(CH₃)(CH₂CF₃)]₄—(CH₂)₅—, —(CH₂)₂—[C(CH₃)(CH₂CF₃)]₄—(CH₂)₃—, —(CH₂)₂—[C(CH₃)(CH₂CF₃)]₄—(CH₂)₄—, —(CH₂)₂—[C(CH₃)(CH₂CF₃)]₄—(CH₂)₅—, —(CH₂)₂—[C(CH₃)(CH₂CF₃)]₄—(CH₂)₆—, —(CH₂)₃—[C(CH₃)(CH₂CF₃)]₄—(CH₂)₂—, —(CH₂)₃—[C(CH₃)(CH₂CF₃)]₄—(CH₂)₄—, —(CH₂)₄—[C(CH₃)(CH₂CF₃)]₄—(CH₂)₂—, —(CH₂)₄—[C(CH₃)(CH₂CF₃)]₄—(CH₂)₃—, —(CH₂)₅—[C(CH₃)(CH₂CF₃)]₄—(CH₂)₂—, —(CH₂)₅—[C(CH₃)(CH₂CF₃)]₄—(CH₂)₃—, —(CH₂)₆—[C(CH₃)(CH₂CF₃)]₄—(CH₂)₂—, —[C(CH₃)(CH₂CF₃)]₅—(CH₂)—, —(CH₂)—[C(CH₃)(CH₂CF₃)5-, —(CH₂)—[C(CH₃)(CH₂CF₃)]₅—(CH₂)—, —(CH₂)—[C(CH₃)(CH₂CF₃)]₅—(CH₂)₂—, —(CH₂)—[C(CH₃)(CH₂CF₃)]₅—(CH₂)₃—, —(CH₂)—[C(CH₃)(CH₂CF₃)]₅—(CH₂)₄—, —(CH₂)—[C(CH₃)(CH₂CF₃)]₅—(CH₂)₅—, —(CH₂)—[C(CH₃)(CH₂CF₃)]₅—(CH₂)₆—, —(CH₂)₂—[C(CH₃)(CH₂CF₃)]₅—(CH₂)—, —(CH₂)₃—[C(CH₃)(CH₂CF₃)]₅—(CH₂)—, —(CH₂)₄—[C(CH₃)(CH₂CF₃)]₅—(CH₂)—, —(CH₂)₅—[C(CH₃)(CH₂CF₃)]₅—(CH₂)—, —(CH₂)₆—[C(CH₃)(CH₂CF₃)]₅—(CH₂)—, —(CH₂)₂—[C(CH₃)(CH₂CF₃)]₅—(CH₂)₂—, —(CH₂)₃—[C(CH₃)(CH₂CF₃)]₅—(CH₂)₃—, —(CH₂)₄—[C(CH₃)(CH₂CF₃)]₅—(CH₂)₄—, —(CH₂)₂—[C(CH₃)(CH₂CF₃)]₅—(CH₂)₃—, —(CH₂)₂—[C(CH₃)(CH₂CF₃)]₅—(CH₂)₄—, —(CH₂)₂—[C(CH₃)(CH₂CF₃)]₅—(CH₂)₅—, —(CH₂)₂—[C(CH₃)(CH₂CF₃)]₅—(CH₂)₆—, —(CH₂)₃—[C(CH₃)(CH₂CF₃)]₅—(CH₂)₂—, —(CH₂)₃—[C(CH₃)(CH₂CF₃)]₅—(CH₂)₄—, —(CH₂)₄—[C(CH₃)(CH₂CF₃)]₅—(CH₂)₂—, —(CH₂)₄—[C(CH₃)(CH₂CF₃)]₅—(CH₂)₃—, —(CH₂)₅—[C(CH₃)(CH₂CF₃)]₅—(CH₂)₂—, —(CH₂)—(CF₂)—O—(CF₂)—O—(CF₂)—(CH₂)—, —(CH₂)₂—(CF₂)—O—(CF₂)—O—(CF₂)—(CH₂)₂—, —(CH₂)₃—(CF₂)—O—(CF₂)—O—(CF₂)—(CH₂)₃—, —(CH₂)₄—(CF₂)—O—(CF₂)—O—(CF₂)—(CH₂)₄—, —(CH₂)—(CF₂)—O—(CF₂)—O—(CF₂)—(CH₂)₂—, —(CH₂)—(CF₂)—O—(CF₂)—O—(CF₂)—(CH₂)₃—, —(CH₂)—(CF₂)—O—(CF₂)—O—(CF₂)—(CH₂)₄—, —(CH₂)—(CF₂)—O—(CF₂)—O—

(CF$_2$)—(CH$_2$)$_5$—,
(CF$_2$)—(CH$_2$)$_6$—,
(CF$_2$)—(CH$_2$)$_7$—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)$_3$—,
(CF$_2$)—(CH$_2$)$_4$—,
(CF$_2$)—(CH$_2$)$_5$—,
(CF$_2$)—(CH$_2$)$_6$—,
(CF$_2$)—(CH$_2$)$_2$—,
(CF$_2$)—(CH$_2$)$_2$—,
(CF$_2$)—(CH$_2$)$_2$—,
(CF$_2$)—(CH$_2$)$_2$—,
(CF$_2$)—(CH$_2$)$_4$—,
(CF$_2$)—(CH$_2$)$_3$—,
(CF$_2$)—(CH$_2$)$_5$—,
(CF$_2$)—(CH$_2$)$_3$—,
(CF$_2$)—(CH$_2$)—,
(CF$_2$)—(CH$_2$)$_2$—,
(CF$_2$)—(CH$_2$)$_3$—,
(CF$_2$)—(CH$_2$)$_4$—,
(CF$_2$)—(CH$_2$)$_2$—,
(CF$_2$)—(CH$_2$)$_3$—,
(CF$_2$)—(CH$_2$)$_4$—,
(CF$_2$)—(CH$_2$)$_5$—,
(CF$_2$)—(CH$_2$)$_6$—,
(CF$_2$)—(CH$_2$)$_7$—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)—,
(CF$_2$)—(CH$_2$)$_3$—,
(CF$_2$)—(CH$_2$)$_4$—,
(CF$_2$)—(CH$_2$)$_5$—,
(CF$_2$)—(CH$_2$)$_6$—,
(CF$_2$)—(CH$_2$)$_2$—,
(CF$_2$)—(CH$_2$)$_2$—,
(CF$_2$)—(CH$_2$)$_2$—,
(CF$_2$)—(CH$_2$)$_3$—,
(CF$_2$)—(CH$_2$)$_4$—,
(CF$_2$)—(CH$_2$)$_3$—,
(CF$_2$)—(CH$_2$)$_5$—,
(CF$_2$)—(CH$_2$)$_3$—,
(CF$_2$)$_2$—(CH$_2$)—,
(CF$_2$)$_2$—(CH$_2$)$_2$—,
(CF$_2$)$_2$—(CH$_2$)$_3$—,
(CF$_2$)$_2$—(CH$_2$)$_4$—,
(CF$_2$)$_2$—(CH$_2$)$_2$—,
(CF$_2$)$_2$—(CH$_2$)$_3$—,
(CF$_2$)$_2$—(CH$_2$)$_3$—,
(CF$_2$)$_2$—(CH$_2$)$_4$—,
(CF$_2$)$_2$—(CH$_2$)$_5$—,
(CF$_2$)$_2$—(CH$_2$)$_6$—,
(CF$_2$)$_2$—(CH$_2$)$_7$—,
(CF$_2$)$_2$—(CH$_2$)—,
(CF$_2$)$_2$—(CH$_2$)—,
(CF$_2$)$_2$—(CH$_2$)—,
(CF$_2$)$_2$—(CH$_2$)—,
(CF$_2$)$_2$—(CH$_2$)—,
(CF$_2$)$_2$—(CH$_2$)—,
(CF$_2$)$_2$—(CH$_2$)—,
(CF$_2$)$_2$—(CH$_2$)$_3$—,

—(CH$_2$)—(CF$_2$)—O—(CF$_2$)—O—
—(CH$_2$)—(CF$_2$)—O—(CF$_2$)—O—
—(CH$_2$)$_2$—(CF$_2$)—O—(CF$_2$)—O—
—(CH$_2$)$_3$—(CF$_2$)—O—(CF$_2$)—O—
—(CH$_2$)$_4$—(CF$_2$)—O—(CF$_2$)—O—
—(CH$_2$)$_5$—(CF$_2$)—O—(CF$_2$)—O—
—(CH$_2$)$_6$—(CF$_2$)—O—(CF$_2$)—O—
—(CH$_2$)$_7$—(CF$_2$)—O—(CF$_2$)—O—
—(CH$_2$)$_2$—(CF$_2$)—O—(CF$_2$)—O—
—(CH$_2$)$_2$—(CF$_2$)—O—(CF$_2$)—O—
—(CH$_2$)$_2$—(CF$_2$)—O—(CF$_2$)—O—
—(CH$_2$)$_3$—(CF$_2$)—O—(CF$_2$)—O—
—(CH$_2$)$_4$—(CF$_2$)—O—(CF$_2$)—O—
—(CH$_2$)$_5$—(CF$_2$)—O—(CF$_2$)—O—
—(CH$_2$)$_6$—(CF$_2$)—O—(CF$_2$)—O—
—(CH$_2$)$_3$—(CF$_2$)—O—(CF$_2$)—O—
—(CH$_2$)$_4$—(CF$_2$)—O—(CF$_2$)—O—
—(CH$_2$)$_3$—(CF$_2$)—O—(CF$_2$)—O—
—(CH$_2$)$_5$—(CF$_2$)—O—(CF$_2$)—O—
—(CH$_2$)—(CF$_2$)—O—(CF$_2$)$_2$—O—
—(CH$_2$)$_2$—(CF$_2$)—O—(CF$_2$)$_2$—O—
—(CH$_2$)$_3$—(CF$_2$)—O—(CF$_2$)$_2$—O—
—(CH$_2$)$_4$—(CF$_2$)—O—(CF$_2$)$_2$—O—
—(CH$_2$)—(CF$_2$)—O—(CF$_2$)$_2$—O—
—(CH$_2$)—(CF$_2$)—O—(CF$_2$)$_2$—O—
—(CH$_2$)—(CF$_2$)—O—(CF$_2$)$_2$—O—
—(CH$_2$)—(CF$_2$)—O—(CF$_2$)$_2$—O—
—(CH$_2$)—(CF$_2$)—O—(CF$_2$)$_2$—O—
—(CH$_2$)—(CF$_2$)—O—(CF$_2$)$_2$—O—
—(CH$_2$)—(CF$_2$)—O—(CF$_2$)$_2$—O—
—(CH$_2$)$_2$—(CF$_2$)—O—(CF$_2$)$_2$—O—
—(CH$_2$)$_3$—(CF$_2$)—O—(CF$_2$)$_2$—O—
—(CH$_2$)$_4$—(CF$_2$)—O—(CF$_2$)$_2$—O—
—(CH$_2$)$_5$—(CF$_2$)—O—(CF$_2$)$_2$—O—
—(CH$_2$)$_6$—(CF$_2$)—O—(CF$_2$)$_2$—O—
—(CH$_2$)$_7$—(CF$_2$)—O—(CF$_2$)$_2$—O—
—(CH$_2$)$_2$—(CF$_2$)—O—(CF$_2$)$_2$—O—
—(CH$_2$)$_2$—(CF$_2$)—O—(CF$_2$)$_2$—O—
—(CH$_2$)$_2$—(CF$_2$)—O—(CF$_2$)$_2$—O—
—(CH$_2$)$_3$—(CF$_2$)—O—(CF$_2$)$_2$—O—
—(CH$_2$)$_3$—(CF$_2$)—O—(CF$_2$)$_2$—O—
—(CH$_2$)$_4$—(CF$_2$)—O—(CF$_2$)$_2$—O—
—(CH$_2$)$_5$—(CF$_2$)—O—(CF$_2$)$_2$—O—
—(CH$_2$)—(CF$_2$)$_2$—O—(CF$_2$)—O—
—(CH$_2$)$_2$—(CF$_2$)$_2$—O—(CF$_2$)—O—
—(CH$_2$)$_3$—(CF$_2$)$_2$—O—(CF$_2$)—O—
—(CH$_2$)$_4$—(CF$_2$)$_2$—O—(CF$_2$)—O—
—(CH$_2$)$_2$—(CF$_2$)$_2$—O—(CF$_2$)—O—
—(CH$_2$)$_2$—(CF$_2$)$_2$—O—(CF$_2$)—O—
—(CH$_2$)$_2$—(CF$_2$)$_2$—O—(CF$_2$)—O—
—(CH$_2$)—(CF$_2$)$_2$—O—(CF$_2$)—O—
—(CH$_2$)—(CF$_2$)$_2$—O—(CF$_2$)—O—
—(CH$_2$)$_3$—(CF$_2$)$_2$—O—(CF$_2$)—O—
—(CH$_2$)$_4$—(CF$_2$)$_2$—O—(CF$_2$)—O—
—(CH$_2$)$_5$—(CF$_2$)$_2$—O—(CF$_2$)—O—
—(CH$_2$)$_6$—(CF$_2$)$_2$—O—(CF$_2$)—O—
—(CH$_2$)$_7$—(CF$_2$)$_2$—O—(CF$_2$)—O—
—(CH$_2$)$_2$—(CF$_2$)$_2$—O—(CF$_2$)—O—
—(CH$_2$)$_2$—(CF$_2$)$_2$—O—(CF$_2$)—O—

(CF$_2$)$_2$—(CH$_2$)$_4$—,
(CF$_2$)$_2$—(CH$_2$)$_5$—,
(CF$_2$)$_2$—(CH$_2$)$_6$—,
(CF$_2$)$_2$—(CH$_2$)$_2$—,
(CF$_2$)$_2$—(CH$_2$)$_2$—,
(CF$_2$)$_2$—(CH$_2$)$_2$—,
(CF$_2$)$_2$—(CH$_2$)$_2$—,
(CF$_2$)$_2$—(CH$_2$)$_4$—,
(CF$_2$)$_2$—(CH$_2$)$_3$—,
(CF$_2$)$_2$—(CH$_2$)$_5$—,
(CF$_2$)$_2$—(CH$_2$)$_3$—,
(CF$_2$)—O—(CF$_2$)—(CH$_2$)—,
(CF$_2$)—O—(CF$_2$)—O—(CF$_2$)—(CH$_2$)$_2$—,
(CF$_2$)—O—(CF$_2$)—O—(CF$_2$)—(CH$_2$)$_3$—,
(CH$_2$)$_4$—(CF$_2$)—O—(CF$_2$)—O—(CF$_2$)—(CH$_2$)$_4$—, —(CH$_2$)—(CF$_2$)—O—(CF$_2$)—O—(CF$_2$)—(CH$_2$)$_2$—,
(CF$_2$)—O—(CF$_2$)—(CH$_2$)$_3$—,
(CF$_2$)—O—(CF$_2$)—O—(CF$_2$)—(CH$_2$)$_4$—,
(CF$_2$)—O—(CF$_2$)—O—(CF$_2$)—(CH$_2$)$_5$—,
—(CH$_2$)—(CF$_2$)—O—(CF$_2$)—O—(CF$_2$)—O—(CF$_2$)—
(CH$_2$)$_6$—, —(CH$_2$)—(CF$_2$)—O—(CF$_2$)—O—(CF$_2$)—
(CF$_2$)—(CH$_2$)$_7$—,
(CF$_2$)—O—(CF$_2$)—(CH$_2$)—,
(CF$_2$)—O—(CF$_2$)—O—(CF$_2$)—(CH$_2$)—,
(CF$_2$)—O—(CF$_2$)—O—(CF$_2$)—O—(CF$_2$)—(CH$_2$)—,
—(CH$_2$)$_5$—(CF$_2$)—O—(CF$_2$)—O—(CF$_2$)—O—(CF$_2$)—
(CH$_2$)—, —(CH$_2$)$_6$—(CF$_2$)—O—(CF$_2$)—O—(CF$_2$)—
(CF$_2$)—(CH$_2$)—, (CH$_2$)$_7$—(CF$_2$)—O—(CF$_2$)—O—
(CF$_2$)—O—(CF$_2$)—(CH$_2$)—,
(CF$_2$)—O—(CF$_2$)—O—(CF$_2$)—(CH$_2$)$_3$—,
(CF$_2$)—O—(CF$_2$)—O—(CF$_2$)—(CH$_2$)$_4$—,
(CH$_2$)$_2$—(CF$_2$)—O—(CF$_2$)—O—(CF$_2$)—(CF$_2$)—
(CH$_2$)$_5$—, —(CH$_2$)$_2$—(CF$_2$)—O—(CF$_2$)—O—(CF$_2$)—
O—(CF$_2$)—(CH$_2$)$_6$—, —(CH$_2$)$_3$—(CF$_2$)—O—(CF$_2$)—
O—(CF$_2$)—O—(CF$_2$)—(CH$_2$)$_2$—, (CH$_2$)$_4$—(CF$_2$)—O—
(CF$_2$)—O—(CF$_2$)—O—(CF$_2$)—(CH$_2$)$_2$—, —(CH$_2$)$_5$—
(CF$_2$)—O—(CF$_2$)—O—(CF$_2$)—O—(CF$_2$)—(CH$_2$)$_2$—,
—(CH$_2$)$_6$—(CF$_2$)—O—(CF$_2$)—O—(CF$_2$)—O—(CF$_2$)—
(CH$_2$)$_2$—, —(CH$_2$)$_3$—(CF$_2$)—O—(CF$_2$)—O—(CF$_2$)—
O—(CF$_2$)—(CH$_2$)$_4$—, —(CH$_2$)$_4$—(CF$_2$)—O—(CF$_2$)—
O—(CF$_2$)—O—(CF$_2$)—(CH$_2$)$_3$—, —(CH$_2$)$_3$—(CF$_2$)—
O—(CF$_2$)—O—(CF$_2$)—O—(CF$_2$)—(CH$_2$)$_5$—, (CH$_2$)$_5$—
(CF$_2$)—O—(CF$_2$)—O—(CF$_2$)—O—(CF$_2$)—(CH$_2$)$_3$—,
—(CH$_2$)—(CF$_2$)$_2$—O—(CF$_2$)$_2$—O—(CF$_2$)$_2$—O—
(CF$_2$)$_2$—(CH$_2$)—, —(CH$_2$)$_2$—(CF$_2$)$_2$—O—(CF$_2$)$_2$—O—
(CF$_2$)$_2$—O—(CF$_2$)$_2$—(CH$_2$)$_2$—, —(CH$_2$)$_3$—(CF$_2$)$_2$—O—
(CF$_2$)$_2$—O—(CF$_2$)$_2$—(CH$_2$)$_3$—, —(CH$_2$)$_4$—
(CF$_2$)$_2$—O—(CF$_2$)$_2$—O—(CF$_2$)$_2$—O—(CF$_2$)$_2$—(CH$_2$)$_4$—,
—(CH$_2$)—(CF$_2$)$_2$—O—(CF$_2$)$_2$—O—(CF$_2$)$_2$—O—
(CF$_2$)$_2$—(CH$_2$)$_2$—, —(CH$_2$)—(CF$_2$)$_2$—O—(CF$_2$)$_2$—O—
(CF$_2$)$_2$—O—(CF$_2$)$_2$—(CH$_2$)$_3$—, —(CH$_2$)—(CF$_2$)$_2$—O—
(CF$_2$)$_2$—O—(CF$_2$)$_2$—O—(CF$_2$)$_2$—(CH$_2$)$_4$—, —(CH$_2$)—
(CF$_2$)$_2$—O—(CF$_2$)$_2$—O—(CF$_2$)$_2$—O—(CF$_2$)$_2$—(CH$_2$)$_5$—,
—(CH$_2$)—(CF$_2$)$_2$—O—(CF$_2$)$_2$—O—(CF$_2$)$_2$—
O—(CF$_2$)$_2$—(CH$_2$)$_6$—, —(CH$_2$)—(CF$_2$)$_2$—O—(CF$_2$)$_2$—
O—(CF$_2$)$_2$—O—(CF$_2$)$_2$—(CH$_2$)$_7$—, —(CH$_2$)$_2$—(CF$_2$)$_2$—
O—(CF$_2$)$_2$—O—(CF$_2$)$_2$—O—(CF$_2$)$_2$—(CH$_2$)—,
—(CH$_2$)$_3$—(CF$_2$)$_2$—O—(CF$_2$)$_2$—O—(CF$_2$)$_2$—O—
(CF$_2$)$_2$—(CH$_2$)—, —(CH$_2$)$_4$—(CF$_2$)$_2$—O—(CF$_2$)$_2$—O—
(CF$_2$)$_2$—O—(CF$_2$)$_2$—(CH$_2$)—, —(CH$_2$)$_5$—(CF$_2$)$_2$—O—
(CF$_2$)$_2$—O—(CF$_2$)$_2$—O—(CF$_2$)$_2$—(CH$_2$)—, —(CH$_2$)$_6$—
(CF$_2$)$_2$—O—(CF$_2$)$_2$—O—(CF$_2$)$_2$—O—(CF$_2$)$_2$—
(CH$_2$)—, —(CH$_2$)$_7$—(CF$_2$)$_2$—O—(CF$_2$)$_2$—O—(CF$_2$)$_2$—
O—(CF$_2$)$_2$—(CH$_2$)—, —(CH$_2$)$_2$—(CF$_2$)$_2$—O—(CF$_2$)$_2$—
O—(CF$_2$)$_2$O—(CF$_2$)$_2$—O—(CF$_2$)$_2$—(CH$_2$)$_4$—,

—(CH₂)₂—(CF₂)₂—O—(CF₂)₂—O—(CF₂)₂—O—(CF₂)₂—(CH₂)₅—, —(CH₂)₂—(CF₂)₂—O—(CF₂)₂—O—(CF₂)₂—O—(CF₂)₂—(CH₂)₆—, —(CH₂)₃—(CF₂)₂—O—(CF₂)₂—O—(CF₂)₂—O—(CF₂)₂—(CH₂)₂—, —(CH₂)₄—(CF₂)₂—O—(CF₂)₂—O—(CF₂)₂—O—(CF₂)₂—(CH₂)₂—, —(CH₂)₅—(CF₂)₂—O—(CF₂)₂—O—(CF₂)₂—O—(CF₂)₂—(CH₂)₂—, —(CH₂)₂—(CF₂)₂—O—(CF₂)₂—O—(CF₂)₂—(CH₂)₆—, —(CH₂)₃—(CF₂)₂—O—(CF₂)₂O—(CF₂)₂—O—(CF₂)₂—(CH₂)₄—, —(CH₂)₄—(CF₂)₂—O—(CF₂)₂—O—(CF₂)₂—O—(CF₂)₂—(CH₂)₃—, —(CH₂)₃—(CF₂)₂—O—(CF₂)₂—O—(CF₂)₂—O—(CF₂)₂—(CH₂)₅—, —(CH₂)₅—(CF₂)₂—O—(CF₂)₂—O—(CF₂)₂—(CH₂)₃—,

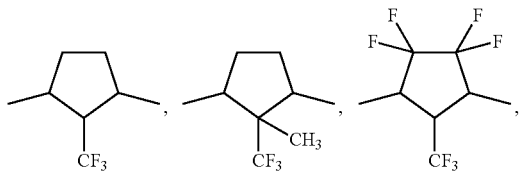

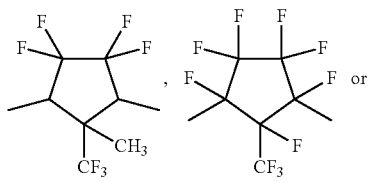

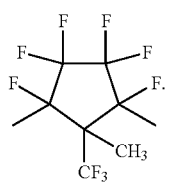

Preferred examples for —R₂— are —(CH₂)₈—, —(CH₂)₁₁—, —(CH₂)₁₂—, —(CH₂)₁₃—. —(CH₂)—(CHOH)—(CH₂)—, —(CH₂)—(CHOH)—(CH₂)₄—, —(CH₂)₄—(CHOH)—(CH₂)—, —(CH₂)—[CH(CH₂OH)]—(CH₂)—, —(CH₂)—[CH(CH₂OH)]—(CH₂)₄—, —(CH₂)₂—[CH(CH₂OH)]—(CH₂)—, —(CH₂)₃—(CHOH)—(CHOH)—(CH₂)₃—, —(CH₂)₃—(CHOH)—(CHOH)—(CH₂)₄—, —(CH₂)₃—(CHOH)—(CH₂)—(CHOH)—(CH₂)₃—, —(CH₂)—(CHOH)—(CH₂)₂—(CHOH)—(CH₂)—, —(CH₂)—(CHOH)—(CH₂)—[CH(CH₂OH)]—(CH₂)₃—, —(CH₂)—(CHOH)—(CH₂)₂—[CH(CH₂OH)]—(CH₂)—, —(CH₂)—(CHOH)—(CHOH)—(CH₂)—(CHOH)—(CHOH)—(CH₂)₃—, —(CH₂)₂—(CHOH)—(CHOH)—(CH₂)—(CHOH)—(CHOH)—(CH₂)₃—, —(CH₂)—(CHOH)—(CH₂)—O—(CH₂)₂—O—(CH₂)—(CHOH)—(CH₂)—, —(CH₂)—(CHOH)—(CH₂)—O—(CH₂)₆—O—(CH₂)—(CHOH)—(CH₂)—, —(CH₂)₃—(CF₂)—(CH₂)₃—, —(CH₂)₅—(CF₂)—(CH₂)₆—, —(CH₂)₆—(CF₂)—(CH₂)₅—, —(CH₂)—(CF₂)₃—(CH₂)—, —(CH₂)₂—(CF₂)₄—(CH₂)₂—, —(CH₂)—[CH(CF₃)]—(CH₂)—, —(CH₂)—[C(CH₃)CF₃]—(CH₂)—, —(CH₂)—[CH(CH₂CF₃)]—(CH₂)—, —(CH₂)—[C(CH₃)(CH₂CF₃)]—(CH₂)—, —(CH₂)₂—(CF₂)₂—O—(CF₂)₂—O—(CF₂)₂—(CH₂)₂—, —(CH₂)—(CF₂)₂—O—(CF₂)₂—O—(CF₂)₂—O—(CF₂)₂—(CH₂)—,

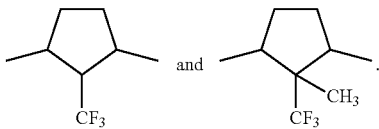

Particularly preferred examples for —R₂— are —(CH₂)₈—, —(CH₂)₁₁—, —(CH₂)₁₂—, —(CH₂)₁₃—, —(CH₂)—(CHOH)—(CH₂)—, —(CH₂)—(CHOH)—(CH₂)₄—, —(CH₂)₄—(CHOH)—(CH₂)—, —(CH₂)—[CH(CH₂OH)]—(CH₂)—, —(CH₂)—[CH(CH₂OH)]—(CH₂)₄—, —(CH₂)₂—[CH(CH₂OH)]—(CH₂)—, —(CH₂)₃—(CHOH)—(CHOH)—(CH₂)₃—, —(CH₂)₃—(CHOH)—(CHOH)—(CH₂)₄—, —(CH₂)₃—(CHOH)—(CH₂)—(CHOH)—(CH₂)₃—, —(CH₂)—(CHOH)—(CH₂)₂—(CHOH)—(CH₂)—, —(CH₂)—(CHOH)—(CH₂)—[CH(CH₂OH)]—(CH₂)₃—, —(CH₂)—(CHOH)—(CH₂)₂—[CH(CH₂OH)]—(CH₂)—, —(CH₂)—(CHOH)—(CHOH)—(CH₂)—(CHOH)—(CHOH)—(CH₂)₃—, —(CH₂)₂—(CHOH)—(CHOH)—(CH₂)—(CHOH)—(CHOH)—(CH₂)₃—, —(CH₂)₃—(CF₂)—(CH₂)₃—, —(CH₂)—(CF₂)₃—(CH₂)—, —(CH₂)₂—(CF₂)₄—(CH₂)₂—, —(CH₂)—[CH(CF₃)]—(CH₂)—, —(CH₂)—[C(CH₃)CF₃]—(CH₂)—, —(CH₂)—[CH(CH₂CF₃)]—(CH₂)—, —(CH₂)—[C(CH₃)(CH₂CF₃)]—(CH₂)—,

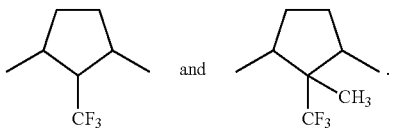

Very particularly preferred examples for —R₂— are —(CH₂)₈—, —(CH₂)₁₁—(CH₂)₁₂—, —(CH₂)₁₃—, especially —(CH₂)₁₂—.

Compounds of formula (I), (I-1), (I-2), (I-3), (I-4), (I-5), (I-6), (I-7), (I-8) and (I-9) with linkers

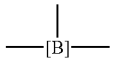

and substituents as described before or preferably described before having a polymerizable group as described before or preferably described before or below are preferred in case the substituent —R₂— corresponds to —(C(R)₂)ₒ— and R and o have a meaning as described before or preferably described before.

The invention therefore relates to compounds of formula (I), (I-1), (I-2), (I-3), (I-4), (I-5), (I-6), (I-7), (I-8) and (I-9) as described before or preferably described before wherein —R₂— is —(C(R)₂)ₒ— and R and o have a meaning as described before.

The substituent —R₂—R₁ is particularly preferably selected when —R₂— has a meaning as described before or preferably or particularly preferably described before and wherein R₁ is a polymerizable group selected from a trialkoxysilyl group, a dialkoxyalkylsilyl group, a silyl group of formula (2), (3) or (4) as described before where the alkyl and/or alkoxy groups are each independently linear or branched having 1 to 6 C atoms, or an alkenyl group of formula (1),

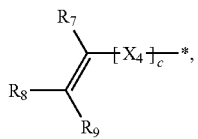
(1)

wherein

X₄ is selected from the group consisting of O, S, C(=O), C(=O)O,

R₇, R₈, R₉ are at each occurrence independently of each other selected from the group consisting of H, F, a linear or branched, non-fluorinated, partially or completely fluorinated alkyl having 1 to 20 C atoms or aryl with 6 to 14 C atoms and c is 0 or 1.

The asterisk "*" denotes the bond to —R₂—.

Preferably, R₈ and R₉ are H.

Preferably, R₇ is H, methyl, ethyl or phenyl.

Preferably, X₄ is C(=O) or C(=O)O.

Preferred alkenyl groups of formula (1) are therefore represented by any one selected from the group consisting of formulae (1-1), (1-2), (1-3), (1-4) and (1-5):

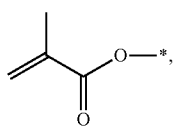
(1-1)

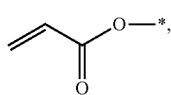
(1-2)

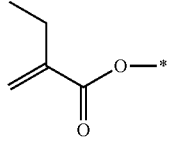
(1-3)

(1-4)

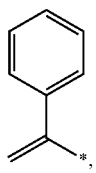
(1-5)

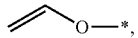
(1-6)

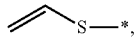
(1-7)

(1-8)

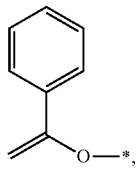

(1-9)

The alkenyl group represented by formula (1-1) is called methacrylate. The alkenyl group represented by formula (1-2) is called acrylate.

The preferred groups R₁ are preferably combined with preferred groups of the linking element —R₂—.

The substituent [—R₂—R₁] is therefore particularly preferably selected from the group consisting of —(CH₂)₈—R₁, —(CH₂)₁₁—R₁, —(CH₂)₁₂—R₁, —(CH₂)₁₃—R₁, —(CH₂)—(CHOH)—(CH₂)—R₁, —(CH₂)—(CHOH)—(CH₂)₄—R₁, —(CH₂)₄—(CHOH)—(CH₂)—R₁, —(CH₂)—[CH(CH₂OH)]—(CH₂)—R₁, —(CH₂)—[CH(CH₂OH)]—(CH₂)₄—R₁, —(CH₂)₂—[CH(CH₂OH)]—(CH₂)—R₁, —(CH₂)₃—(CHOH)—(CHOH)—(CH₂)₃—R₁, —(CH₂)₃—(CHOH)—(CHOH)—(CH₂)₄—R₁, —(CH₂)₃—(CHOH)—(CH₂)—(CHOH)—(CH₂)₃—R₁, —(CH₂)—(CHOH)—(CH₂)₂—(CHOH)—(CH₂)—R₁, —(CH₂)—(CHOH)—(CH₂)—[CH(CH₂OH)]—(CH₂)₃—R₁, —(CH₂)—(CHOH)—(CH₂)₂—[CH(CH₂OH)]—(CH₂)—R₁, —(CH₂)—(CHOH)—(CHOH)—(CH₂)—(CHOH)—(CHOH)—(CH₂)₃—R₁, —(CH₂)₂—(CHOH)—(CHOH)—(CH₂)—(CHOH)—(CHOH)—(CH₂)₃—R₁, —(CH₂)₃—(CF₂)—(CH₂)₃—R₁, —(CH₂)—(CF₂)₃—(CH₂)—R₁, —(CH₂)₂—(CF₂)₄—(CH₂)₂—R₁, —(CH₂)—[CH(CF₃)]—(CH₂)—R₁, —(CH₂)—[C(CH₃)CF₃]—(CH₂)—R₁, —(CH₂)—[CH(CH₂CF₃)]—(CH₂)—R₁, —(CH₂)—[C(CH₃)(CH₂CF₃)]—(CH₂)—R₁,

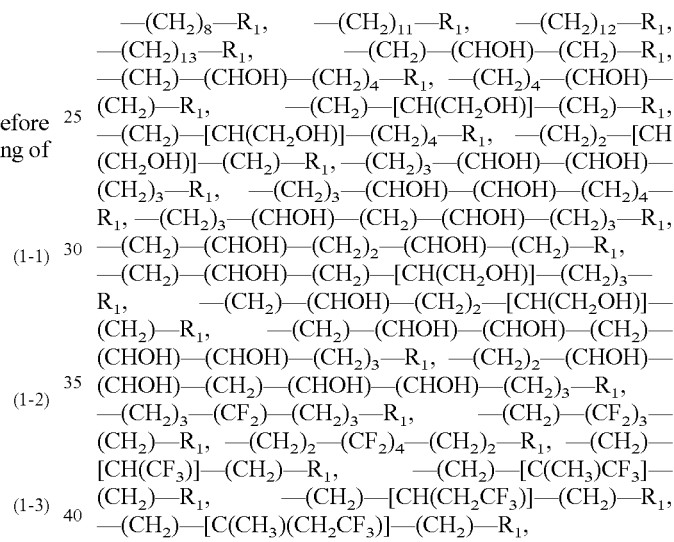

wherein R₁ is selected from the group consisting of triethoxysilyl, diethoxymethylsilyl or an alkenyl of formula (1-1), (1-2), (1-3), (1-4), (1-5), (1-6), (1-7), (1-8) or (1-9) or wherein R₁ is preferably selected from the group consisting of an alkenyl of formula (1-1), (1-2) or (1-3).

Very particularly preferably, the compounds of formula (I), (I-1), (I-2), (I-3), (I-4), (I-5), (I-6), (I-7), (I-8) and (I-9) as described before or preferably described before comprise a polymerizable group R₁ which is a methacryl or an acryl group represented by formula (I-1) and (1-2).

The invention therefore relates further to compounds of formula (I), (I-1), (I-2), (I-3), (I-4), (I-5), (I-6), (I-7), (I-8) and (I-9) as described before or preferably described before wherein R₁ is an acryl or methacryl group.

Examples for compounds of formula (I), (I-1), (I-2), (I-3), (I-4), (I-5), (I-6), (I-7), (I-8) and/or (I-9) are the following compounds M-001 to M-147:

M-001
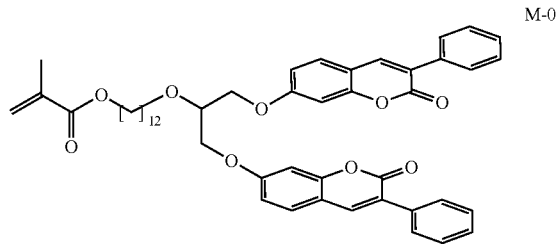
M-002
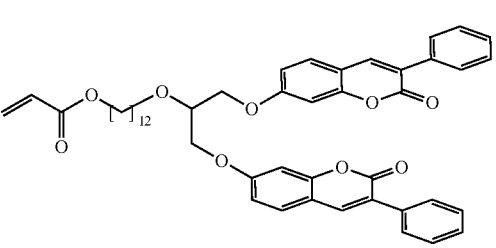
M-003
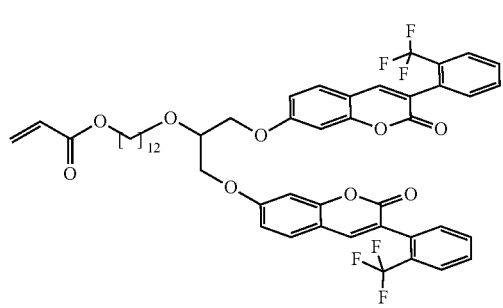
M-004
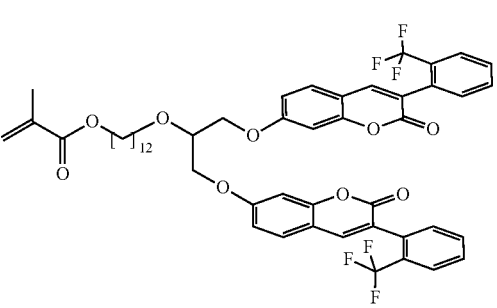
M-005
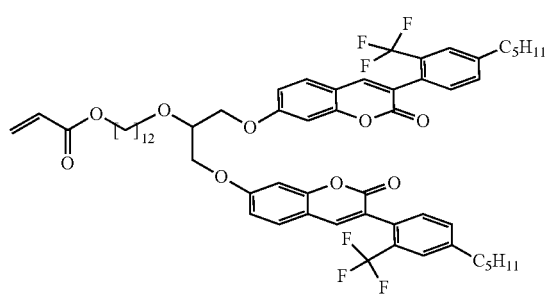
M-006
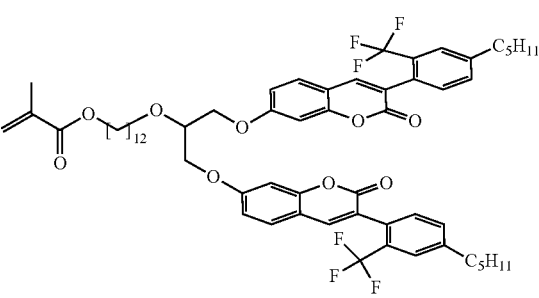
M-007
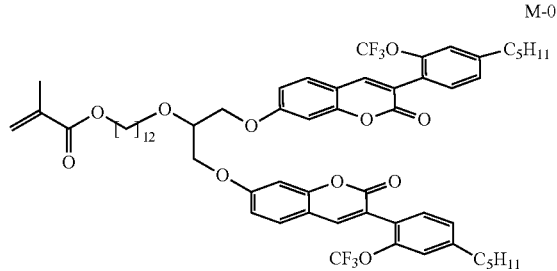
M-008
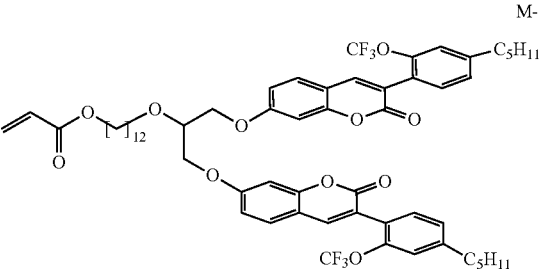
M-009
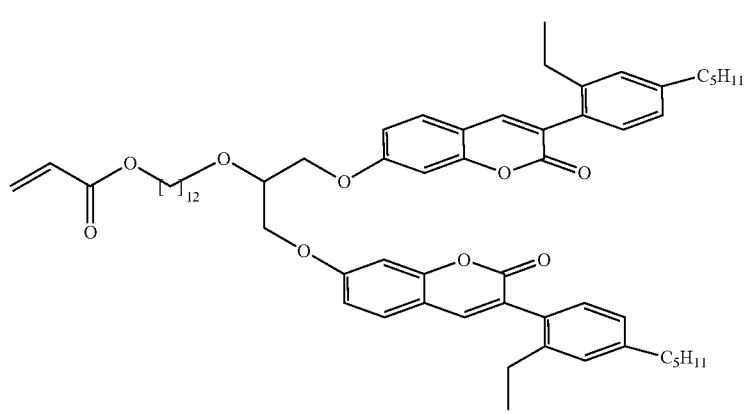

-continued
M-010
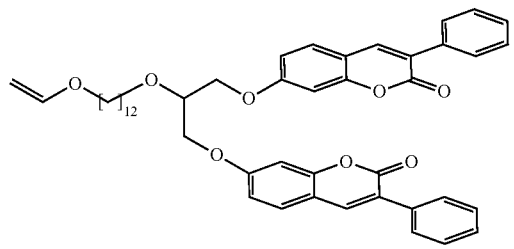
M-011
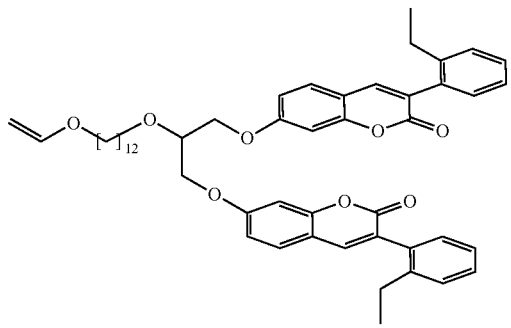
M-012
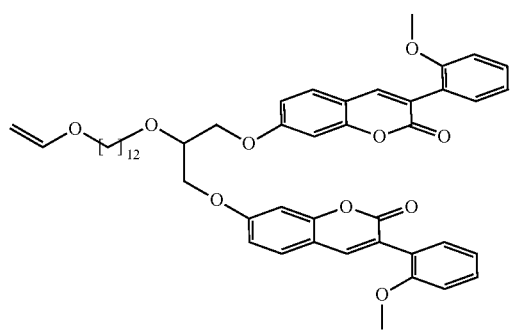
M-013
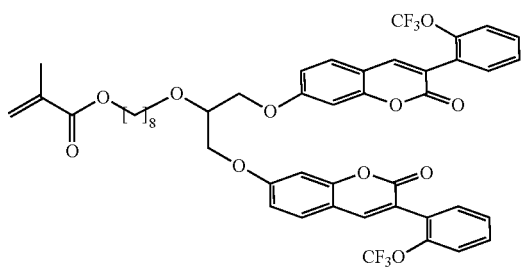
M-014
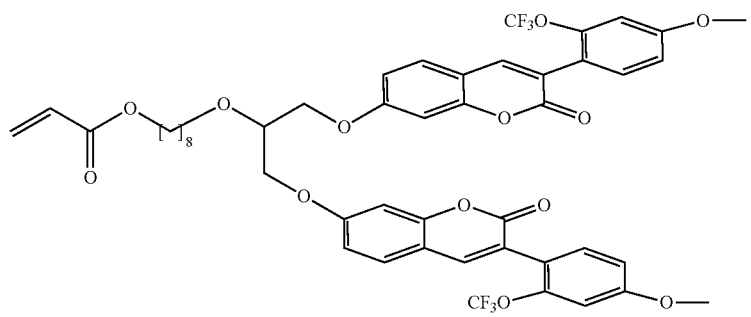
M-015
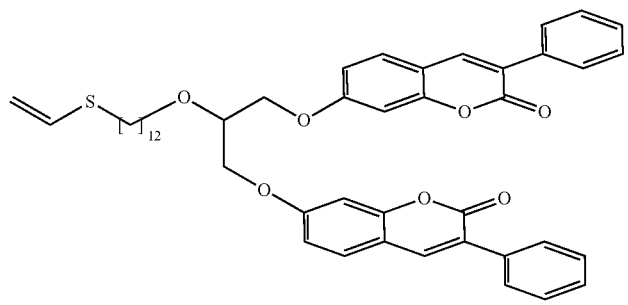

-continued
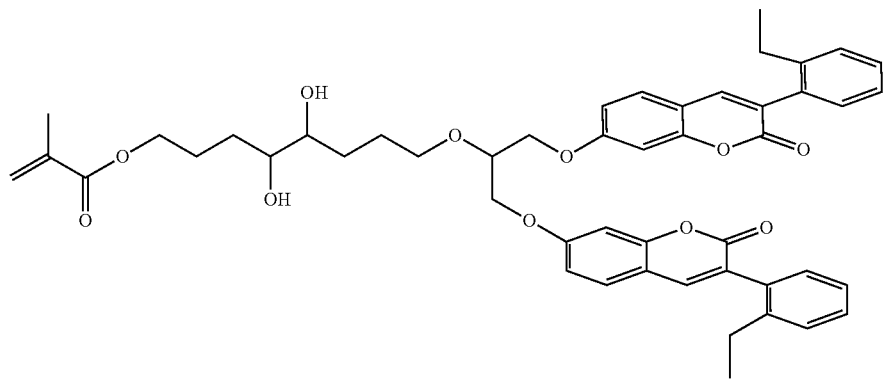
M-016
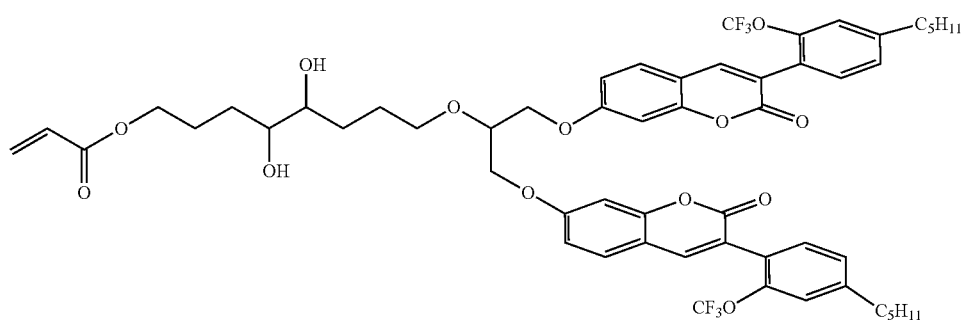
M-017
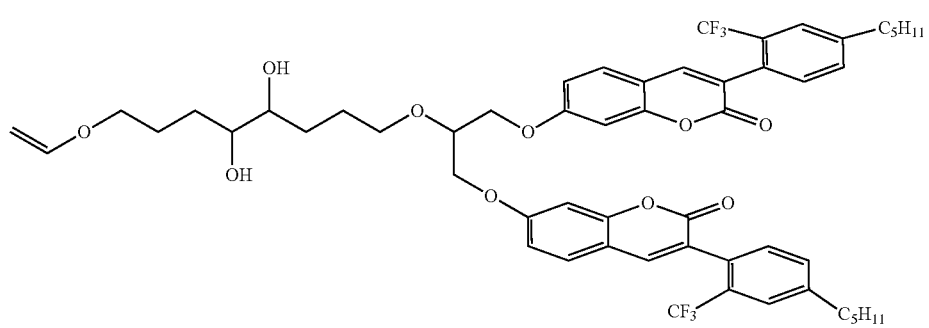
M-018
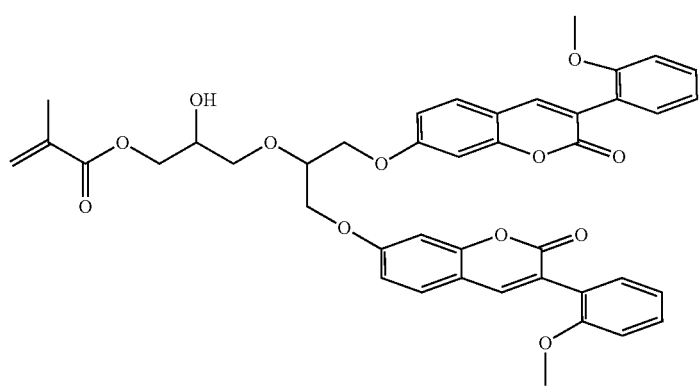
M-019

M-020
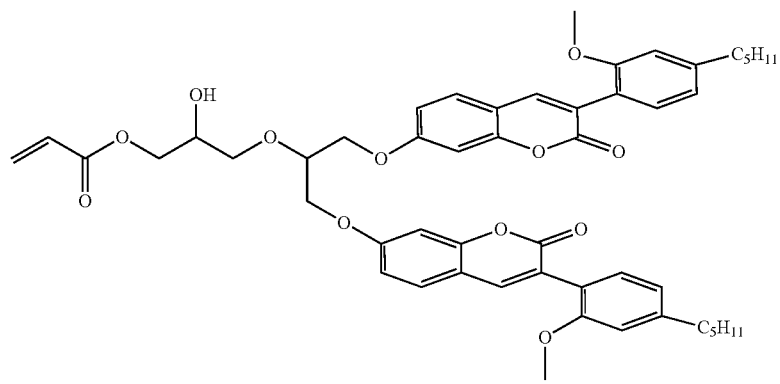
M-021
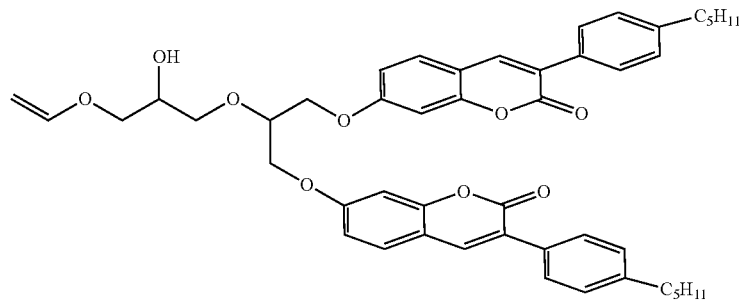
M-022
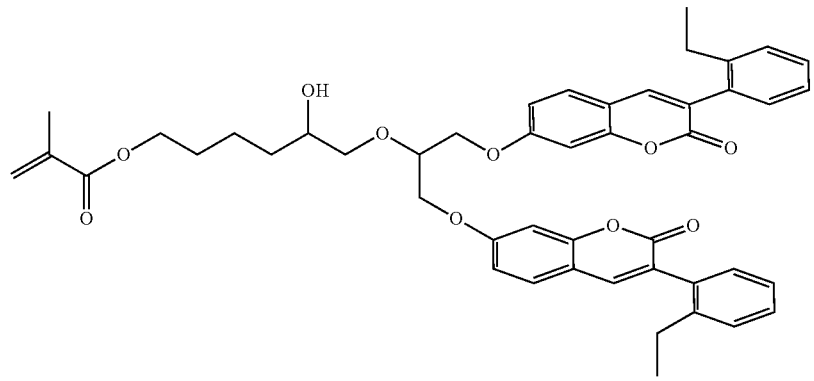
M-023
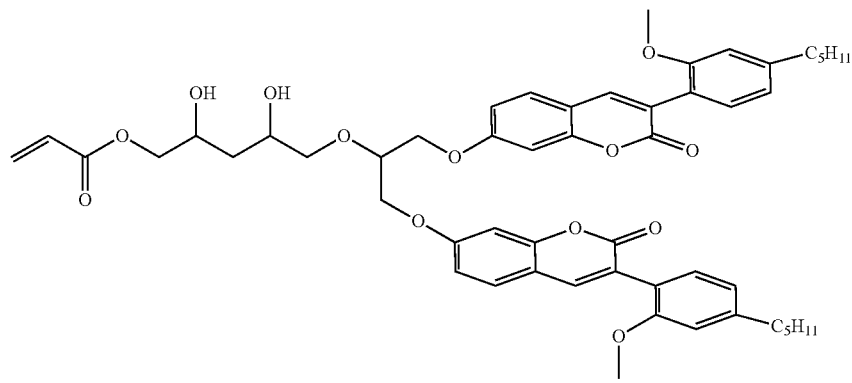

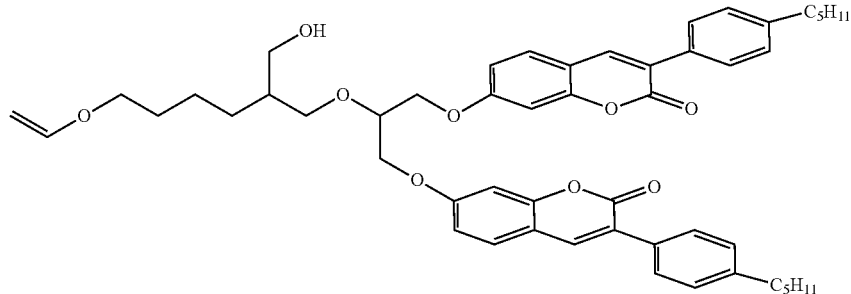
M-024
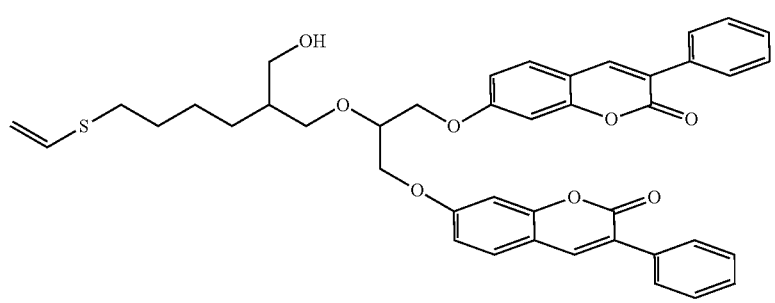
M-025
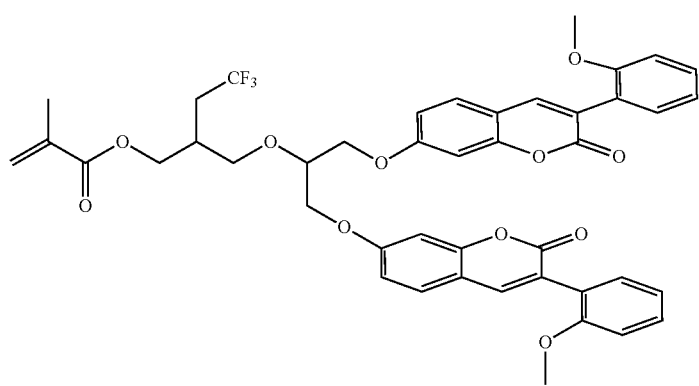
M-026
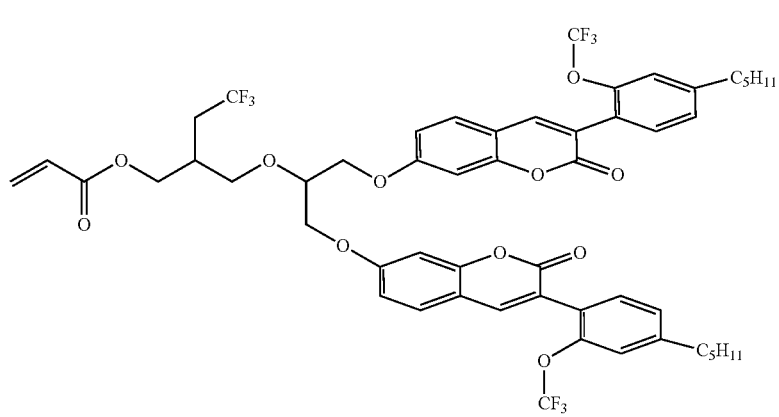
M-027

M-028
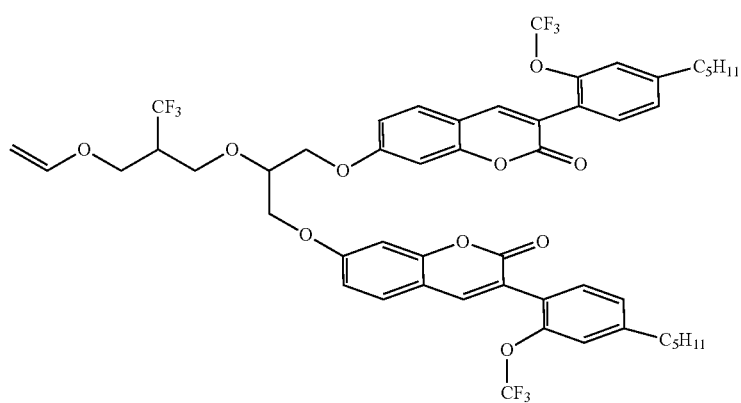
M-029
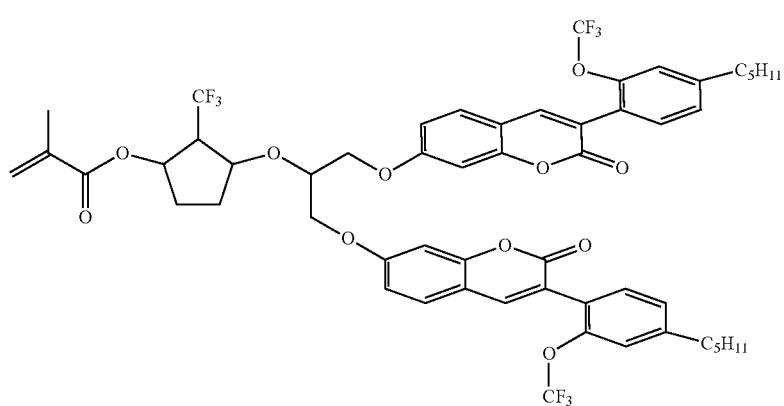
M-030
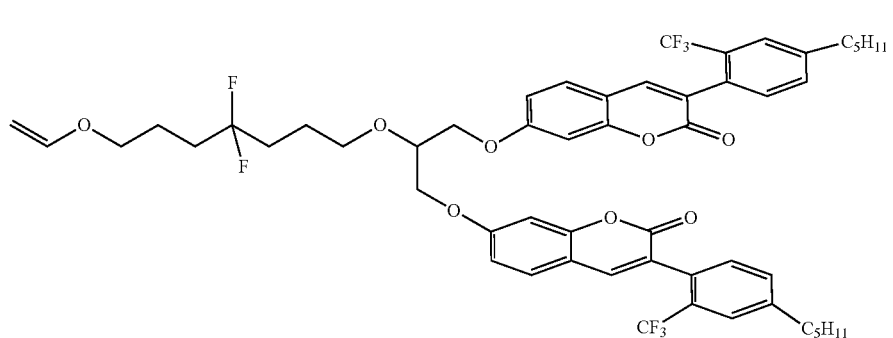
M-031
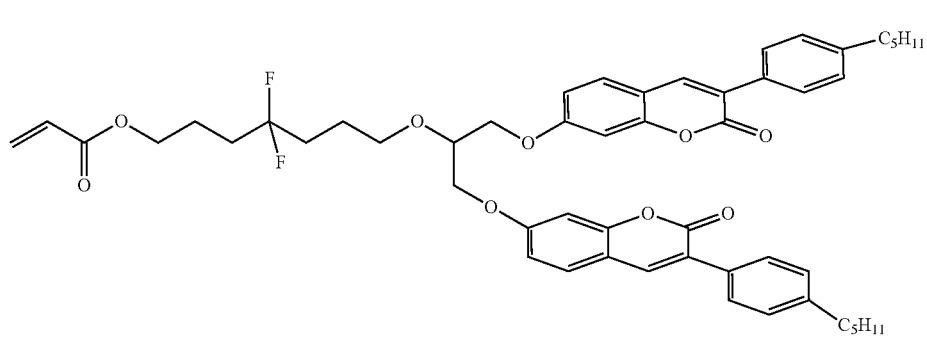

-continued
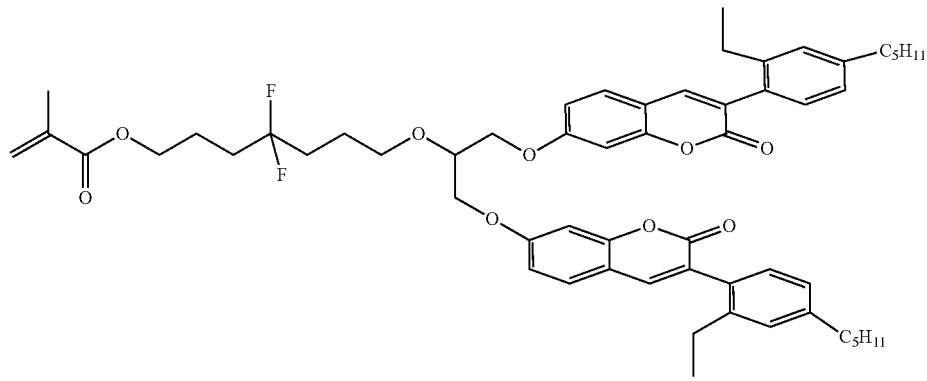
M-032
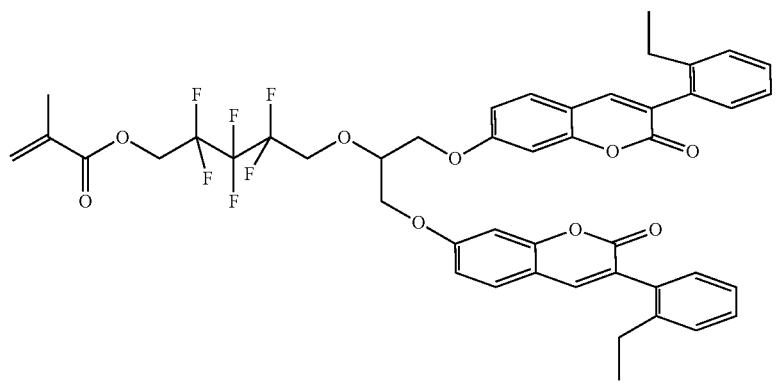
M-033
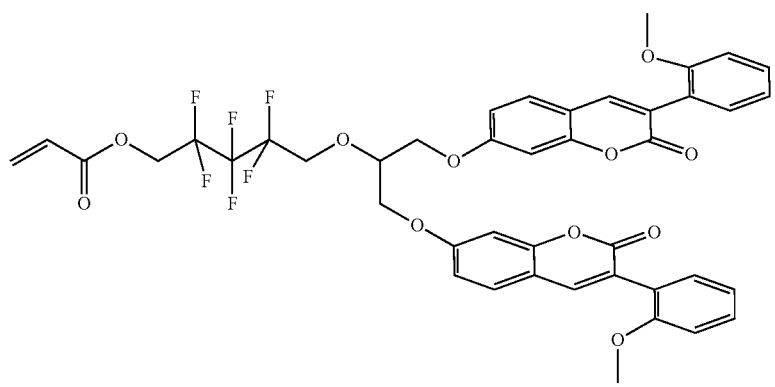
M-034
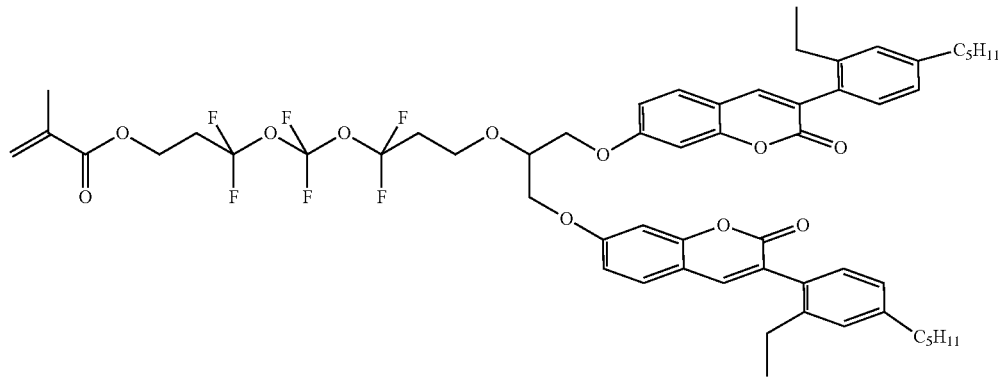
M-035

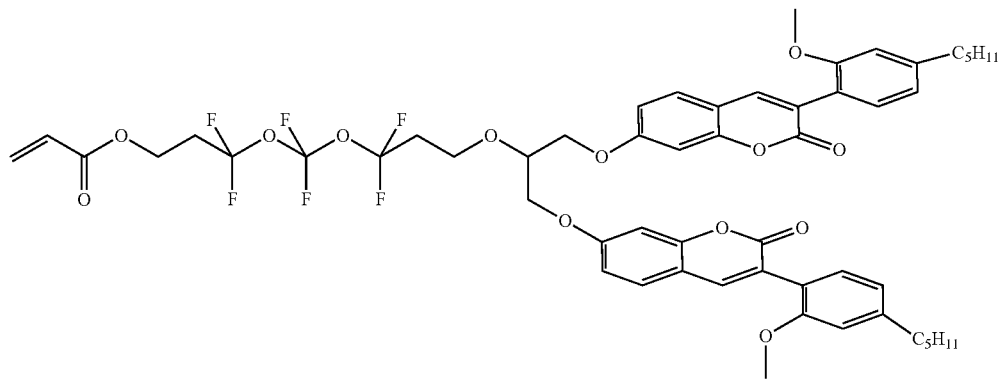
M-036
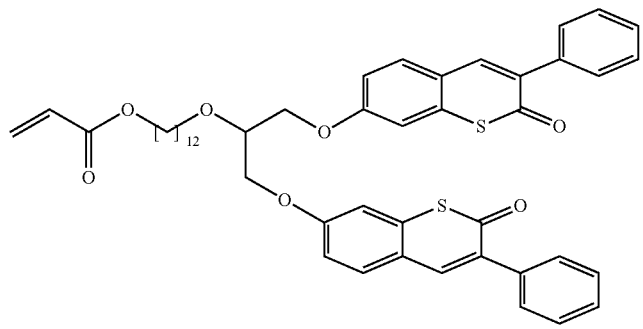
M-037
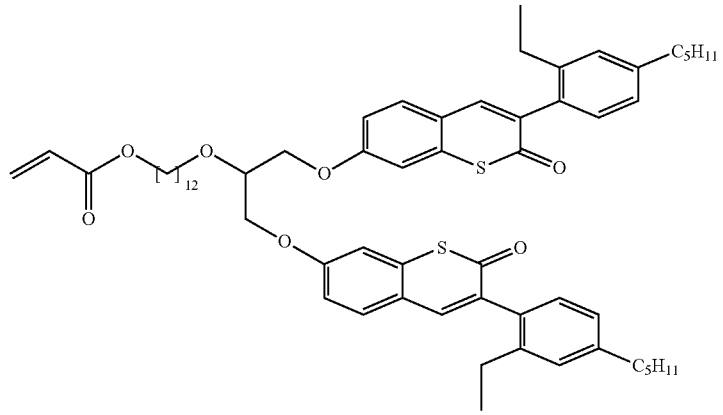
M-038
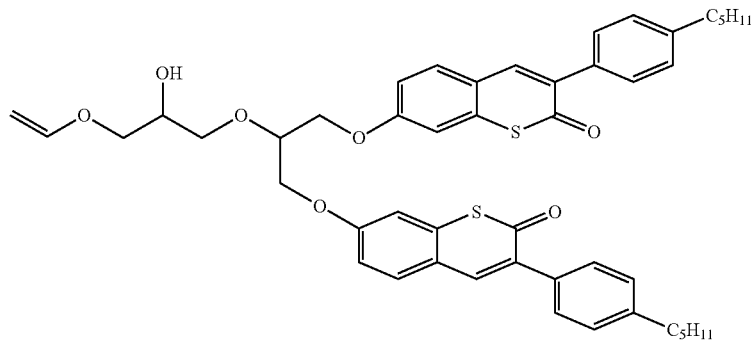
M-039

-continued
M-040
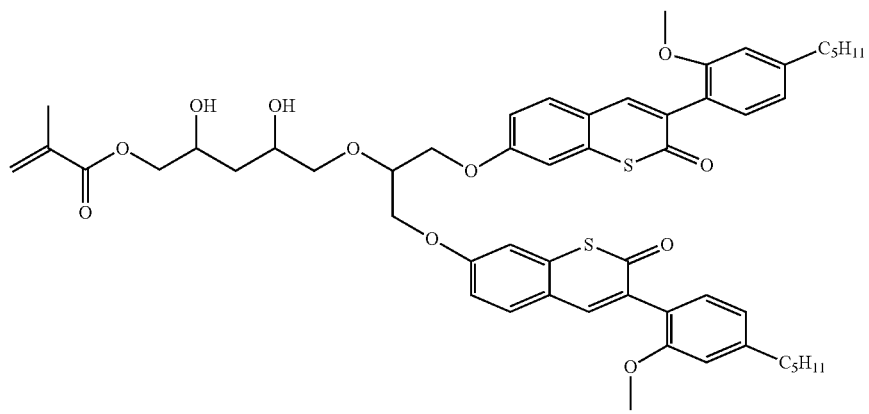
M-041
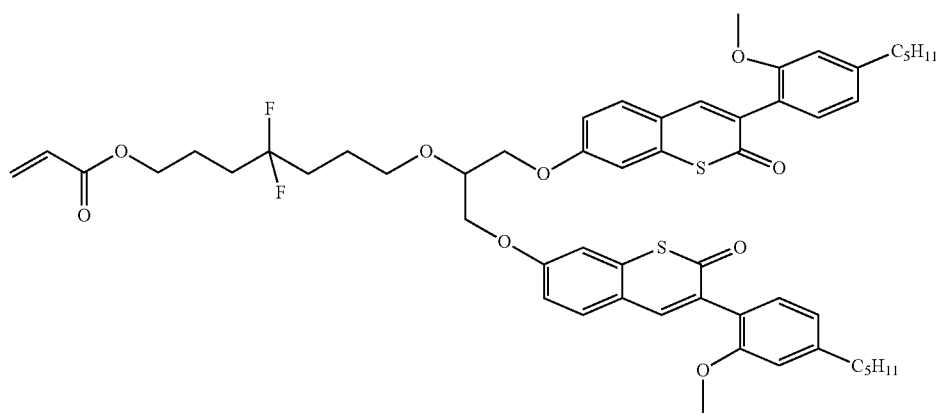
M-042
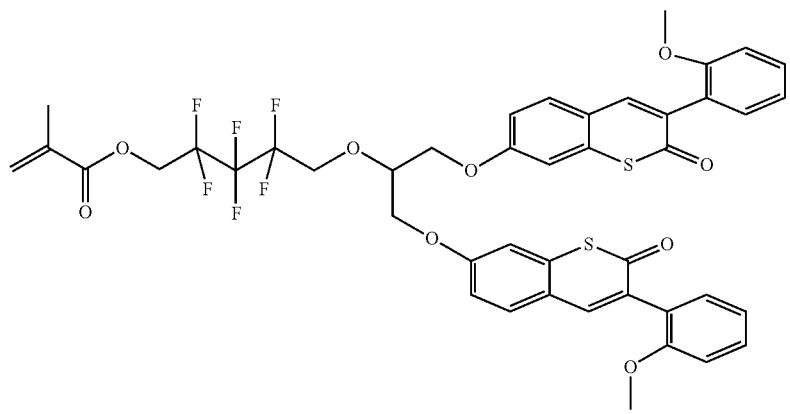
M-043  M-044
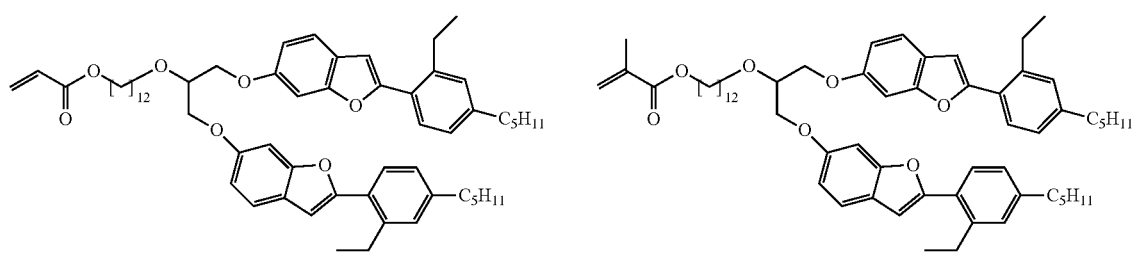

-continued
M-045
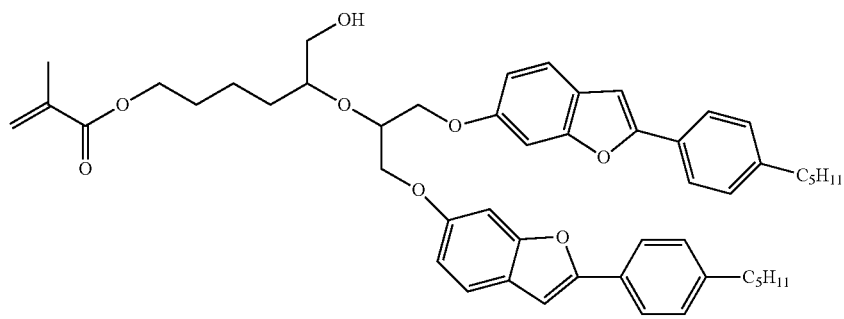
M-046
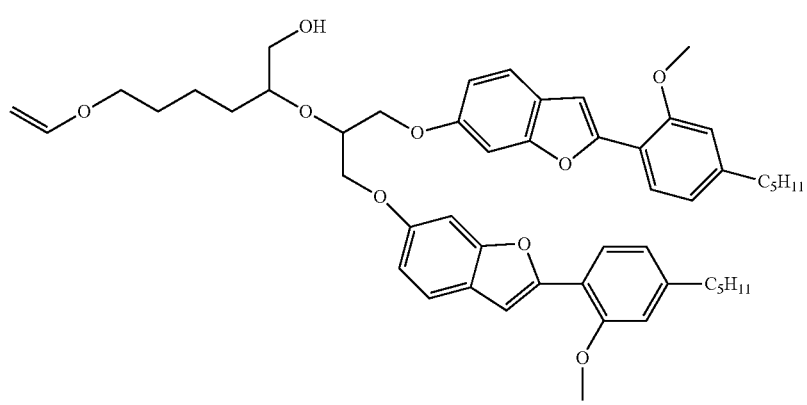
M-047
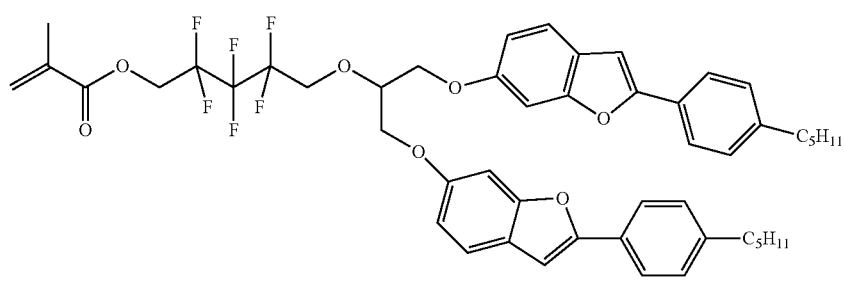
M-048
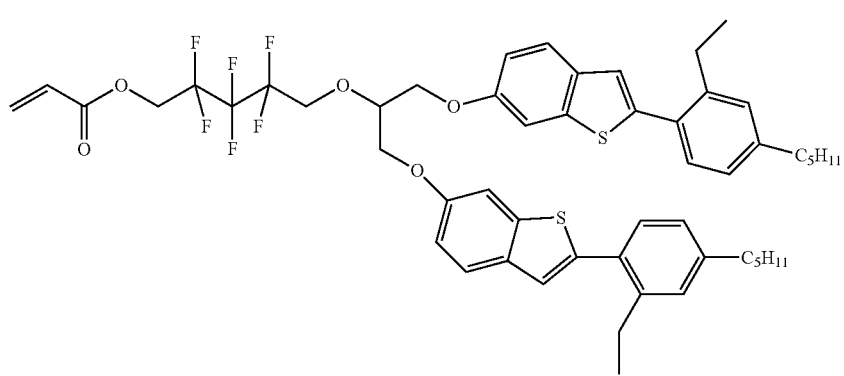

-continued
M-049
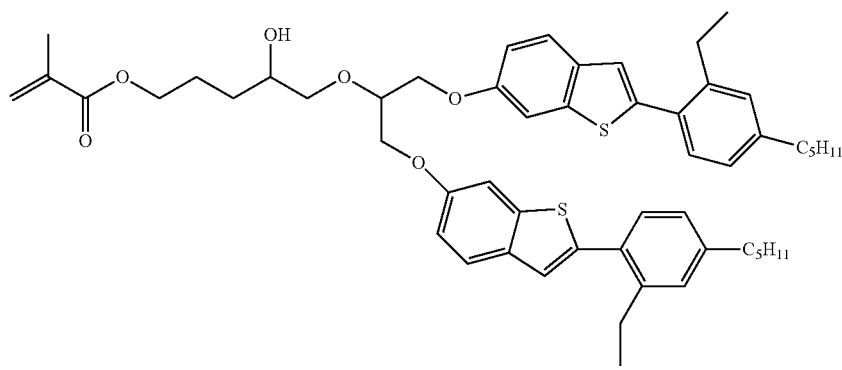
M-050
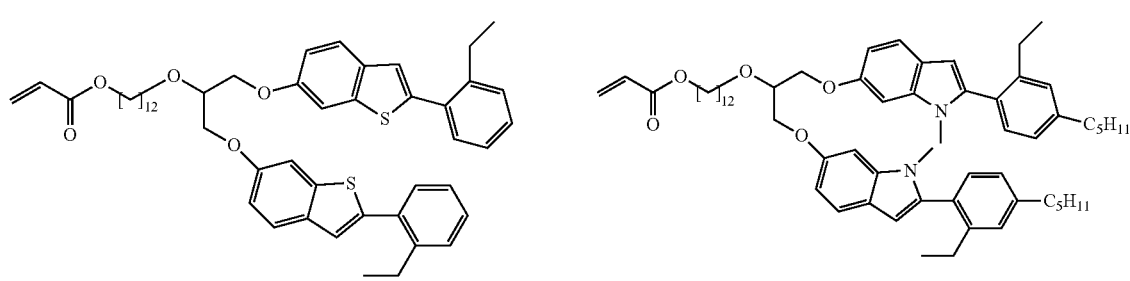
M-051
M-052
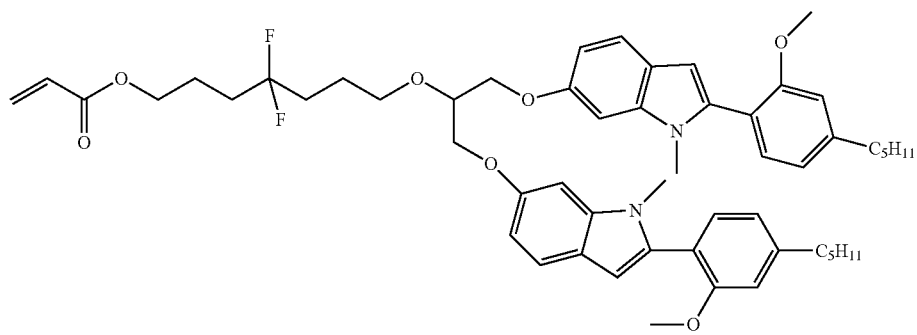
M-053
M-054
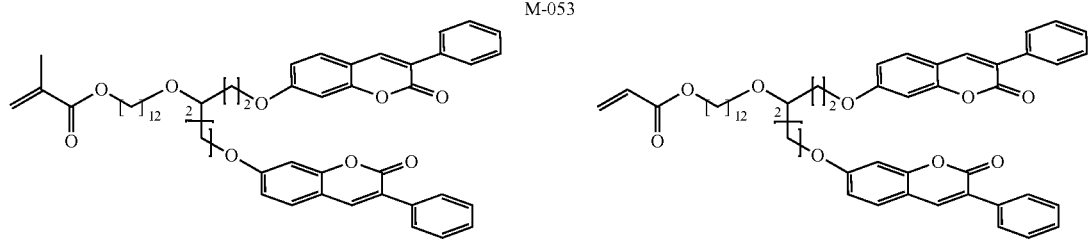
M-055
M-056
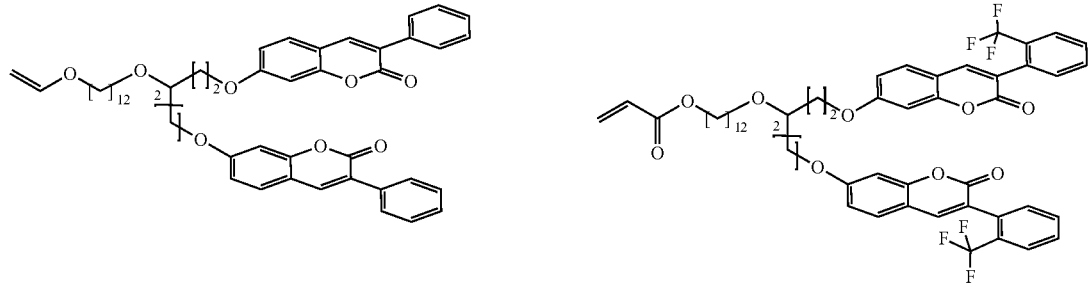

-continued
M-057
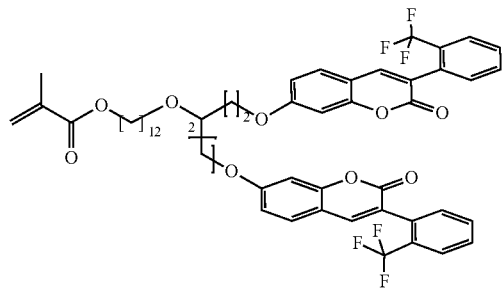
M-058
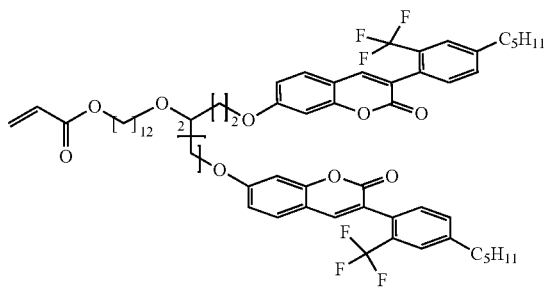
M-059
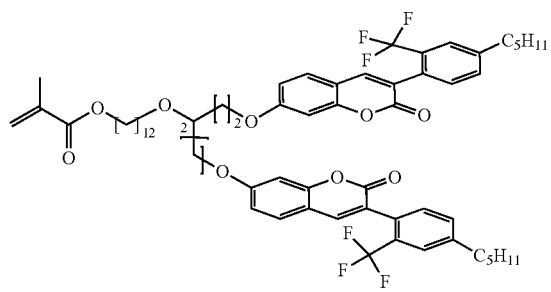
M-060
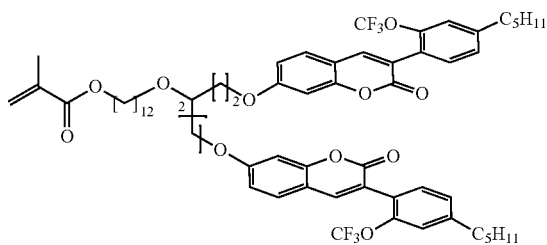
M-061
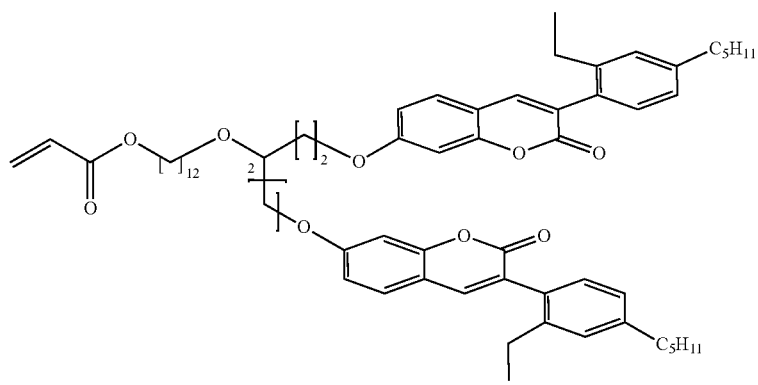
M-062
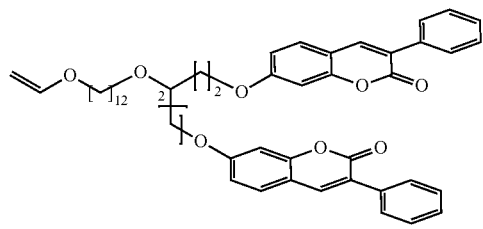
M-063
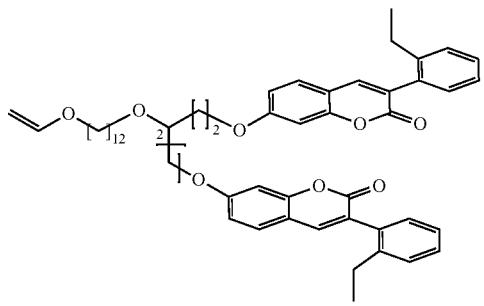

-continued
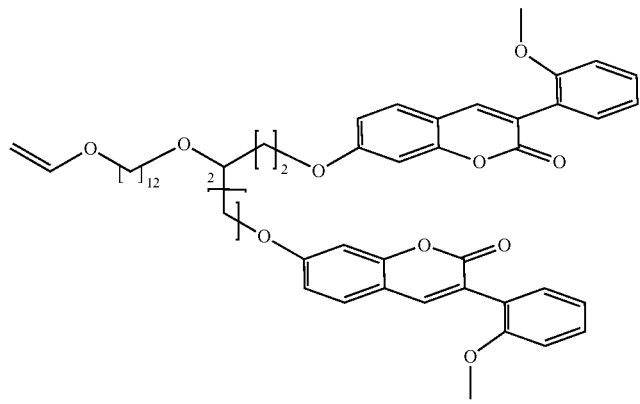
M-064
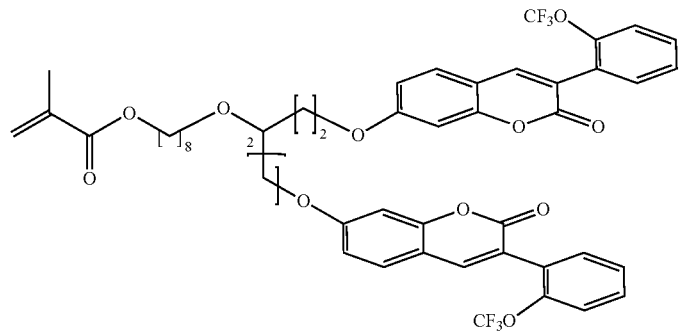
M-065
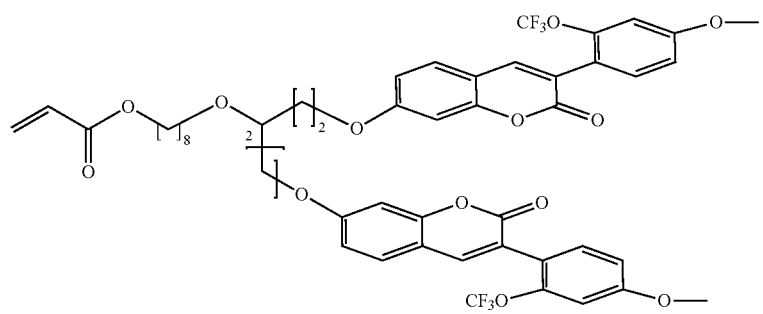
M-066
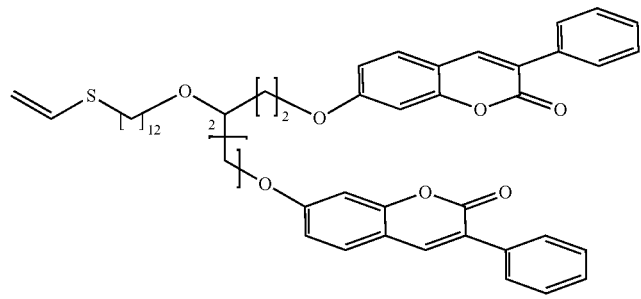
M-067

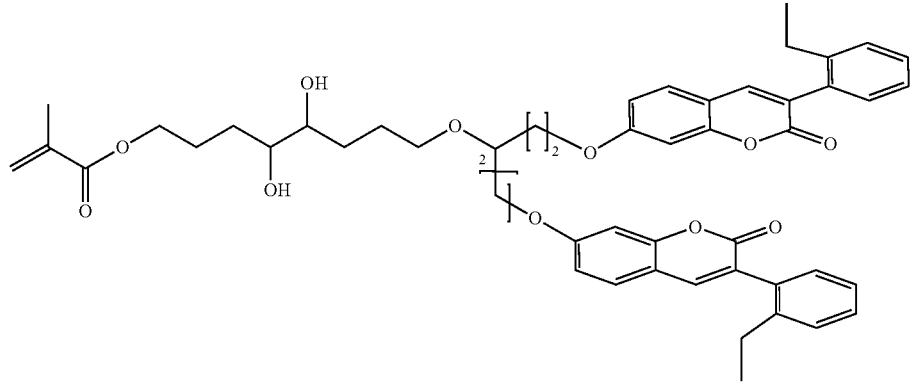
M-068
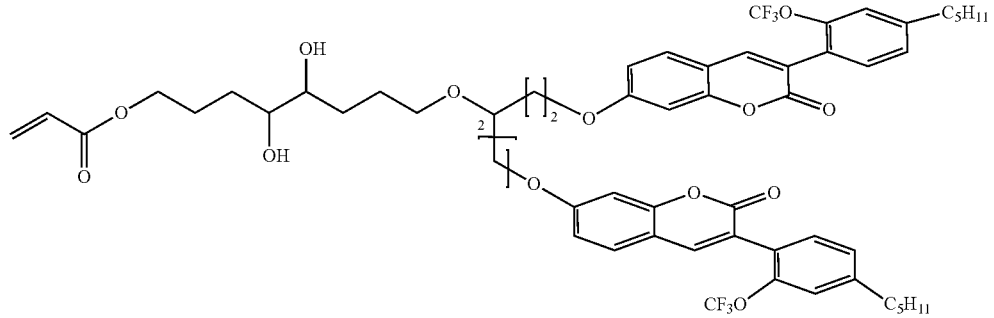
M-069
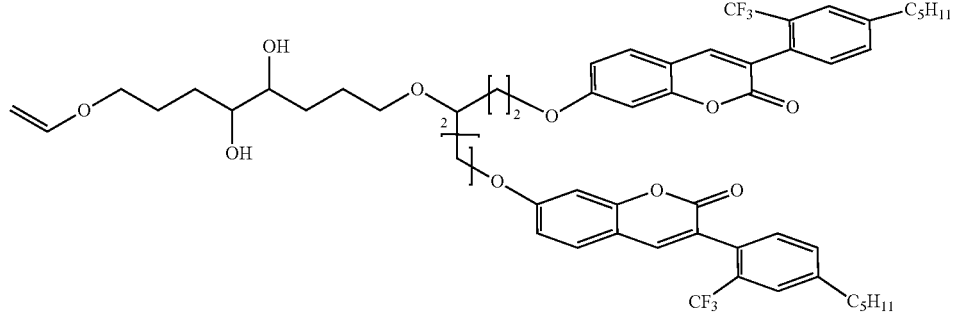
M-070
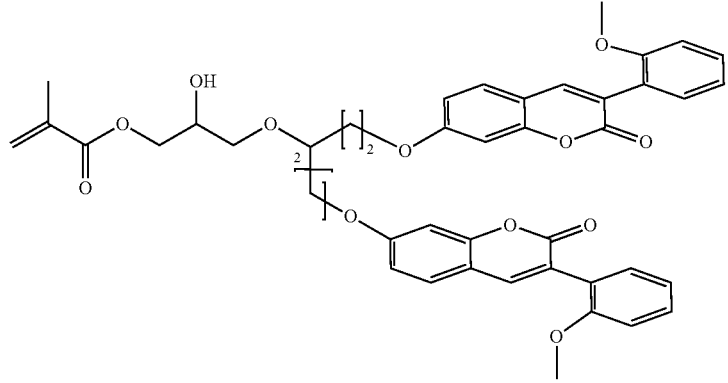
M-071

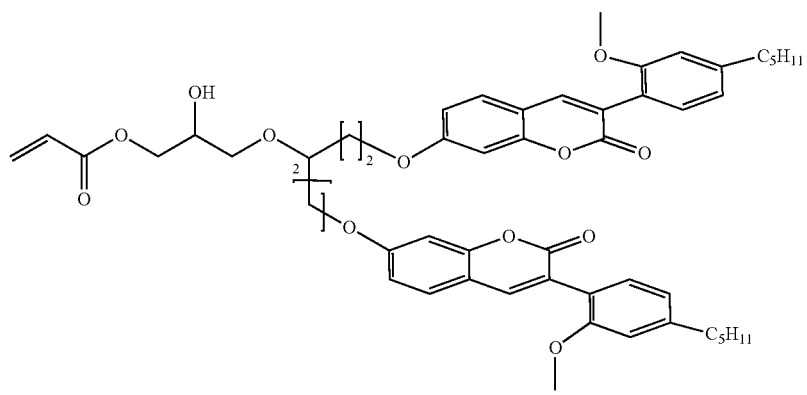
M-072
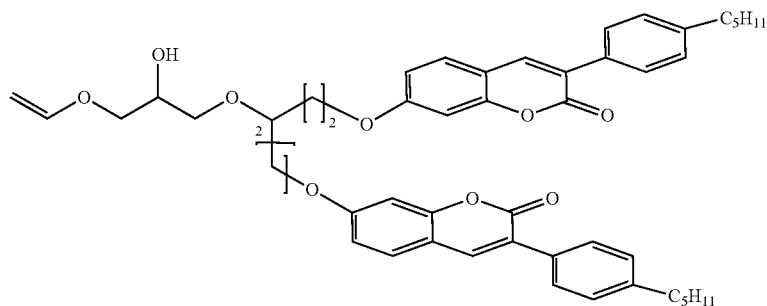
M-073
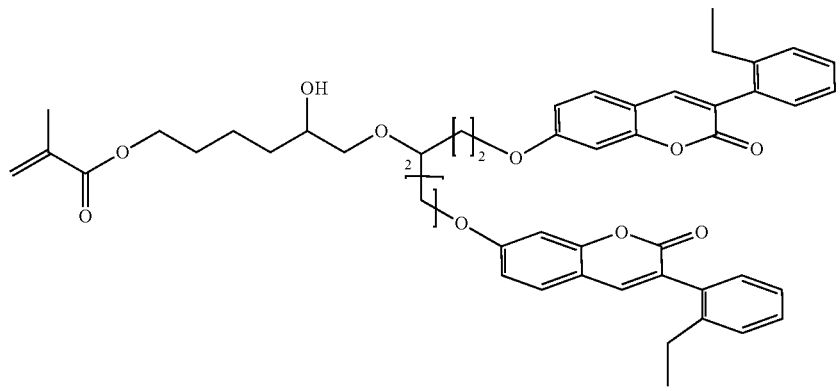
M-074
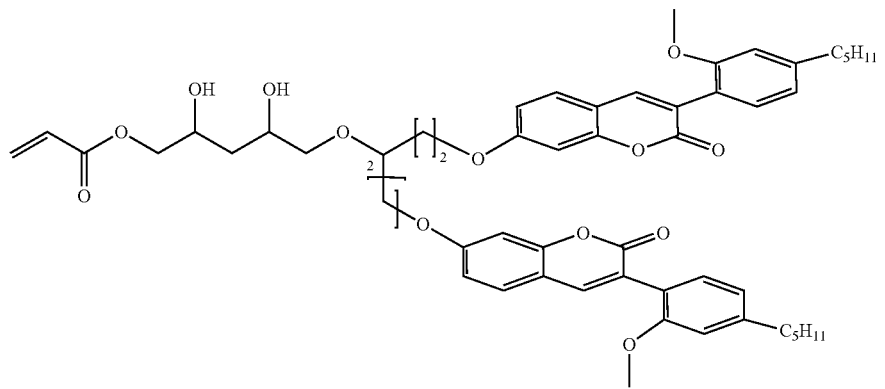
M-075

M-076
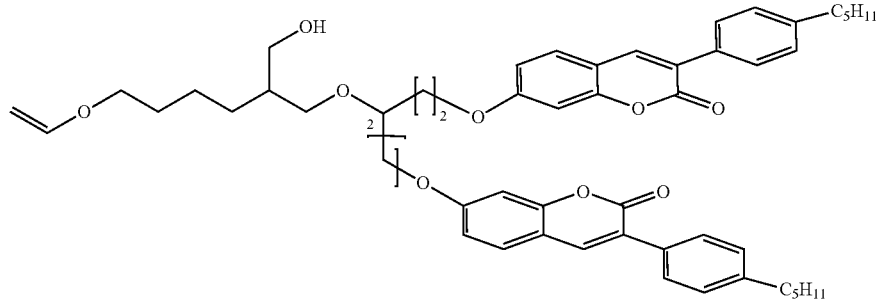
M-077
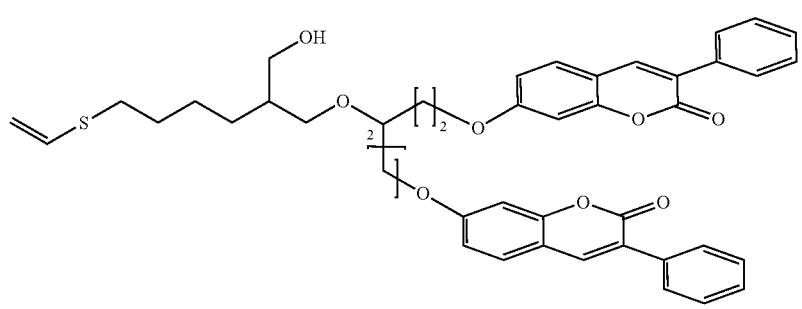
M-078
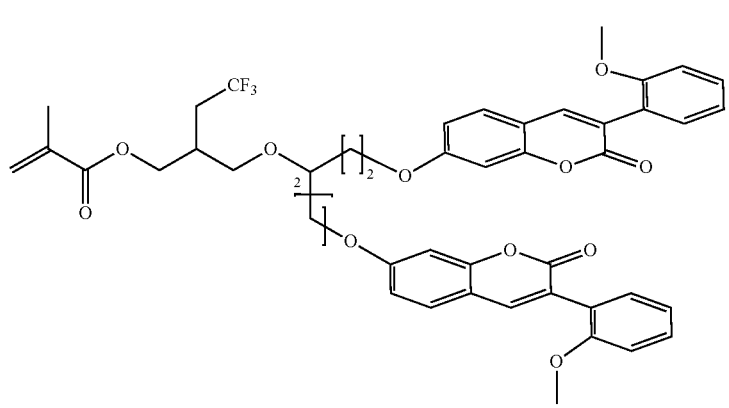
M-079
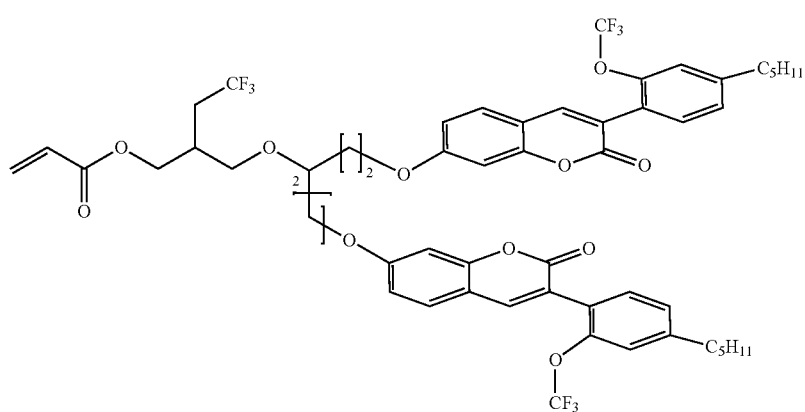

M-080
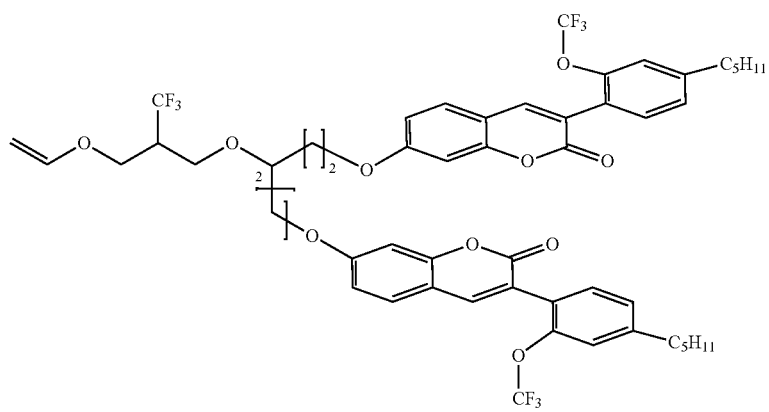
M-081
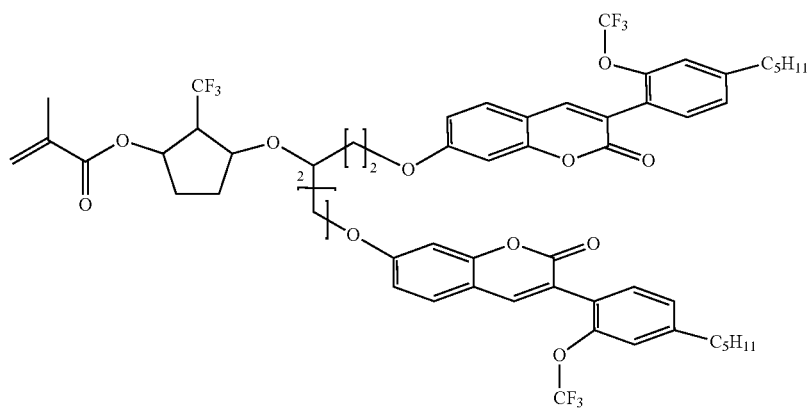
M-082
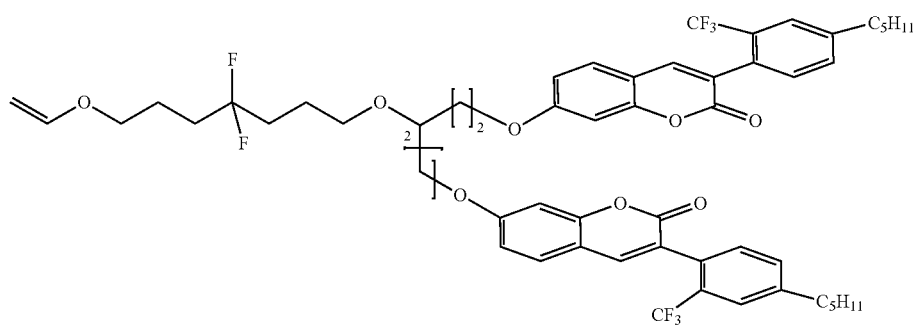
M-083
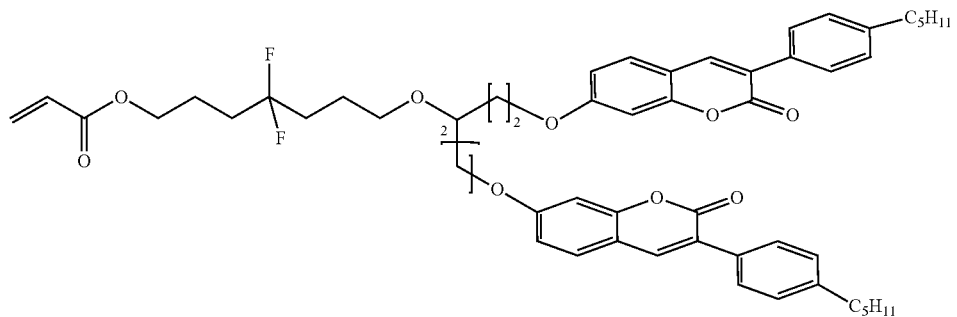

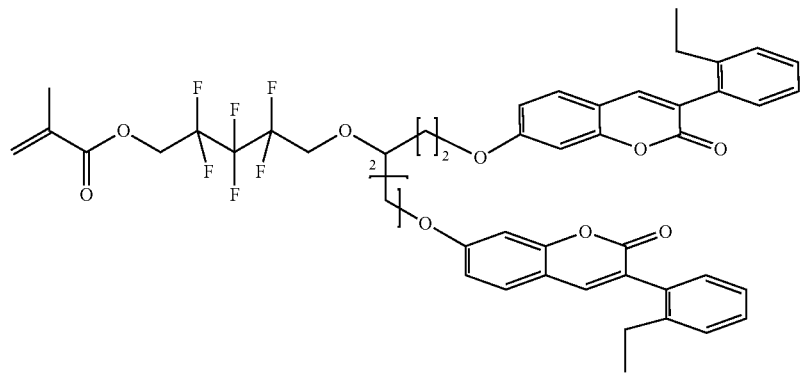
M-084
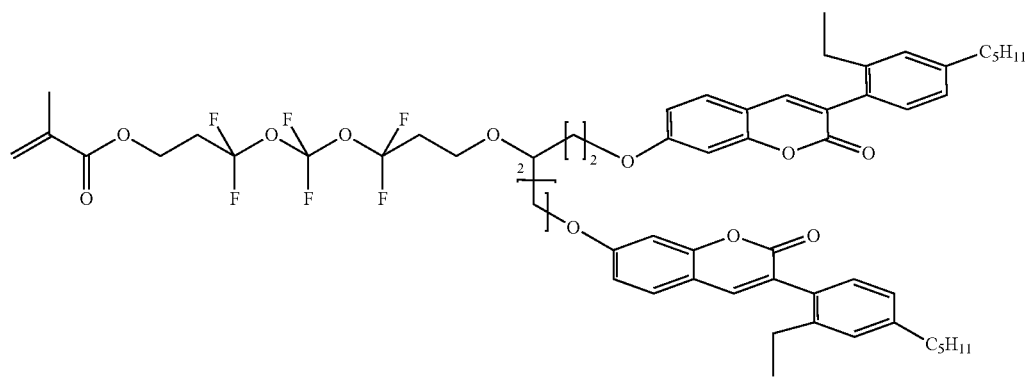
M-085
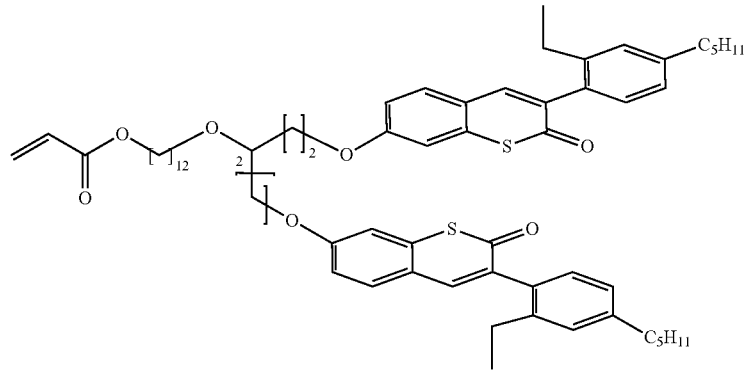
M-086
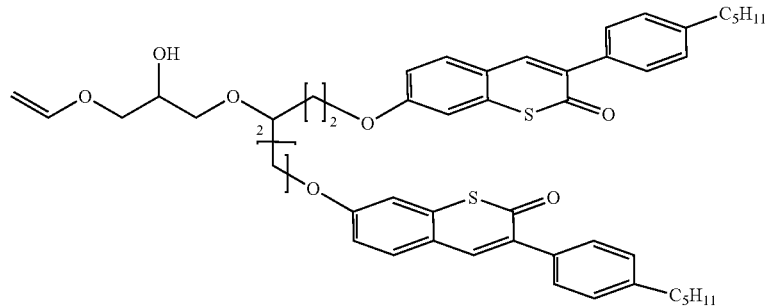
M-087

M-088
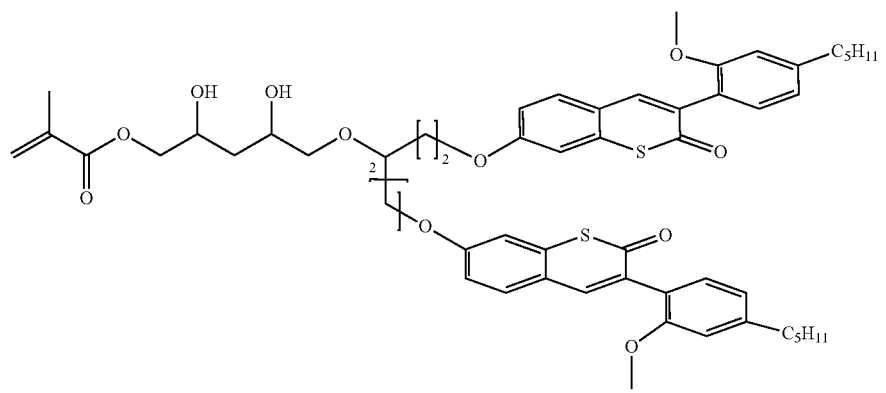
M-089
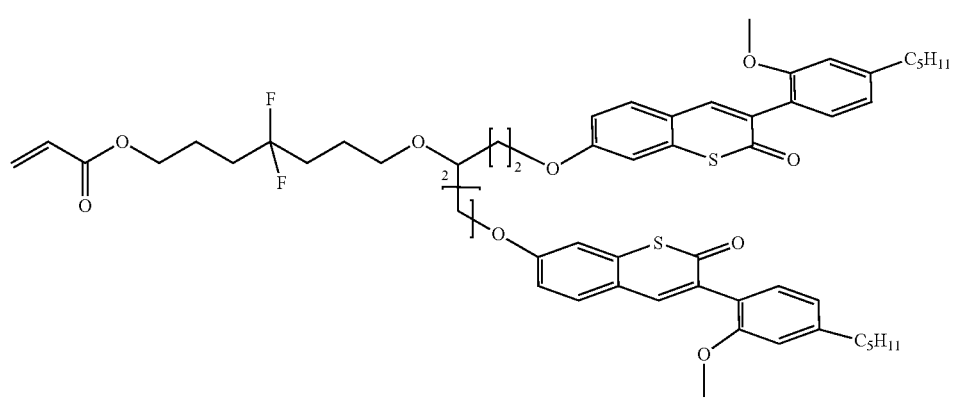
M-090
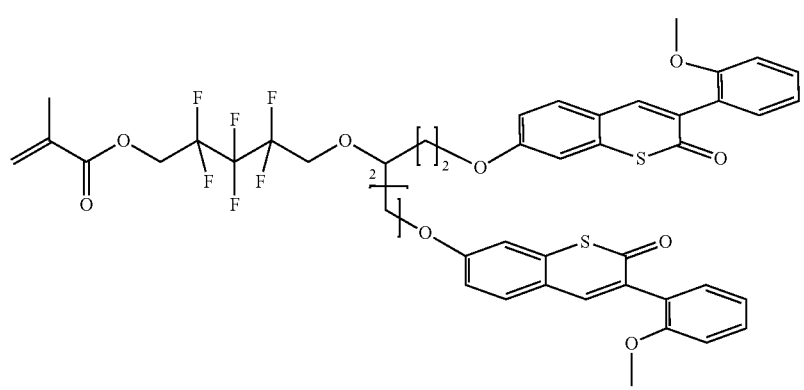
M-091
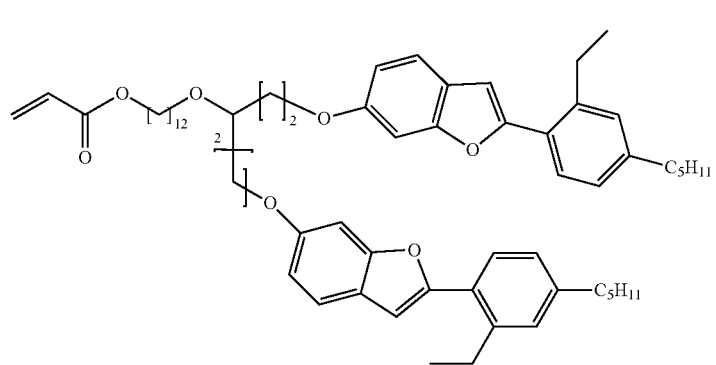

-continued
M-092
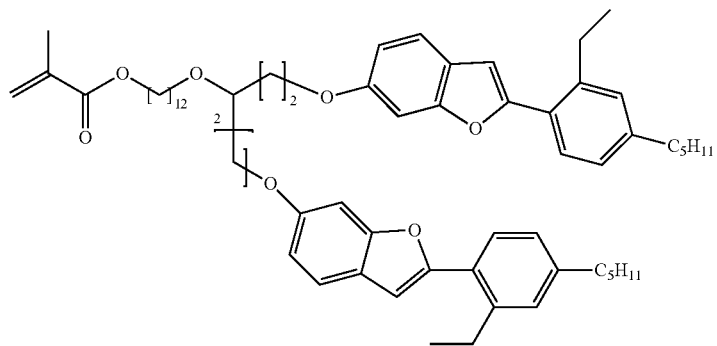
M-093
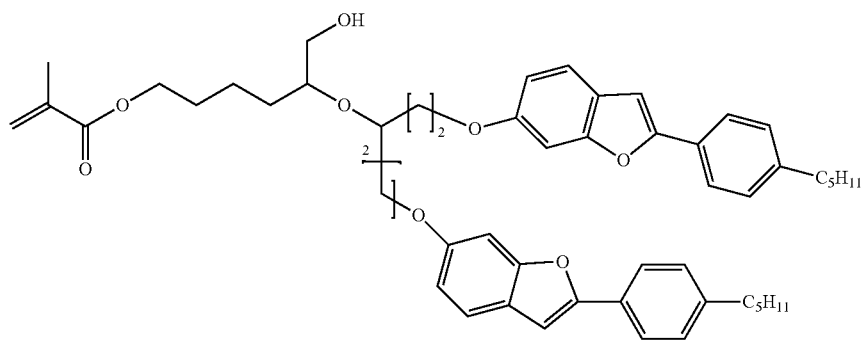
M-094
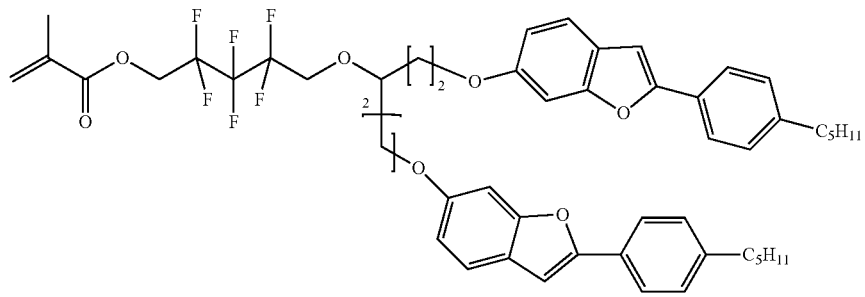
M-095
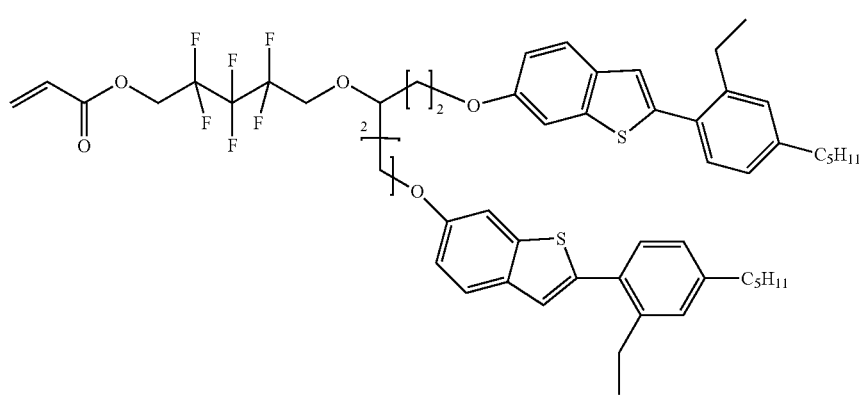

M-096
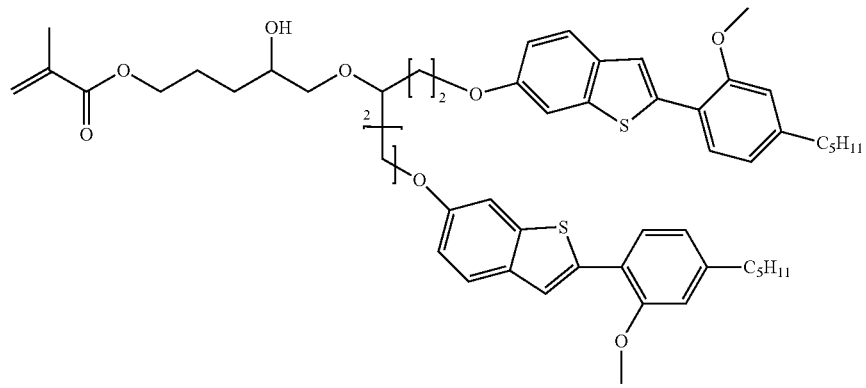
M-097
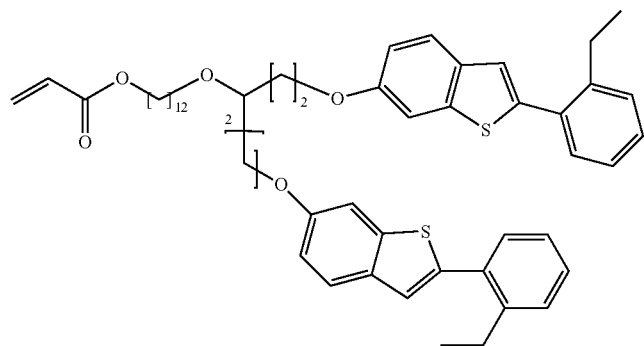
M-098
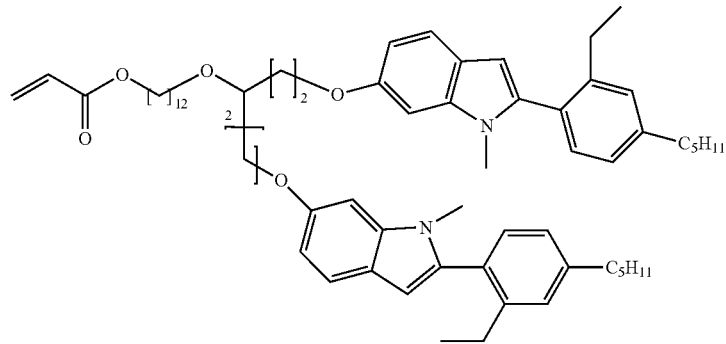
M-099
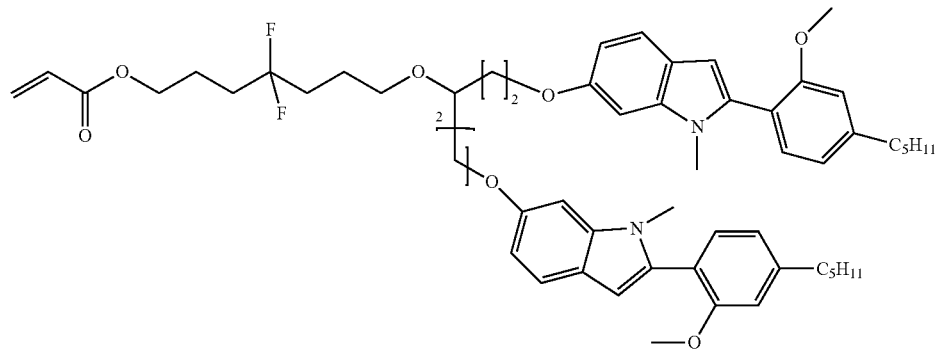

-continued
M-100
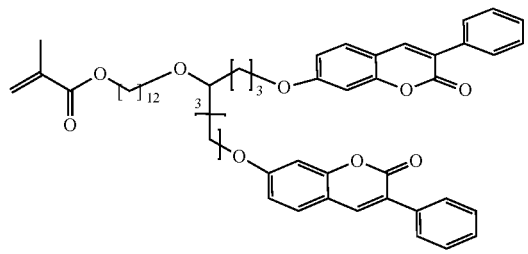
M-101
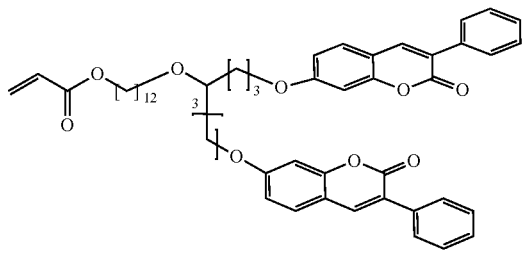
M-102
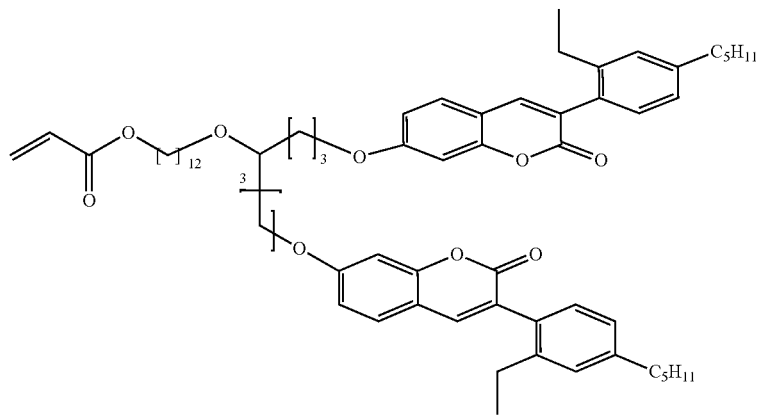
M-103
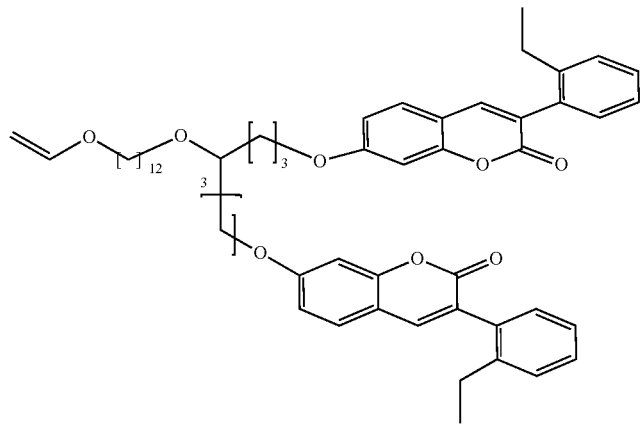
M-104
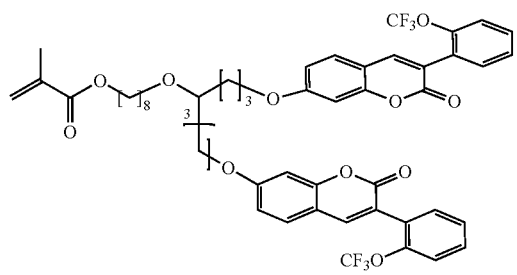
M-105
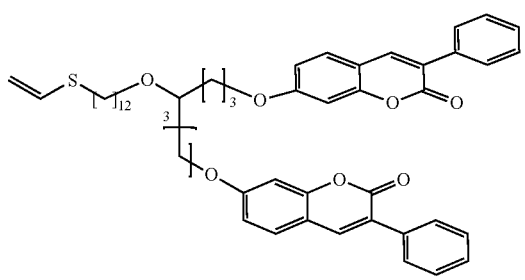

-continued
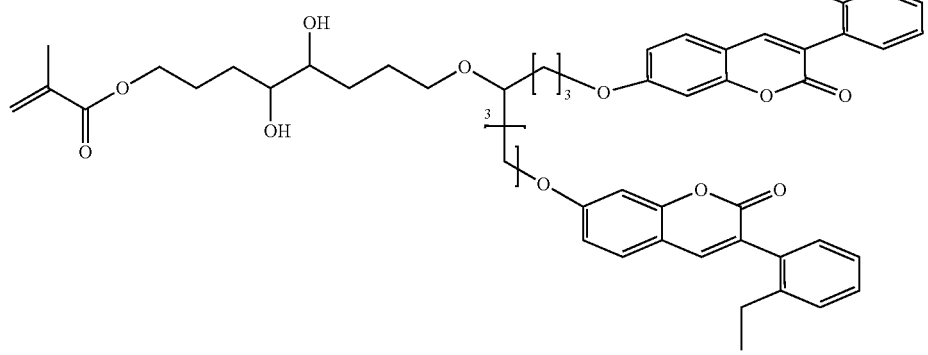
M-106
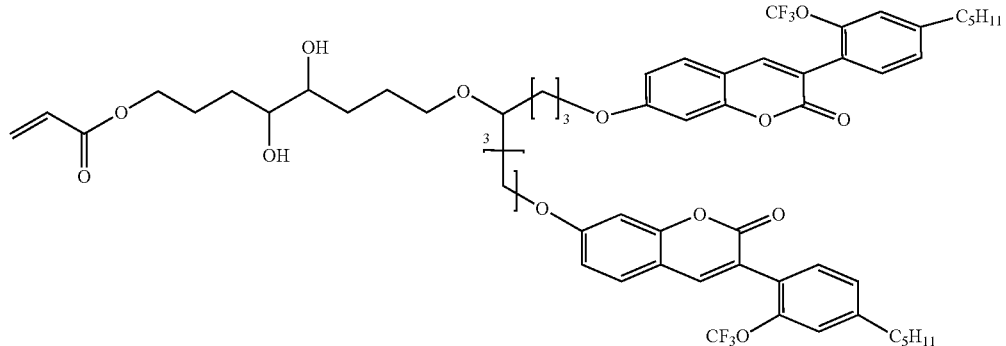
M-107
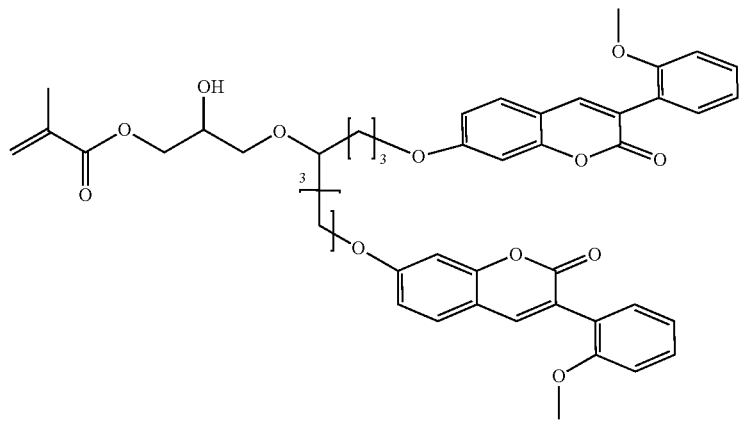
M-108
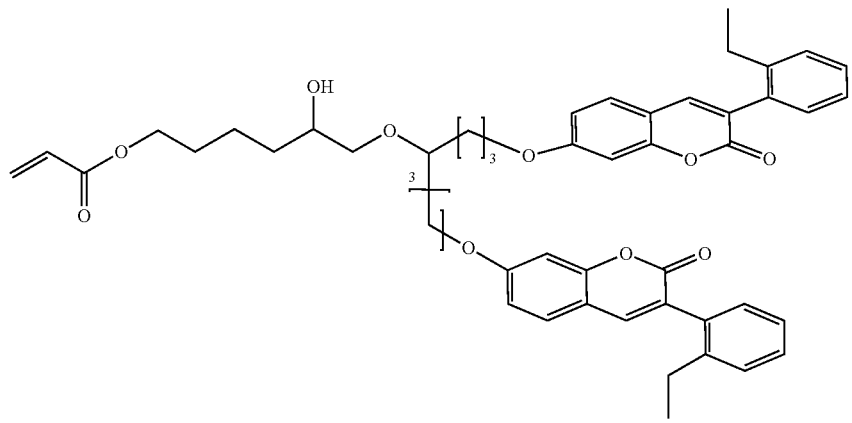
M-109

-continued
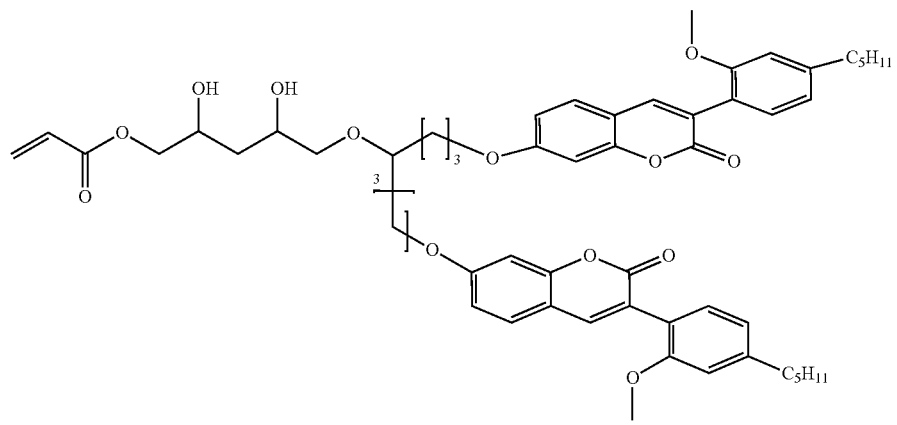
M-110
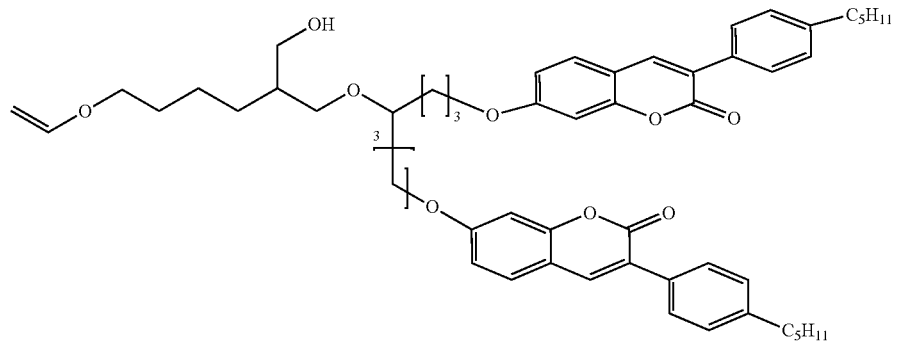
M-111
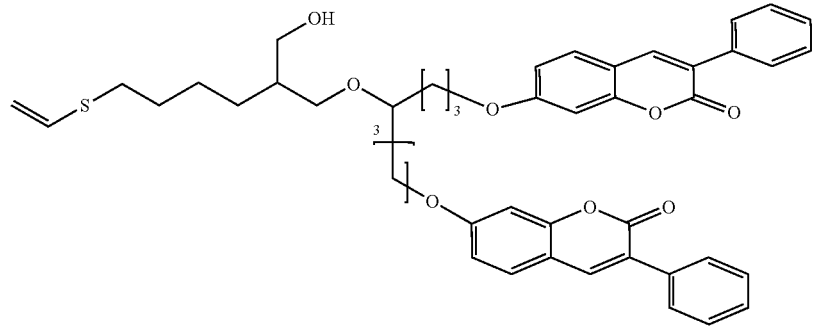
M-112
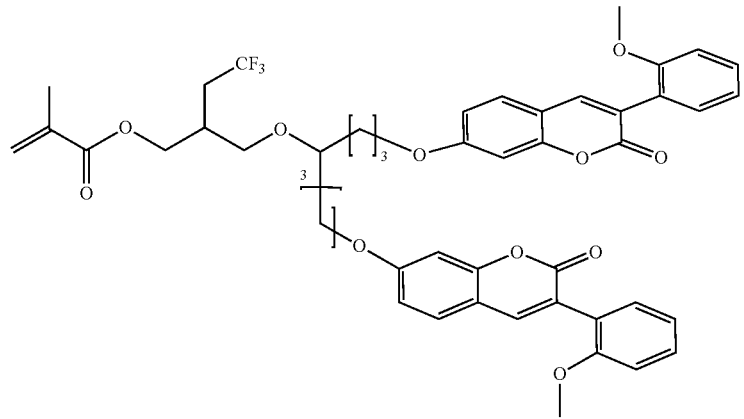
M-113

M-114
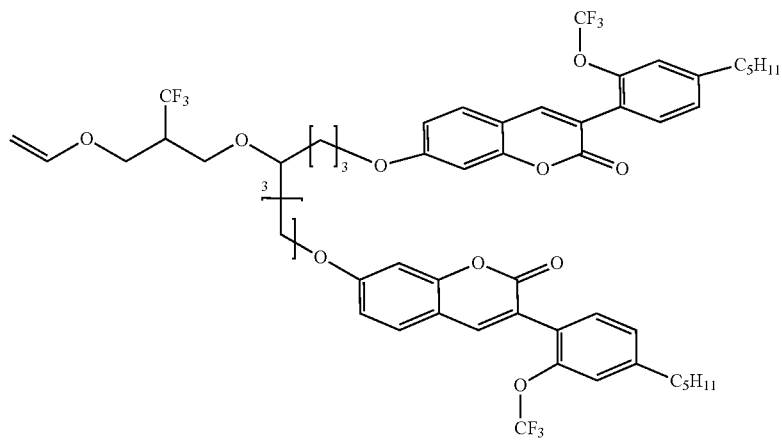
M-115
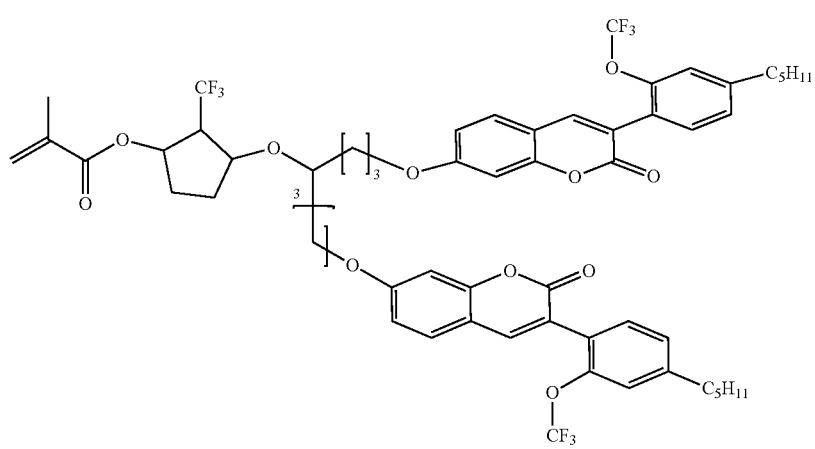
M-116
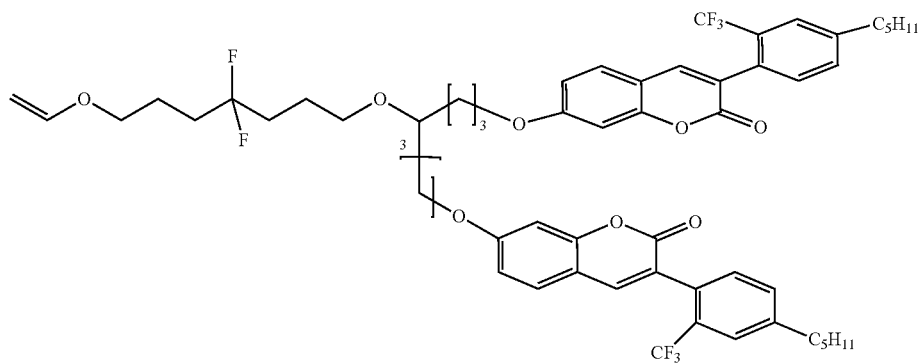
M-117
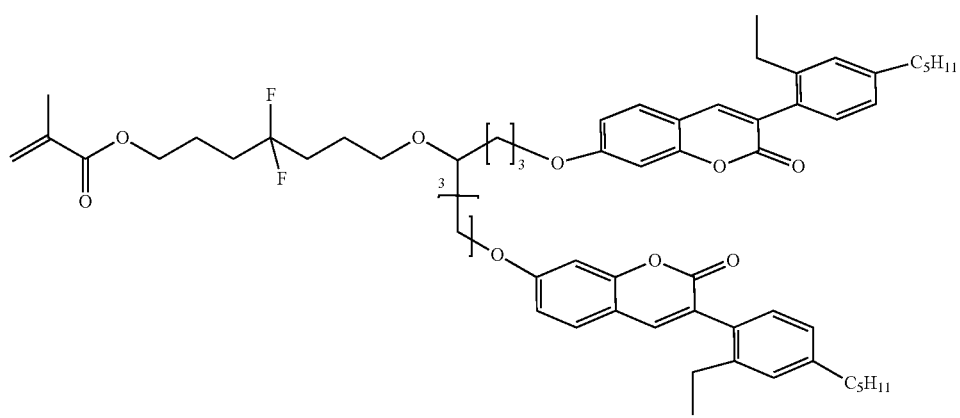

-continued
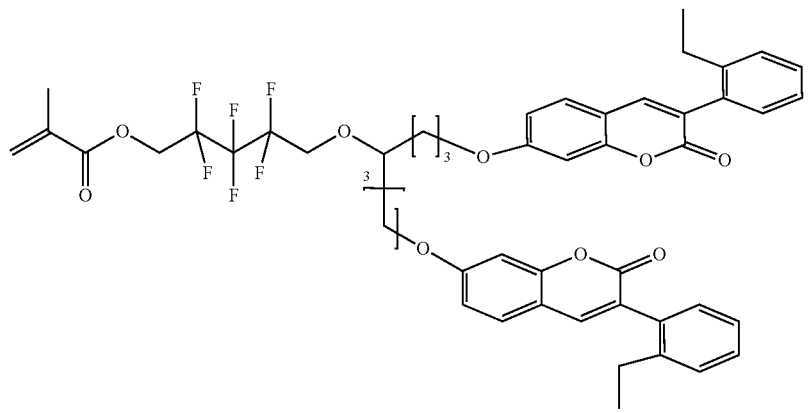
M-118
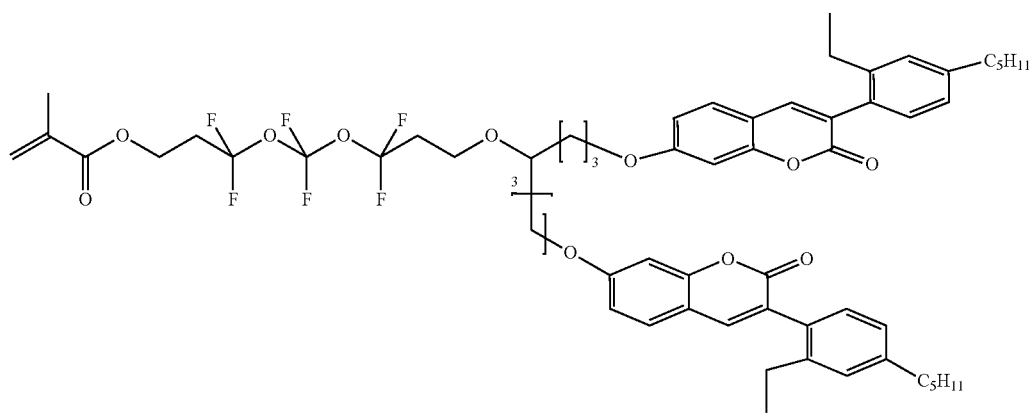
M-119
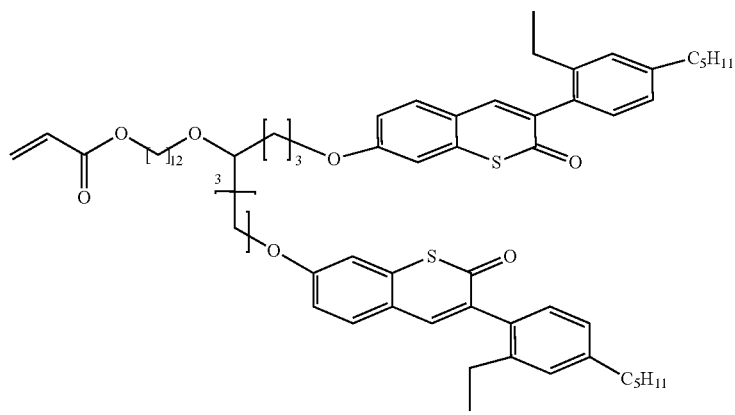
M-120
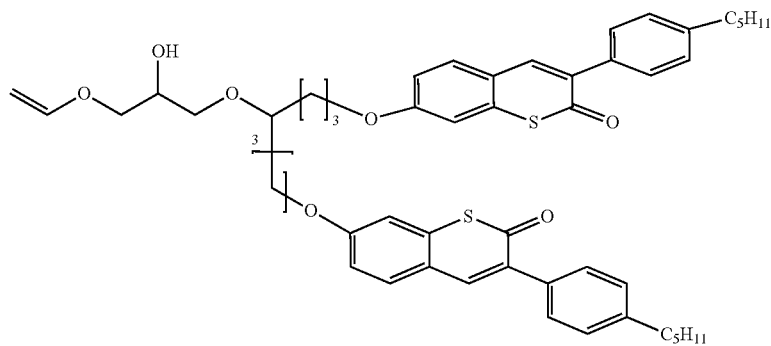
M-121

-continued
M-122
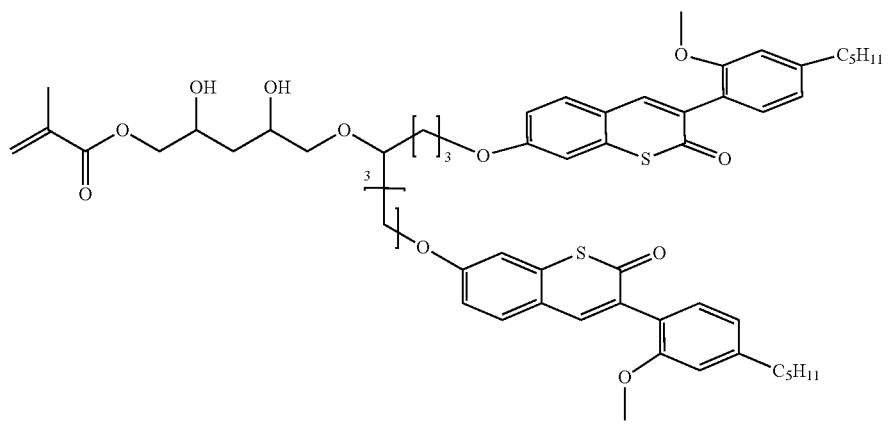
M-123
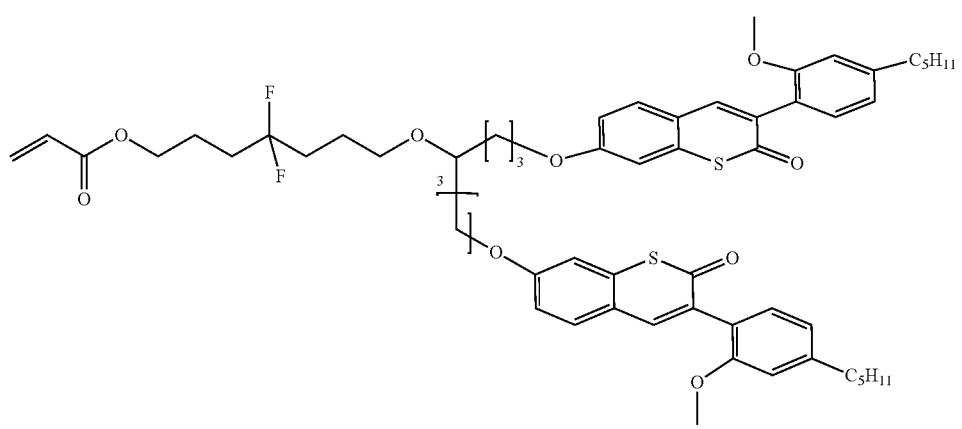
M-124
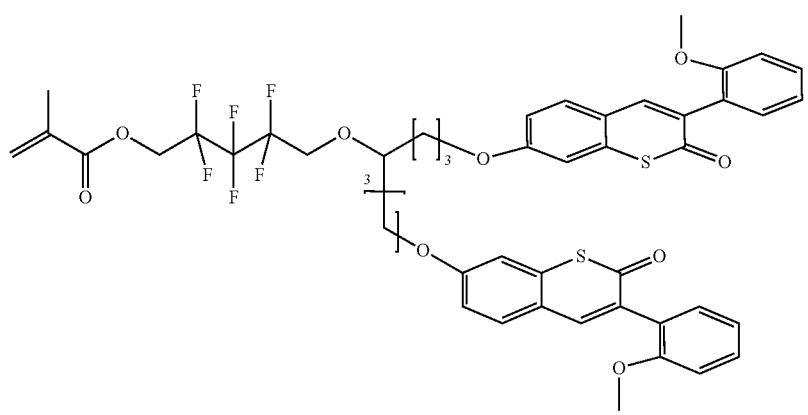
M-125
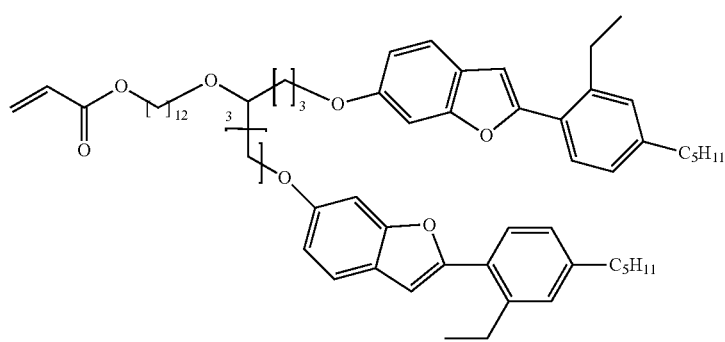

M-126
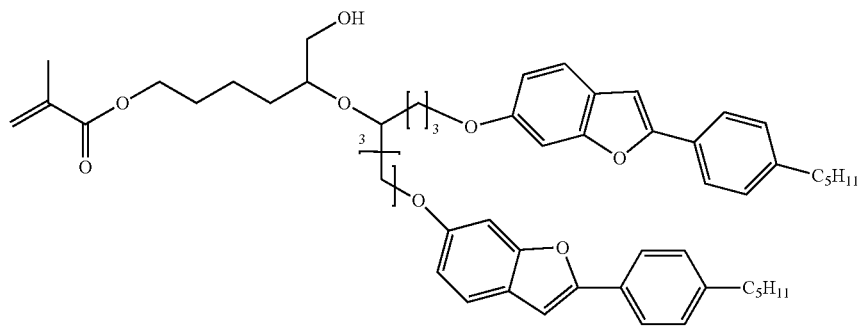
M-127
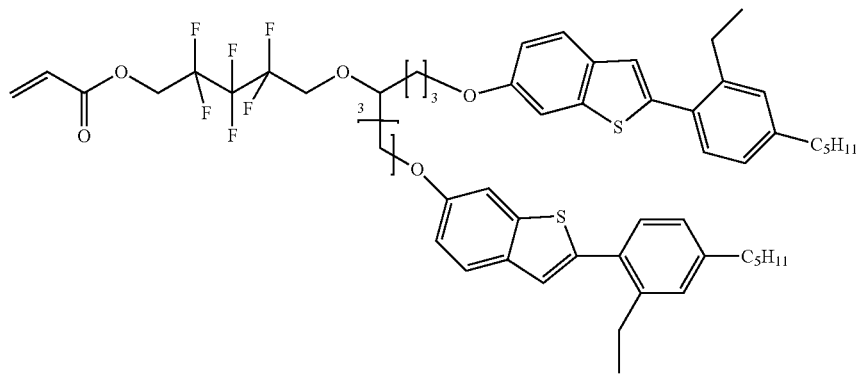
M-128
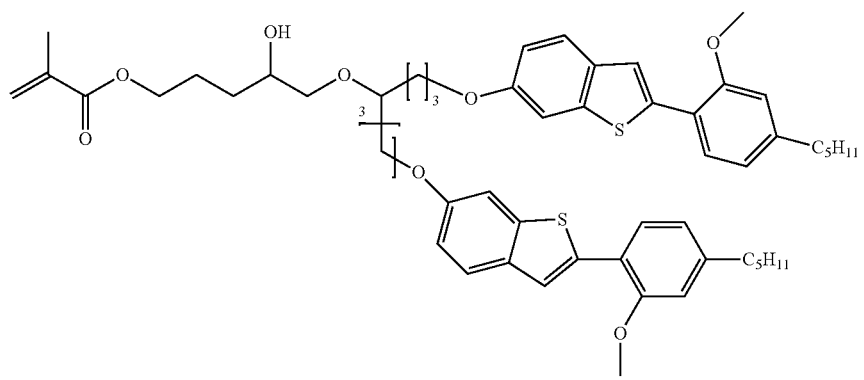
M-129
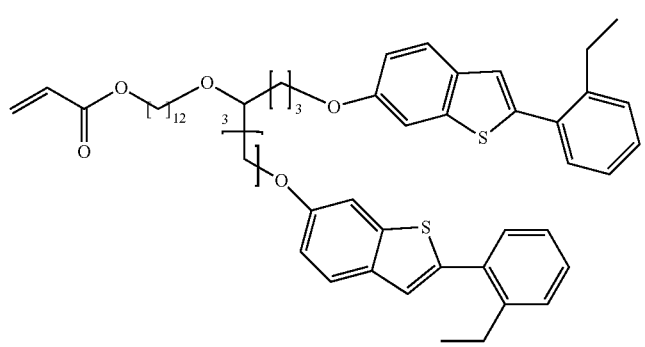

-continued
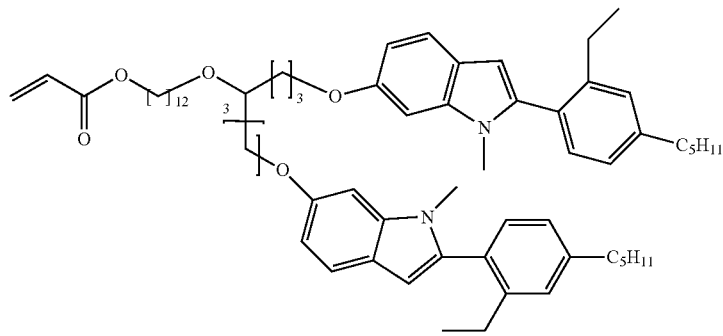
M-130
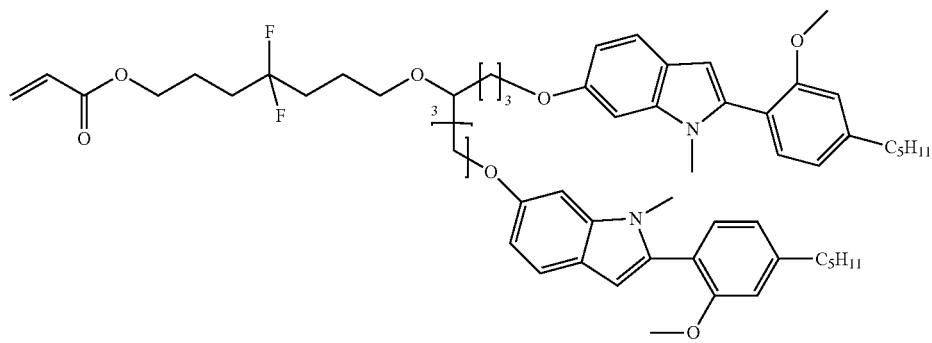
M-131
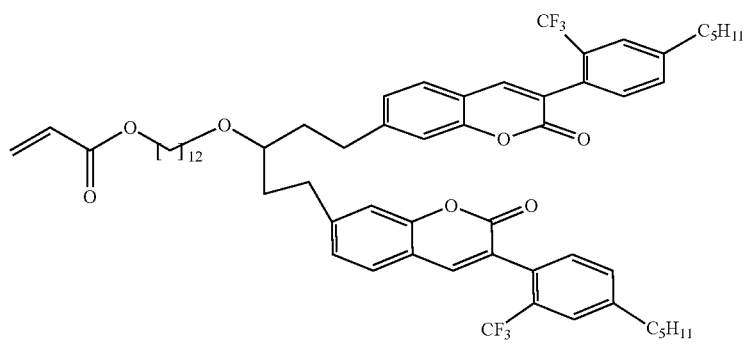
M-132
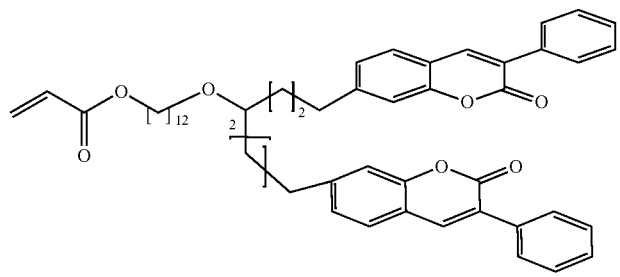
M-133
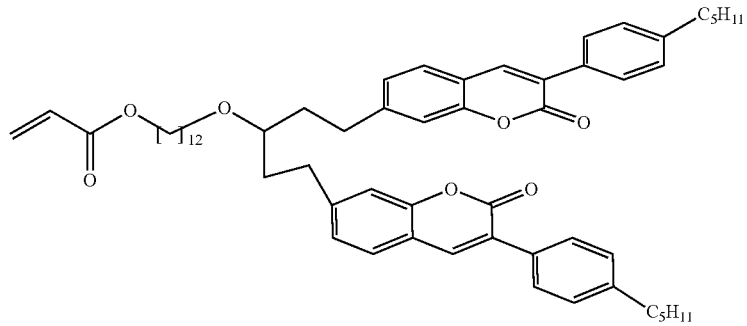
M-134

-continued
M-135
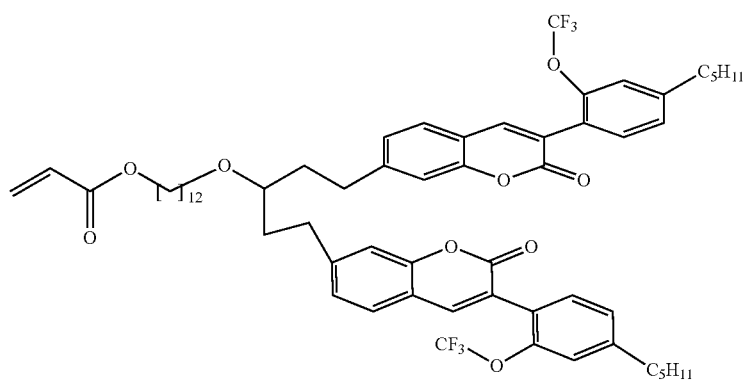
M-136
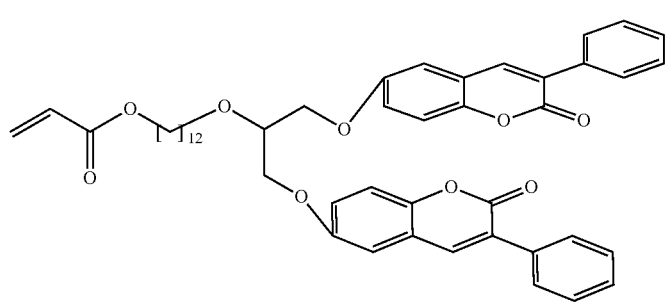
M-137
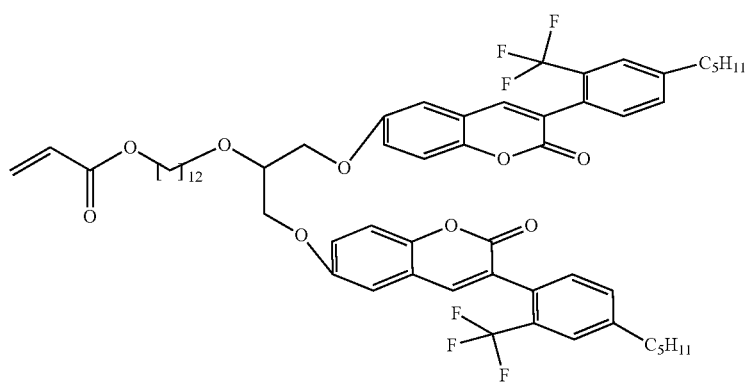
M-138
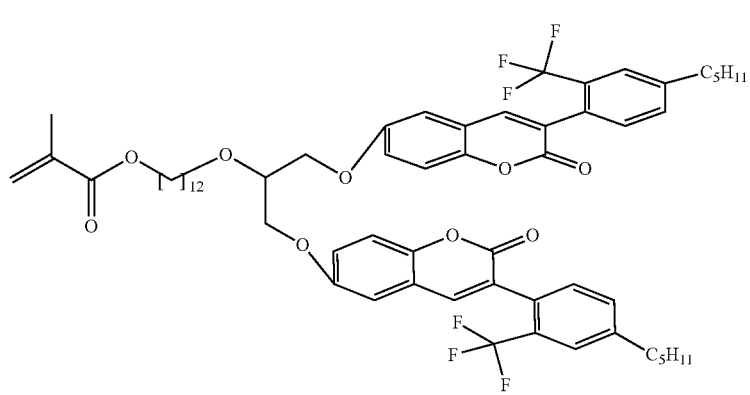

-continued
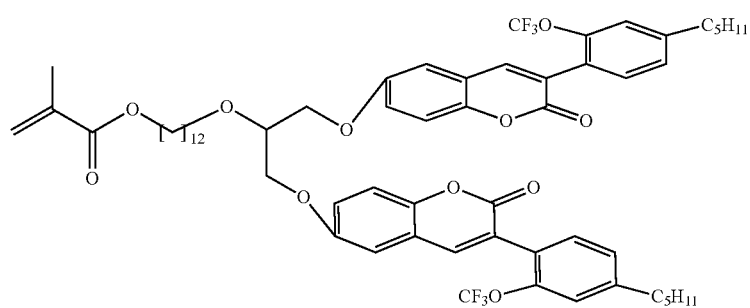
M-139
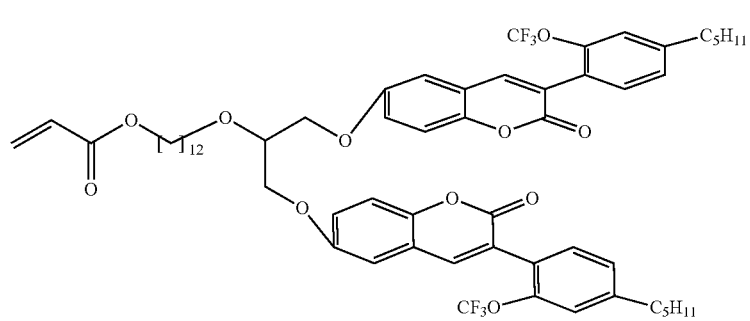
M-140
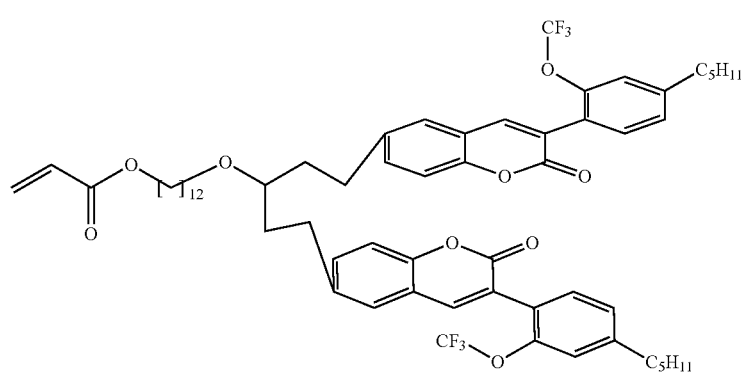
M-141
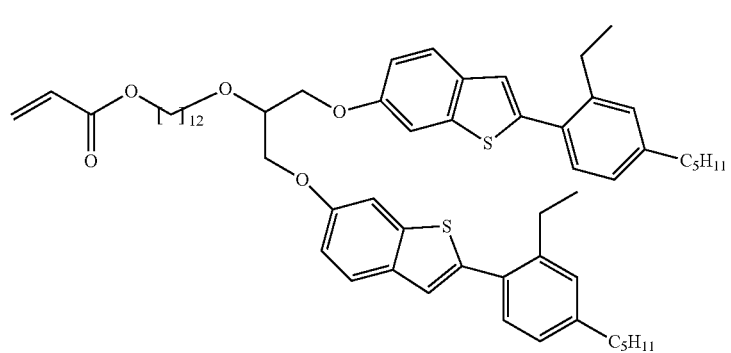
M-142

-continued
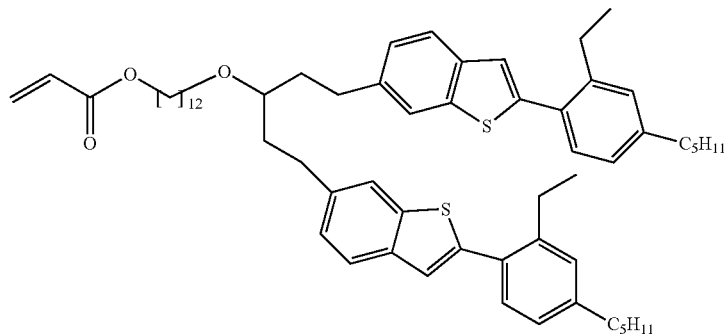
M-143
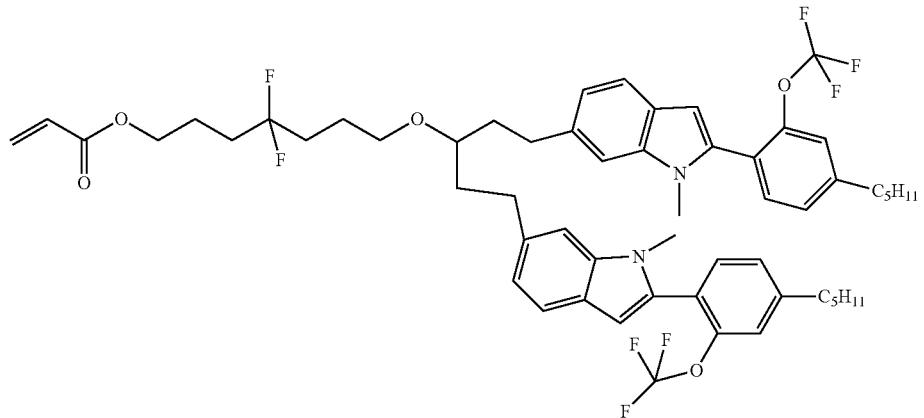
M-144
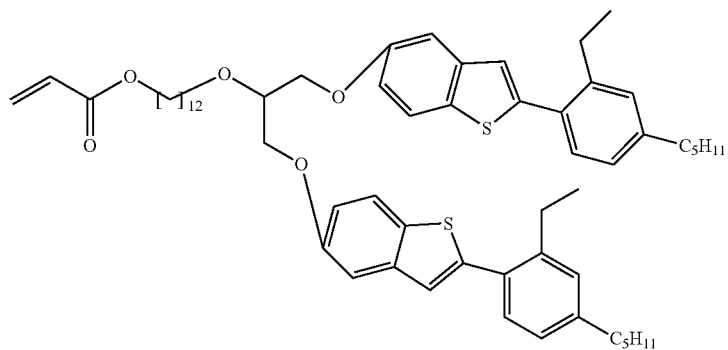
M-145
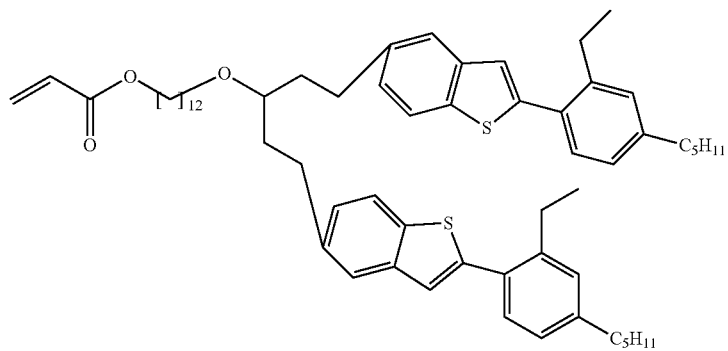
M-146

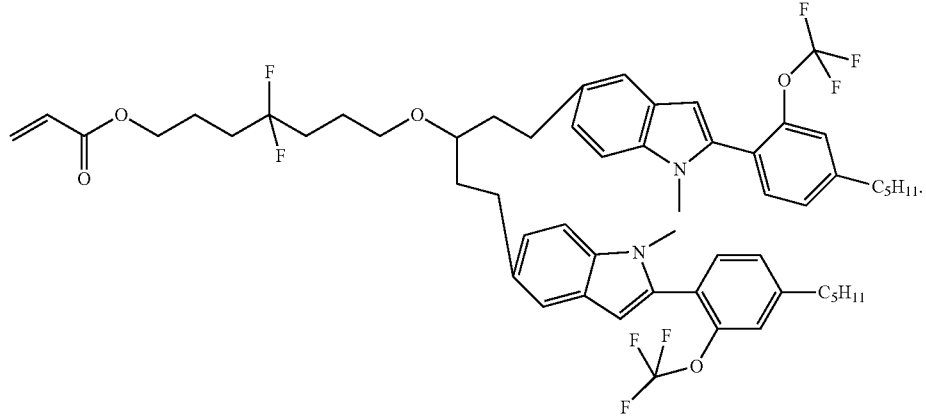
M-147
The compounds of the present application may be synthesized by methods well known to the skilled person. Preferably, all syntheses are carried out under an inert atmosphere using dried solvents.
An exemplary reaction sequence is shown in Scheme 1 for the compound M-003:
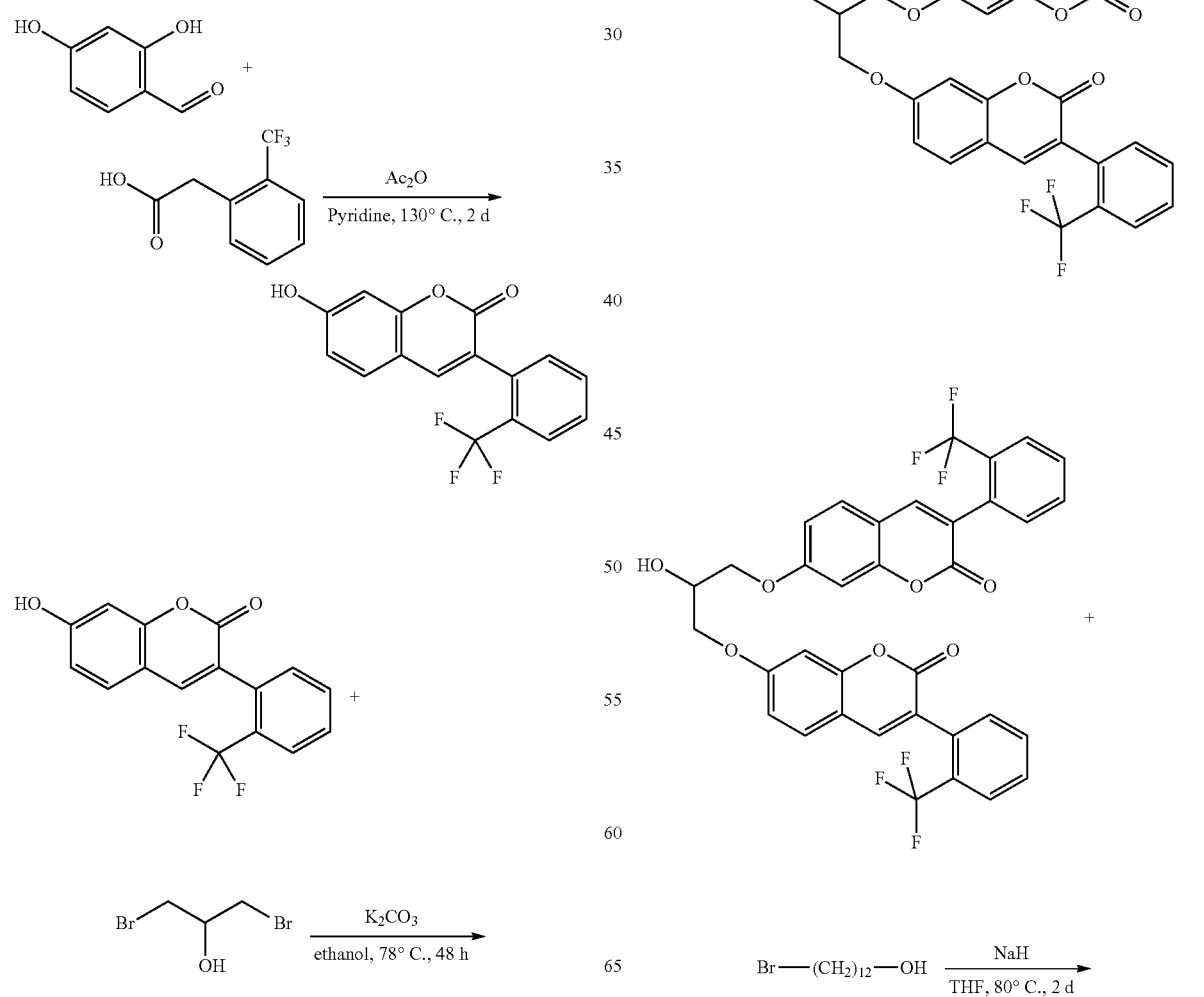

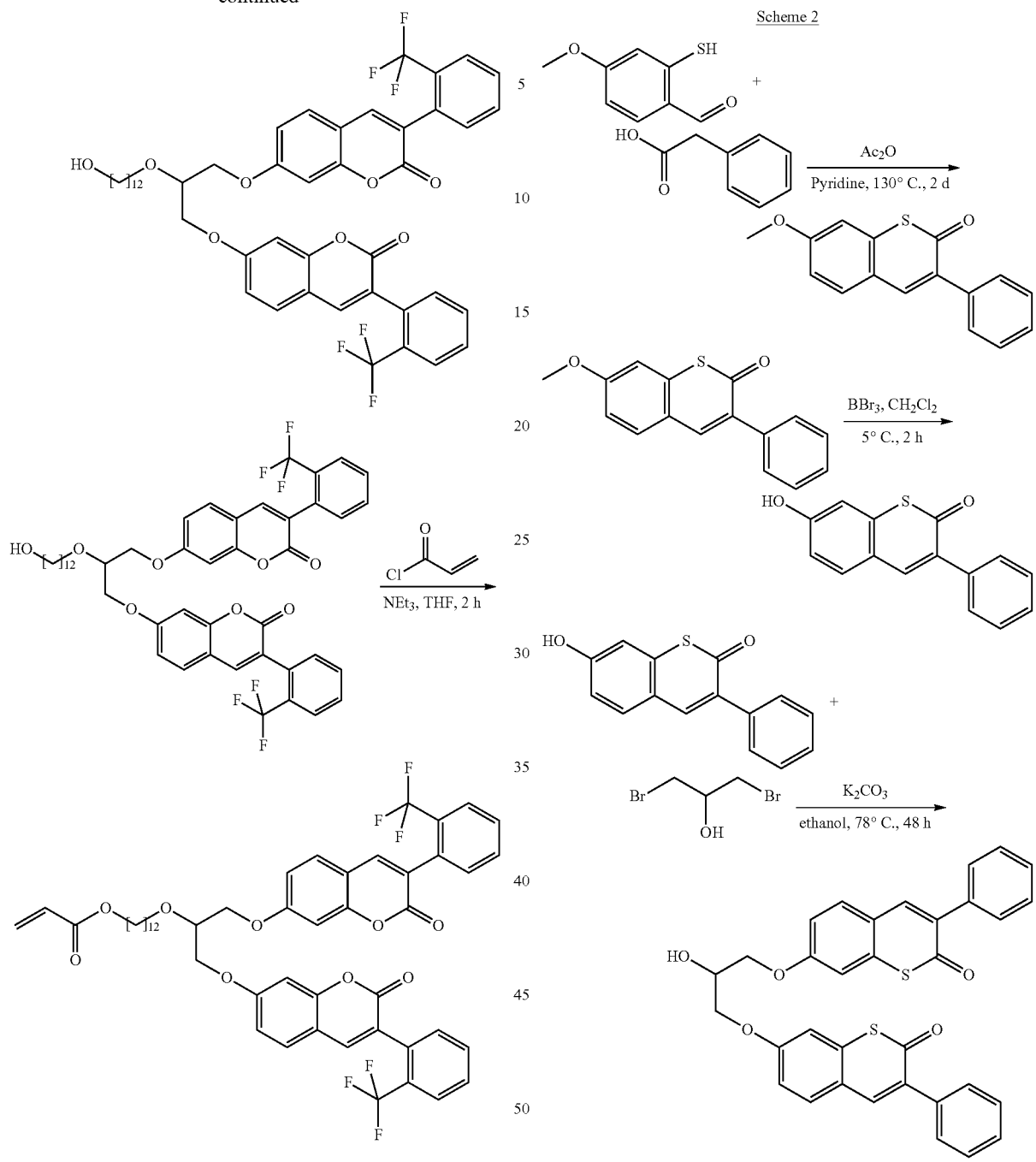

The first type of reaction is a Pechmann reaction.

The second type of reaction is a Williamson ether synthesis.

The third type of reaction is a Williamson ether synthesis.

The fourth type of reaction is an esterification reaction.

All these types of reaction and their reaction conditions are well known to a skilled person and can be easily optimized for the specific starting materials forming the compounds of formula (I). More details can be found in the experimental section.

An exemplary reaction sequence is shown in Scheme 2 for the compound M-037.

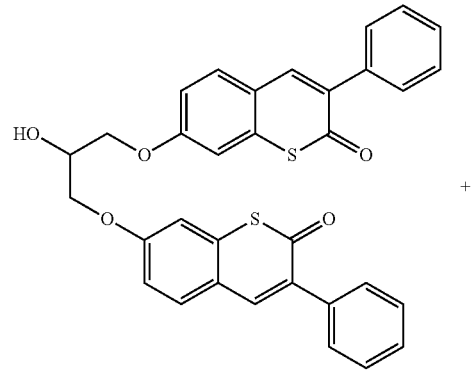

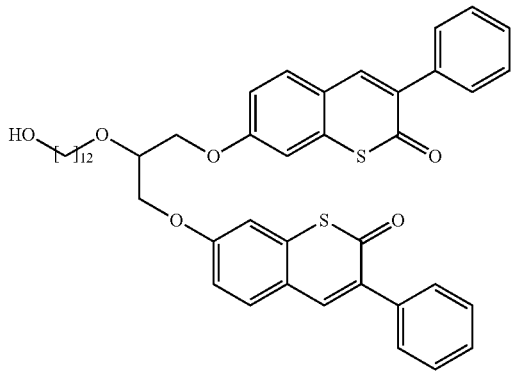

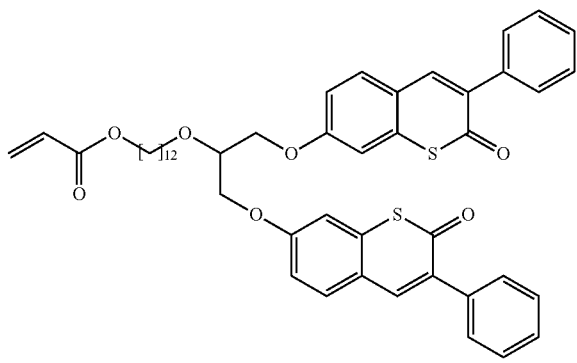

The first type of reaction is a Pechmann reaction.
The second type of reaction is a Williamson ether synthesis.
The third type of reaction is a Williamson ether synthesis.
The fourth type of reaction is an esterification reaction.
All these types of reaction and their reaction conditions are well known to a skilled person and can be easily optimized for the specific starting materials forming the compounds of formula (I). More details can be found in the experimental section.

As described before, the compounds of formula (I), (I-1), (I-2), (I-3), (I-4), (I-5), (I-6), (I-7), (I-8) and/or (I-9) as described before or preferably described before contain a polymerizable group and are predestinated as monomers for an oligomerization or a polymerization.

The invention is therefore further directed to an oligomer or polymer comprising polymerized compounds of formula (I), (I-1), (I-2), (I-3), (I-4), (I-5), (I-6), (I-7), (I-8) and/or (I-9) as described before or preferably described before.

The term "polymer" generally means a molecule of high relative molecular mass, the structure of which essentially comprises the multiple repetition of units derived, actually or conceptually, from molecules of low relative molecular mass (PAC, 1996, 68, 2291). The term "polymer" includes homopolymers and co-polymers. The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having ≥30 repeating units, and an oligomer means a compound with >1 and <30 repeating units.

Above and below, in formulae showing a polymer, an oligomer, a compound of formula (I) or a monomeric unit formed from a compound of formula (I), an asterisk ("*") denotes a linkage to the adjacent repeating unit in the polymer chain or oligomer chain or to a terminal end group.

Suitable terminal end groups are known to the skilled artisan and depend on the polymerization method used.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

Unless stated otherwise, the molecular weight is given as the number average molecular weight Mn or weight average molecular weight Mw, which is determined by gel permeation chromatography (GPC) against polystyrene standards in eluent solvents such as tetrahydrofuran, trichloromethane (TCM, chloroform), chlorobenzene or 1,2,4-trichloro-benzene.

Unless stated otherwise, tetrahydrofuran is used as solvent. The degree of polymerization (n) means the number average degree of polymerization given as n=Mn/Mu, wherein Mu is the molecular weight of the single repeating unit as described in J. M. G. Cowie, *Polymers: Chemistry & Physics of Modern Materials*, Blackie, Glasgow, 1991.

In the polymers according to the present invention, the total number of repeating units n is preferably ≥30, very preferably ≥100, most preferably ≥200, and preferably up to 5000, very preferably up to 3000, most preferably up to 2000, including any combination of the aforementioned lower and upper limits of n.

The polymers of the present invention include homopolymers, statistical co-polymers, random co-polymers, alternating co-polymers and block co-polymers, and combinations of the aforementioned.

Throughout the description and claims of this specification, the words "comprise" and "contain" and variations of the words, for example "comprising" and "comprises", mean "including but not limited to", and are not intended to (and do not) exclude other components Preferably the polymerizable group $R_1$ forms the regioregular, alternated, regiorandom, statistical, block or random homopolymer or co-polymer backbone or is part of the polymer backbone where $R_1$ has a meaning as described or preferably described before. Particularly preferably, such oligomer or polymer comprises a constitutional unit $M^o$ of formulae (1-p-1), (1-p-1)

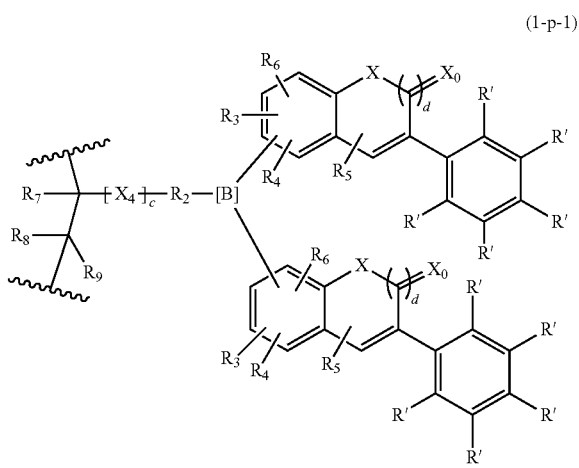

wherein
—R$_2$—, R$_3$, R$_4$, R$_5$, R$_6$, R$_7$, R$_8$, R$_9$, X, X$_0$, R',

X$_4$ and c have a meaning or a preferred meaning as described or preferably described before. Combinations are excluded where two O atoms or an O atom and a S atom are directly linked to each other as known for a skilled artisan in the field of organic chemistry.

The co-polymer may be an oligomer or polymer comprising one or more polymerized compounds of formula (I), (I-1), (I-2), (I-3), (I-4), (I-5), (I-6), (I-7), (I-8) or (I-9) or a constitutional unit M$^0$ of formulae (1-p-1), which may be the same or different from one another, and one or more constitutional units M$^2$, which may be the same or different from one another.

Said one or more constitutional units M$^2$ are chemically different from the units M$^0$. Preferably, said one or more constitutional units M$^2$ are derived by polymerization of one or more monomers selected from the group consisting of styrene, ethoxyethyl methacrylate (EOEMA), methyl methacrylate (MMA), n-alkyl acrylates (the n-alkyl group comprising 2-20 C-atoms), n-alkyl methacrylates (the n-alkyl group comprising 2-20 C-atoms), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA), 2-[3'-2'H-benzotriazol-2'-yl)-4'-hydroxyphenyl]ethyl methacrylate (BTPEM), trialkoxyalkenylsilane, dialkoxyalkylalkenylsilane or a silane of formula (10) and (11), (10)

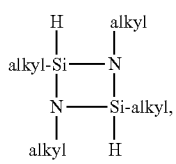

(11)

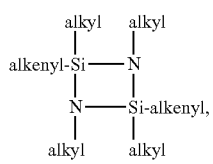

where the alkyl and/or alkoxy groups are at each occurrence independently of each other linear or branched having 1 to 6 C atoms and where the alkenyl group is at each occurrence independently linear having 2 to 4 C atoms.

Particularly preferably, said one or more constitutional units M$^2$ are derived by polymerization of one or more monomers selected from the group consisting of styrene, ethoxyethyl methacrylate (EOEMA), methyl methacrylate (MMA), n-alkyl acrylates (the n-alkyl group comprising 2-20 C-atoms), n-alkyl methacrylates (the n-alkyl group comprising 2-20 C-atoms), ethoxyethyl methacrylate (EOEMA), methyl methacrylate (MMA), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA) and 2-[3'-2'H-benzotriazol-2'-yl)-4'-hydroxyphenyl]ethyl methacrylate (BTPEM) in combination with inventive monomers containing an alkenyl group of formula (1) as described or preferably described before.

Particularly preferably, said one or more constitutional units M$^2$ are derived by polymerization of one or more monomers selected from the group consisting of trialkoxyalkenylsilane, dialkoxyalkylalkenylsilane or a silane of formula (10) and (11), (10)

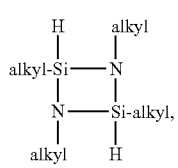

(11)

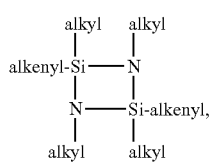

where the alkyl and/or alkoxy groups are at each occurrence independently of each other linear or branched having 1 to 6 C atoms and where the alkenyl group is at each occurrence independently linear having 2 to 4 C atoms in combination with inventive monomers containing a polymerizable group containing at least one Si atom.

Alternatively the oligomer or polymer according to the invention is a homopolymer, i.e. an oligomer or polymer comprising one or more constitutional unit M$^0$ of formula (1-p-1), wherein all constitutional units M$^0$ are the same.

Exemplary polymeric compounds may be selected from the following formulae (P-001) to (P-147):

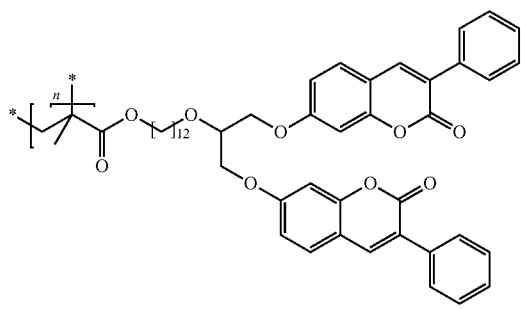
P-001
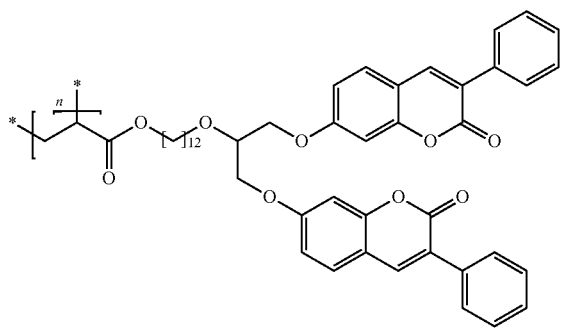
P-002
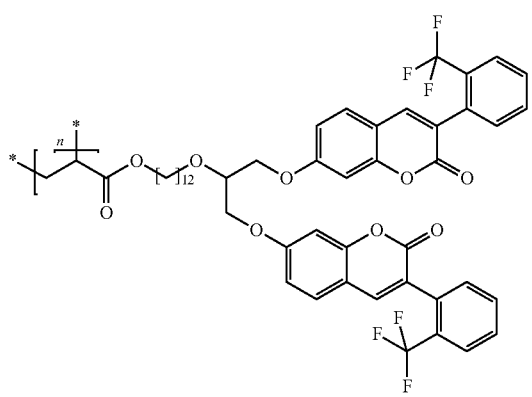
P-003
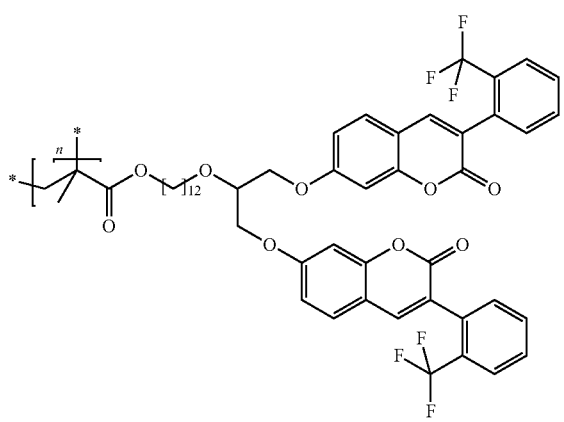
P-004
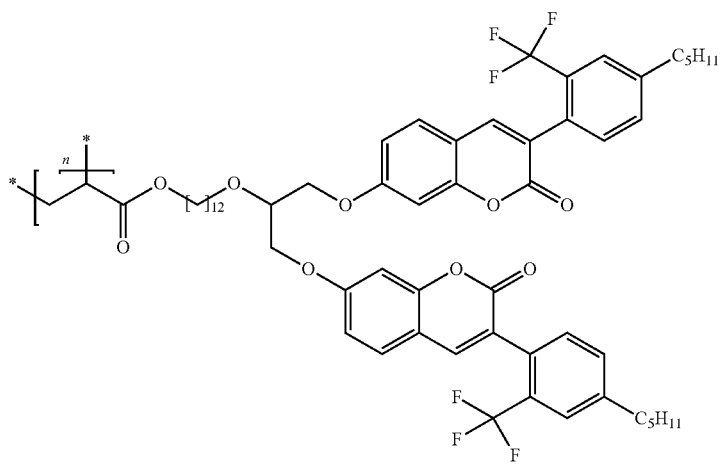
P-005

P-006
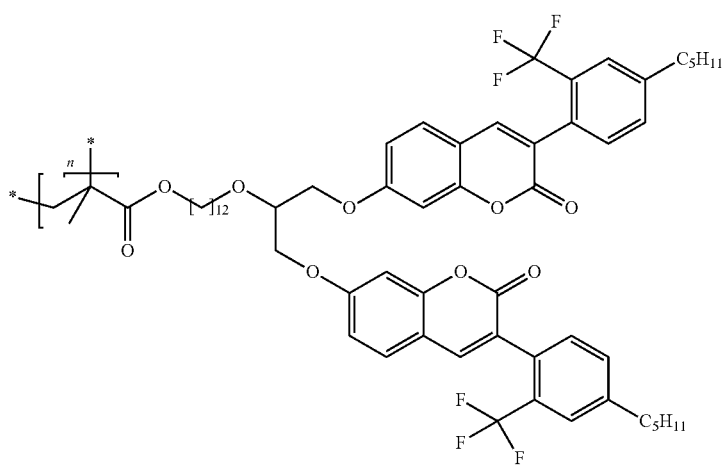
P-007
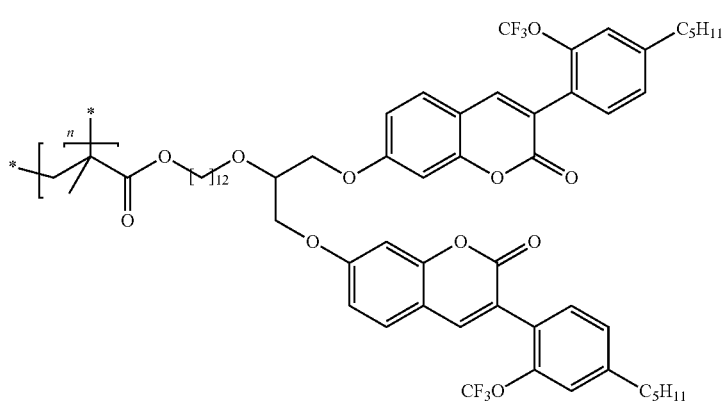
P-008
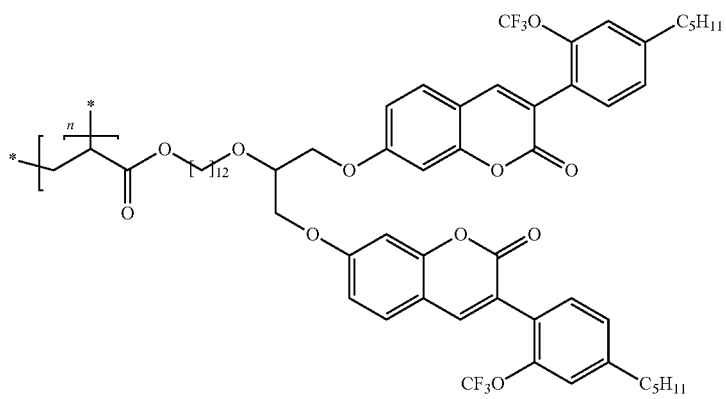

-continued
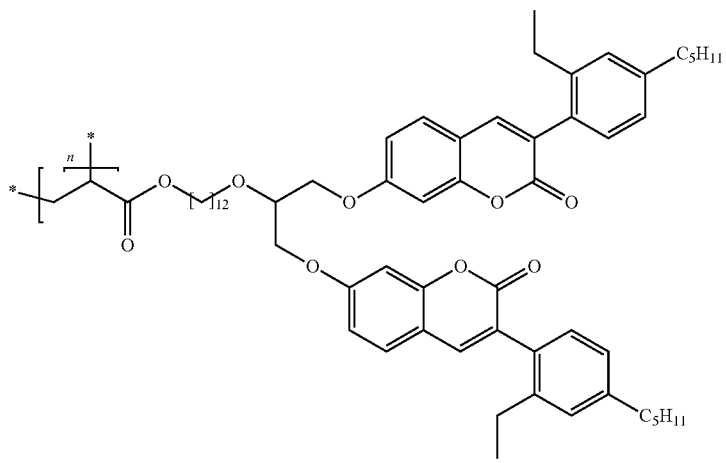
P-009
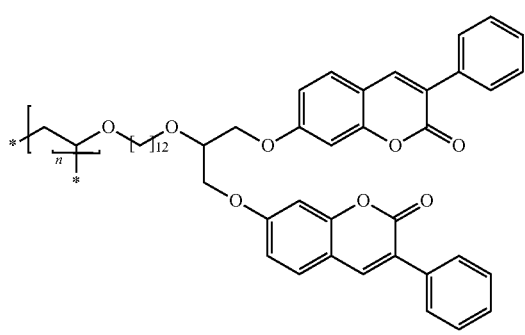
P-010
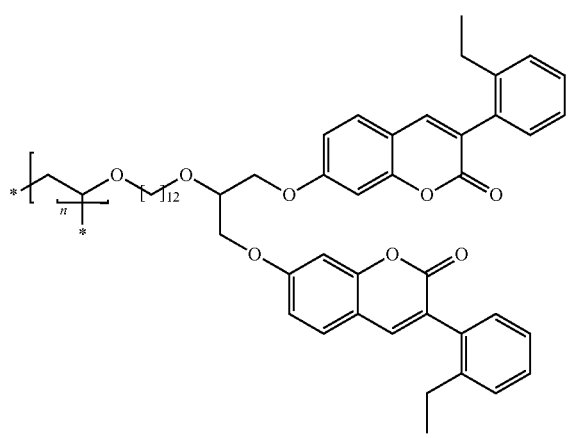
P-011
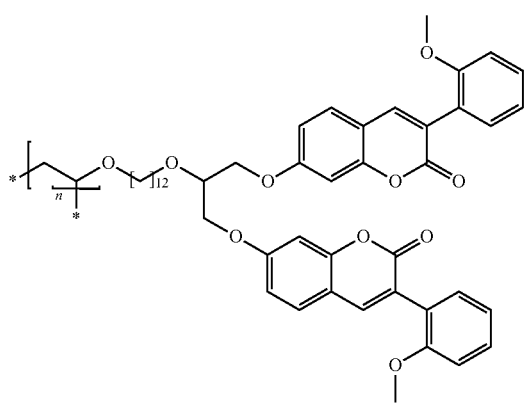
P-012
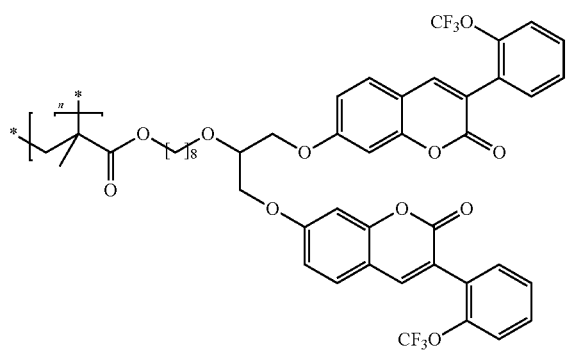
P-013

-continued
P-014
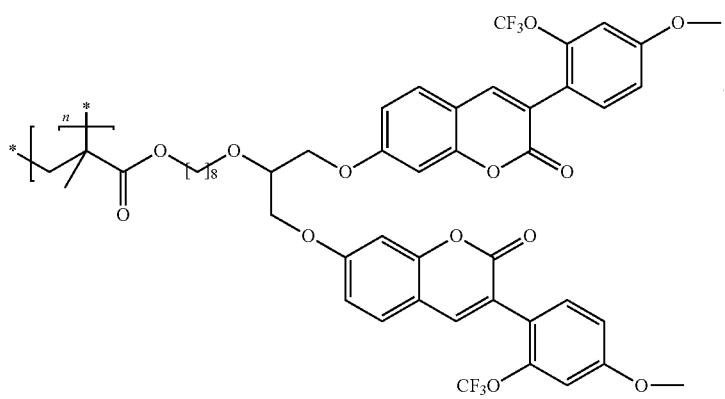
P-015
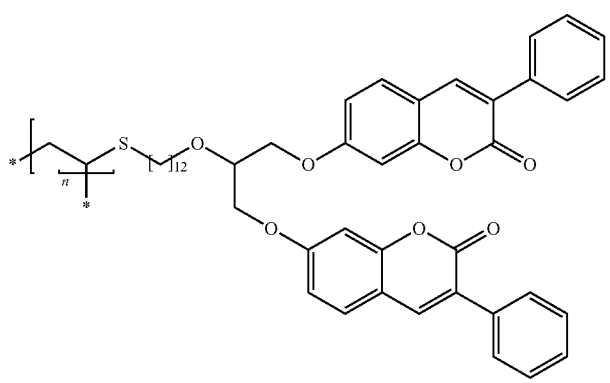
P-016
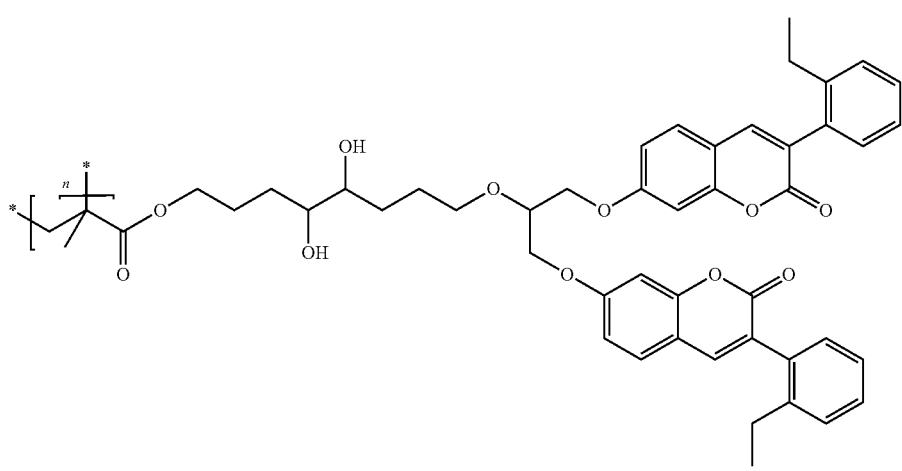
P-017
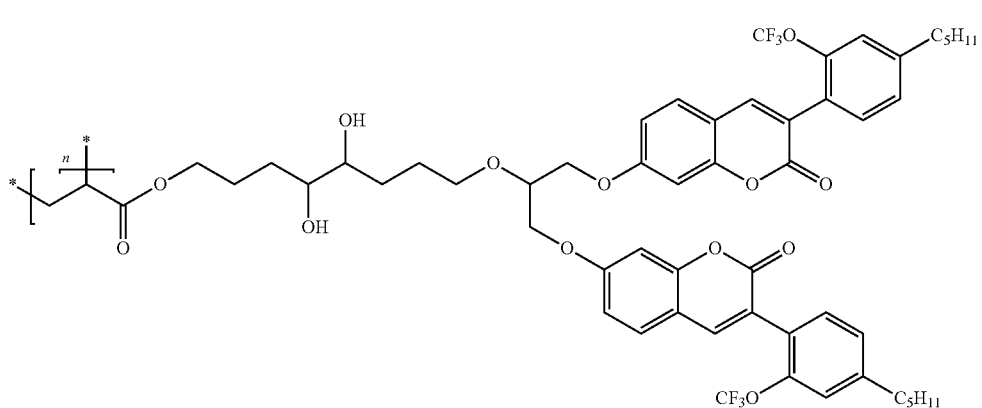

-continued
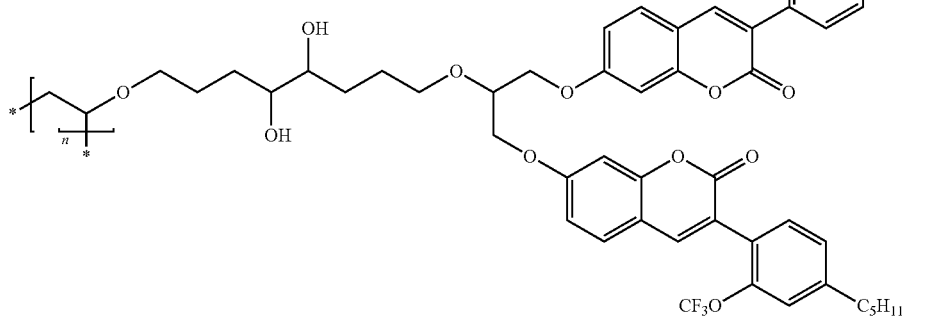
P-018
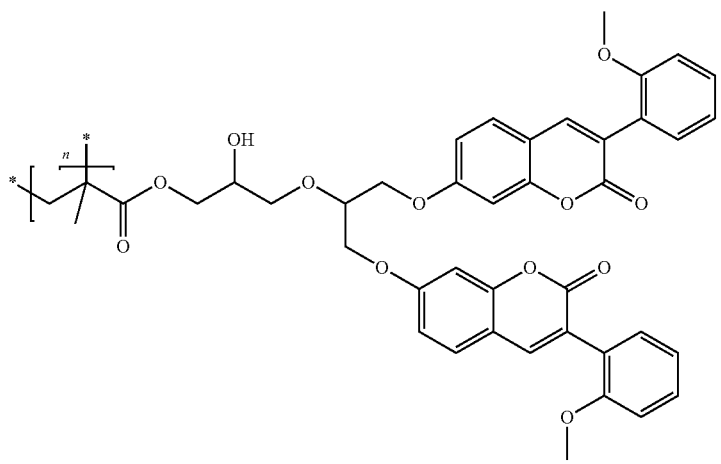
P-019
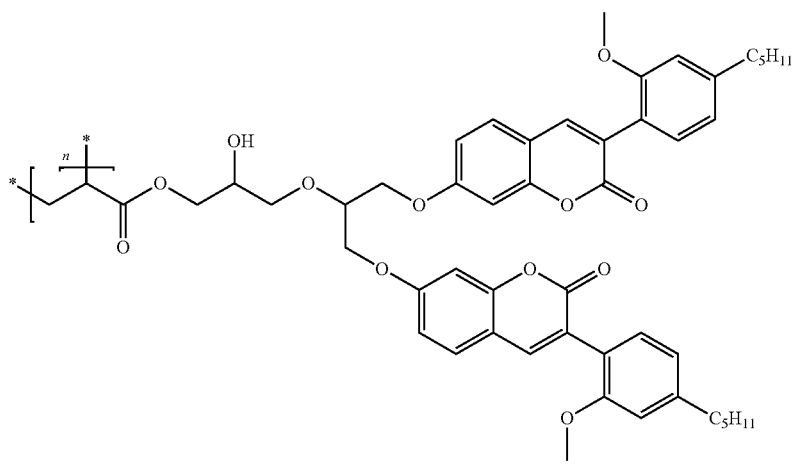
P-020

-continued
P-021
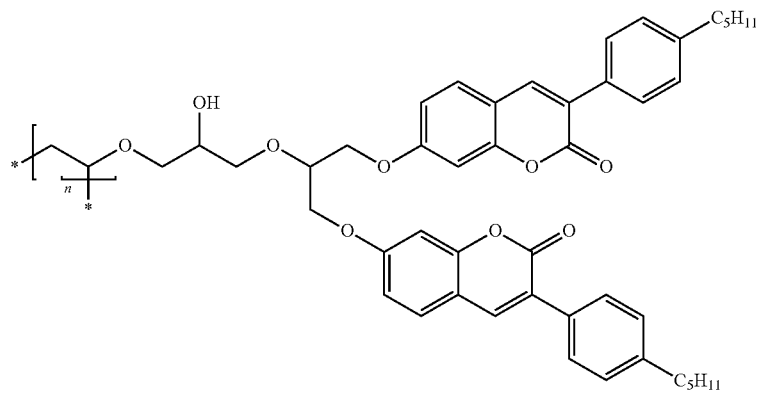
P-022
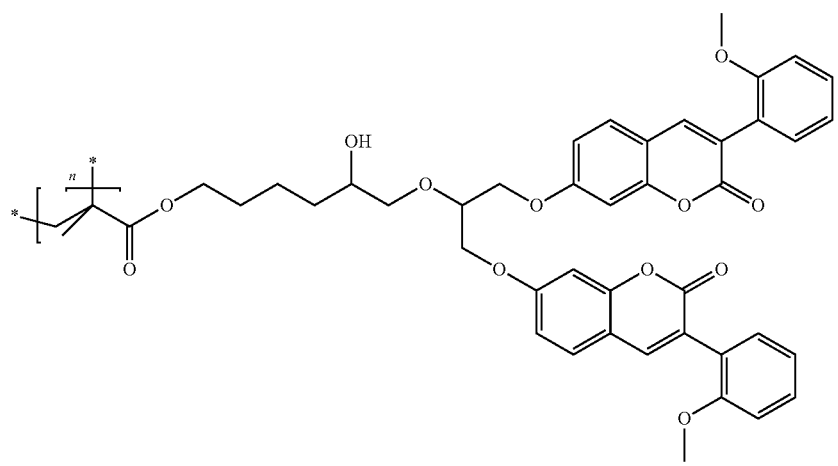
P-023
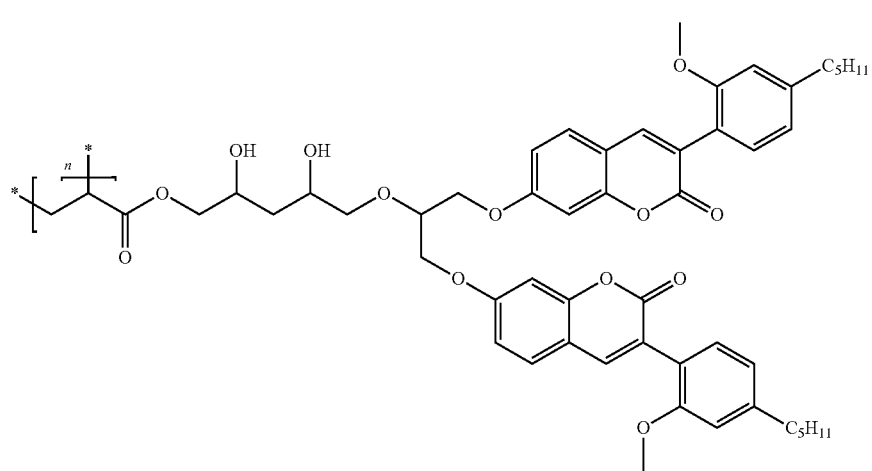

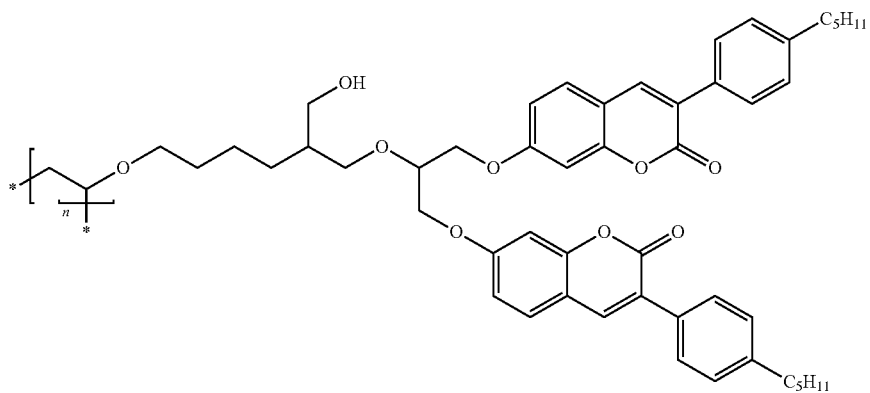
P-024
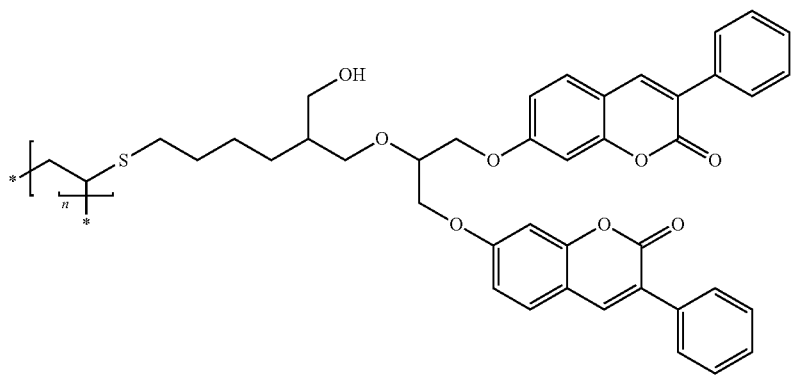
P-025
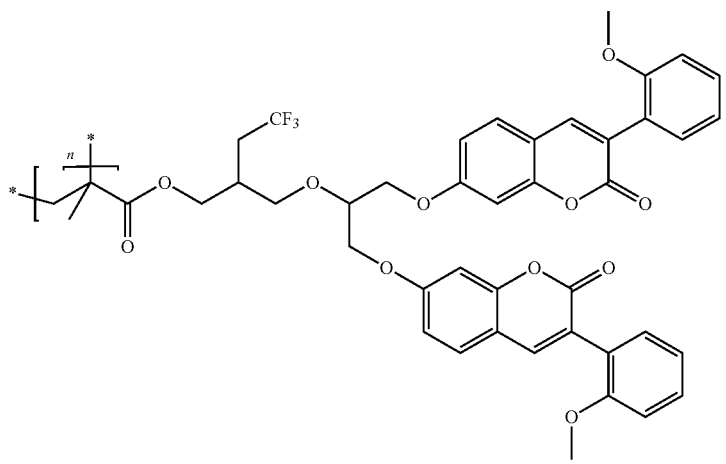
P-026

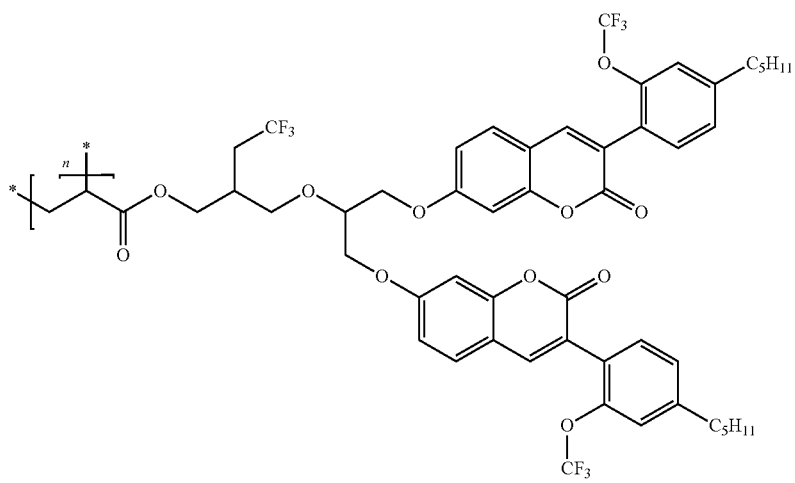
P-027
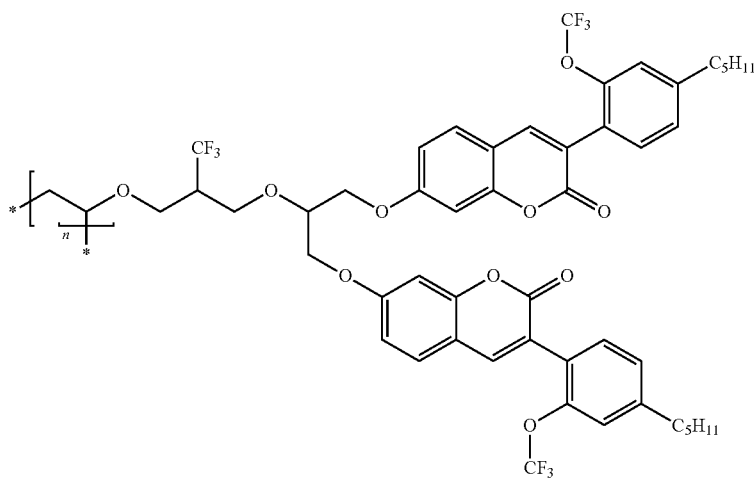
P-028
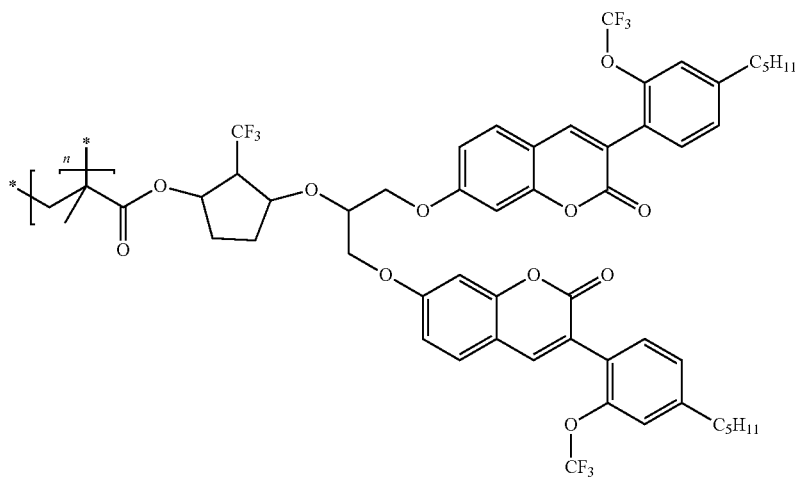
P-029

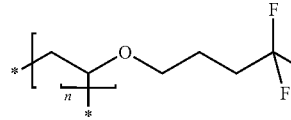 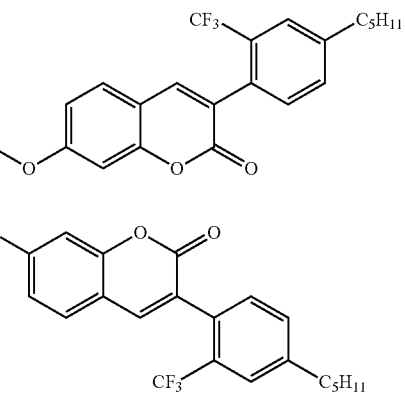
P-030
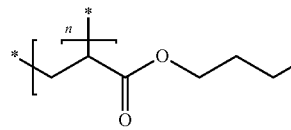 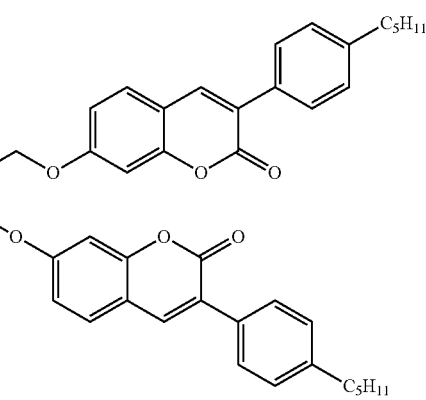
P-031
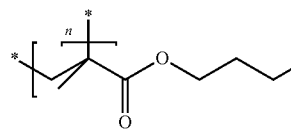 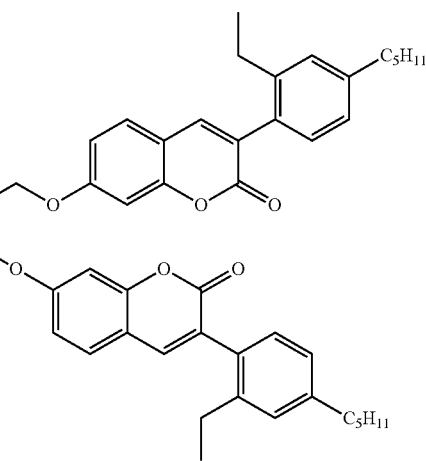
P-032

-continued
P-033
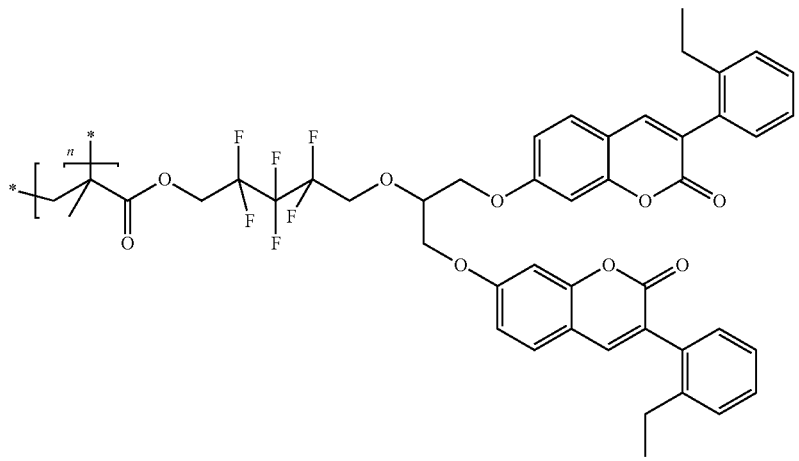
P-034
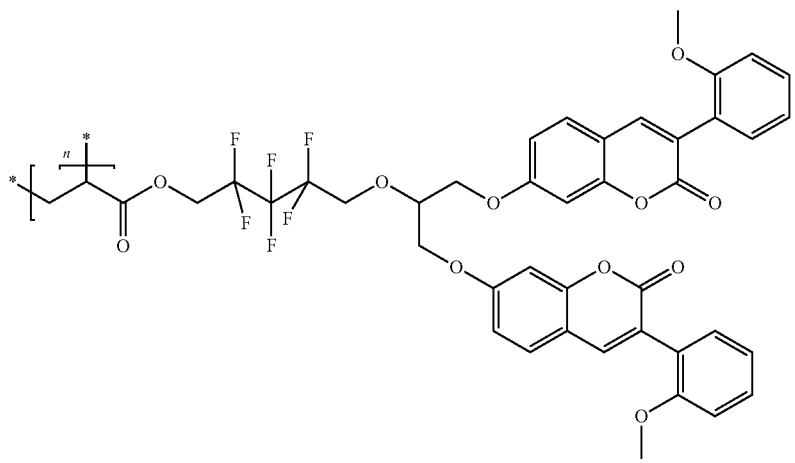
P-035
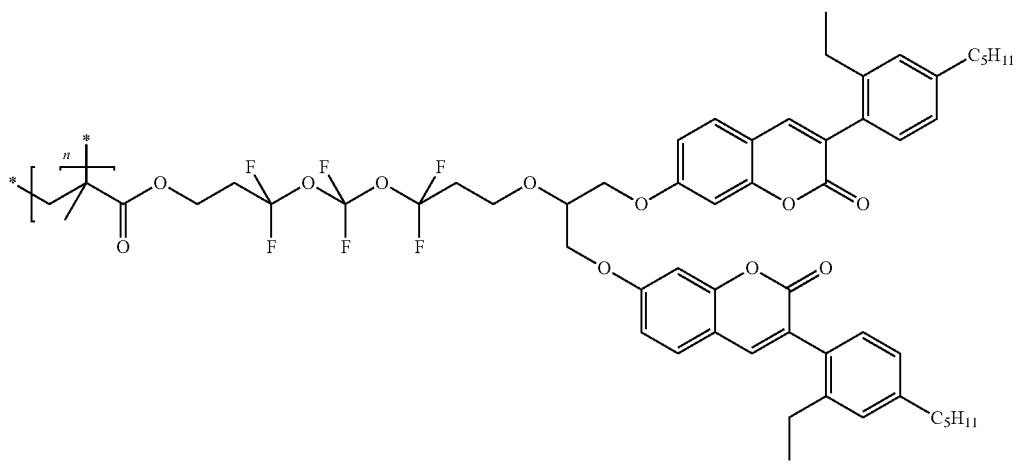

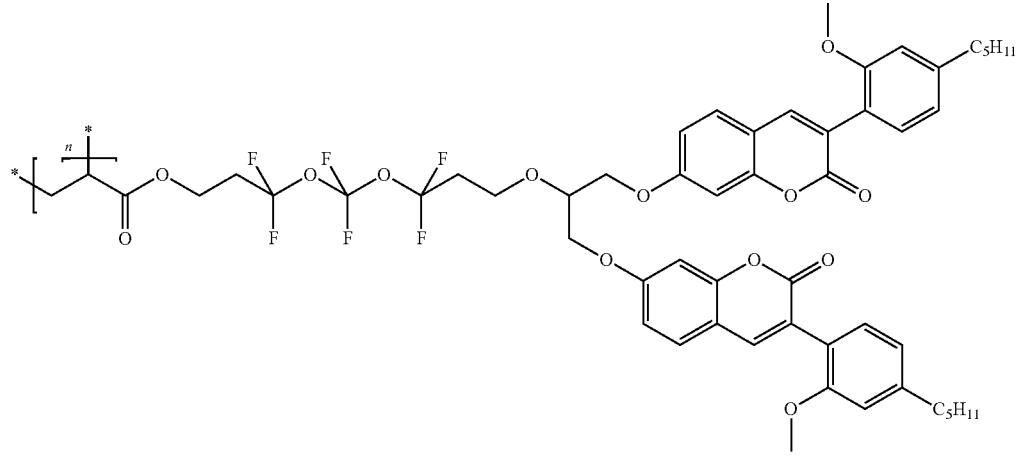
P-036
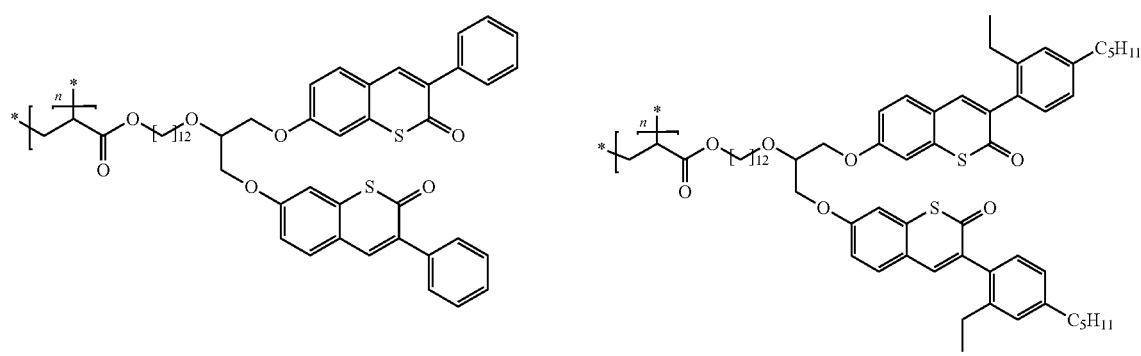
P-037
P-038
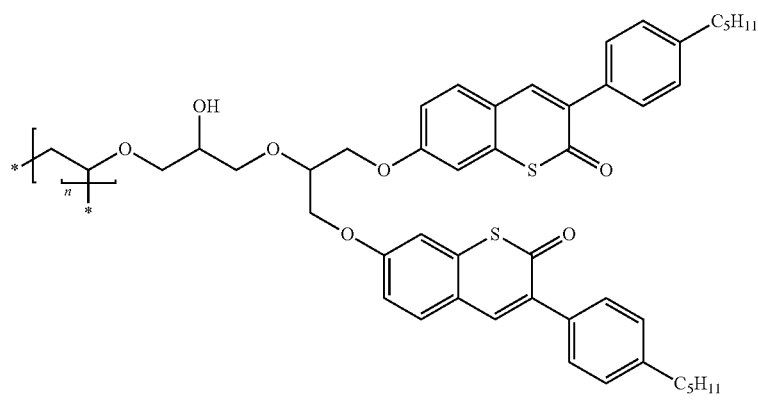
P-039

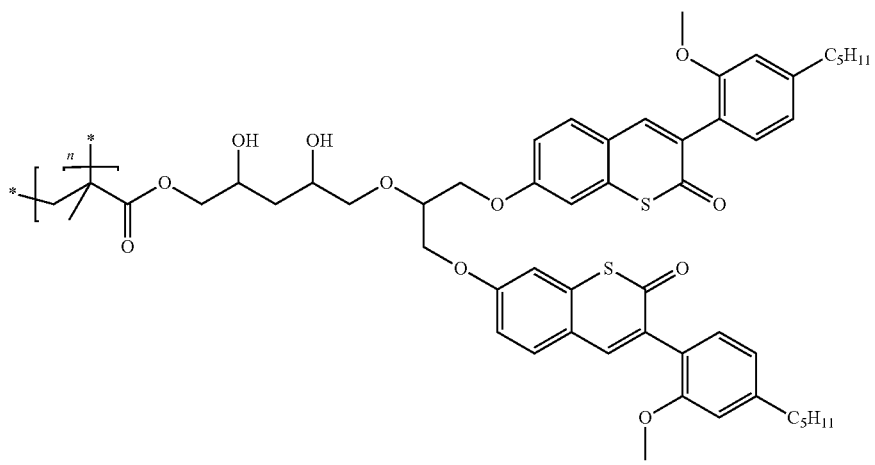
P-040
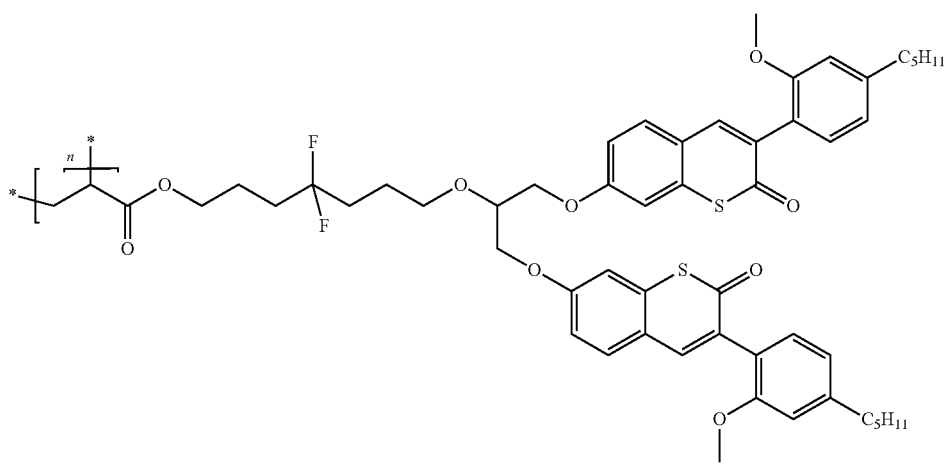
P-041
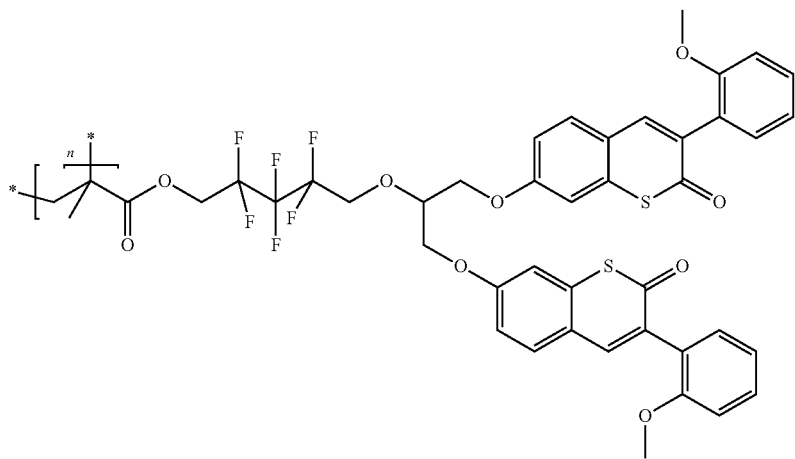
P-042

P-043
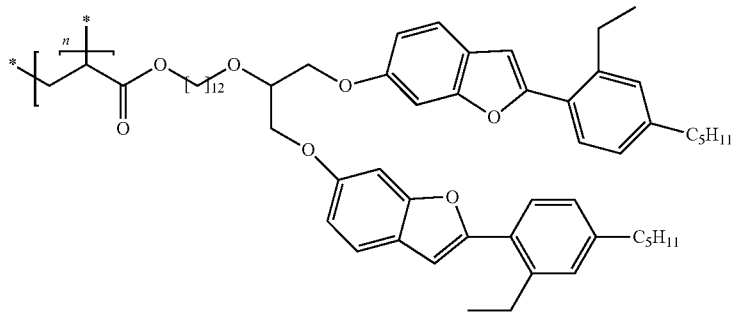
P-044
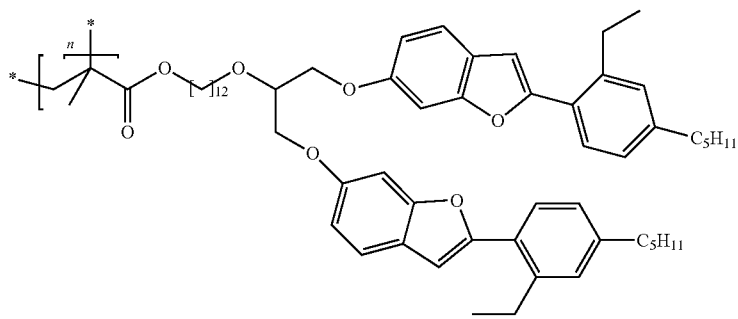
P-045
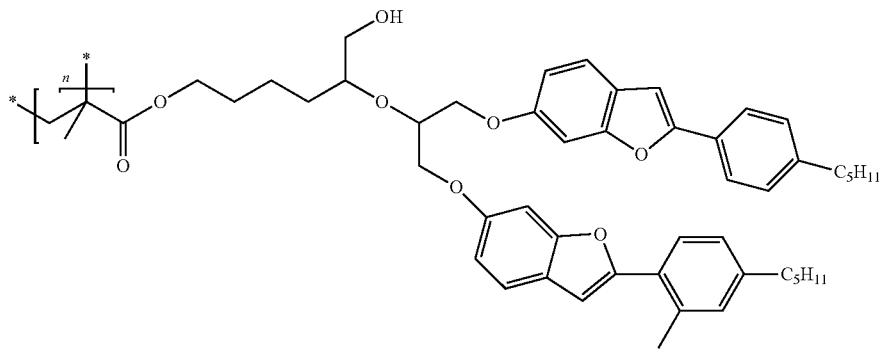
P-046
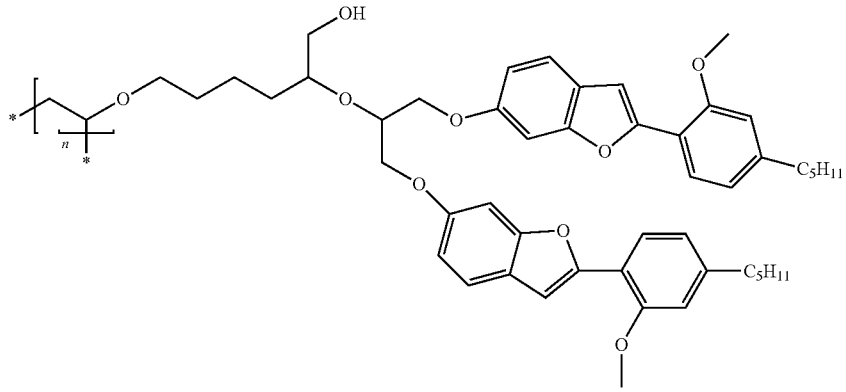

-continued
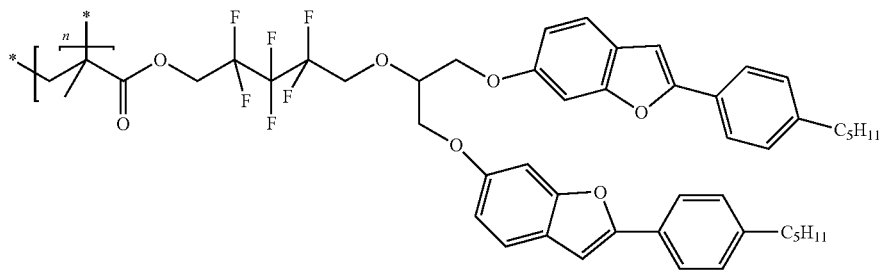
P-047
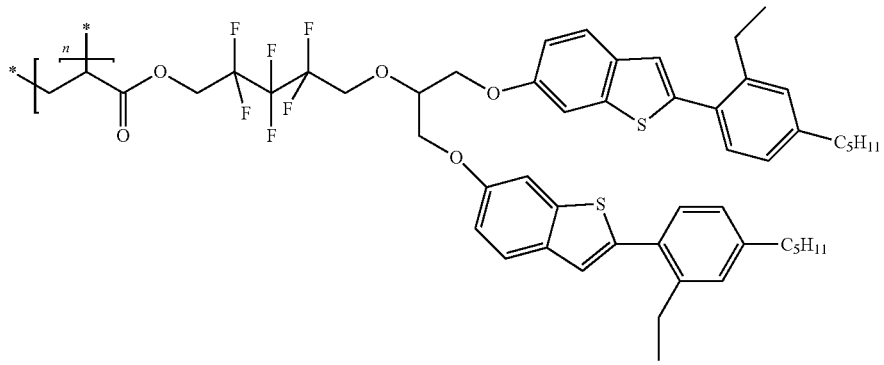
P-048
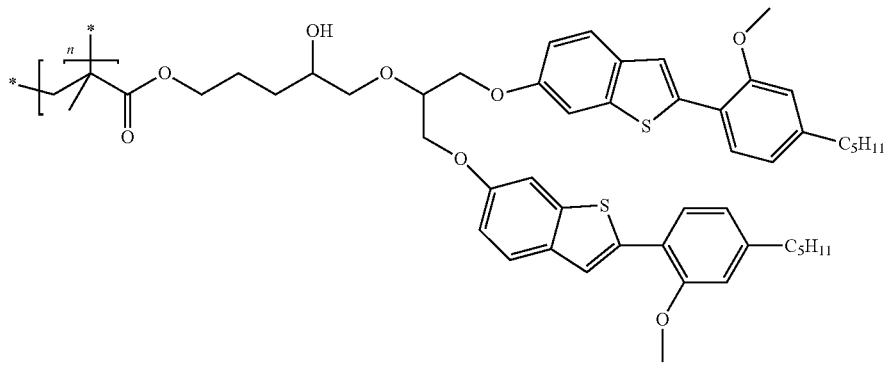
P-049
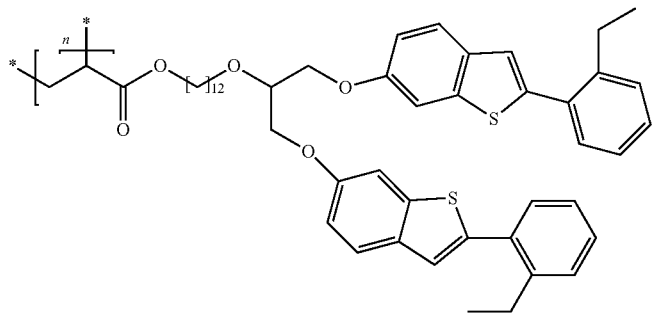
P-050
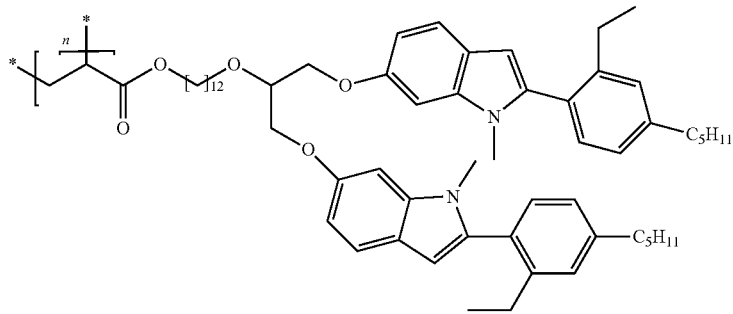
P-051

P-052
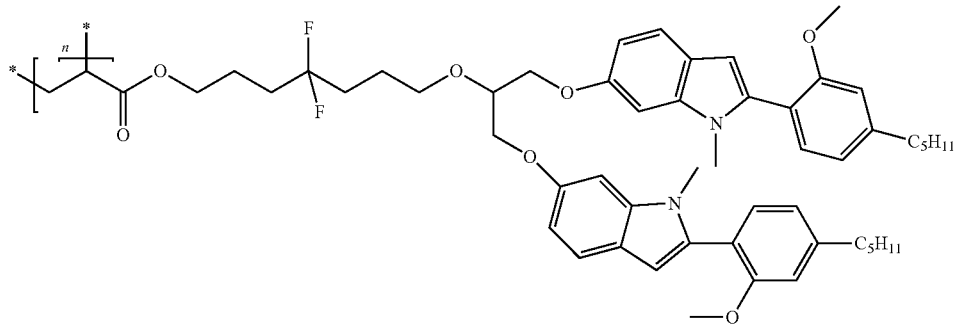
P-053
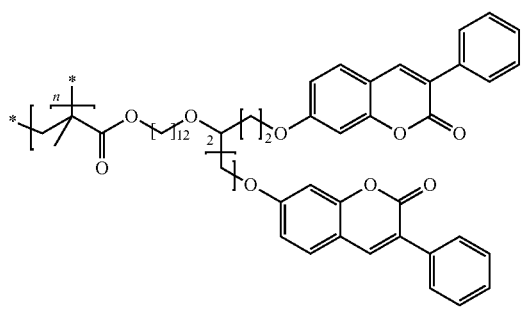
P-054
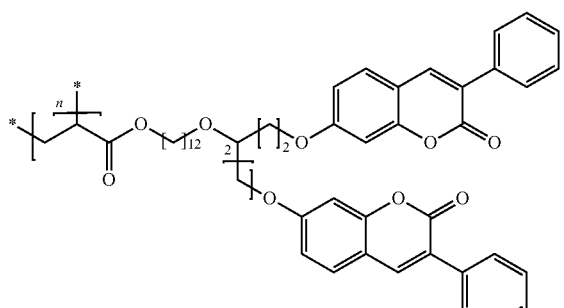
P-055
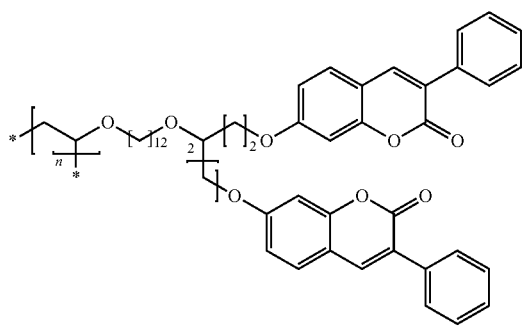
P-056
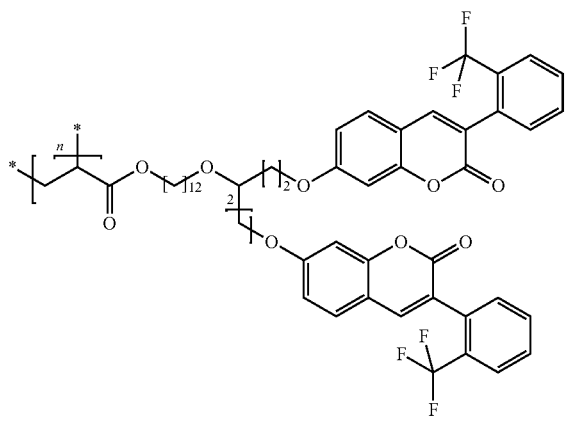
P-057
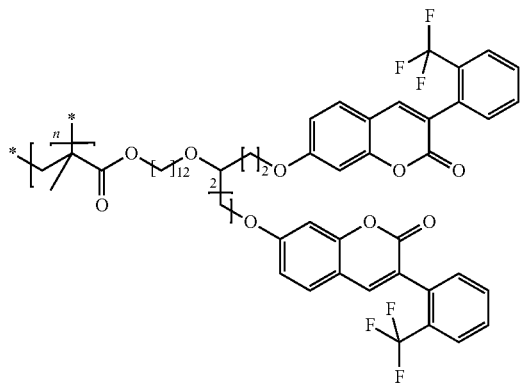
P-058
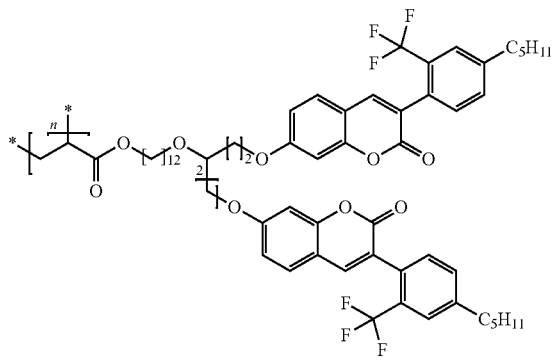

-continued
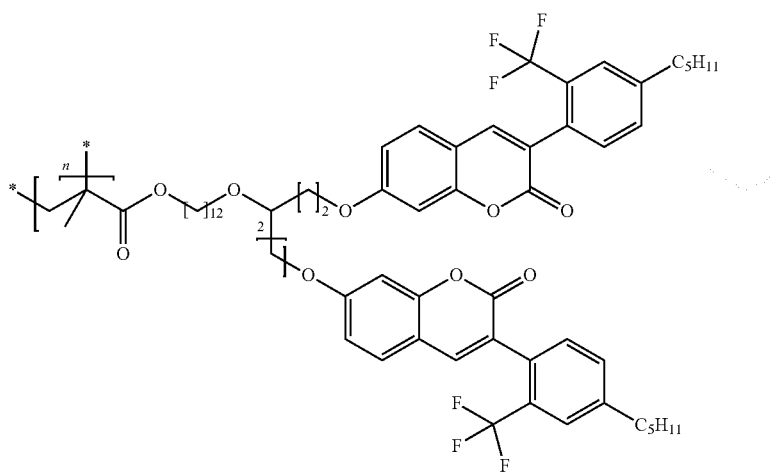
P-059
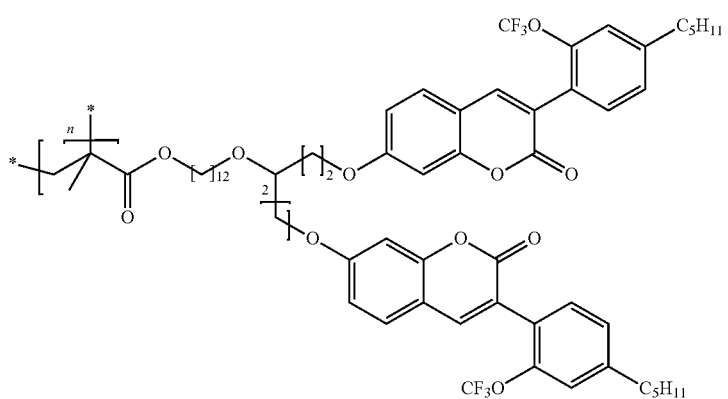
P-060
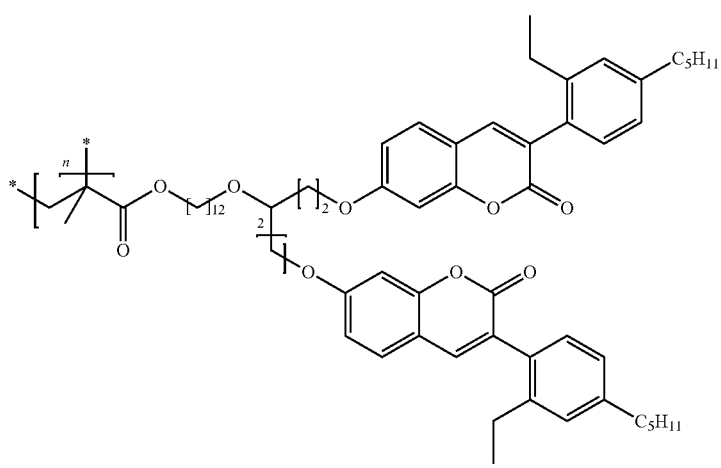
P-061

-continued
P-062
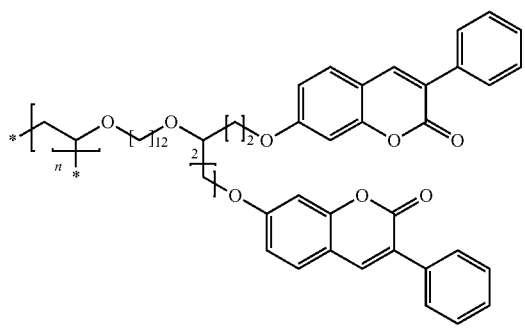
P-063
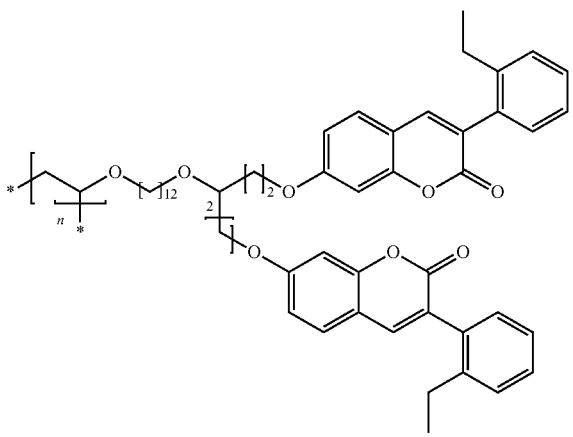
P-064
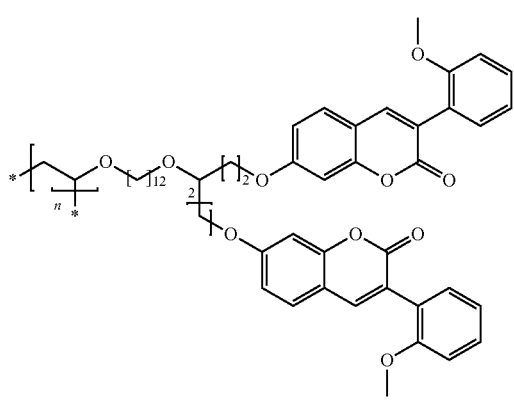
P-065
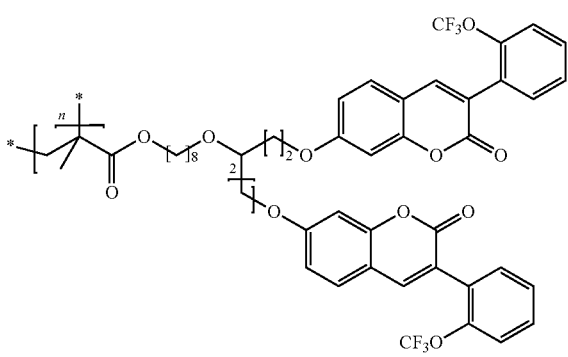
P-066
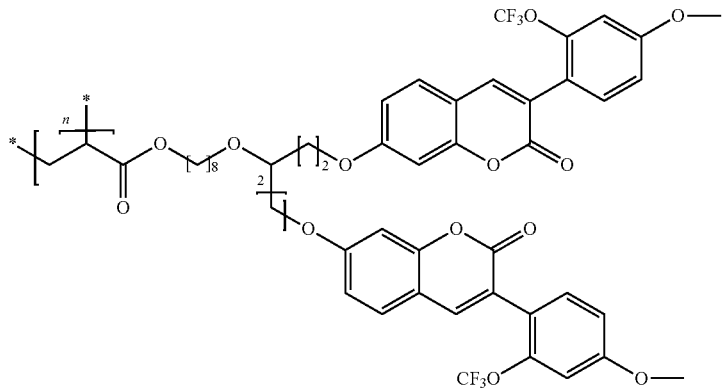
P-067
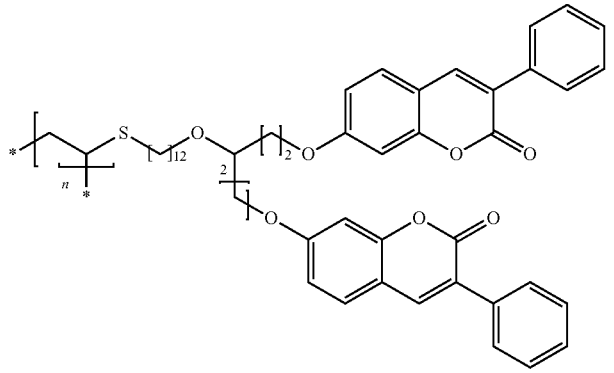

-continued
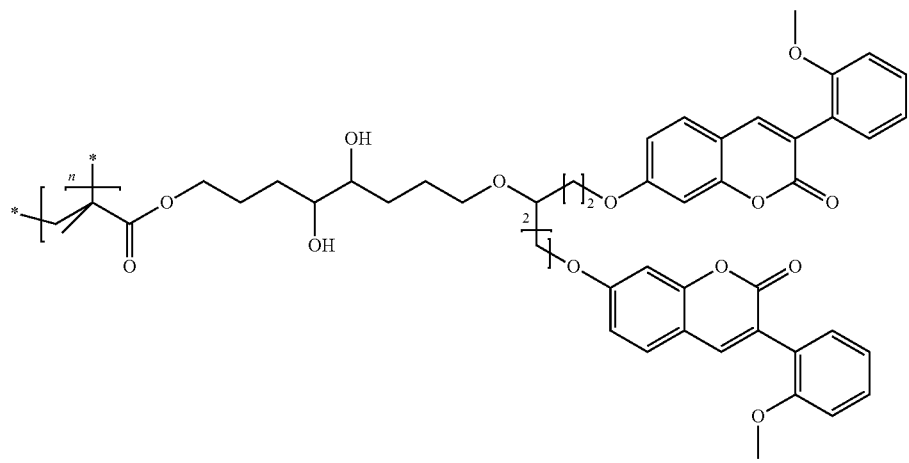
P-068
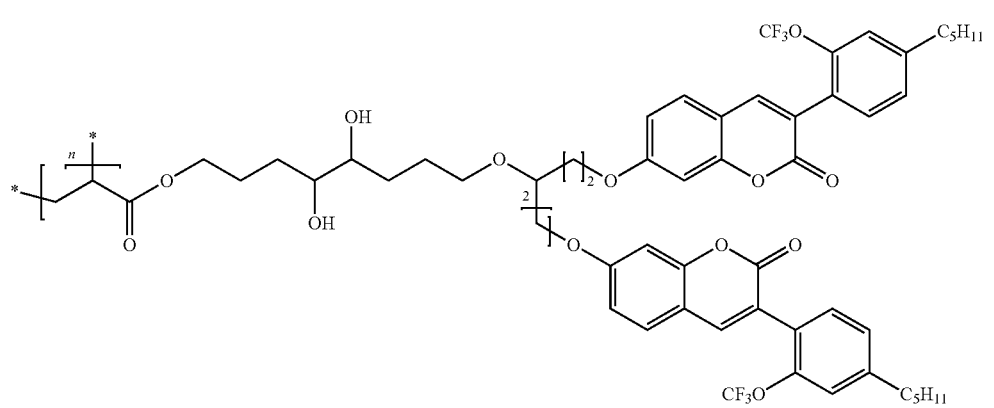
P-069
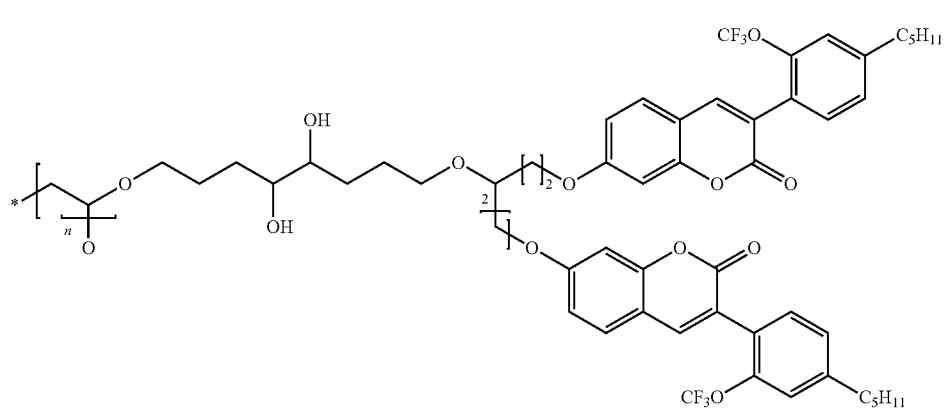
P-070

-continued
P-071
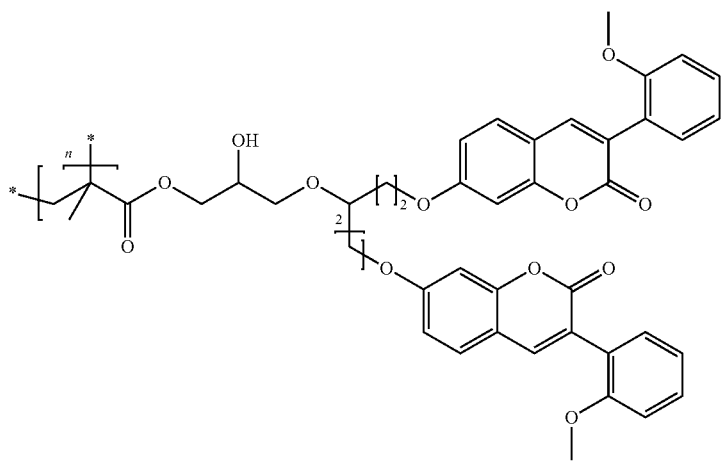
P-072
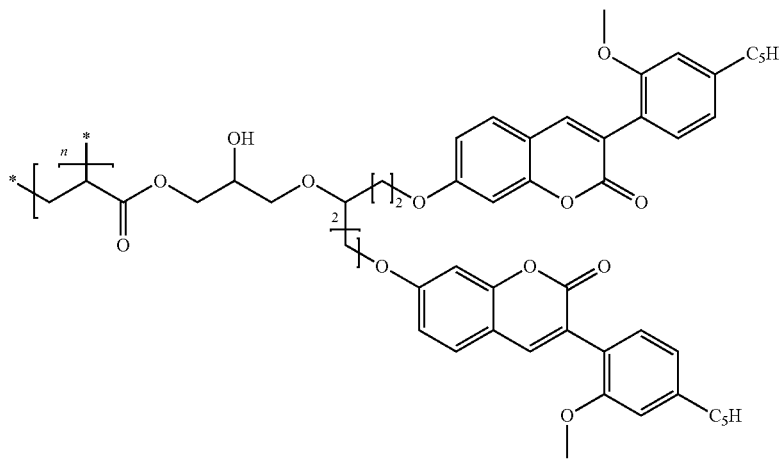
P-073
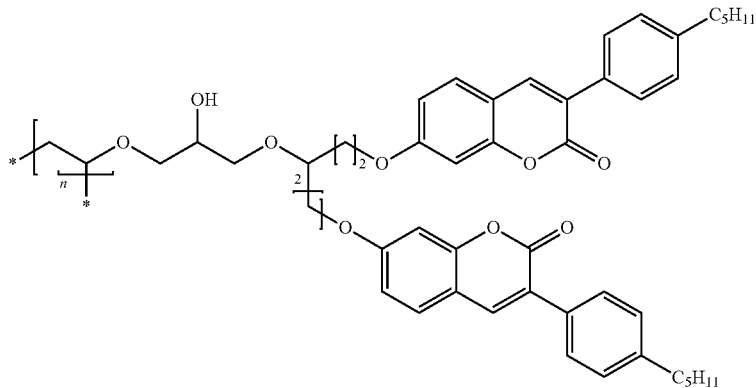

-continued
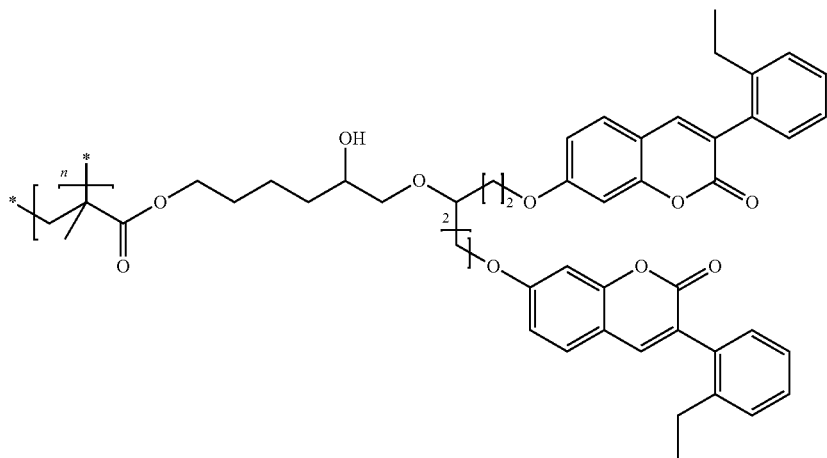
P-074
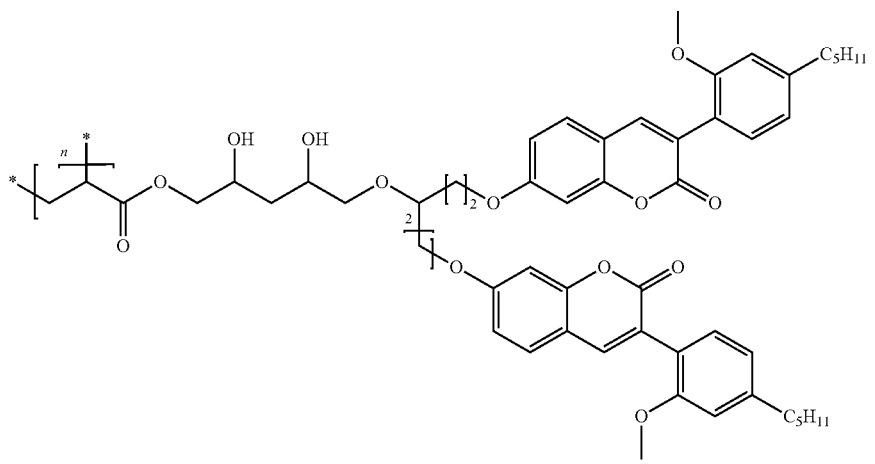
P-075
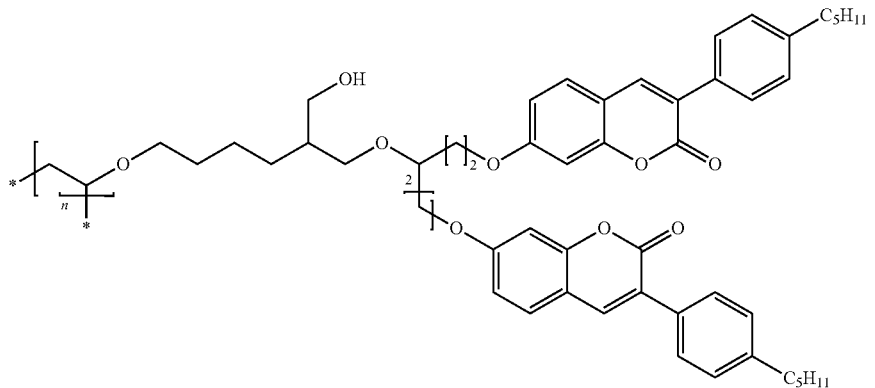
P-076

-continued
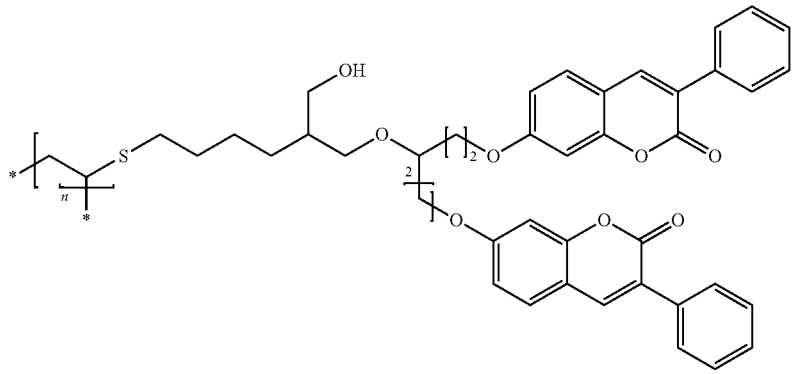
P-077
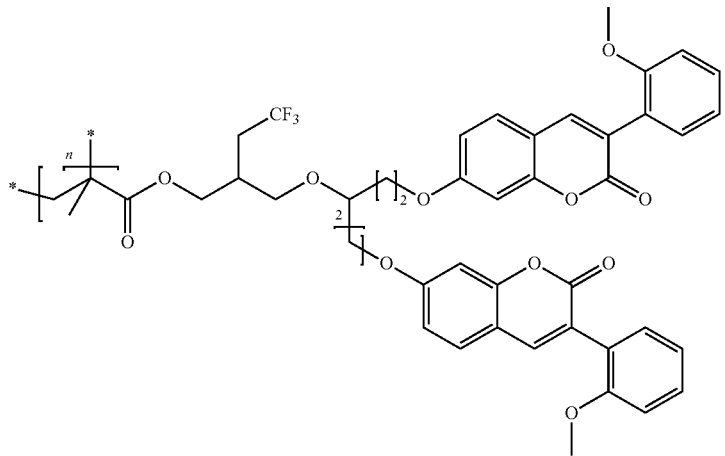
P-078
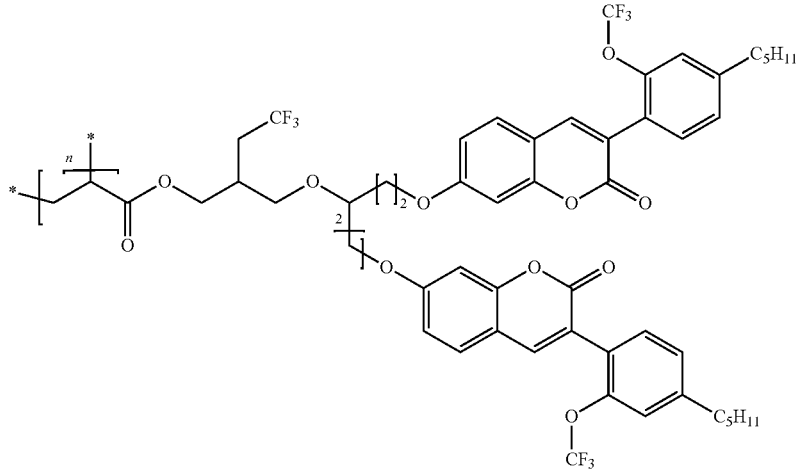
P-079

-continued
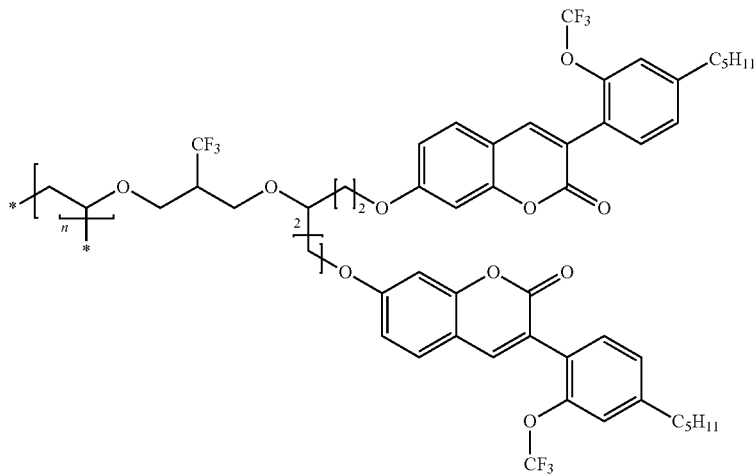
P-080
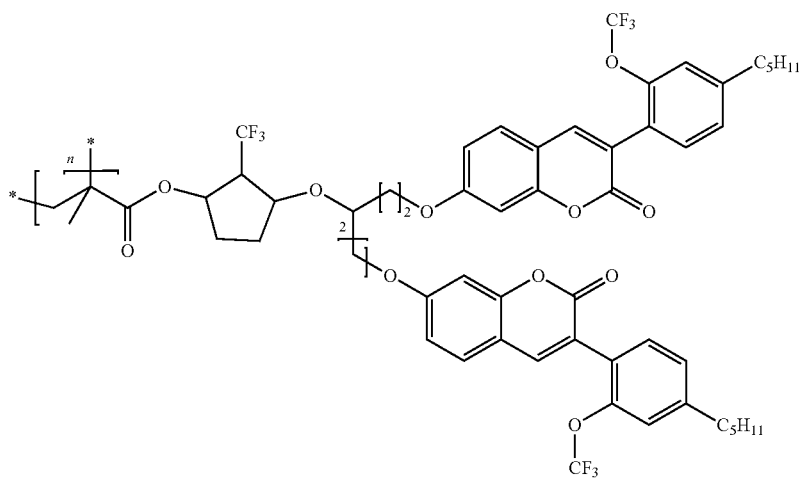
P-081
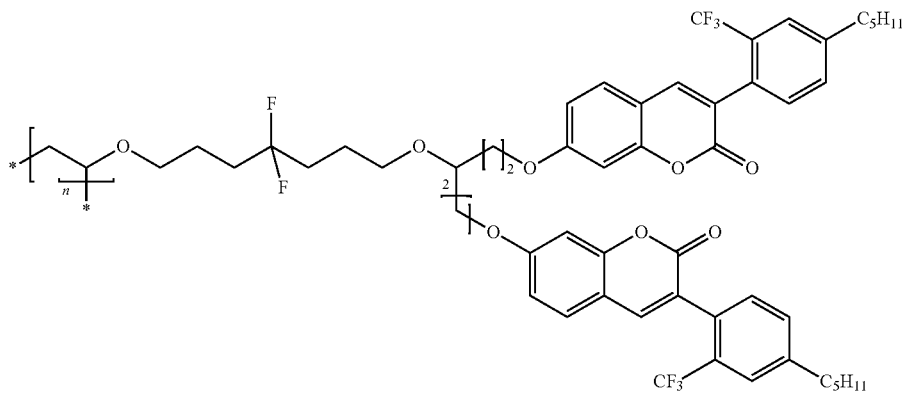
P-082

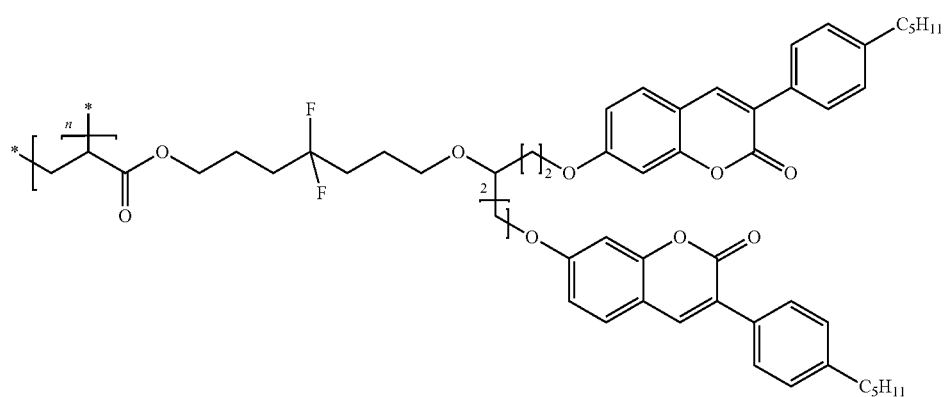
P-083
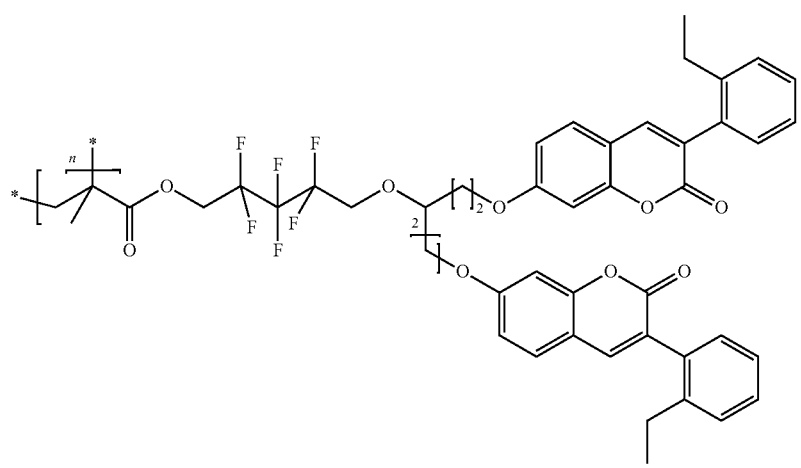
P-084
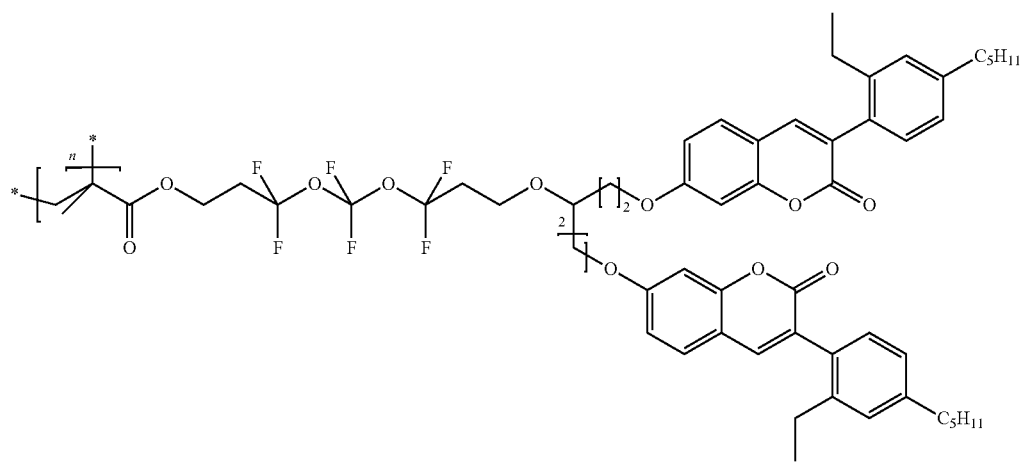
P-085

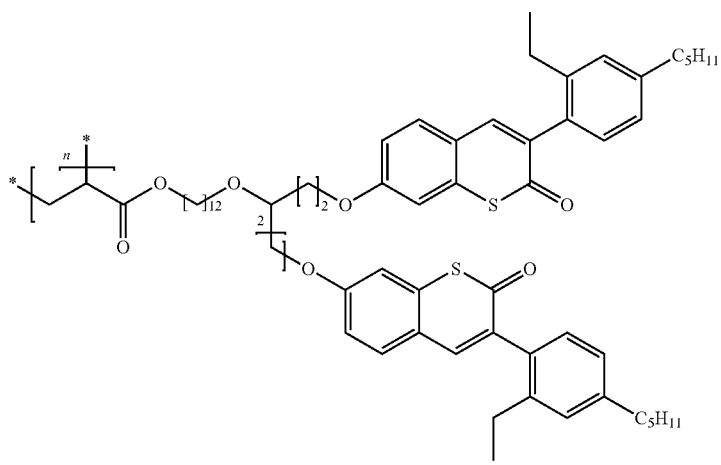
P-086
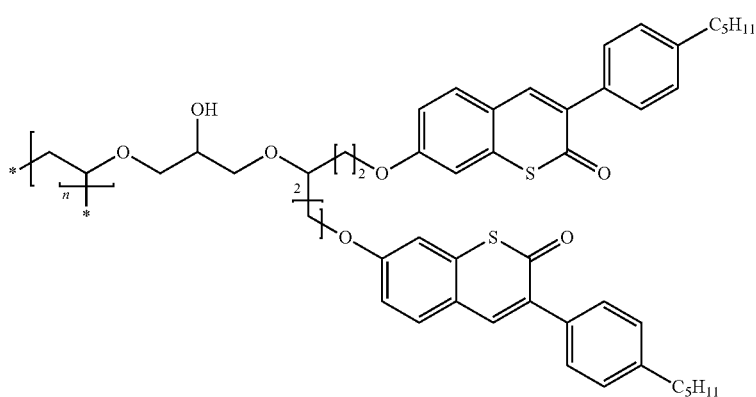
P-087
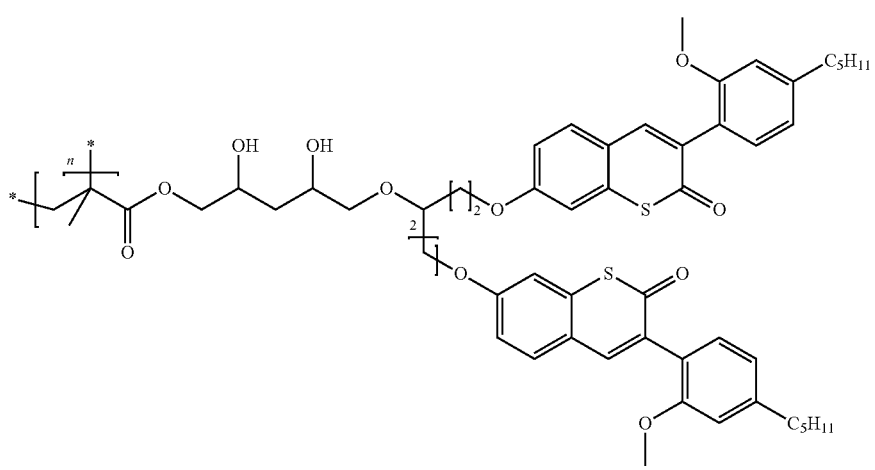
P-088

-continued
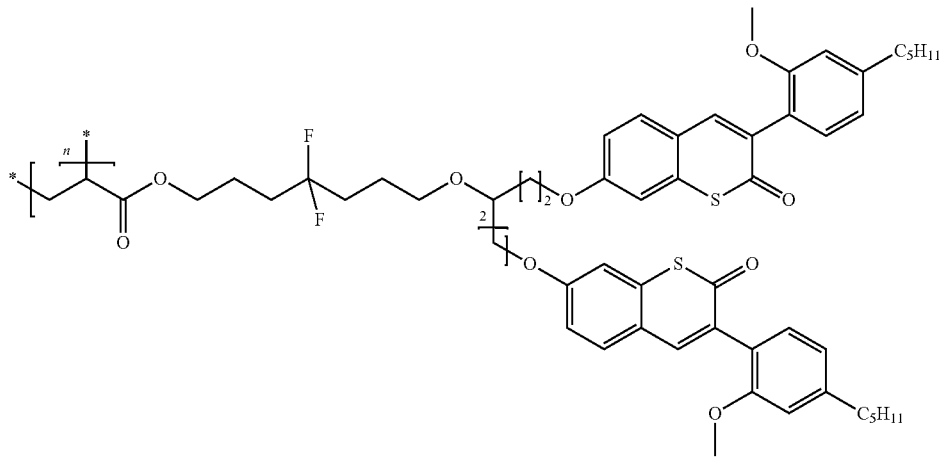
P-089
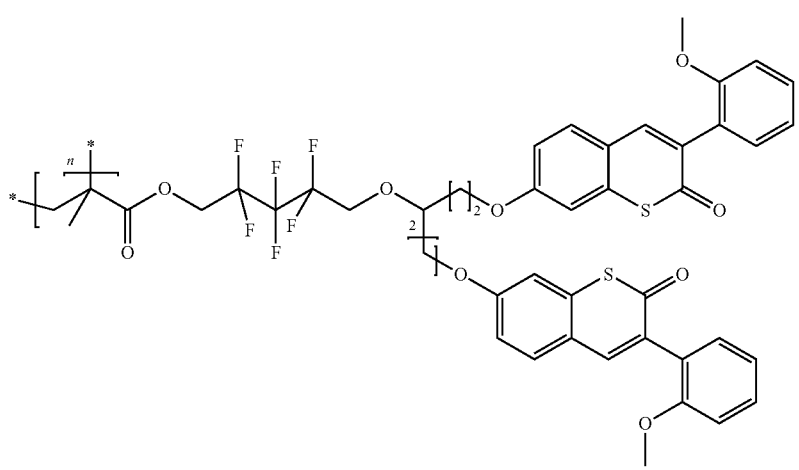
P-090
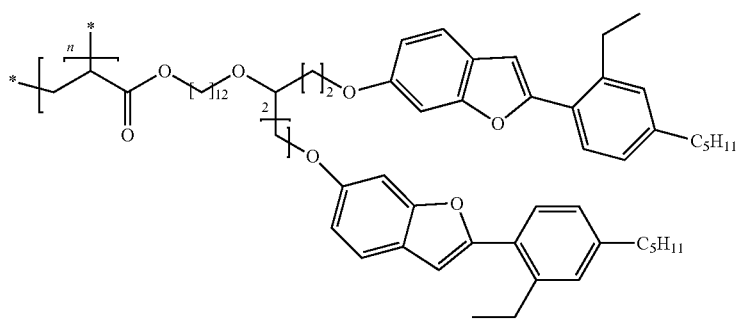
P-091
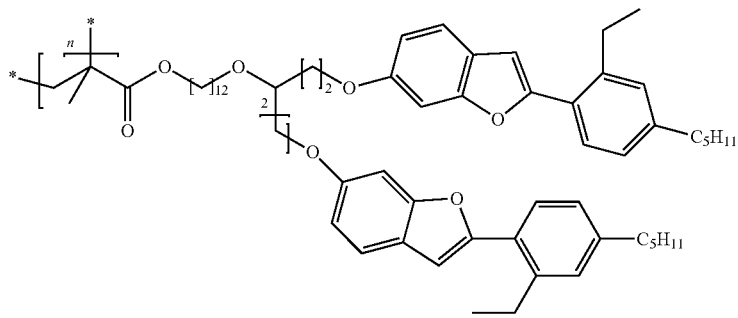
P-092

-continued
P-093
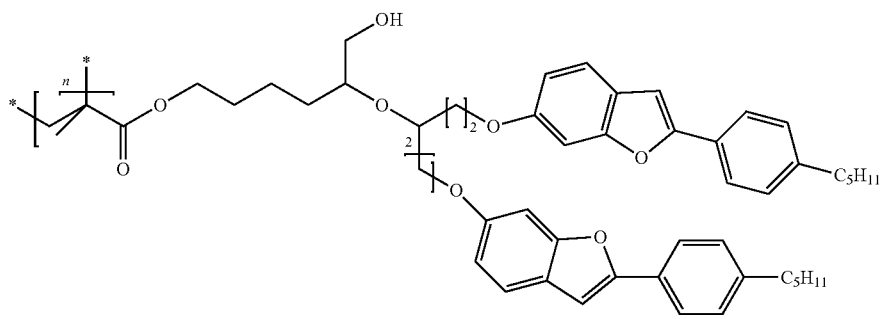
P-094
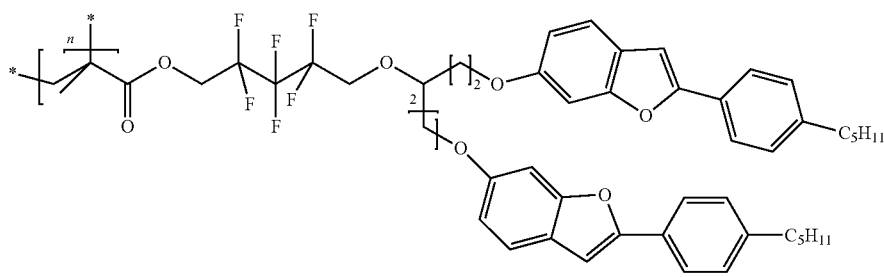
P-095
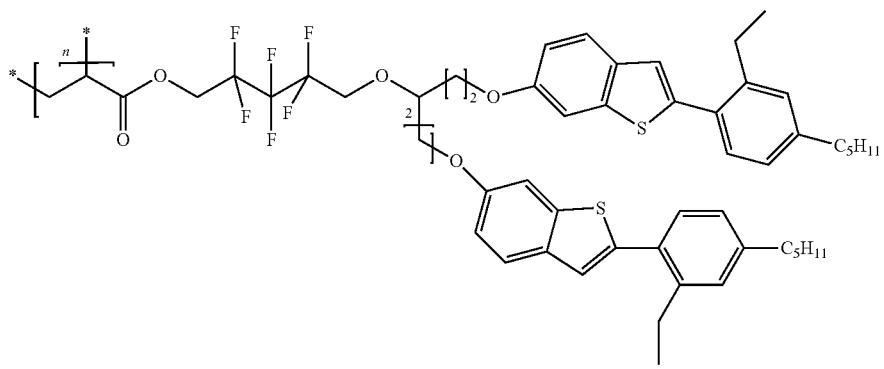
P-096
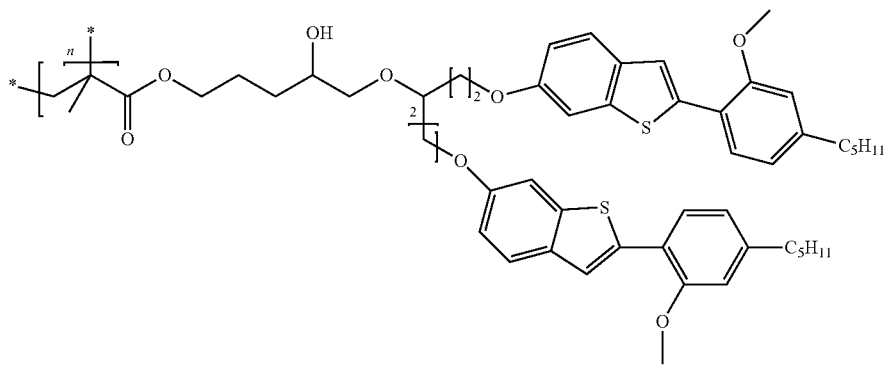
P-097
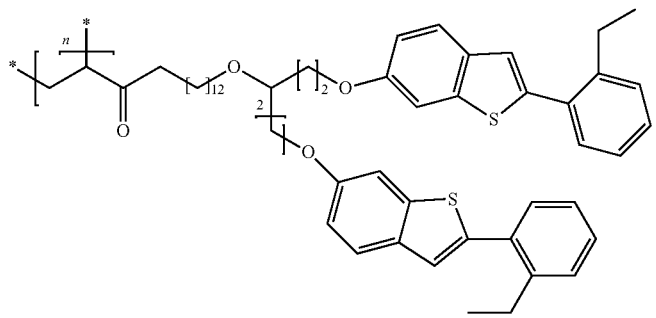

-continued
P-098
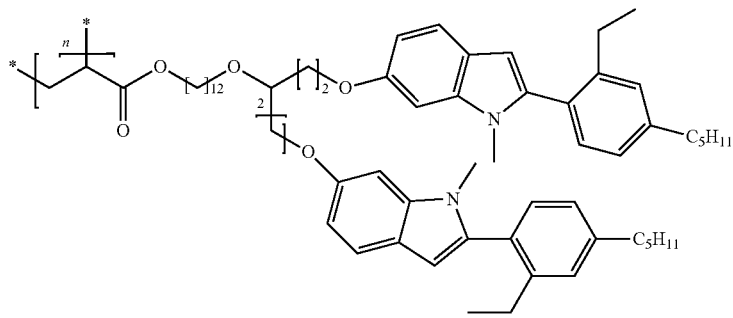
P-099
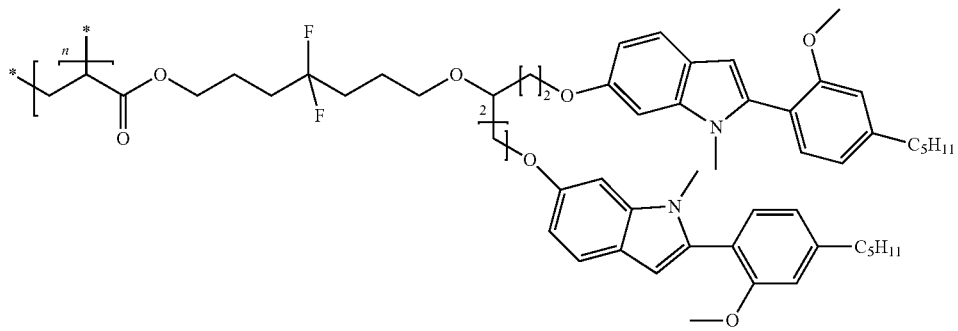
P-100
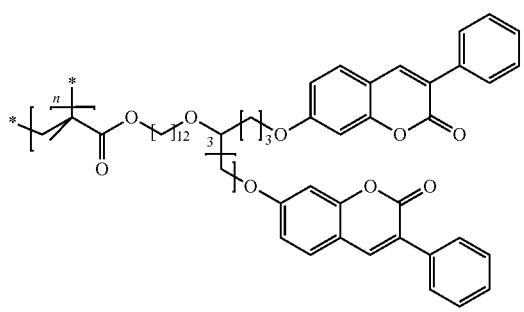
P-101
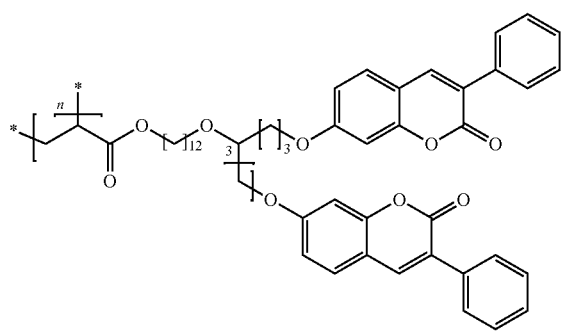
P-102
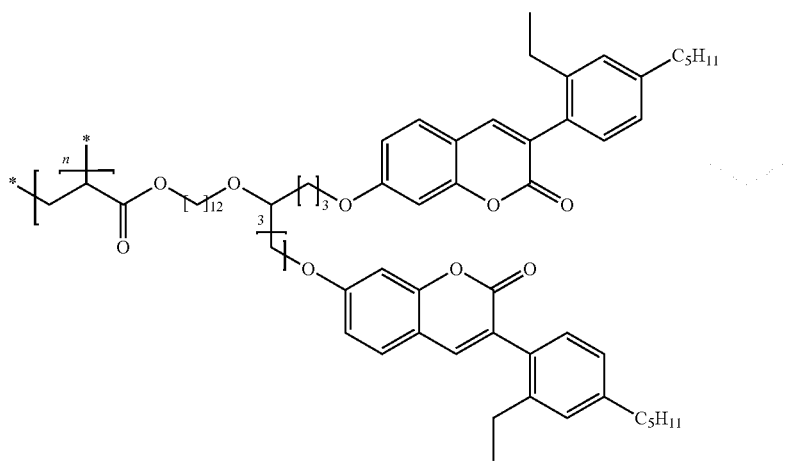

-continued
P-103
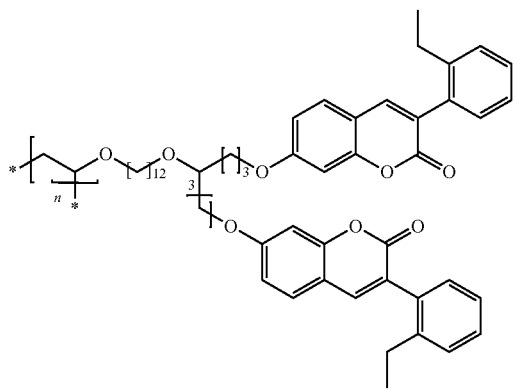
P-104
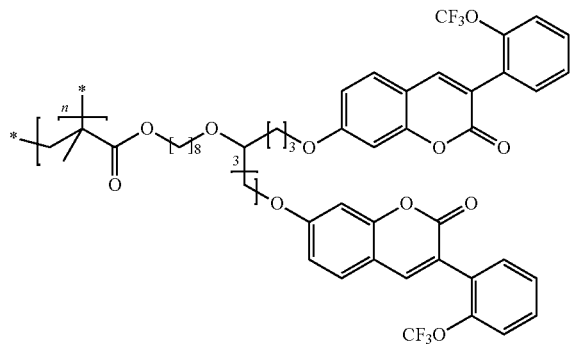
P-105
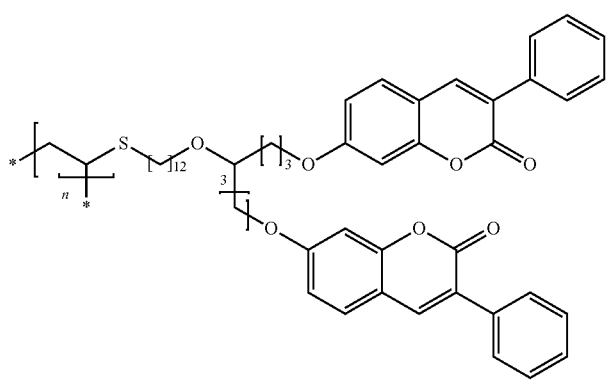
P-106
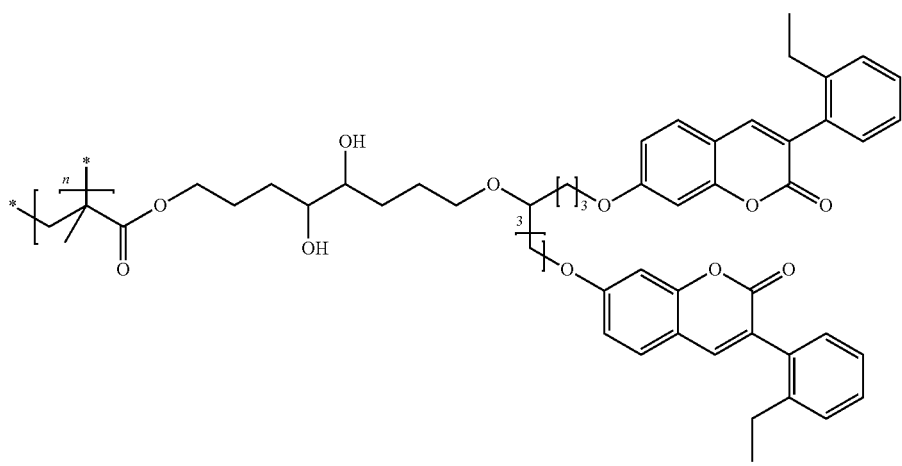
P-107
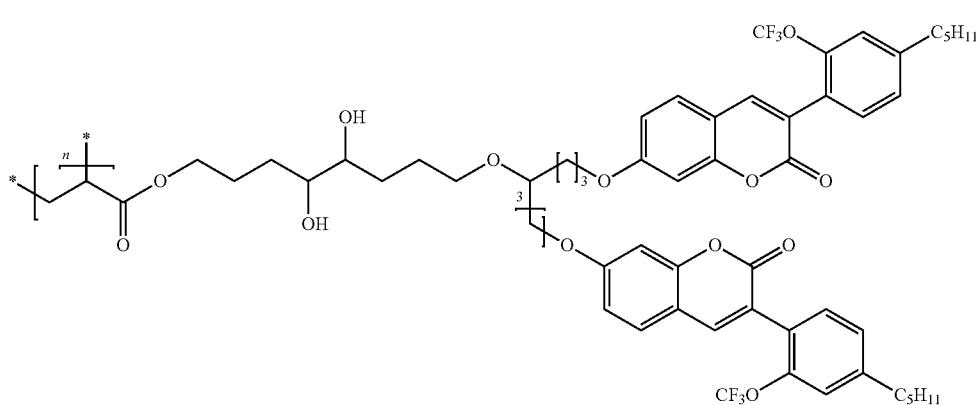

-continued
P-108
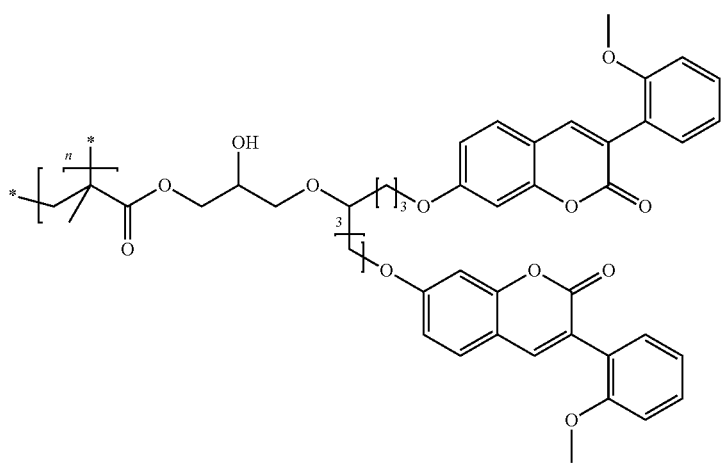
P-109
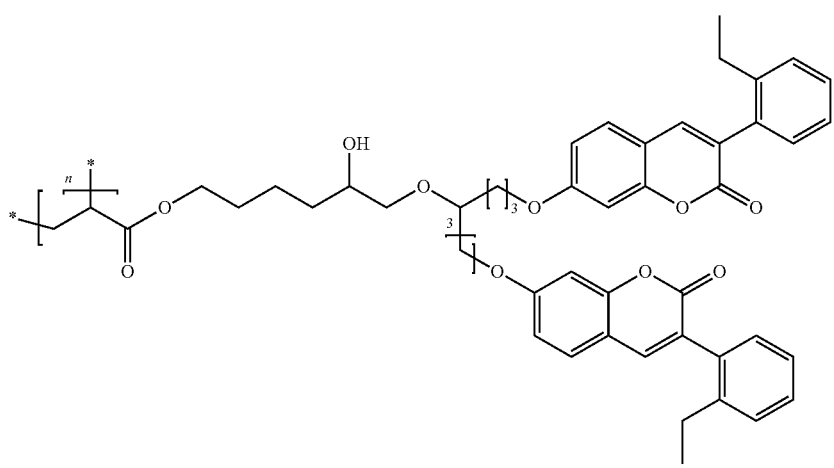
P-110
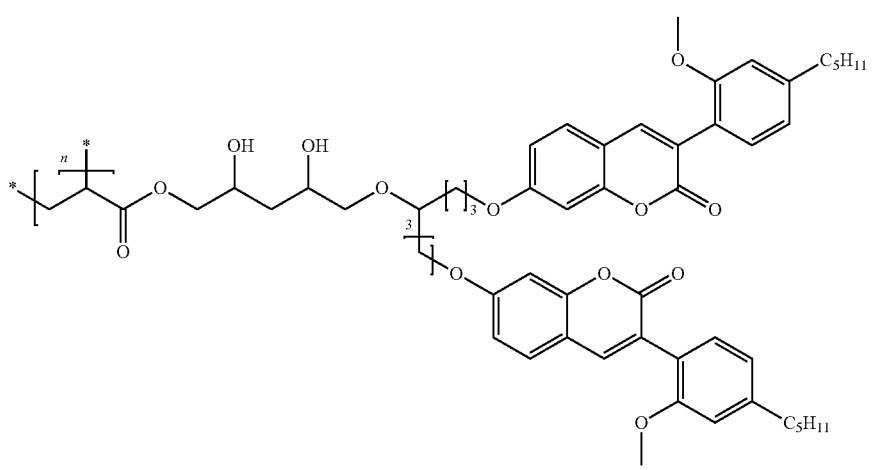

-continued
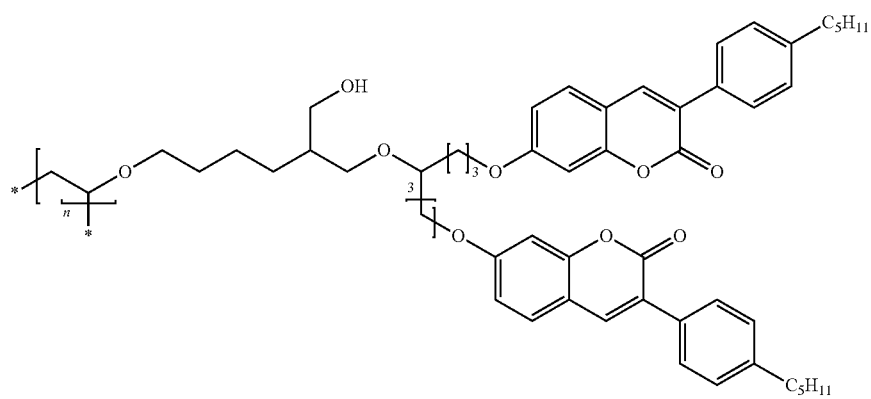
P-111
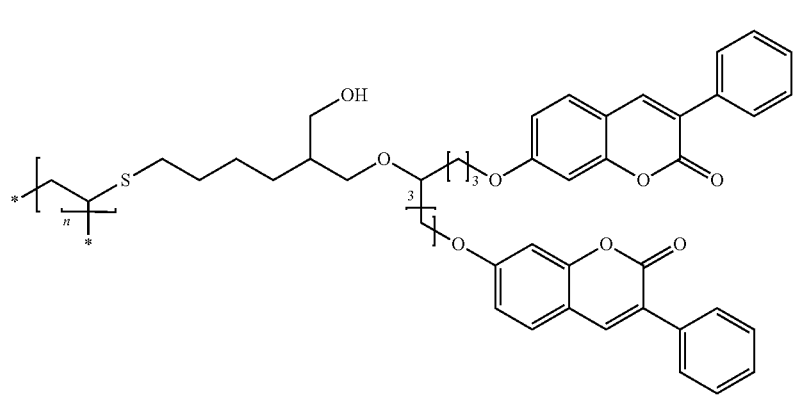
P-112
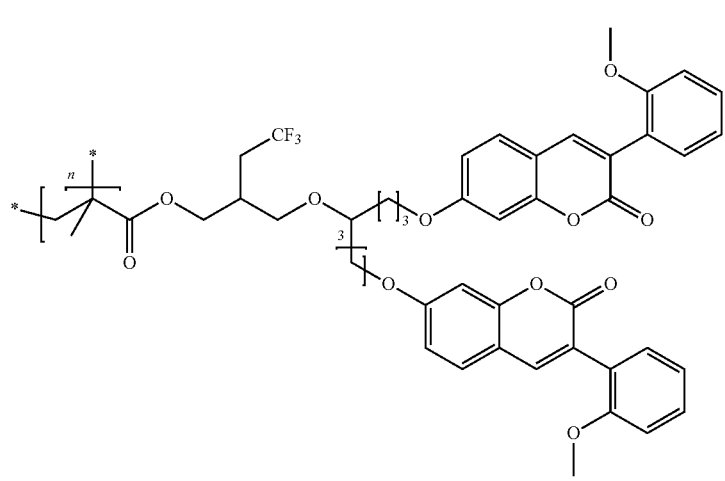
P-113

-continued
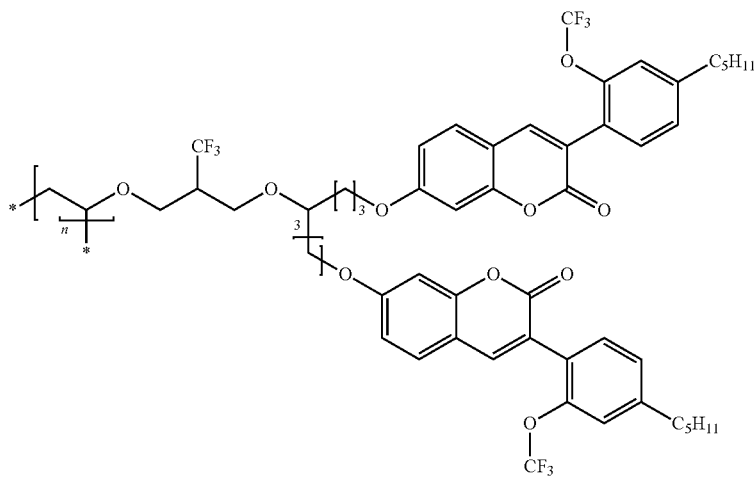
P-114
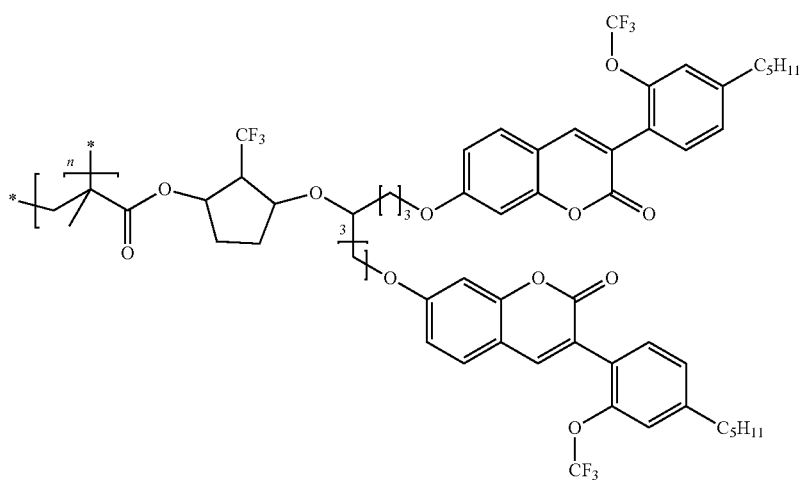
P-115
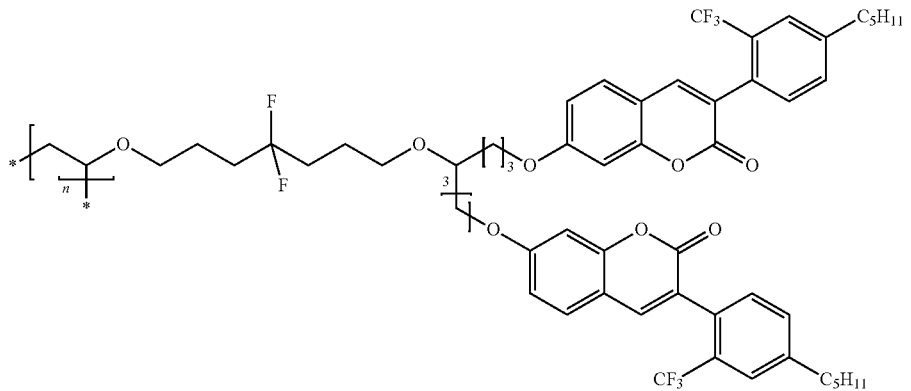
P-116

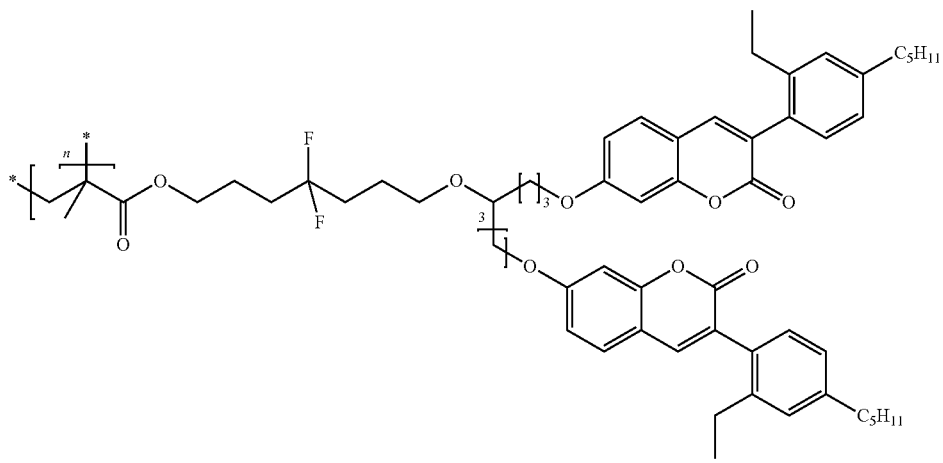
P-117
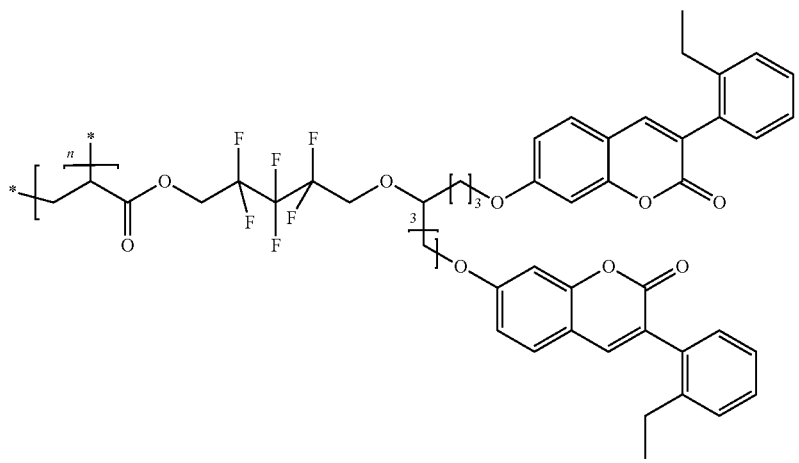
P-118
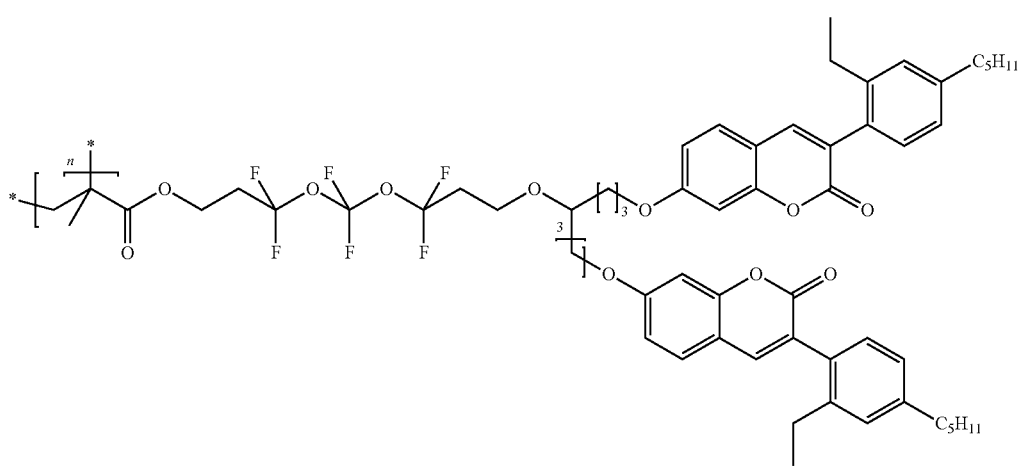
P-119

P-120
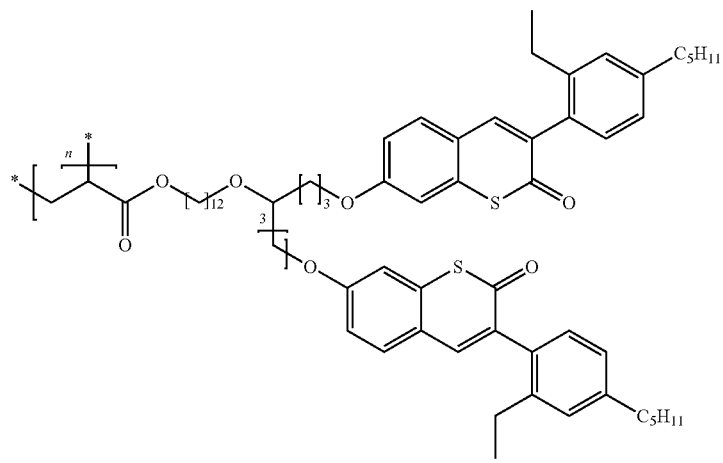
P-121
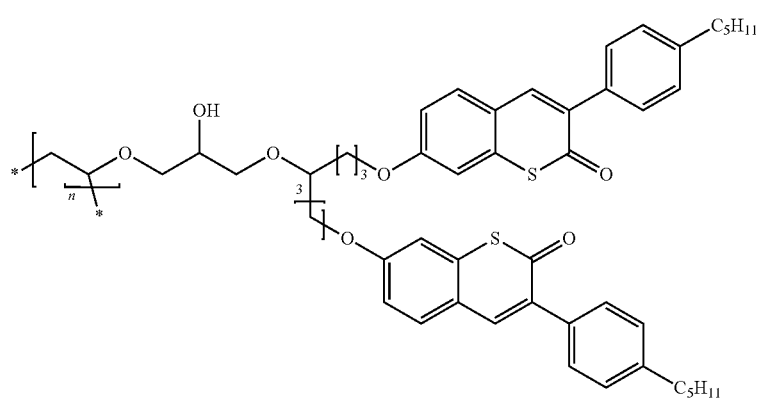
P-122
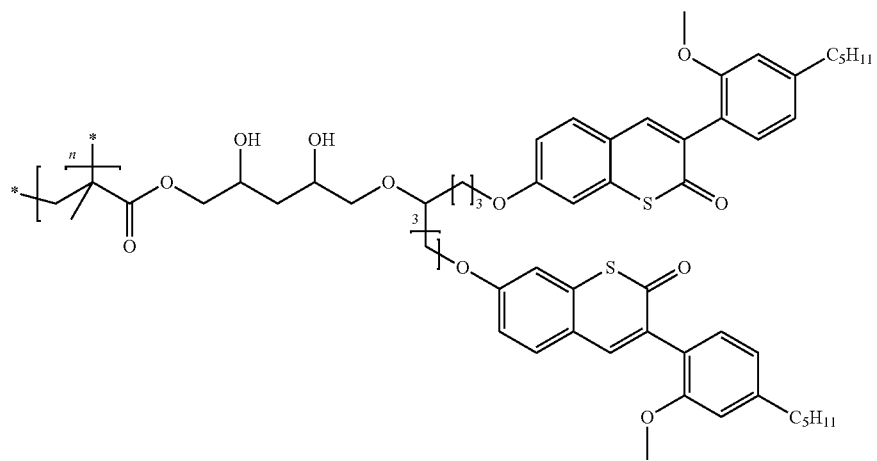

-continued
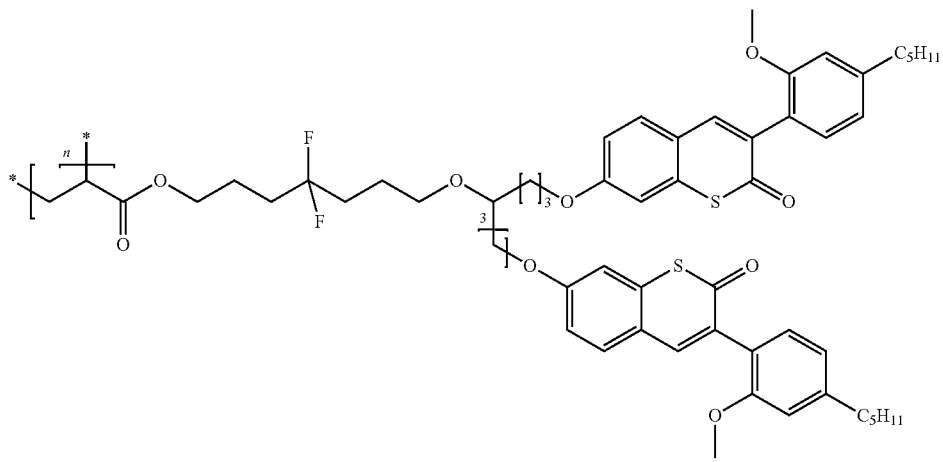
P-123
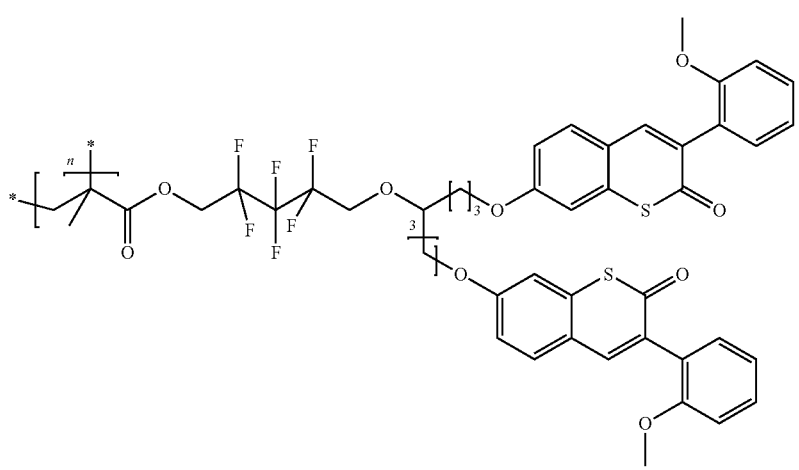
P-124
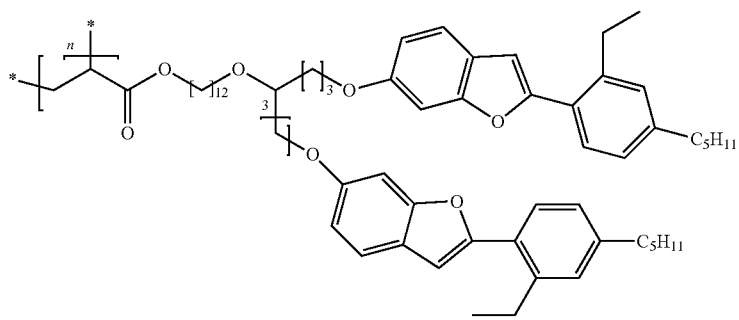
P-125
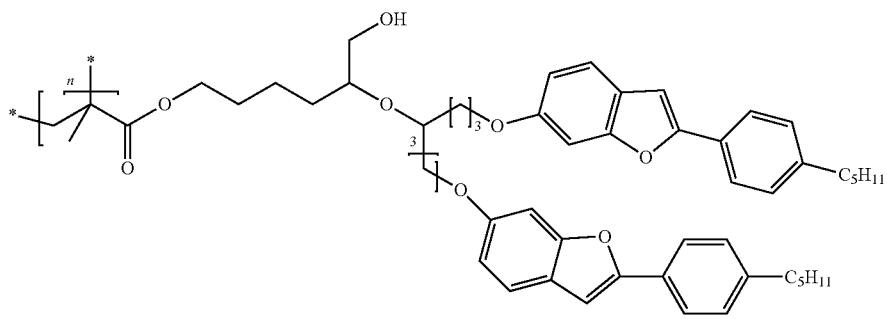
P-126

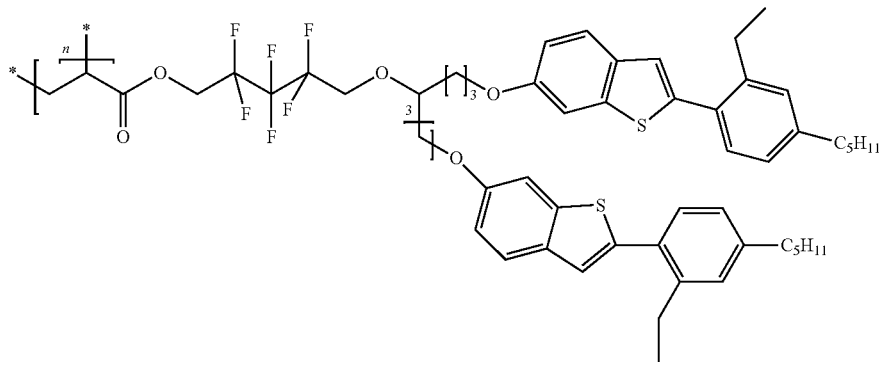
P-127
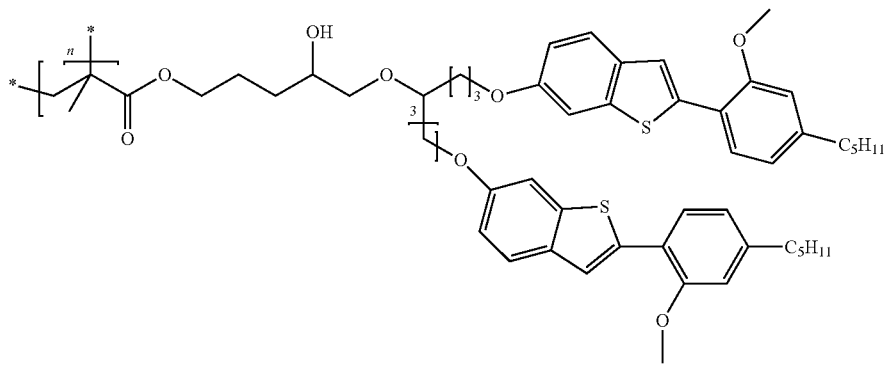
P-128
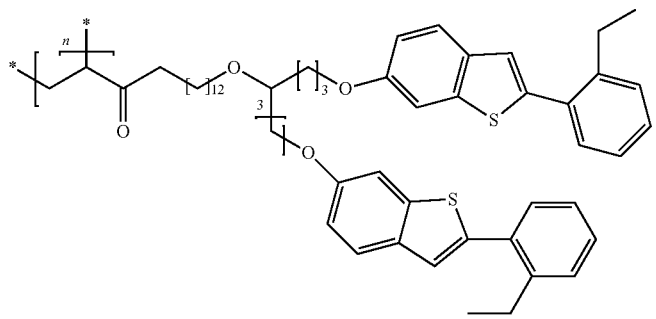
P-129
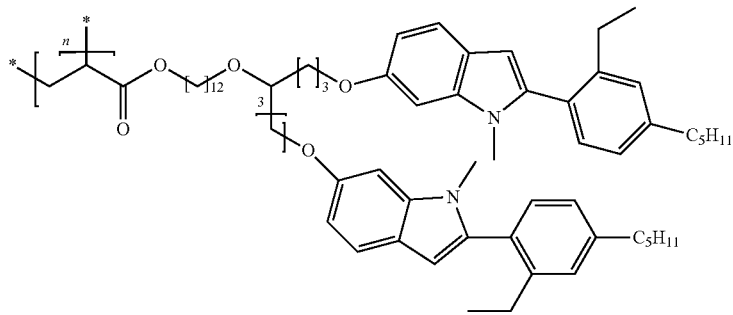
P-130

-continued
P-131
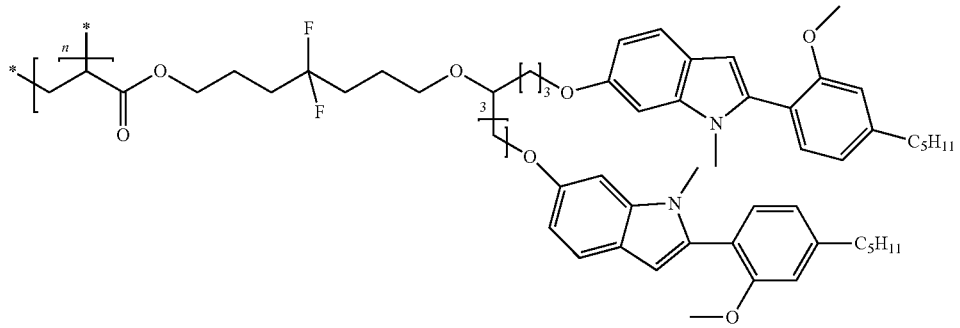
P-132
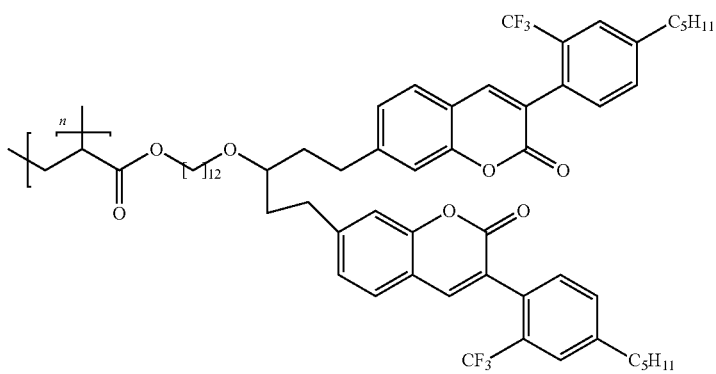
P-133
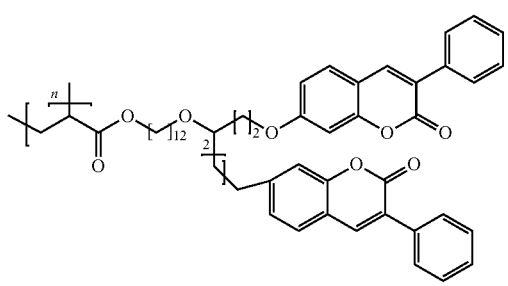
P-134
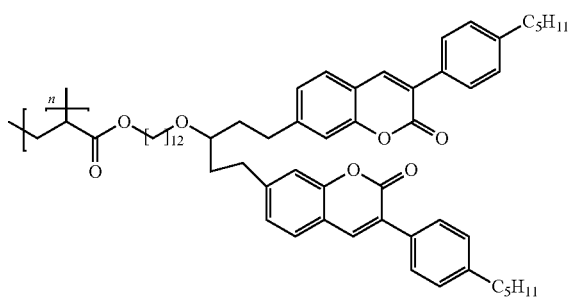
P-135
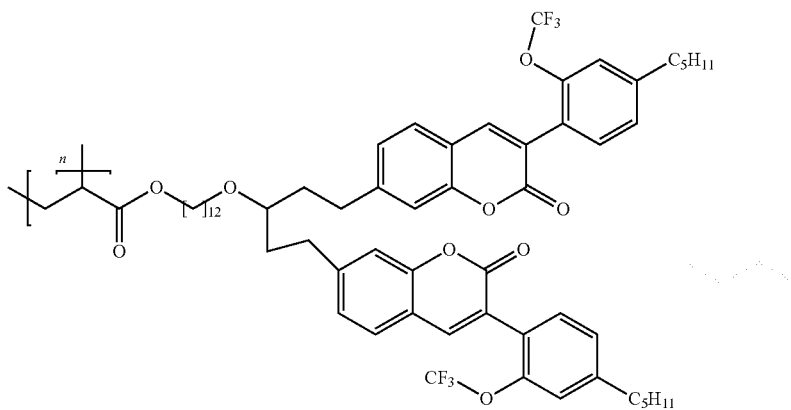

-continued
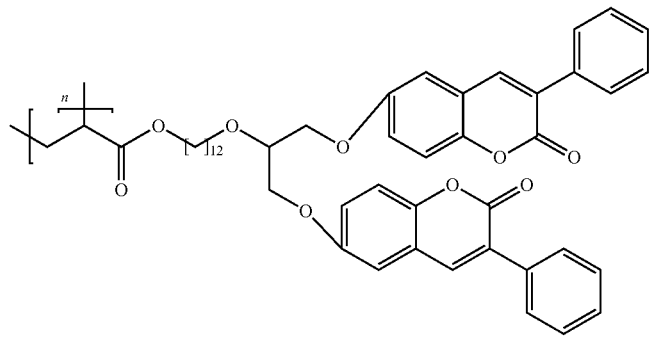
P-136
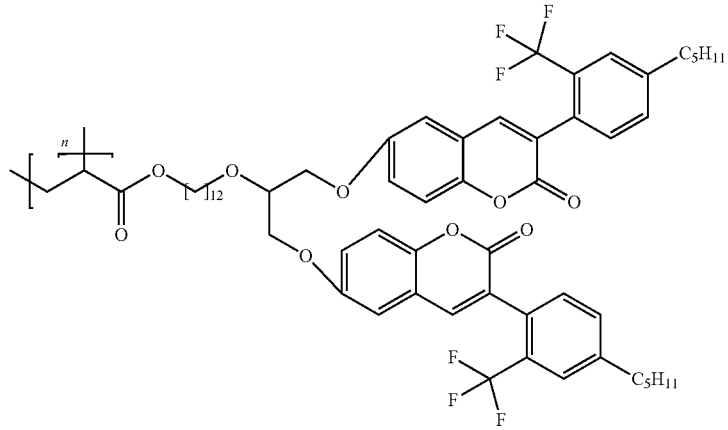
P-137
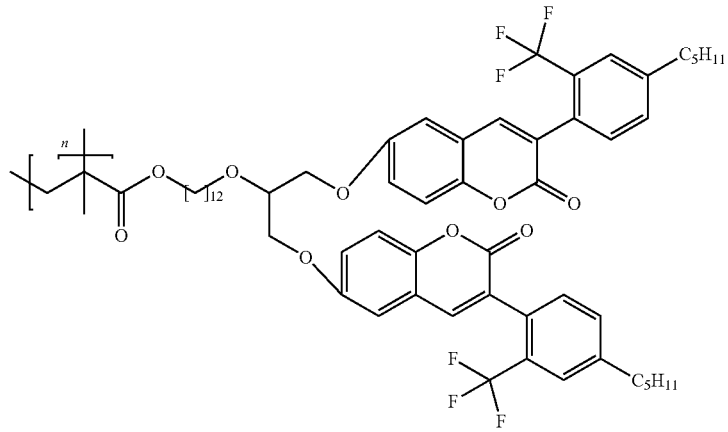
P-138
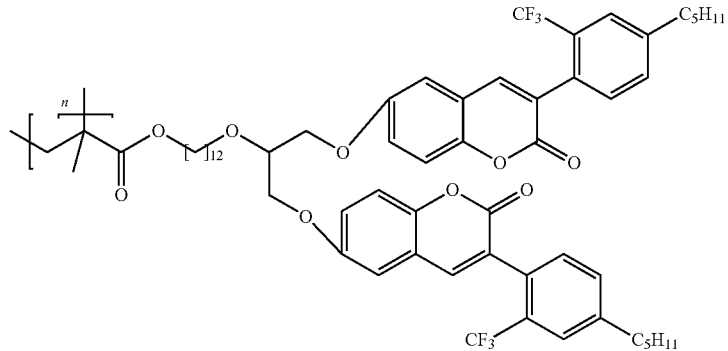
P-139

-continued
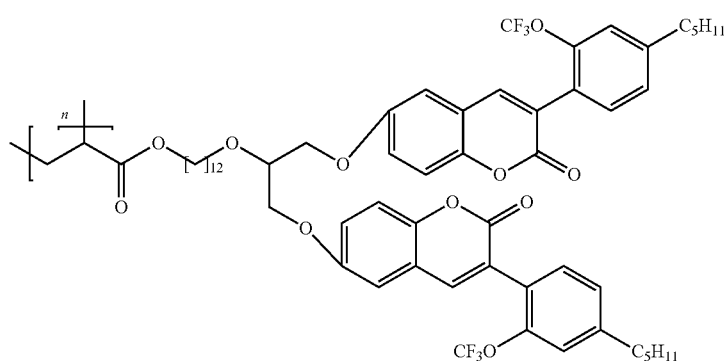
P-140
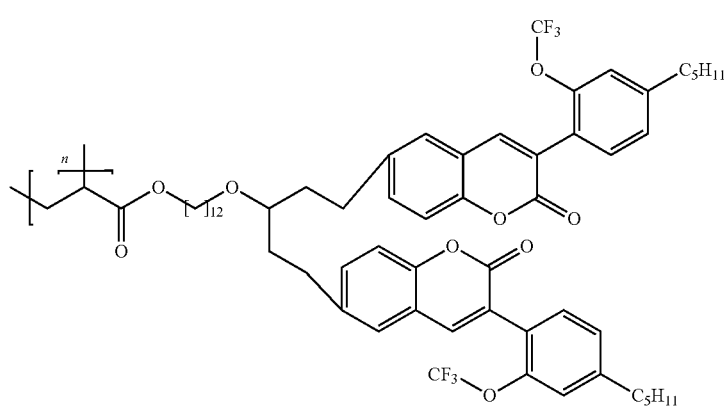
P-141
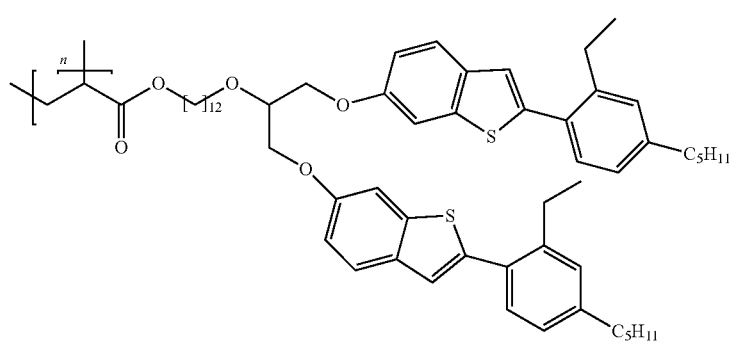
P-142
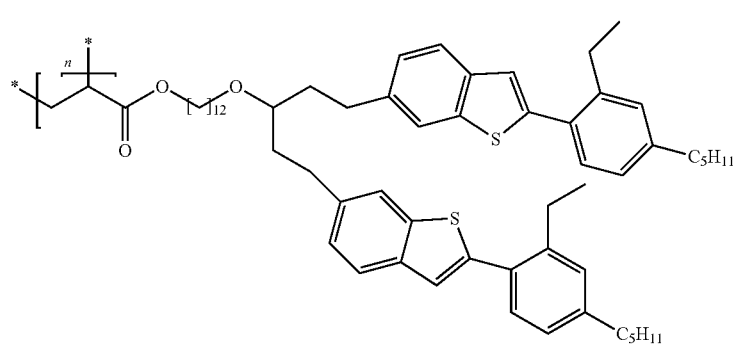
P-143

-continued
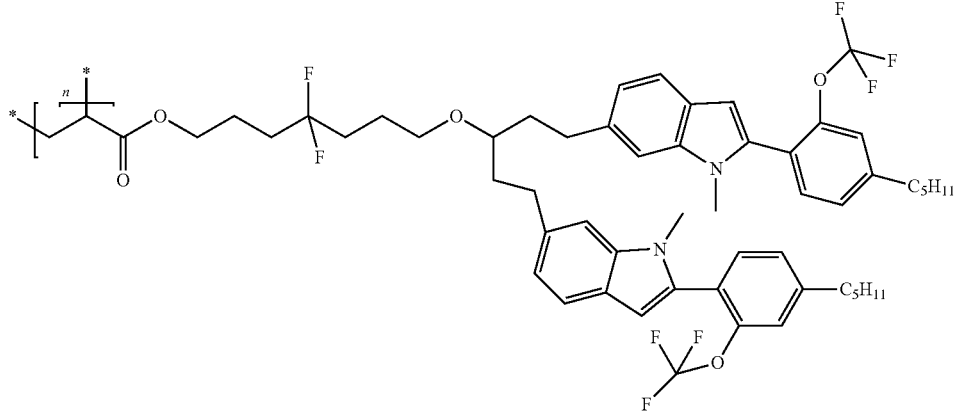
P-144
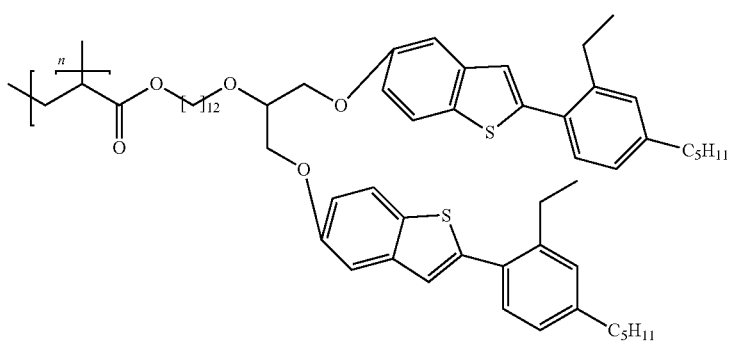
P-145
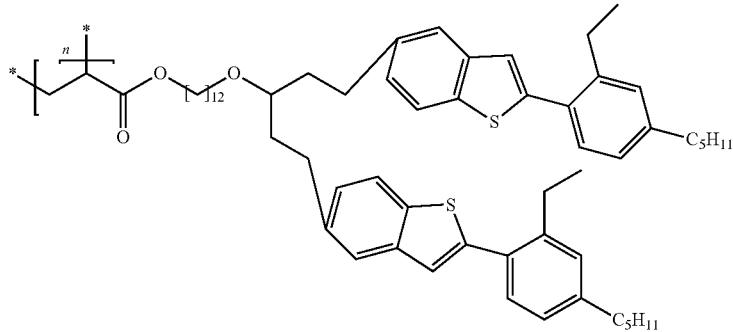
P-146
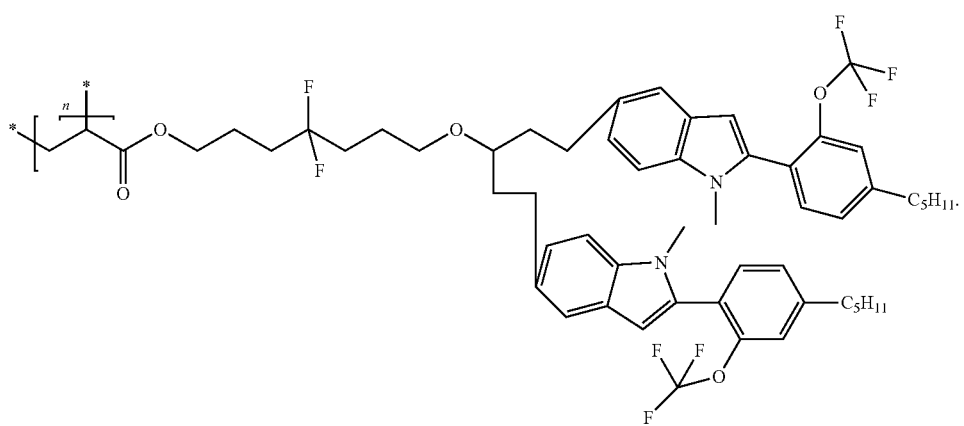
P-147

The letter n gives the degree of polymerization as explained before.

Preferably a co-polymer according to the invention as described before or preferably described before comprises the one or more constitutional units $M^0$ in a molar ratio m1 and the one or more constitutional units $M^2$ in a molar ratio m2, wherein the ratio m1:m2 is at least 0.01 and at most 100.

The oligomers or polymers according to the invention as described before or preferably described may be cross-linked.

The oligomers and polymers of the present invention may be made by any suitable method. It is, however, preferred that the present oligomers and polymers are made by radical polymerization, wherein the polymerization reaction is started by means of a suitable radical polymerization initiator. For the purposes of the present invention the type of radical polymerization initiator is not particularly limited and may be any suitable radical generating compound. Such compounds are well known to the skilled person. Suitable polymerization initiators may be selected from thermal initiators or photoinitiators, i.e. compounds that generate radicals by exposure to heat or irradiation with light of a suitable wavelength. Examples of suitable thermal polymerization initiators may be selected from the groups of compounds comprising one or more peroxide groups, i.e. compounds comprising a group —O—O—, and/or compounds comprising one or more azo groups, i.e. compounds comprising a group —N=N—.

Suitable polymerization initiators comprising one or more peroxide groups may, for example, be selected from the groups consisting of t-butyl(peroxy-2-ethyl-hexanoate), di-(tert-butylcyclohexyl)peroxydicarbonate and benzoylperoxide.

Suitable polymerization initiators comprising one or more azo groups may, for example, be selected from the group consisting of 1,1'-azobis(cyclohexancarbonitrile) and 2,2'azobis(cyclohexanecarbonitrile) (AIBN).

A suitable example of a photoinitiator is dimethylaminobenzoate/camphorquinone.

If a photoinitiator is used as polymerization initiator, it is preferred that the wavelength required to decompose said photoinitiator is different from the wavelength needed to irradiate the compound of the present application so as to change its optical properties.

Preferably, the radical initiators are used in an amount of at least 0.0001 eq and of at most 0.1 eq of the main monomer. Such radical initiators could be thermal initiators, e.g. azobisisobutyronitrile (AIBN) or photochemical initiators like dimethylaminobenzoate/camphorquinone.

The present invention is also directed to a composition comprising at least one compound of formula (I), (I-1), (I-2), (I-3), (I-4), (I-5), (I-6), (I-7), (I-8) or (I-9) as described or preferably described before and/or an oligomer or polymer as described before or preferably described before.

A composition comprising at least one compound of formula (I), (I-1), (I-2), (I-3), (I-4), (I-5), (I-6), (I-7), (I-8) or (I-9) as described or preferably described before and an oligomer or polymer as described before is primarily used for the synthesis of block co-polymers with the condition that the oligomer or polymer has at least one reactive group left which may react with the monomers.

Depending upon the intended use such composition may comprise further different components. Such further components may, for example, be selected from the group consisting of UV absorbers, antioxidants and cross-linkers.

The compositions may include or comprise, essentially consist of or consist of the said requisite or optional constituents. All compounds or components which can be used in the compositions are either known and commercially available or can by synthesized by known processes.

The UV absorber that may be used in the present composition is not particularly limited and can easily be selected from those generally known to the skilled person. Generally suitable UV absorbers are characterized by being unsaturated compounds, preferably compounds comprising one or more selected from group consisting of olefinic groups, aryl groups and heteroaryl groups; these groups may be present in any combination.

Suitable UV-absorbers for use in the present composition may, for example, be selected from those comprising a group selected from benzotriazole, benzophenone and triazine. Suitable UV-absorbers are, for example, disclosed in U.S. Pat. Nos. 5,290,892; 5,331,073 and 5,693,095.

Suitable cross-linkers may be used to impart elastomeric properties to the present composition and the articles produced therewith. Typically any suitable di- or tri-functional monomer may be used as crosslinker.

Preferred cross-linker may be selected from the following group of compounds

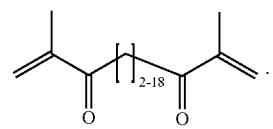

Ethylene glycol dimethacrylate (EGDMA) is particularly preferred.

Suitable antioxidants are phenyl acrylate derivatives bearing a hindered phenol moiety. A preferred antioxidant is

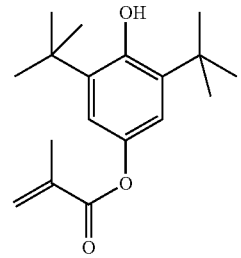

The compounds of formula (I) according to the invention and their oligomers or polymers as described before or preferably described before are particularly well suited for use in optically active devices.

Hence the present invention is also directed to articles e.g. blanks which may be transformed into optically active devices comprising at least one compound of formula (I) as described before or preferably described before or at least one oligomer or polymer as described before or preferably described before.

Preferred articles are blanks which may be transformed into optically active devices or the optically active devices as such. Preferred optically active devices are ophthalmic devices. Examples of such ophthalmic devices include lenses, keratoprostheses, and cornea inlays or rings. More preferably, said article is a blank which may be transformed into an eye-implant or the eye-implant as such. More preferably, said eye-implant is a lens. Most preferably, such article is a blank which may be transformed into an intraocular lens or the intraocular lens as such, which may, for example, be a posterior chamber intraocular lens or an anterior chamber intraocular lens.

A blank of this invention may be produced as a step in the manufacturing process used to create an intraocular lens. For example, without limitation, a manufacturing process may include the steps of polymer synthesis, polymer sheet casting, blank cutting, optic lathe cutting, optic milling, haptic milling or attachment, polishing, solvent extraction, sterilization and packaging.

The present articles according to the invention as described before or preferably described before may be formed by a process comprising the steps of
- providing a composition comprising at least one compound of formula (I) as defined herein and/or an oligomer or polymer as defined herein; and
- subsequently forming the article of said composition.

Intraocular lenses in accordance with the present invention are believed to show particularly advantageous properties in that they are flexible enough so as to be rolled or folded and consequently requiring a much smaller incision for them to be inserted into the eye. It is believed that this will allow for improved healing of the eye, particularly in respect to the time for the eye to heal.

The type of intraocular lens is not limited in any way. It may, for example, comprise one or more optic and one or more haptic components, wherein the one or more optic components serve as lens and the one or more haptic components are attached to the one or more optic components and hold the one or more optic components in place in the eye. The present intraocular lens may be of a one-piece design or of multi-piece design, depending on whether the one or more optic components and the one or more haptic components are formed from a single piece of material (one-piece design) or are made separately and then combined (multi-piece design). The present intraocular lens is also designed in such a way that it allows to be, for example, rolled up or folded small enough so that it fits through an incision in the eye, said incision being as small as possible, for example, at most 3 mm in length.

Additionally, intraocular lenses in accordance with the present invention allow for the non-invasive adjustment of the optical properties, particularly the refractive power, after implantation of the lens into the eye, thus reducing the need for post-surgery vision aids or reducing or totally avoiding follow-up surgery.

In order to change the optical properties and particularly the refractive power of the intraocular lens it is exposed to irradiation having a wavelength of at least 200 nm and of at most 1500 nm. Hence, the present invention is also directed to a process of changing the optical properties of an article as defined or preferably defined herein, said process comprising the steps of
- providing an article as defined herein; and
- subsequently exposing said article to irradiation having a wavelength of at least 200 nm and at most 1500 nm.

Preferably, said irradiation has a wavelength of at least 250 nm or 300 nm, more preferably of at least 350 nm, even more preferably of at least 400 nm, still even more preferably of at least 450 nm, and most preferably of at least 500 nm. Preferably, said irradiation has a wavelength of at most 1400 nm or 1300 nm or 1200 nm or 1100 nm or 1000 nm, more preferably of at most 950 nm or 900 nm, even more preferably of at most 850 nm, still even more preferably of at most 800 nm and most preferably of at most 750 nm.

EXAMPLES

The following examples are intended to show the advantages of the present compounds in a non-limiting way.

Unless indicated otherwise, all syntheses are carried out under an inert atmosphere using dried (i.e. water-free) solvents. Solvents and reagents are purchased from commercial suppliers.

DCM is used to denote dichloromethane. DMF is used to denote dimethylformamide. EE is used to denote ethyl acetate. THF is used to denote tetrahydrofuran.

Co-polymer-properties can be investigated on blanks, prepared by bulk polymerization of the monomers. Co-monomers, cross-linkers and initiators therefore can be purchased from commercial sources. All chemicals are of highest purity available and can be used as received.

Synthesis of Precursor Materials

Example 1

General Remarks & General Synthetic Procedures (GSP 1) for the Synthesis of Acetic Acid 3-phenyl-coumarin-7-yl Ester:

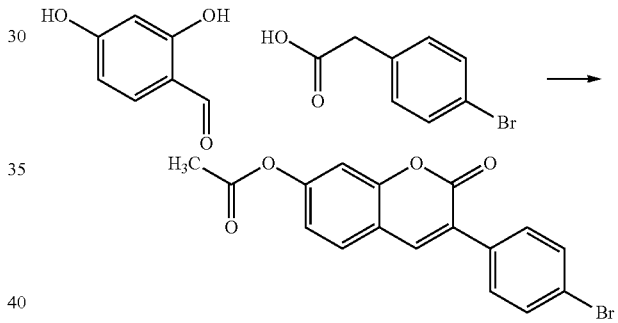

2 g (14.2 mmol) 2,4-Dihydroxy-benzaldehyde and 3.1 g (14.2 mmol) 4 bromophenyl-acetic acid are dissolved in 4.5 ml acetic anhydride and 4.4 ml pyridine. The batch is stirred at 135° C. for 72 h and is then cooled to room temperature. The solid which has precipitated out is filtered off with suction and rinsed neutral with water. The residue is dried at 40° C. in vacuo. The yield of 3-(4-bromophenyl)-2-oxo-2H-chromen-7-yl acetate is 4.9 g (13.6 mmol) (96% of theory).

1H NMR (500 MHz, DMSO-d6) δ 8.31 (s, 1H), 7.82 (d, 1H, J=8.5 Hz), 7.71-7.66 (m, 4H), 7.32 (d, 1H, J=2.0 Hz), 7.20 (dd, 1H, J=8.4 Hz, J=2.1 Hz), 2.32 (s, 3H).

Analogously, other derivatives are prepared in the same manner: $R_1$ means reactant 1, $R_2$ means reactant 2, [P] means product

| No. | | | Yield [%] |
|---|---|---|---|
| 1a | R1 | 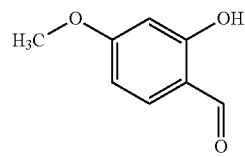 | |

-continued
| No. | | | Yield [%] |
|---|---|---|---|
| | R2 | 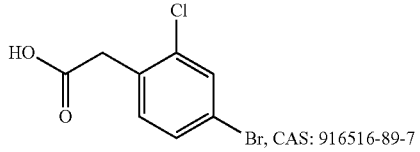 Br, CAS: 916516-89-7 | |
| | [P] | 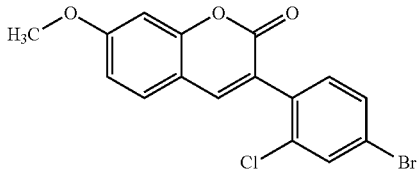 | 68 |
| 1b | R1 | 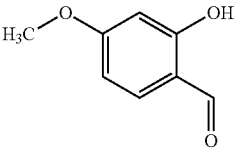 | |
| | R2 | 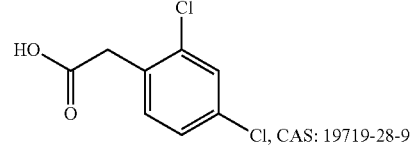 Cl, CAS: 19719-28-9 | |
| | [P] | 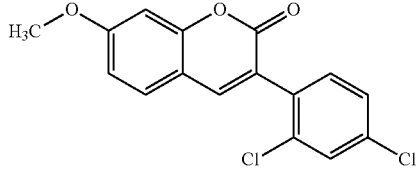 [SMILES: COc1ccc2cc(-c3ccc(Cl)cc3Cl)c(=O)oc2c1] | 89 |
| 1c | R1 | 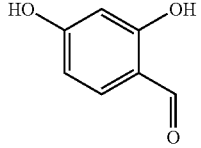 | |
| | R2 | 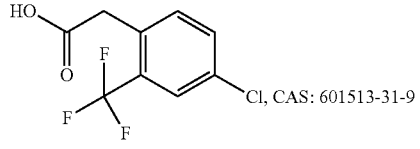 Cl, CAS: 601513-31-9 | |
| | [P] | 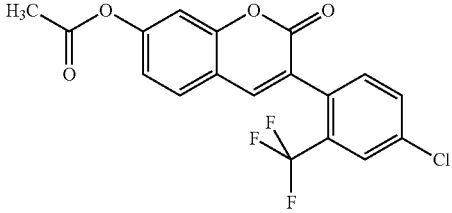 [SMILES: CC(=O)Oc1ccc2cc(-c3ccc(Cl)cc3C(F)(F)F)c(=O)oc2c1] | 57 |
| 1d | R1 | 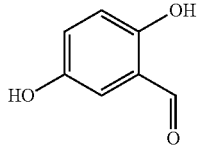 | |

-continued
| No. | | | Yield [%] |
|---|---|---|---|
| | R2 | 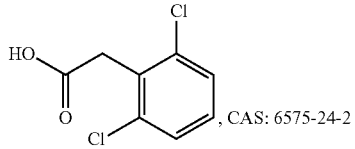, CAS: 6575-24-2 | |
| | [P] | 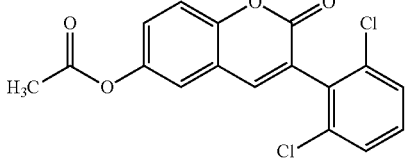 | 73 |
| 1e | R1 | 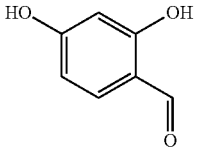 | |
| | R2 | 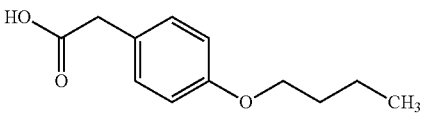 | |
| | [P] | 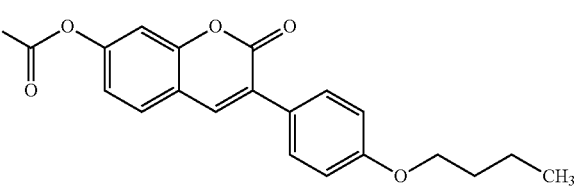 | 99 |
| 1f | R1 | 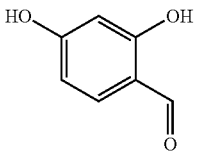 | |
| | R2 | 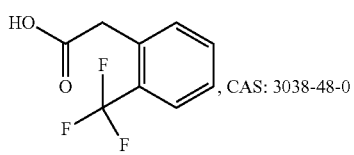, CAS: 3038-48-0 | |
| | [P] | 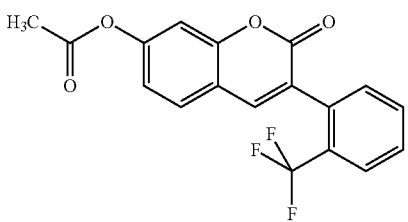 | 64 |
| 1g | R1 | 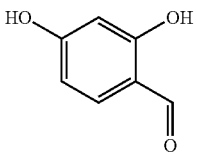 | |

-continued
| No. | | | Yield [%] |
|---|---|---|---|
| | R2 | 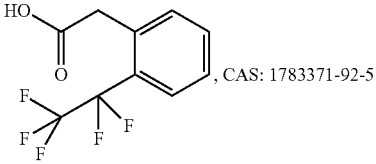 , CAS: 1783371-92-5 | |
| | [P] | 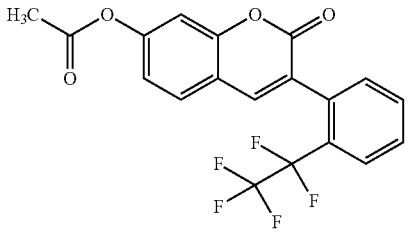 [SMILES: CC(=O)Oc1ccc2cc(-c3ccccc3C(F)(F)C(F)(F)F)c(=O)oc2c1] | 69 |
| 1h | R1 | 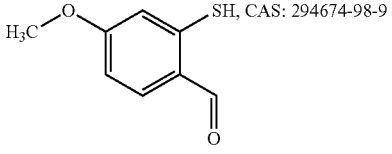 SH, CAS: 294674-98-9 | |
| | R2 | 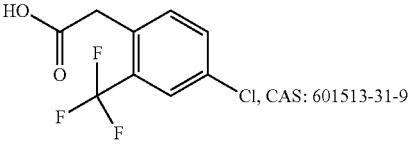 Cl, CAS: 601513-31-9 | |
| | [P] | 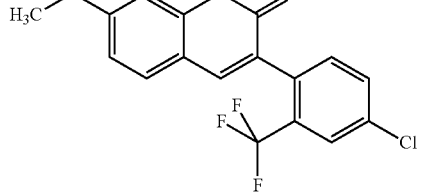 | 60 |
| 1i | R1 | 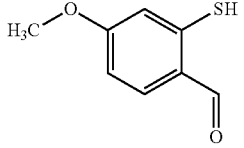 | |
| | R2 | 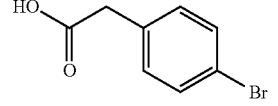 | |
| | [P] | 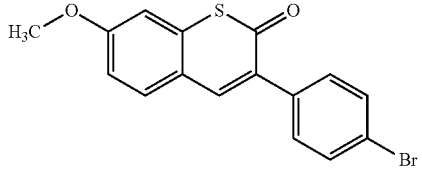 [SMILES: COc1ccc2cc(-c3ccc(Br)cc3)c(=O)sc2c1] | 65 |

-continued

| No. | | | Yield [%] |
|---|---|---|---|
| 1j | R1 | 2,4-dihydroxybenzaldehyde | |
| | R2 | 2-(4-bromo-2-(trifluoromethoxy)phenyl)acetic acid | |
| | [P] | 3-(4-bromo-2-(trifluoromethoxy)phenyl)-2-oxo-2H-chromen-7-yl acetate | 69 |
| 1k | R1 | 2,4-dihydroxybenzaldehyde | |
| | R2 | 2-(2-(trifluoromethoxy)phenyl)acetic acid | |
| | [P] | 2-oxo-3-(2-(trifluoromethoxy)phenyl)-2H-chromen-7-yl acetate | 75 |
| 1l | R1 | 2,4-dihydroxybenzaldehyde | |
| | R2 | 2-(4-(trifluoromethoxy)phenyl)acetic acid | |

| No. | | | Yield [%] |
|---|---|---|---|
| | [P] | (7-acetoxy-3-(4-(trifluoromethoxy)phenyl)-2H-chromen-2-one) | 91 |
| 1m | R1 | 2,4-dihydroxybenzaldehyde | |
| | R2 | 4-hydroxyphenylacetic acid | |
| | [P] | (7-acetoxy-3-(4-acetoxyphenyl)-2H-chromen-2-one) | 69 |
| 1n | R1 | 2,4-dihydroxybenzaldehyde | |
| | R2 | 2-(5-bromo-2-methoxyphenyl)acetic acid | |
| | [P] | (7-acetoxy-3-(5-bromo-2-methoxyphenyl)-2H-chromen-2-one) | 67 |

-continued

| No. | | | Yield [%] |
|---|---|---|---|
| 1o | R1 | 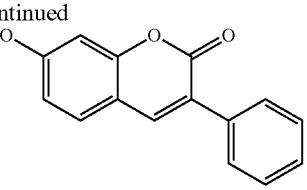 | |
| | R2 | (2-methoxy-4-bromo-phenylacetic acid structure) | |
| | [P] | (7-acetoxy-3-(2-methoxy-4-bromophenyl)coumarin structure) | 58 |
| 1p | R1 | (4-formyl-3-hydroxyphenyl dimethylthiocarbamate structure), CAS: 1356543-46-8 | |
| | R2 | (4-chloro-2-trifluoromethylphenylacetic acid structure), CAS: 601513-31-9 | |
| | [P] | (7-acetylthio-3-(4-chloro-2-trifluoromethylphenyl)coumarin structure) | 62 |

Example 2

General Remarks & General Synthetic Procedures (GSP 2) for the Deprotection of the Acetate Derivative to the Phenol Derivative:

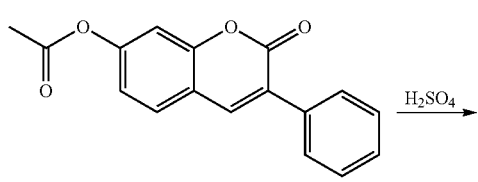

-continued (7-hydroxy-3-phenyl-coumarin structure)

7.0 mmol acetic acid 3-phenyl-coumarin-7-yl ester are suspended in a mixture of 14 ml ethanol and 10 ml sulfuric acid (20%, aq.) and refluxed for 2 h. The batch is then cooled to room temperature, and the precipitated solid is filtered off with suction and rinsed neutral with water. The yield is 6.8 mmol, 97% of theory.

1H NMR (500 MHz, DMSO-d6) δ 10.59 (s, 1H), 8.16 (s, 1H), 7.70 (dd, 2H, J=7.3 Hz, J=1.7 Hz), 7.61 (d, 1H, J=8.5

Hz), 7.45 (t, 2H, J=7.5 Hz), 7.39 (t, 1H, J=7.3 Hz), 6.83 (dd, 1H, J=8.5 Hz, J=2.2 Hz), 6.77 (d, 1H, J=2.2 Hz).

Analogously, other 7-hydroxy-3-phenyl-coumarin derivatives are prepared in the same manner:

| No. | Reactant | Product | Yield [%] |
|---|---|---|---|
| 2a | | | 99 |
| 2b | | | 90 |
| 2c | | | 89 |
| 2d | | | 99 |
| 2e | | | 80 |
| 2f | | | 59 |
| 2g | | | 75 |

-continued

| No. | Reactant | Product | Yield [%] |
|---|---|---|---|
| 2h | 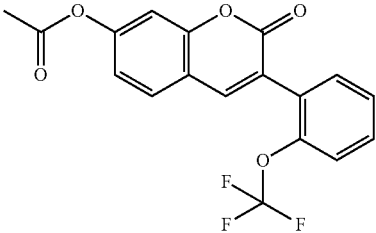 [SMILES: CC(=O)Oc1ccc2cc(-c3ccccc3OC(F)(F)F)c(=O)oc2c1] | 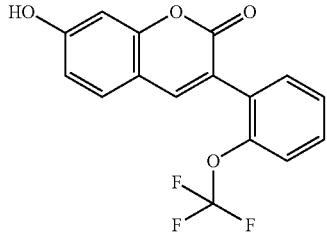 [SMILES: O=c1oc2cc(O)ccc2cc1-c1ccccc1OC(F)(F)F] | 89 |

Example 3

General Remarks & General Synthetic Procedures (GSP 3) for the Suzuki Coupling of Halogenated 2-oxo-3-phenyl-2H-chromen-7-yl Acetate Derivatives:

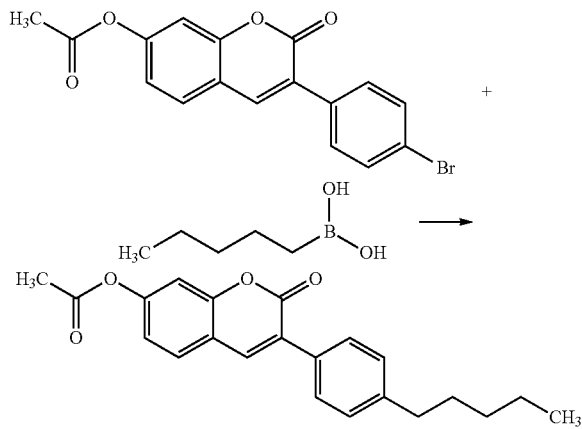

3.0 g (8.4 mmol) of acetic acid 3-(4-bromophenyl)-coumarin-7-yl ester, 1.0 g (8.8 mmol) of n-pentylboronic acid and 3.7 g (17.5 mmol) of tri-potassium phosphate trihydrate are dissolved in 80 ml of toluene and degassed. 171 mg (0.4 mmol) of 2-dicyclohexylphoshino-2',6'-dimethoxy-1,1'-biphenyl [S-Phos] and 47 mg (0.2 mmol) of palladium(II) acetate are added. The reaction mixture is subsequently stirred at 110° C. for 24 h under a protective-gas atmosphere. The cooled solution is diluted with ethyl acetate and washed with water, dried and evaporated. The product is purified by column chromatography on silica gel (heptane/ethyl acetate). Yield: 2.5 g (7.1 mmol), 85% of theory.

Under the basic conditions, deprotection of the acetate group to the corresponding phenol could be observed during several Suzuki coupling reactions. To complete the deprotection step, the crude organic phase after workup is refluxed with a 1:2 mixture sulfuric acid (~20%):ethanol until completion. Then column chromatography of the obtained residue, as described above, is done.

1H NMR (500 MHz, DMSO-d6) δ 8.23 (s, 1H), 7.81 (d, 1H, J=8.4 Hz), 7.64 (d, 2H, J=8.2 Hz), 7.34-7.25 (m, 3H), 7.18 (dd, 1H, J=8.4 Hz, J=2.2 Hz), 7.20 (dd, 1H, J=8.4 Hz, J=2.1 Hz), 2.62 (t, 2H, J=7.6 Hz), 2.32 (s, 3H), 1.64-1.58 (m, 2H), 1.37-1.24 (m, 4H), 0.87 (t, 3H, J=7.0 Hz).

Analogously, other Suzuki derivatives are prepared in the same manner:

R1 means reactant 1, R2 means reactant 2, [P] means product

| No. | | | Yield [%] |
|---|---|---|---|
| 3a | R1 | 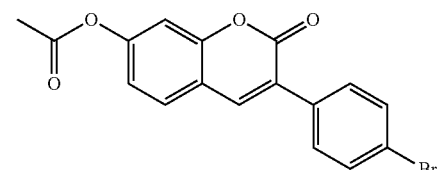 | |
| | R2 | 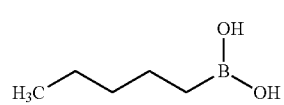 | |
| | [P] | 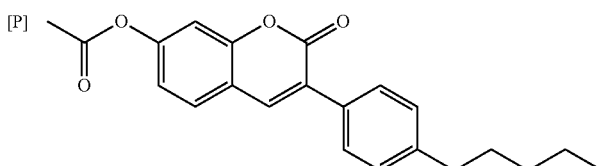 | 85 |

| No. | | | Yield [%] |
|---|---|---|---|
| 3b | R1 | 7-acetoxy-3-(4-chloro-2-(trifluoromethyl)phenyl)-2H-chromen-2-one | |
| | R2 | pentylboronic acid (H₃C-(CH₂)₄-B(OH)₂) | |
| | [P] | 7-acetoxy-3-(4-pentyl-2-(trifluoromethyl)phenyl)-2H-chromen-2-one | 94 |
| 3c | R1 | 3-(4-bromophenyl)-7-methoxy-2H-thiochromen-2-one | |
| | R2 | pentylboronic acid | |
| | [P] | 7-methoxy-3-(4-pentylphenyl)-2H-thiochromen-2-one | 92 |
| 3d | R1 | 3-(4-bromo-2-ethylphenyl)-7-methoxy-2H-chromen-2-one | |
| | R2 | pentylboronic acid | |
| | [P] | 3-(2-ethyl-4-pentylphenyl)-7-methoxy-2H-chromen-2-one | 90 |

-continued
| No. | | | Yield [%] |
|---|---|---|---|
| 3e | R1 | 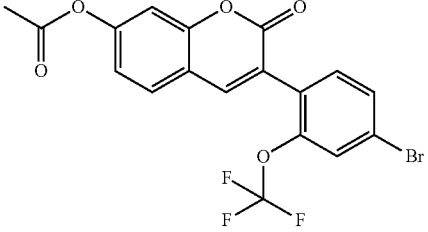 [SMILES: CC(=O)Oc1ccc2cc(-c3ccc(Br)cc3OC(F)(F)F)c(=O)oc2c1] | |
| | R2 | 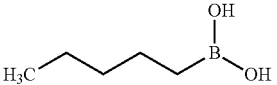 | |
| | [P] | 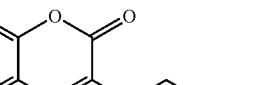 | 90 |
| 3f | R1 | 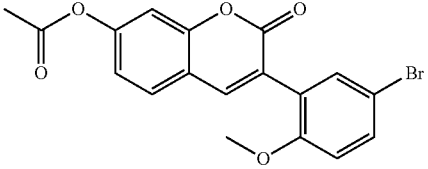 [SMILES: COc1ccc(Br)cc1-c1cc2ccc(OC(C)=O)cc2oc1=O] | |
| | R2 | 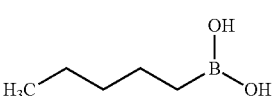 | |
| | [P] | 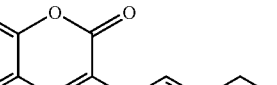 | 95 |
| 3g | R1 | 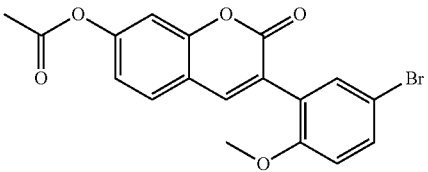 [SMILES: COc1ccc(Br)cc1-c1cc2ccc(OC(C)=O)cc2oc1=O] | |
| | R2 |  | |
| | [P] | 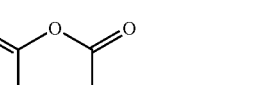 | 84 |

| No. | | | Yield [%] |
|---|---|---|---|
| 3h | R1 | 7-acetyloxy-3-(4-bromo-2-(trifluoromethoxy)phenyl)-2H-chromen-2-one | |
| | R2 | ethylboronic acid (H₃C-CH₂-B(OH)₂) | |
| | [P] | 7-hydroxy-3-(4-ethyl-2-(trifluoromethoxy)phenyl)-2H-chromen-2-one | 95 |
| 3i | R1 | 7-methoxy-3-(2,4-dichlorophenyl)-2H-chromen-2-one | |
| | R2 | ethylboronic acid (H₃C-CH₂-B(OH)₂) | |
| | [P] | 7-methoxy-3-(2,4-diethylphenyl)-2H-chromen-2-one | 28 |
| 3j | R1 | 7-methoxy-3-(2-bromo-4-(trifluoromethyl)phenyl)-2H-chromen-2-one | |
| | R2 | ethylboronic acid (H₃C-CH₂-B(OH)₂) | |

| No. | | Yield [%] |
|---|---|---|
| [P] | 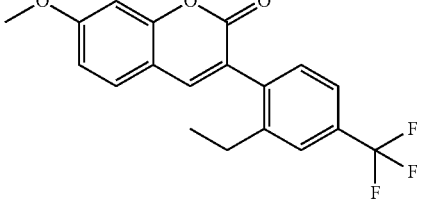 | 79 |
| 3k R1 | 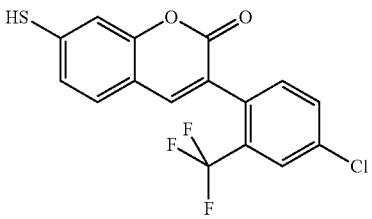 [SMILES: O=c1oc2cc(S)ccc2cc1-c1ccc(Cl)cc1C(F)(F)F] | |
| R2 | 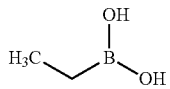 | |
| [P] | 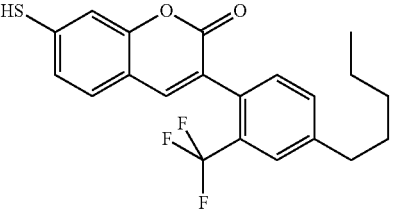 [SMILES: CCCCCc1ccc(-c2cc3ccc(S)cc3oc2=O)c(C(F)(F)F)c1] | 62 |

Example 4

General Remarks & General Synthetic Procedures (GSP 4) for the Deprotection of the Methyl Ether Derivatives to the Corresponding Phenol Derivatives:

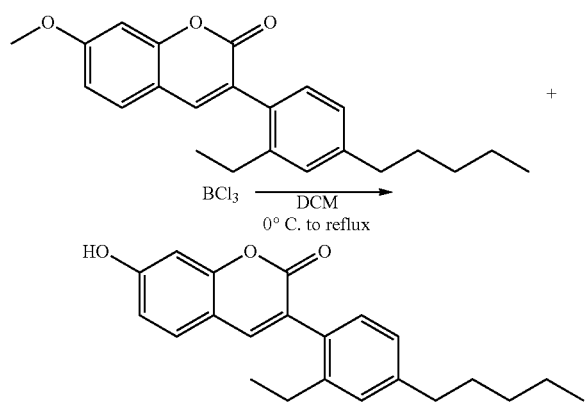

To a solution of 3-(2-ethyl-4-pentylphenyl)-7-methoxy-2H-chromen-2-one (300 mg, 0.973 mmol) in 10 ml DCM is added $BCl_3$ (2.0 equiv.) at 0° C. The solution is warmed to room temperature overnight and refluxed for additional one hour. After cooling down the reaction mixture to room temperature, it is poured on an ice/water mixture, extracted with EE, dried with $MgSO_4$ and evaporated. The residue is purified via column chromatography using heptane/EE as eluent. 182.3 mg (0.51 mmol) of 3-(2-ethyl-4-pentylphenyl)-7-hydroxy-2H-chromen-2-one is isolated (83% of theory).

Alternatively, the deprotection of the methylethers may be done in the presence of $BBr_3$.

1H NMR (500 MHz, DMSO-d6) δ 10.58 (s, 1H), 7.85 (s, 1H), 7.54 (d, 2H, J=8.5 Hz), 7.16-7.06 (m, 3H), 7.10 (d, 1H, j=2.2 Hz), 6.81 (dd, 1H, J=8.5 Hz, J=2.3 Hz), 6.76 (d, 1H, J=2.3 Hz), 2.63 (q, 2H, J=7.6 Hz), 2.49-2.45 (m, 2H), 1.21 (t, 3H, J=7.6 Hz), 1.07 (t, 3H, J=7.5 Hz).

Analogously, other phenol derivatives are prepared in the same manner:

| No. | Reactant 1 | Product | Yield [%] |
|---|---|---|---|
| 4a | (7-methoxy-coumarin with 2-ethyl-4-trifluoromethylphenyl) | (7-hydroxy-coumarin with 2-ethyl-4-trifluoromethylphenyl) | Quant. |
| 4b | (7-methoxy-coumarin with 2,4-diethylphenyl) | (7-hydroxy-coumarin with 2,4-diethylphenyl) | 83 |
| 4c | (7-methoxy-coumarin with 2-(pentafluoroethyl)phenyl) | (7-hydroxy-coumarin with 2-(pentafluoroethyl)phenyl) | 75 |

Example 5

General Remarks & General Synthetic Procedures (GSP 5) for the Synthesis of 1,3-Bis(3-[4-pentyl-2-trifluoromethylphenyl]coumarin-7-yl]oxy-glycerol:

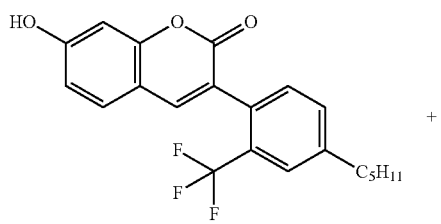

+

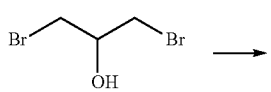

→

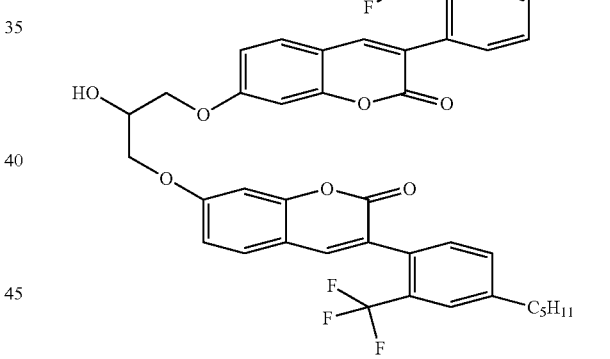

A mixture of 7-hydroxy-3-(4-pentyl-2-trifluoromethylphenyl)coumarin (4.15 g; 11.0 mmol), 1,3-dibromo-2-propanol (562 μl; 5.5 mmol) and potassium carbonate (761 mg; 5.5 mmol) in ethanol (3.22 ml; 55.1 mmol) is heated under reflux for 48 h. After cooling to room temperature, the precipitate is filtered and evaporated to dryness. The residual oil is purified by column chromatography on silica gel (heptane/ethyl acetate [1/0-2/1]) to yield 1,3-Bis(3-[4-pentyl-2-trifluoromethylphenyl]coumarin-7-yl]oxy-glycerol (2.77 g; 3.4 mmol; 62% of theory).

$^1$H NMR (500 MHz, DMSO-d6) δ 7.96 (s, 2H), 7.68 (d, J=8.7 Hz, 2H), 7.64 (s, 2H), 7.57 (d, J=8.0 Hz, 2H), 7.44 (d, J=7.9 Hz, 2H), 7.12 (d, J=2.3 Hz, 2H), 7.05 (dd, J=8.6, 2.4 Hz, 2H), 5.57 (d, J=4.6 Hz, 1H), 4.30-4.18 (m, 5H), 2.75-2.69 (m, 4H), 1.64 (p, J=7.5 Hz, 4H), 1.39-1.28 (m, 8H), 0.89 (t, J=7.0 Hz, 6H).

Analogously, other derivatives are prepared in the same manner:

R1 means reactant 1, R2 means reactant 2, [P] means product

| No. | | | Yield [%] |
|---|---|---|---|
| 5a | R1 | 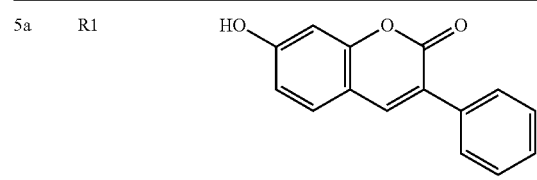 | |
| | R2 | 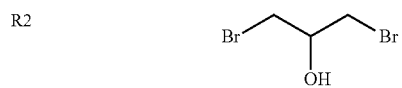 | |
| | [P] | 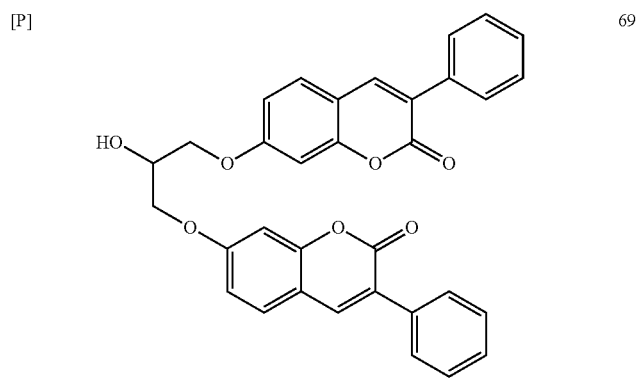 | 69 |
| 5b | R1 | 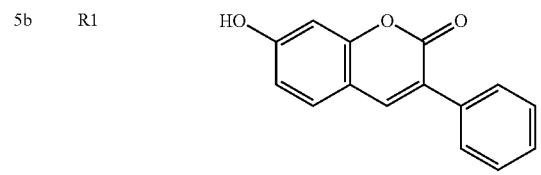 | |
| | R2 | 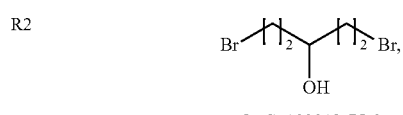
CAS: 128813-75-2 | |
| | [P] | 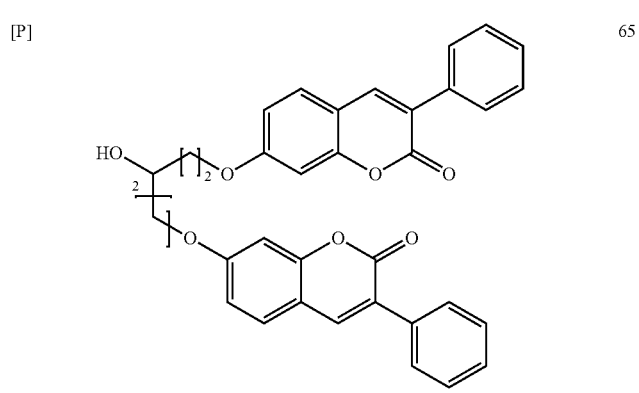 | 65 |
| 5c | R1 | 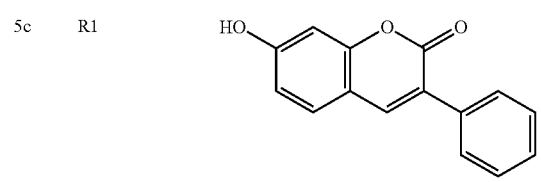 | |

| No. | | | Yield [%] |
|---|---|---|---|
| | R2 |  CAS: 861322-73-8 | |
| | [P] | 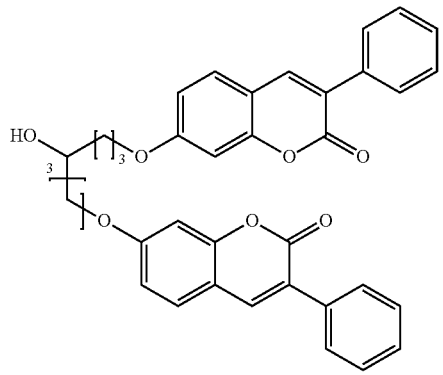 | 52 |
| 5d | R1 | 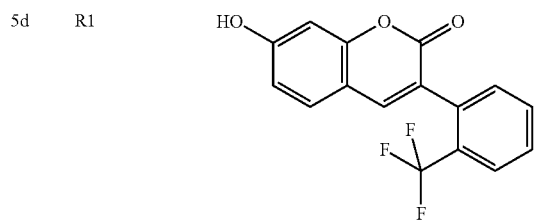 | |
| | R2 | 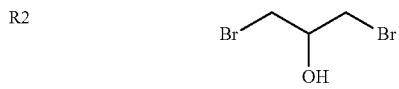 | |
| | [P] | 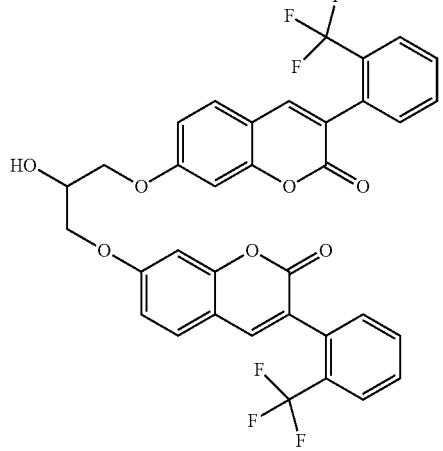 | 55 |
| 5e | R1 | 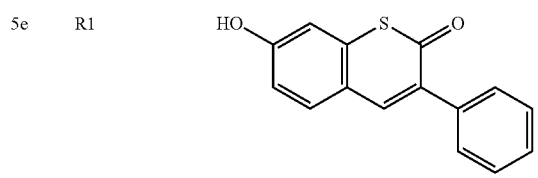 | |
| | R2 | 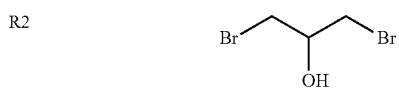 | |

| No. | | | Yield [%] |
|---|---|---|---|
| | [P] | 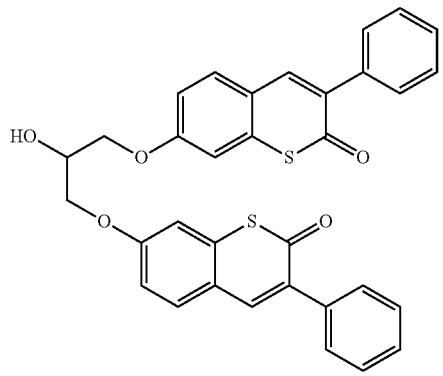 [SMILES: O=c1sc2cc(OCC(O)COc3ccc4cc(-c5ccccc5)c(=O)sc4c3)ccc2cc1-c1ccccc1] | 71 |
| 5f | R1 | 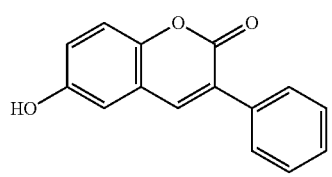 | |
| | | CAS: 6468-47-9 | |
| | R2 | 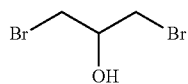 | |
| | [P] | 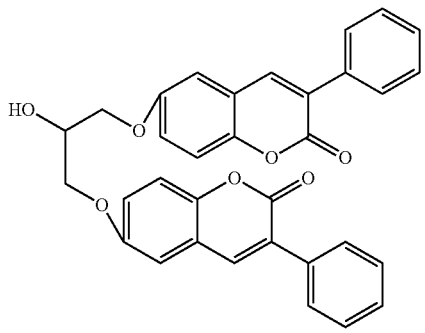 [SMILES: O=c1oc2ccc(OCC(O)COc3ccc4oc(=O)c(-c5ccccc5)cc4c3)cc2cc1-c1ccccc1] | 52 |
| 5g | R1 | 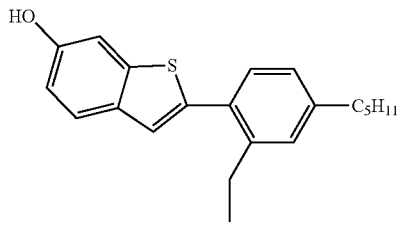 | |
| | R2 | 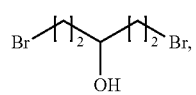 | |
| | | CAS: 128813-75-2 | |

| No. | | Yield [%] |
|---|---|---|
| [P] | 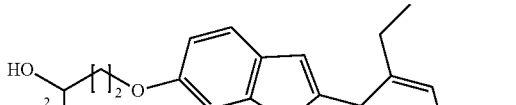 | 43 |

1,3-Bis(3-phenylcoumarin)-7-yloxy-glycerol

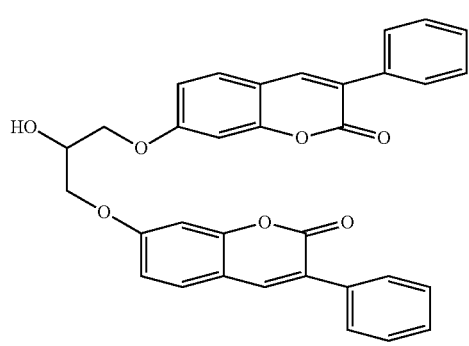 [SMILES: O=c1oc2cc(OCC(O)COc3ccc4cc(-c5ccccc5)c(=O)oc4c3)ccc2cc1-c1ccccc1]

$^1$H NMR (500 MHz, DMSO-d6) δ 8.20 (s, 2H), 7.73-7.68 (m, 6H), 7.45 (t, J=7.4 Hz, 4H), 7.40 (t, J=7.3 Hz, 2H), 7.08 (d, J=2.3 Hz, 2H), 7.04 (dd, J=8.6, 2.4 Hz, 2H), 5.57 (d, J=4.6 Hz, 1H), 4.29-4.17 (m, 5H).

1,3-Bis(2-(trifluoromethyl)phenyl]coumarin)-7-yloxy-glycerol

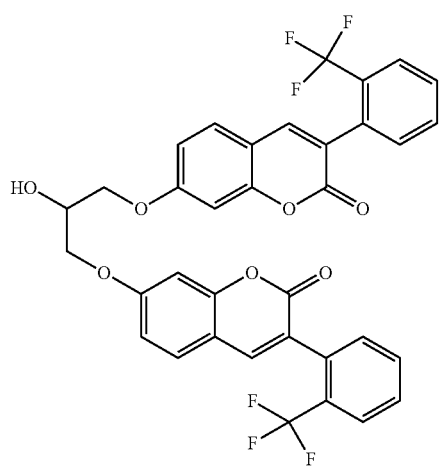 [SMILES: O=c1oc2cc(OCC(O)COc3ccc4cc(-c5ccccc5C(F)(F)F)c(=O)oc4c3)ccc2cc1-c1ccccc1C(F)(F)F]

$^1$H NMR (500 MHz, DMSO-d6) δ 8.00 (s, 2H), 7.85 (d, J=7.8 Hz, 2H), 7.76 (t, J=7.5 Hz, 2H), 7.72-7.65 (m, 4H), 7.56 (d, J=7.6 Hz, 2H), 7.14 (d, J=2.3 Hz, 2H), 7.06 (dd, J=8.6, 2.4 Hz, 2H), 5.61 (d, J=4.6 Hz, 1H), 4.31-4.18 (m, 5H).

Example 6

General Remarks & General Synthetic Procedures (GSP 5.2) for the Synthesis of 3-phenylcoumarin-7-yl trifluoromethanesulfonate:

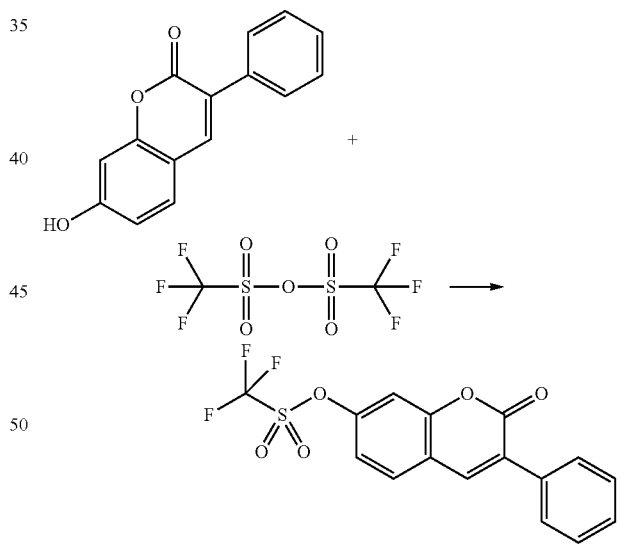

A solution of trifluoromethanesulfonic anhydride (4.50 ml; 27.3 mmol) in dichloromethane (anhydrous) (6.70 ml; 104.9 mmol) is added dropwise to a stirring solution of 7-hydroxy-3-phenylcoumarin (5.00 g; 21.0 mmol) and triethylamine (8.82 ml; 63.0 mmol) in dichloromethane (anhydrous) (26.80 ml; 419.7 mmol) at ca. 0° C. for 1 h. The solidified reaction is quenched with water. The mixture is stirred for 10 min and allowed to warm to room temperature. The solid is filtered off and recrystallized from 2-propanol to afford 3-phenylcoumarin-7-yl trifluoromethanesulfonate (6.60 g; 17.8 mmol; 85% of theory).

$^1$H NMR (500 MHz, DMSO-d6) δ 8.33 (s, 1H), 7.99 (d, J=8.7 Hz, 1H), 7.81 (d, J=2.4 Hz, 1H), 7.74 (dd, J=8.2, 1.4 Hz, 2H), 7.56 (dd, J=8.6, 2.4 Hz, 1H), 7.53-7.44 (m, 3H).

Analogously, other derivatives are prepared in the same manner:

R1 means reactant 1, [P] means product

Example 7

General Remarks & General Synthetic Procedures (GSP 5.3) for the Synthesis of 7-[3-hydroxy-5-[3-[4-pentyl-2-(trifluoromethyl)phenyl]coumarin-7-yl]penta-1,4-diynyl]-3-[4-pentyl-2-(trifluoromethyl)phenyl]coumarin:

| No. | | Yield [%] |
|---|---|---|
| 6a | R1 | |
| | [P] | 84 |
| 6b | R1 | |
| | [P] | 91 |
| 6c | R1 | |
| | [P] | 93 |

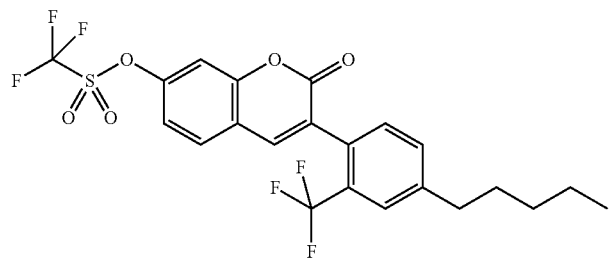 [SMILES: CCCCCc1ccc(-c2cc3ccc(OS(=O)(=O)C(F)(F)F)cc3oc2=O)c(C(F)(F)F)c1]
+
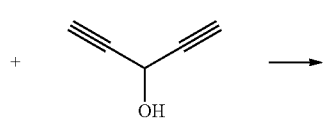
→

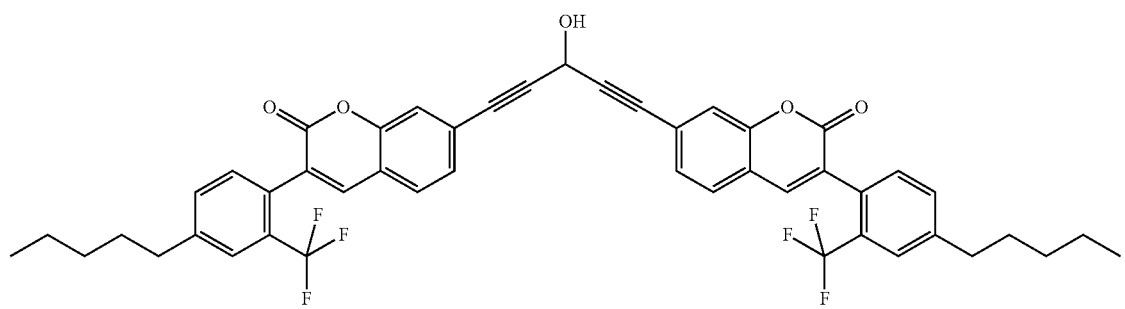

3-(4-Pentyl-2-(trifluoromethyl)phenyl)coumarin-7-yl trifluoromethanesulfonate (20.00 g; 39.34 mmol) is dissolved in tetrahydrofuran (anhydrous) (79.67 ml; 983.42 mmol) and diisopropylamine (13.27 ml; 94.41 mmol), then argon is passed through the solution for 5 minutes. The solution is heated to 50° C. Bis(triphenylphosphine)palladium chloride (1.38 g; 1.97 mmol), copper(I) iodide (114.67 mg; 590.05 μmol) and penta-1,4-diyn-3-ol (1.82 g; 21.64 mmol) are added under argon and the reaction is stirred until TLC showed complete consumption of the starting material. The reaction is quenched with water, diluted with Methyl-tert-butylether, washed with HCl, water and brine, dried over $MgSO_4$ and evaporated. The residue is purified by column chromatography on silica gel (heptane/ethyl acetate, 4/1) to yield 7-[3-hydroxy-5-[3-[4-pentyl-2-(trifluoromethyl)phenyl]coumarin-7-yl]penta-1,4-diynyl]-3-[4-pentyl-2-(trifluoromethyl)phenyl]coumarin (24.45 g; 30.7 mmol; 78%).

Analogously, other derivatives are prepared in the same manner:

R1 means reactant 1, $R_2$ means reactant 2, [P] means product

| No. | | | Yield [%] |
|---|---|---|---|
| 7a | R1 | ![structure] | |
| | R2 | ![structure] | |
| | [P] | ![structure] | 64 |

| No. | | Yield [%] |
|---|---|---|
| 7b | R1 (7-trifluoromethylsulfonyloxy-3-(4-pentylphenyl)coumarin) | |
| | R2 (penta-1,4-diyn-3-ol) | |
| | [P] bis-coumarin diyne dimer | 91 |
| 7c | R1 (7-trifluoromethylsulfonyloxy-3-[4-pentyl-2-(trifluoromethoxy)phenyl]coumarin) | |
| | R2 (penta-1,4-diyn-3-ol) | |
| | [P] bis-coumarin diyne dimer with OCF₃ | 86 |

Example 8

General Remarks & General Synthetic Procedures (GSP 5.4) for the Synthesis of 7-[3-Hydroxy-5-[3-[4-pentyl-2-(trifluoromethyl)phenyl]coumarin-7-yl]pentyl]-3-[4-pentyl-2-(trifluoromethyl)phenyl]coumarin:

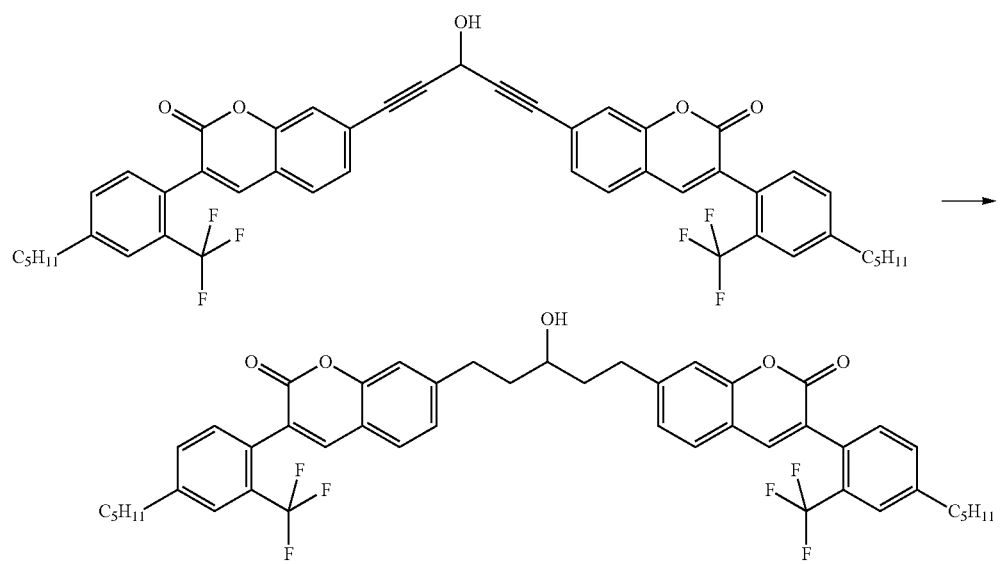

7-[3-Hydroxy-5-[3-[4-pentyl-2-(trifluoromethyl)phenyl]coumarin-7-yl]penta-1,4-diynyl]-3-[4-pentyl-2-(trifluoromethyl)phenyl]coumarin (20.00 g; 25.10 mmol) and palladium on charcoal (6 g; 56 mmol) are stirred in tetrahydrofuran (140 ml; 983.42 mmol) under hydrogen atmosphere over night. The reaction is filtered and evaporated. The residue is purified by column chromatography on silica gel (heptane/ethyl acetate, 4/1) to yield 7-[3-Hydroxy-5-[3-[4-pentyl-2-(trifluoromethyl)phenyl]coumarin-7-yl]pentyl]-3-[4-pentyl-2-(trifluoromethyl)phenyl]coumarin (18.99 g; 23.6 mmol; 94%).

Analogously, other derivatives are prepared in the same manner:

R1 means reactant 1, [P] means product

| No. | | | Yield [%] |
|---|---|---|---|
| 8a | R1 | ![structure] | |
| | [P] | ![structure] | 95 |
| 8b | R1 | ![structure] | |

| No. | | Yield [%] |
|---|---|---|
| | [P] (bis-coumarin with central OH, C5H11 substituents) | 93 |
| 8c | R1 (bis-coumarin with diyne-OH linker, OCF3 and C5H11 substituents) | 35 |
| | [P] (bis-coumarin with central OH linker, OCF3 and C5H11 substituents) | 95 |

Example 9

General Remarks & General Synthetic Procedures (GSP 6) for the Synthesis of 1,3-bis(7-[2-(trifluoromethyl)phenyl] coumarin)-yloxy-2-(dodecan-12-ol)-glycerol-ether:

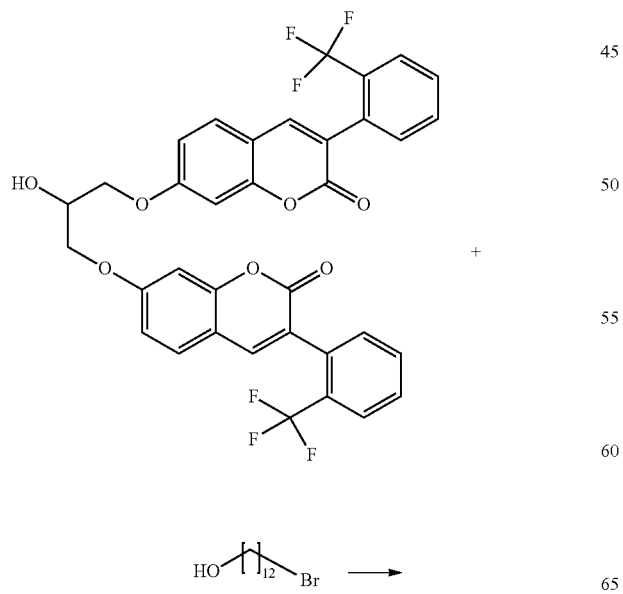

+

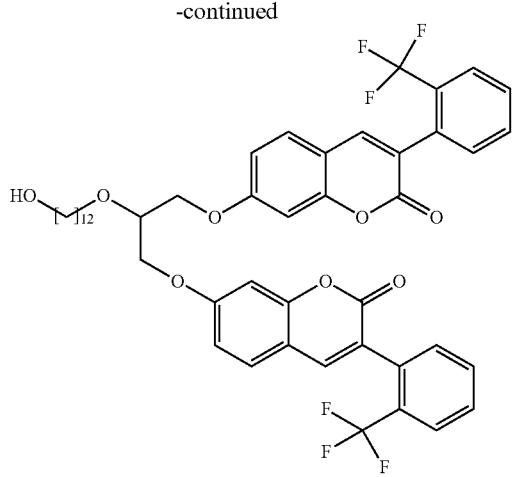

To a solution of 1,3-bis(2-(trifluoromethyl)phenyl]coumarin)-7-yloxy-glycerol (200 mg; 302 μmol) in tetrahydrofuran (2.42 ml; 29.9 mmol) is added sodium hydride (60% in mineral oil) (23.9 mg; 630 mmol) under an atmosphere of argon. Then 12-bromo-dodecan-1-ol (83.3 mg; 310 mmol) in THF is added dropwise to the reaction mixture at room temperature. The reaction mixture is heated to 85° C. Work-up by column chromatography on silica gel yields 1,3-bis(7-[2-(trifluoromethyl)phenyl]coumarin)-yloxy-2-(dodecan-12-ol)-glycerol-ether (100 mg; 125 μmol; 39% of theory).

Analogously, other derivatives are prepared in the same manner: R1 means reactant 1, $R_2$ means reactant 2, [P] means product

| No. | | | Yield [%] |
|---|---|---|---|
| 9a | R1 | | |
| | R2 | | |
| | [P] | | 46 |
| 9b | R1 | | |
| | R2 | | |

-continued
| No. | | Yield [%] |
|---|---|---|
| [P] | 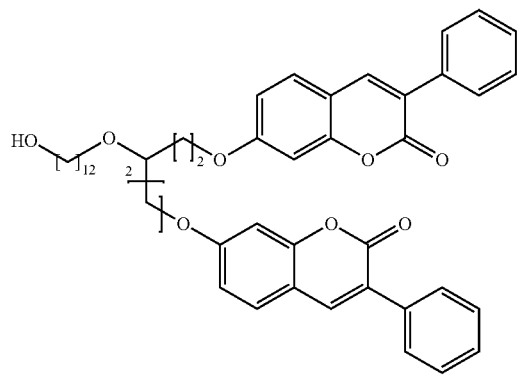 | 59 |
| 9c | R1 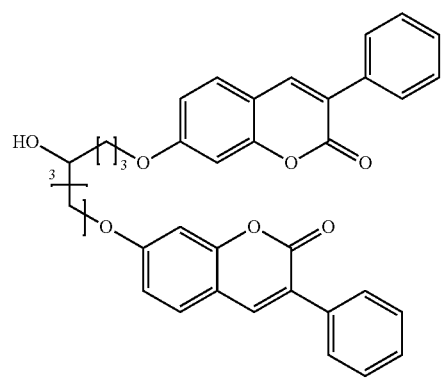 | |
| | R2 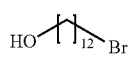 | |
| [P] | 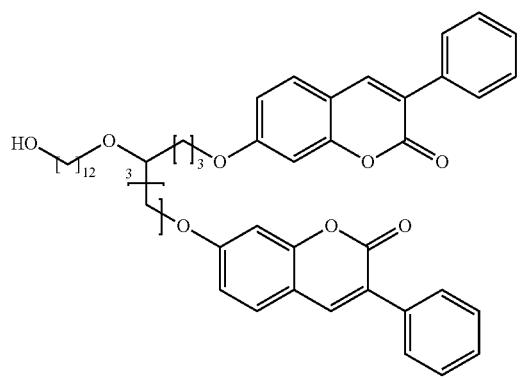 | 37 |

| No. | | | Yield [%] |
|---|---|---|---|
| 9d | R1 | 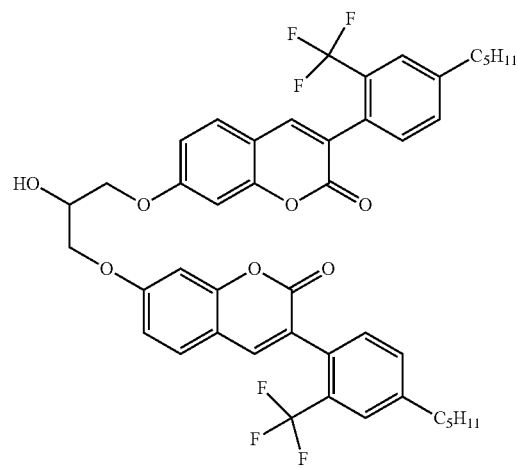 | |
| | R2 | 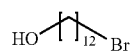 | |
| | [P] | 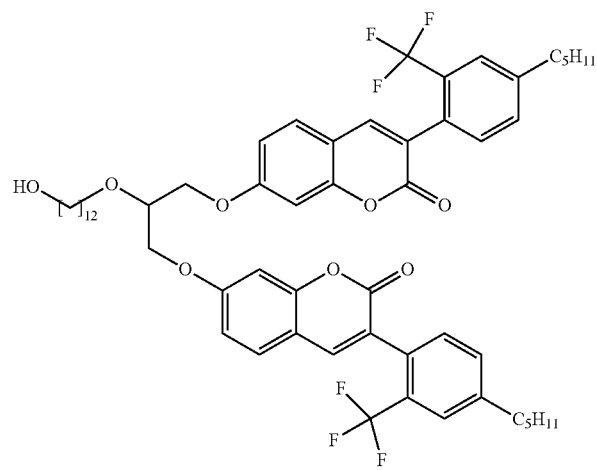 | 65 |
| 9e | R1 | 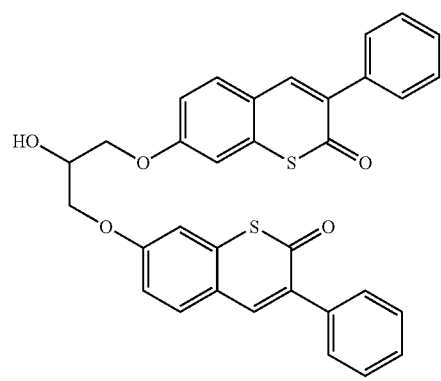 [SMILES: O=c1sc2cc(OCC(O)COc3ccc4cc(-c5ccccc5)c(=O)sc4c3)ccc2cc1-c1ccccc1] | |
| | R2 | 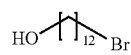 | |

| No. | | Yield [%] |
|---|---|---|
| | [P] 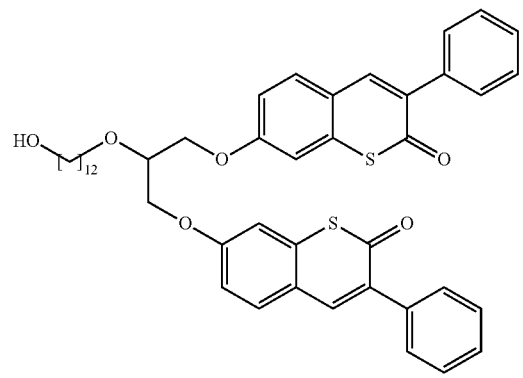 | 24 |
| 9f | R1 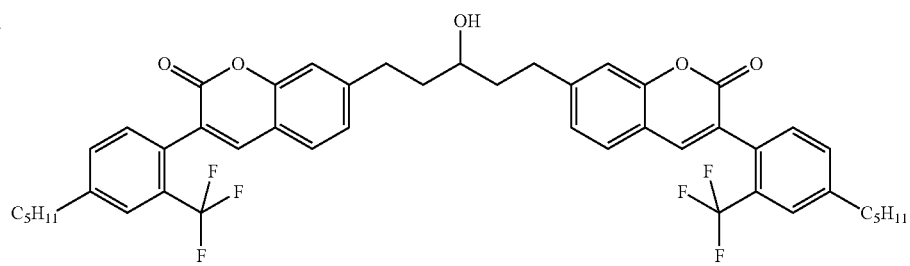 | |
| | R2 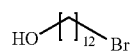 | |
| | [P] 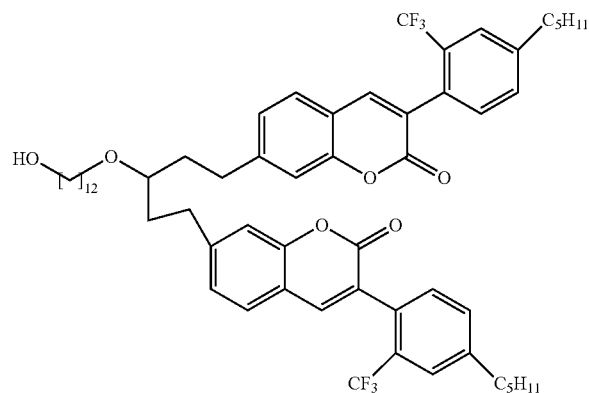 | 63 |
| 9g | R1 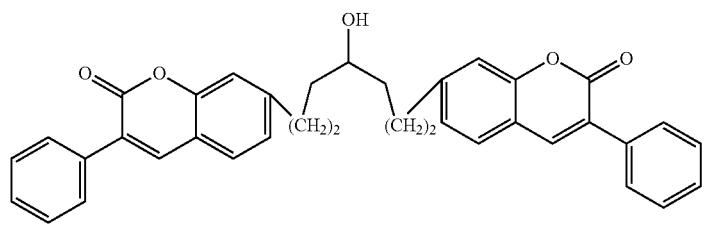 | |
| | R2 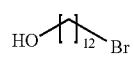 | |

US 11,001,576 B2
253 254
-continued
| No. | | Yield [%] |
|---|---|---|
| | [P] 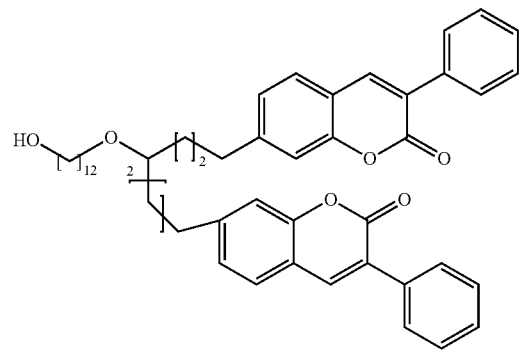 | 54 |
| 9h | R1 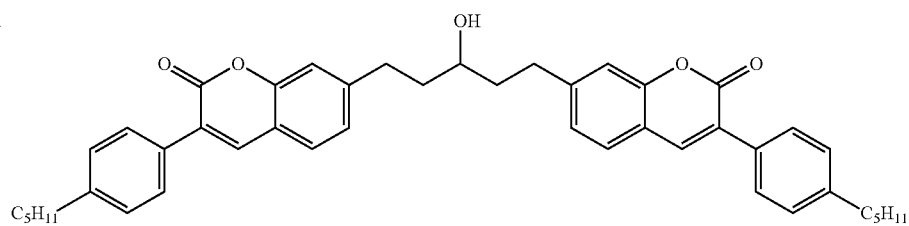 | |
| | R2 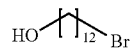 | |
| | [P] 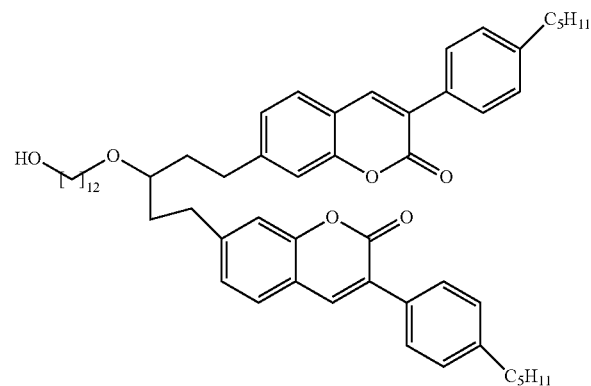 | 77 |
| 9i | R1 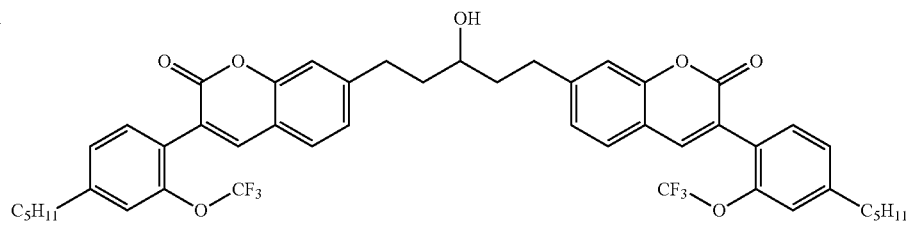 | |
| | R2 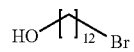 | |

-continued
| No. | | | Yield [%] |
|---|---|---|---|
| | [P] | 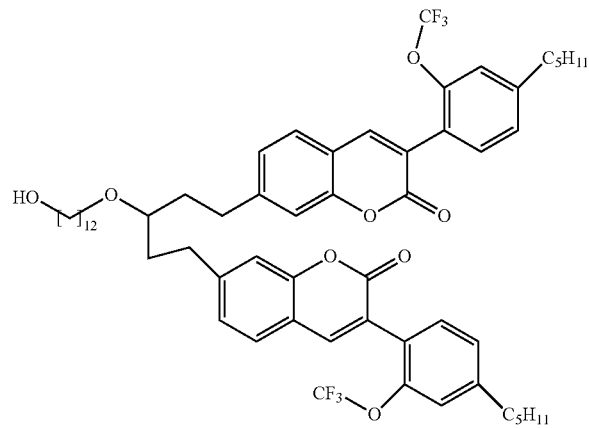 | 71 |
| 9k | R1 | 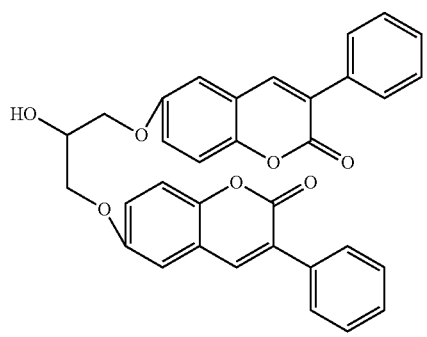 [SMILES: O=c1oc2ccc(OCC(O)COc3ccc4oc(=O)c(-c5ccccc5)cc4c3)cc2cc1-c1ccccc1] | |
| | R2 | 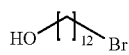 | |
| | [P] | 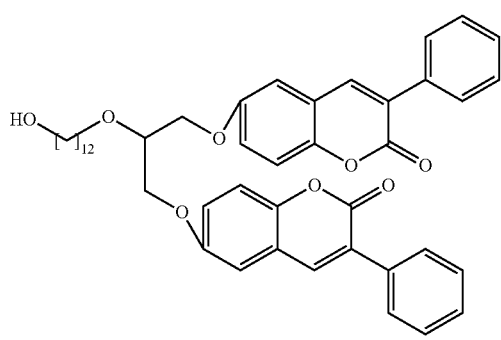 | 59 |
| 9l | R1 | 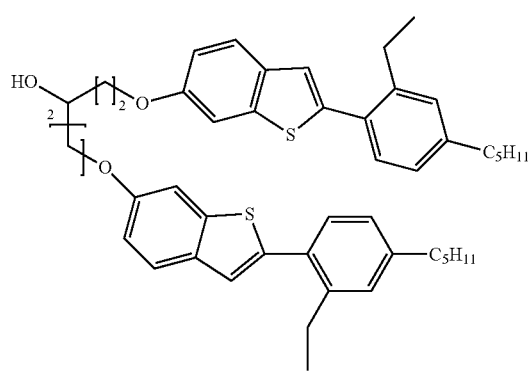 | |

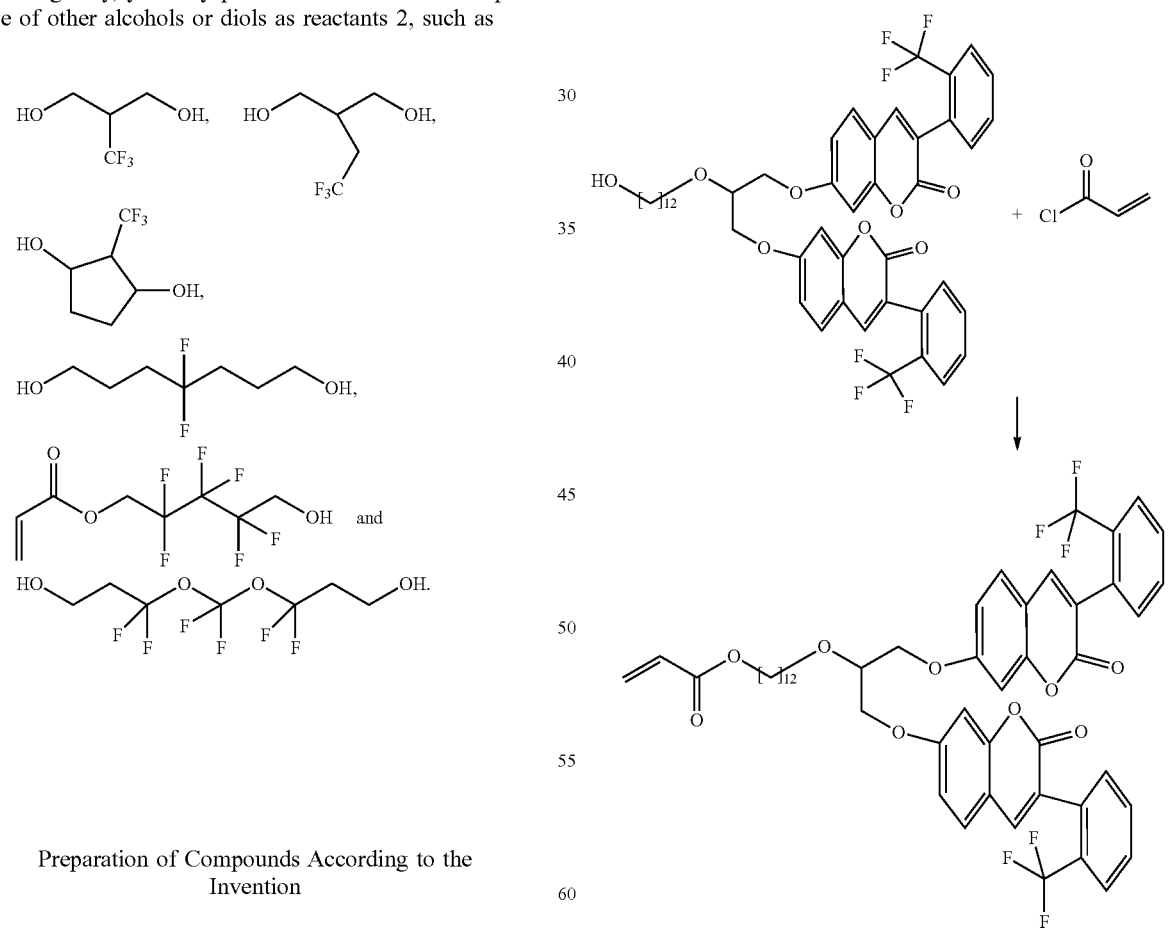

Analogously, you may perform the reaction in the presence of other alcohols or diols as reactants 2, such as Preparation of Compounds According to the Invention Example 10

General Remarks & General Synthetic Procedures (GSP 7) for the Esterification with Acryloyl Chloride or Methacryloyl Chloride to the Corresponding Monomer:

The corresponding aliphatic alcohol is dissolved in dry THF and the solution is cooled with an ice-bath. Triethylamine (4.00 equivs.) is added and the solution is stirred for a few minutes. Then acryloyl chloride or methacryloyl chloride (1.05-2.00 equivs.) is added at ice-bath temperature, while precipitating a colourless solid. The solution is stirred for several hours and is monitored via TLC. Upon completion of the reaction, the suspension is filtrated and washed with THF. The filtrate is evaporated under reduced pressure and purified via column chromatography using cyclohexane/ethyl acetate.

Analogously, other phenol derivatives are prepared in the same manner with acryloyl chloride or methacryloyl chloride: R means reactant, [P] means product

| No. | | Yield [%] |
|---|---|---|
| 10a | R | |
| | [P] | |
| 10b | R | |

| No. | | Yield [%] |
|---|---|---|
| | [P] 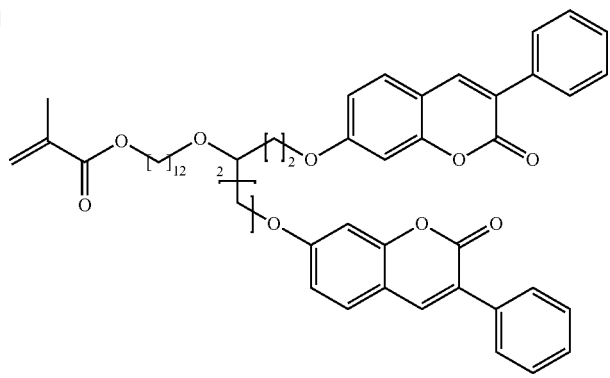 | |
| 10c | R 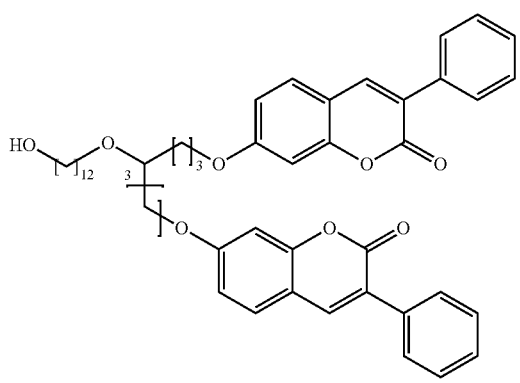 | |
| | [P] 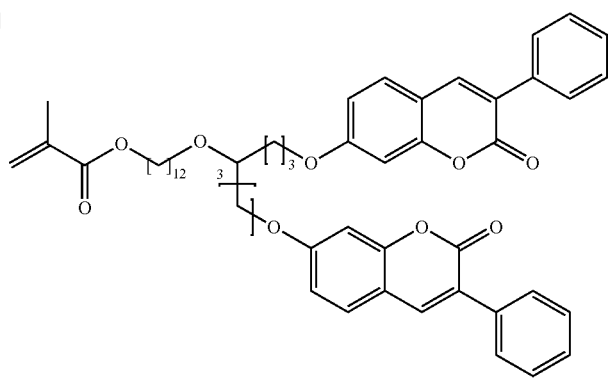 | |
| 10d | R 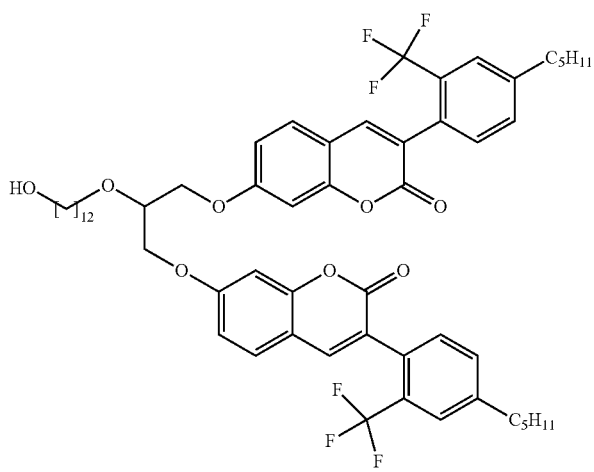 | |

| No. | Yield [%] |
|---|---|
[P]
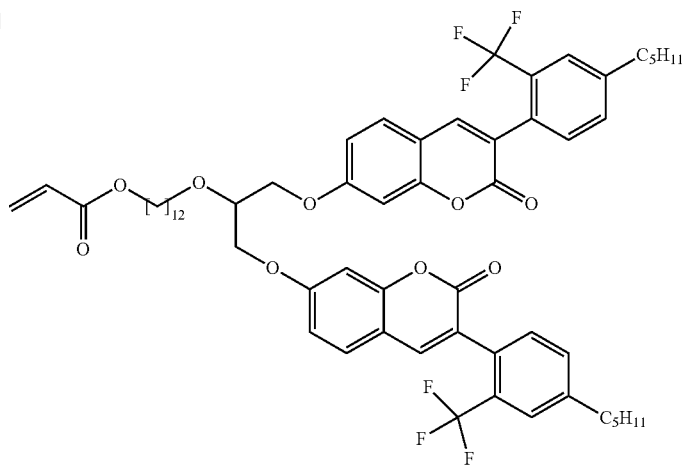
10e R
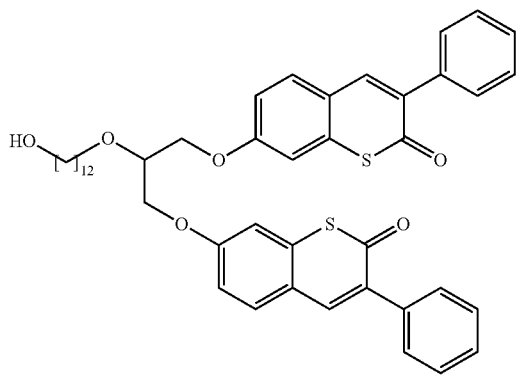
[P]
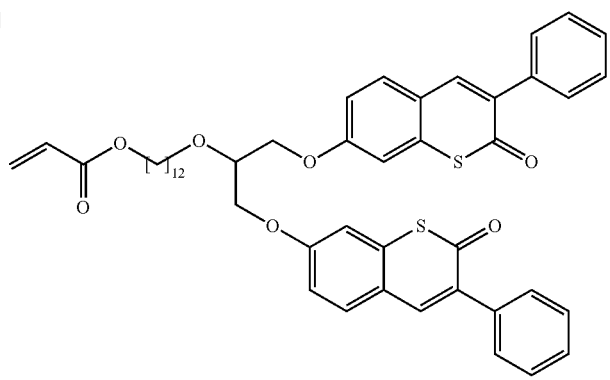

| No. | | Yield [%] |
|---|---|---|
| 10f | R 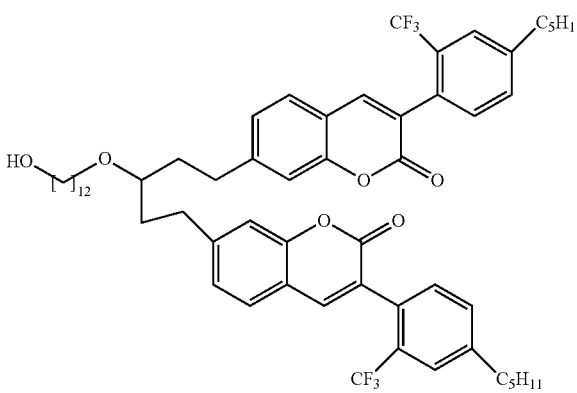 | |
| | [P] 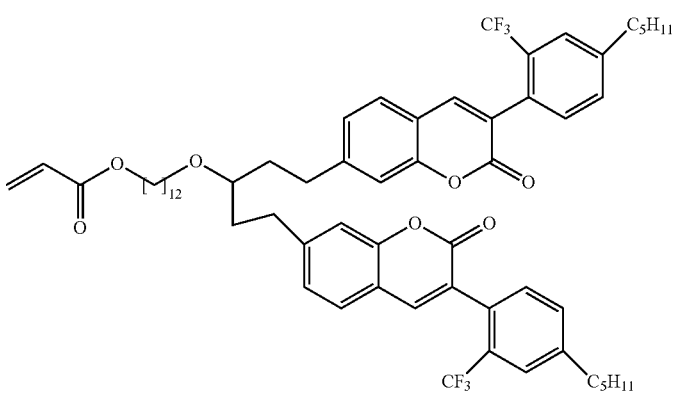 | 84 |
| 10g | R 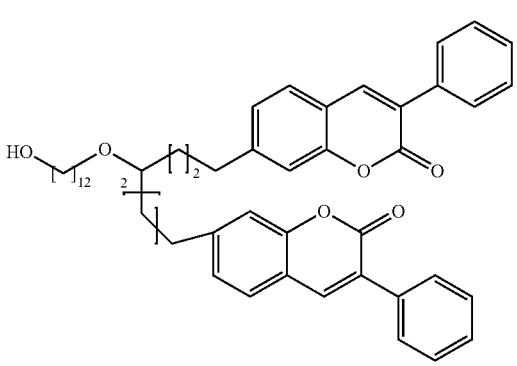 | 54 |
| | [P] 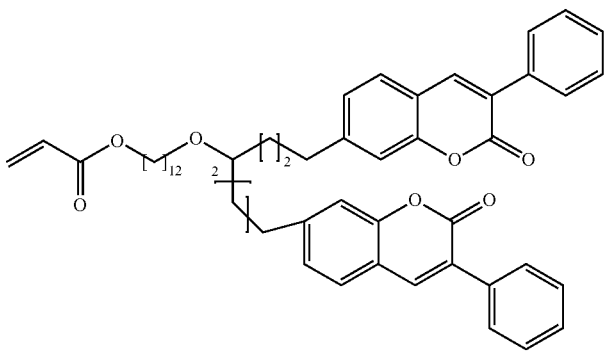 | |

| No. | | Yield [%] |
|---|---|---|
| 10h | R 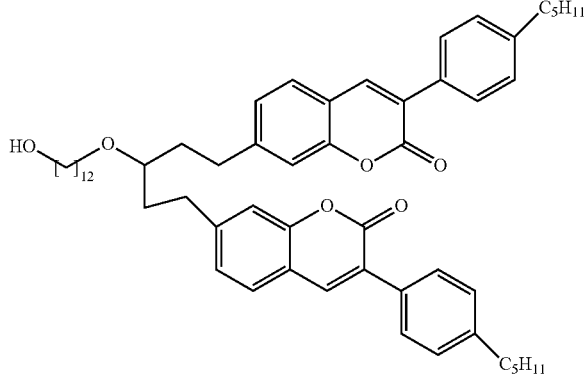 | 77 |
| [P] | 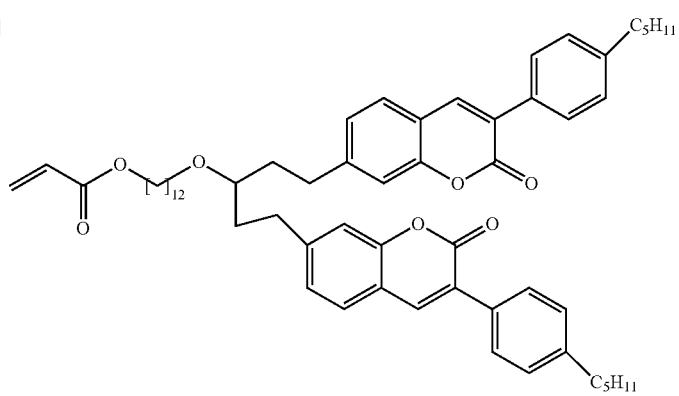 | |
| 10i | R 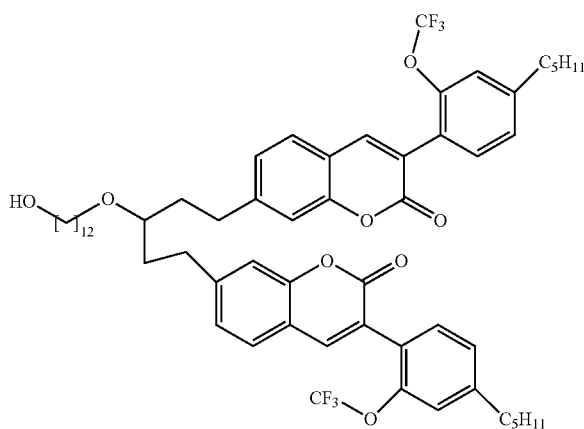 | |

-continued
| No. | | Yield [%] |
|---|---|---|
| | [P] 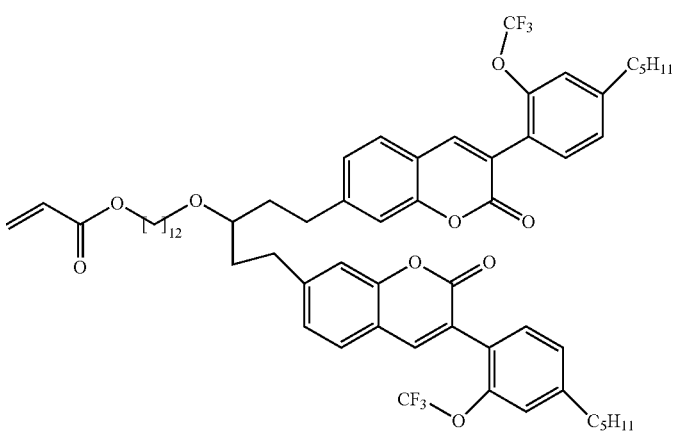 | 82 |
| 10k | R 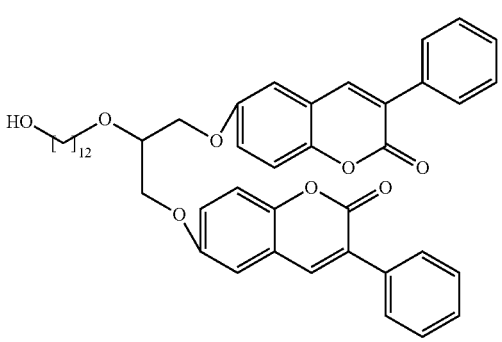 | |
| | [P] 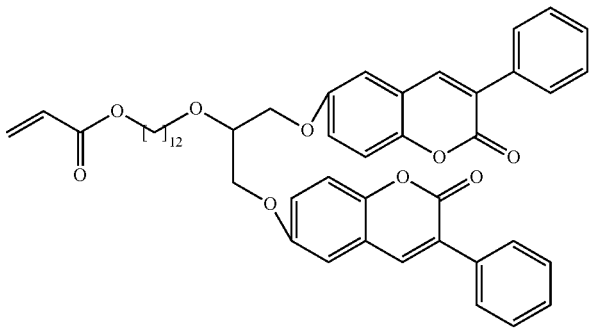 | 93 |
| 10l | R 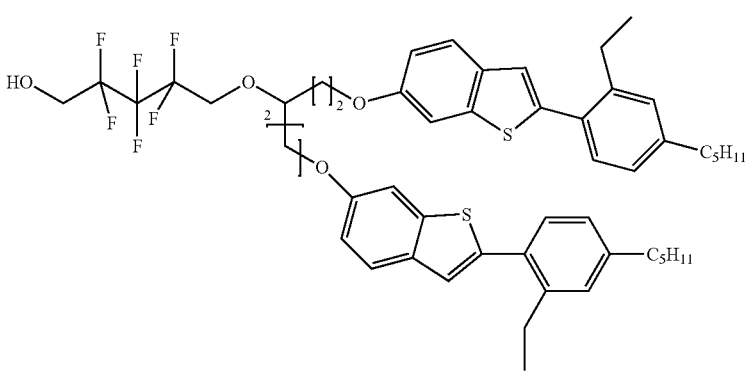 | |

| No. | | Yield [%] |
|---|---|---|
| [P] | (structure shown) | 89 |

Example 11

General Remarks & General Synthetic Procedures (GSP 8) for the Solvent Polymerization of the Monomers:

The corresponding monomer is dissolved in dry N,N-dimethylformamide in a Schlenck-tube with a stirring bar. The solution is degassed performing three times freeze-evacuate-thaw cycles. After that, azoisobutyronitrile (AIBN, 0.05 equiv.) is added in one portion to the degassed solution, which is heated up to 65° C. in an oil bath for a minimum of three days. The solution is cooled to room temperature and is then poured dropwise into cold methanol (100 ml methanol/100 mg monomer) while stirring. The precipitated polymer is collected on a frit or the solution is centrifuged several times to obtain the final polymer material.

Examples of polymers within this invention are given in the following table:

| No. | | |
|---|---|---|
| 11a | (structure shown) | M-003 |
| | (structure shown) | P-003 |

-continued
| No. | | |
|---|---|---|
| 11b | 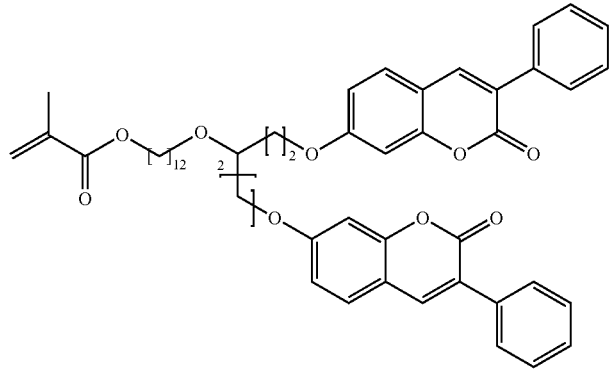 | M-053 |
| | 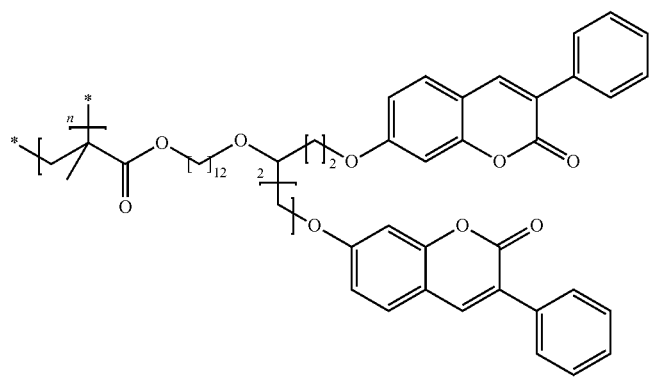 | P-053 |
| 11c | 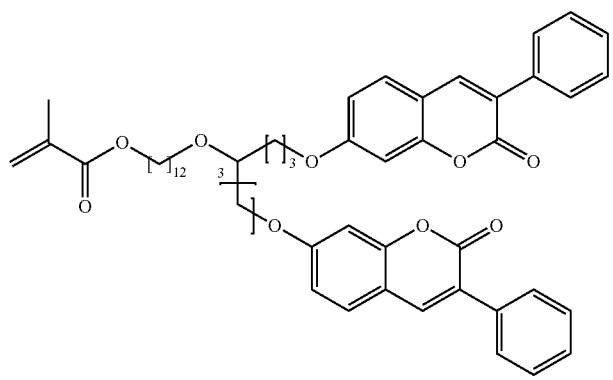 | M-100 |
| | 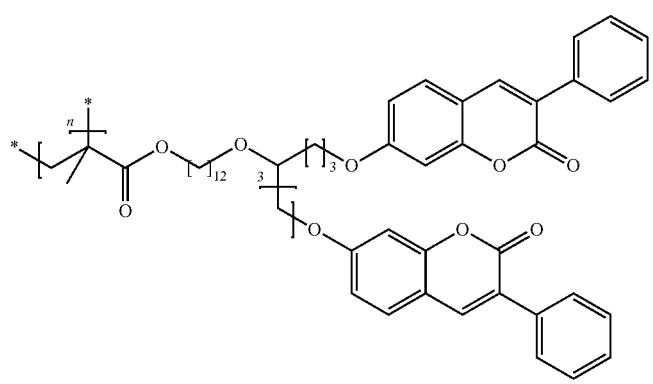 | P-100 |

-continued
| No. | | |
|---|---|---|
| 11d | 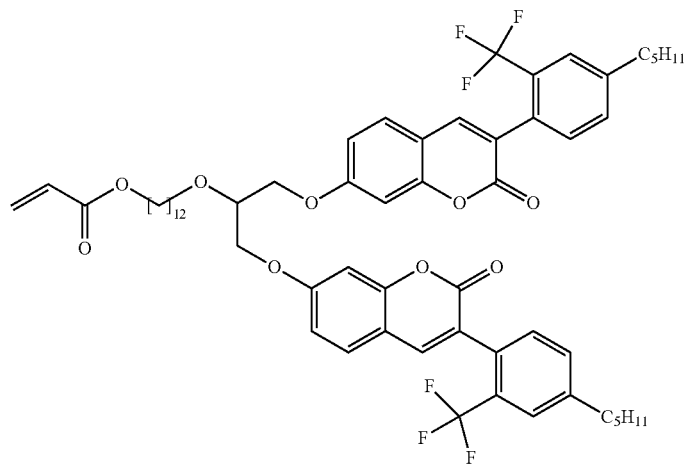 | M-005 |
| | 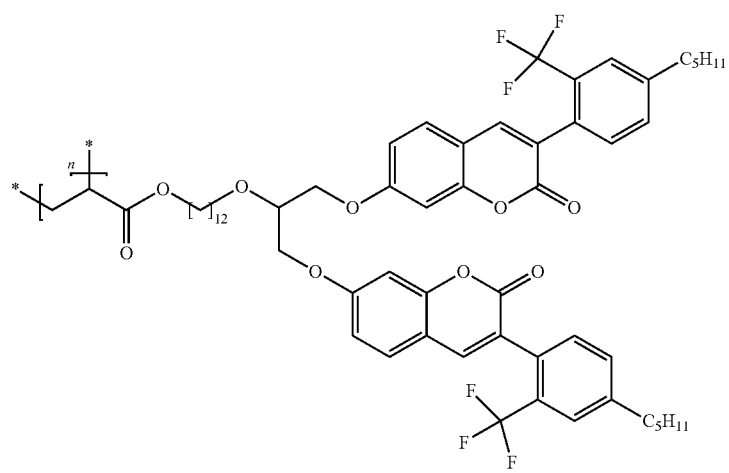 | P-005 |
| 11e | 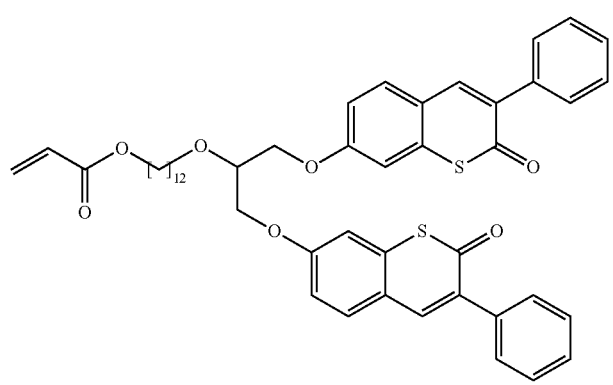 | M-037 |

-continued
| No. | | |
|---|---|---|
| | 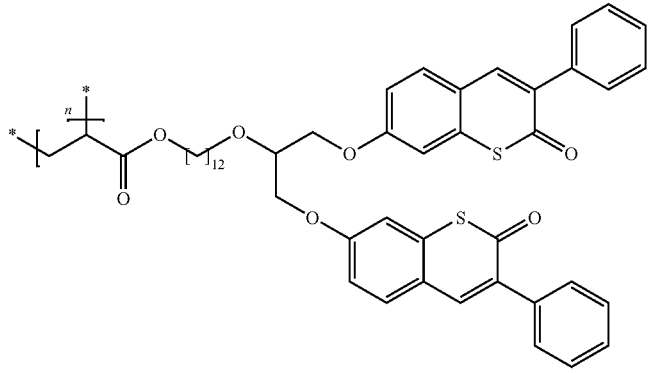 | P-037 |
| 11f | 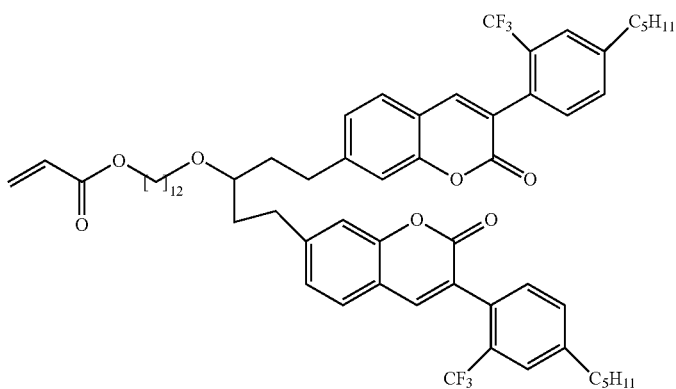 | M-132 |
| | 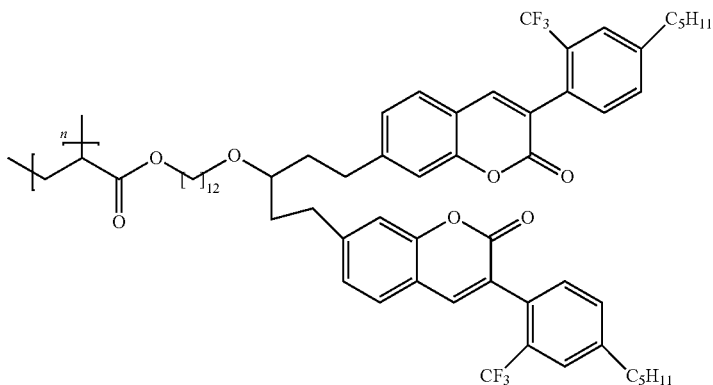 | P-132 |
| 11g | 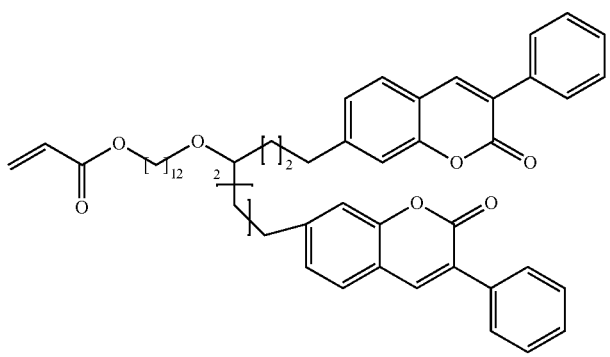 | M-133 |

| No. | | |
|---|---|---|
| | 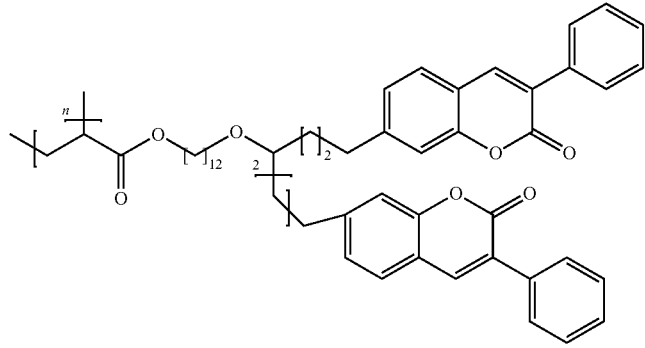 | P-133 |
| 11h | 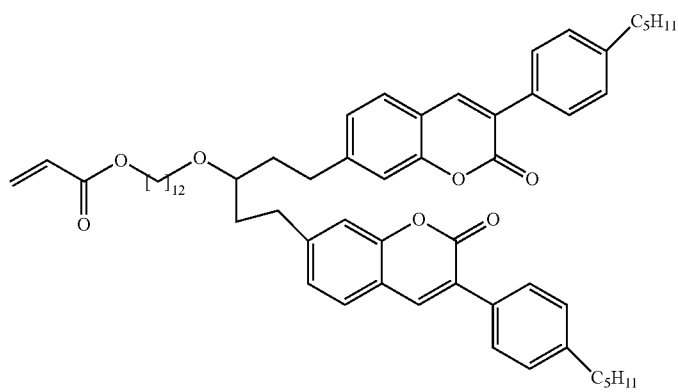 | M-134 |
| | 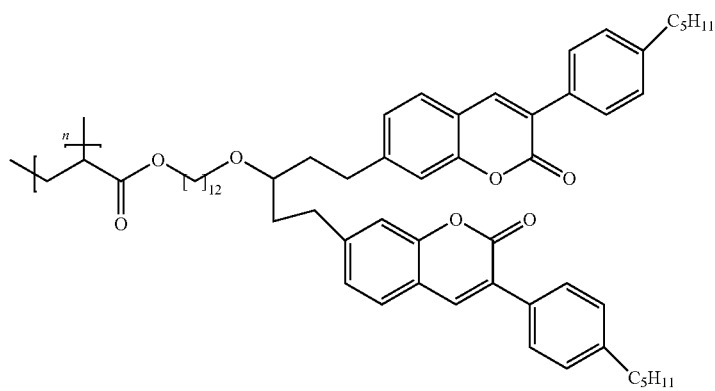 | P-134 |
| 11i | 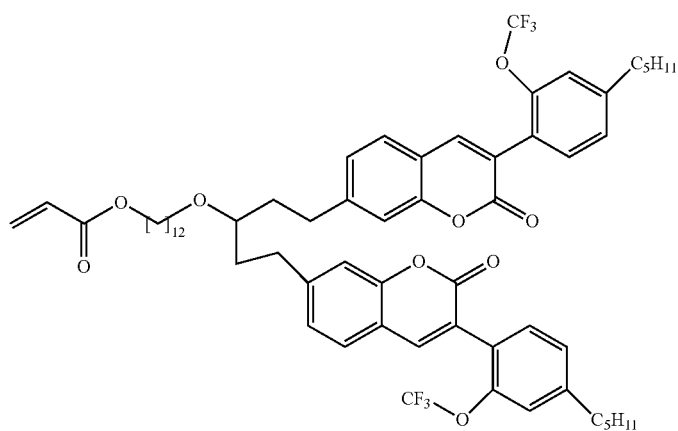 | M135 |

| No. | | |
|---|---|---|
| | 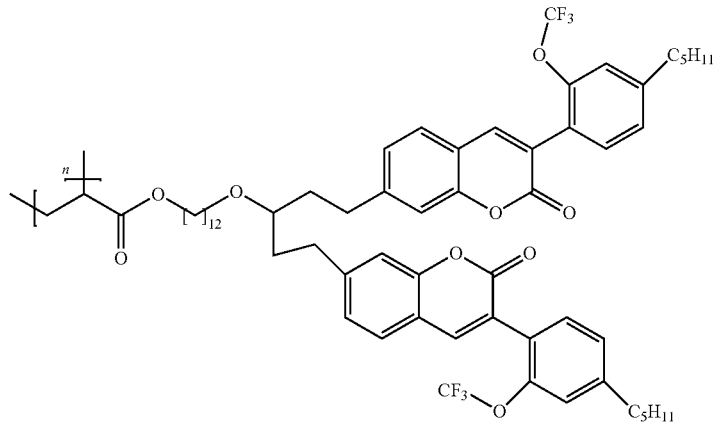 | P-135 |
| 11k | 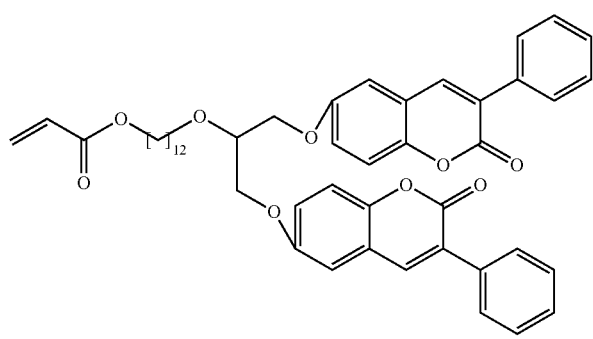 | M-136 |
| | 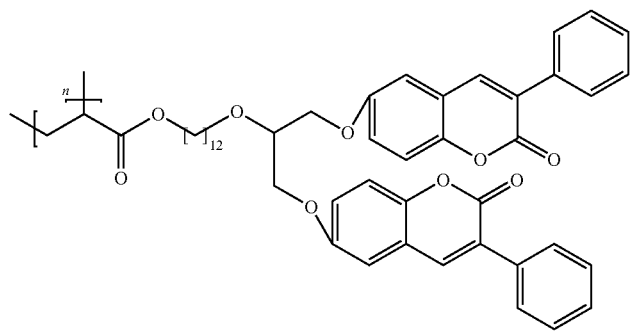 | P-136 |
| 11l | 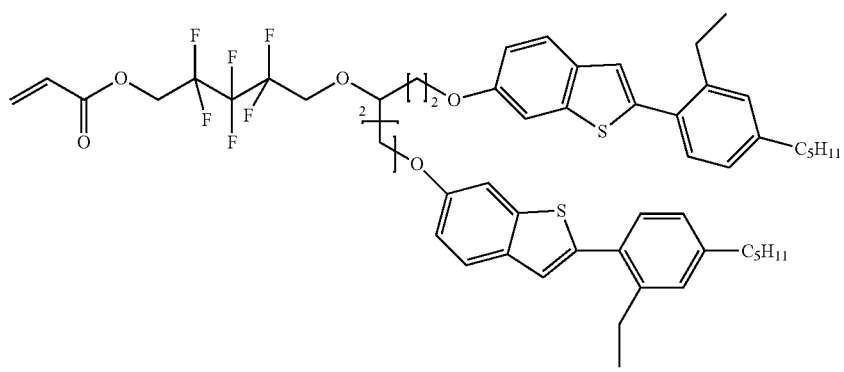 | M-095 |

| No. | |
|---|---|
| 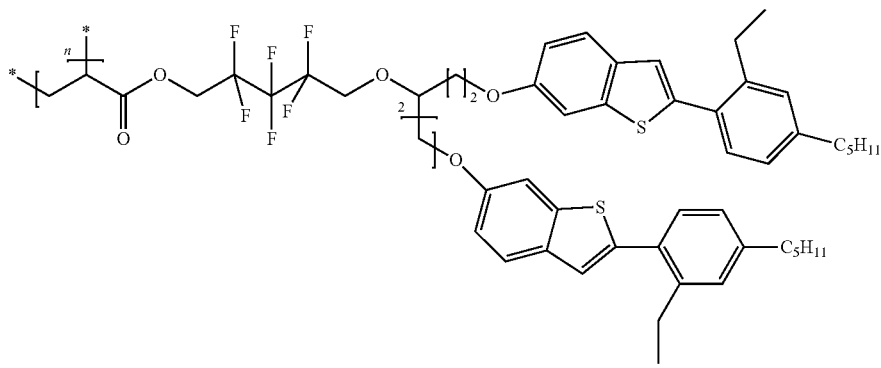 | P-095 |

Reference Example 12—Synthetic Procedures (GSP 9) for the Solvent Polymerization of Methacrylic Acid 10-[3-phenylcoumarin-7-yloxy]-decyl Ester, Used as Reference Monomer, Known from M. Schraub Et Al./European Polymer Journal 51 (2014) 21-27)

1.00 g (2.1 mmol) Methacrylic acid 10-[3-phenylcoumarin-7-yloxy]-decyl ester is dissolved in dimethylformamide (10 ml). The solution is degassed by three freeze-pump-thaw cycles. 12 mg (0.07 mmol) azobisisobutyronitrile are added to the solution and the reaction vessel is then placed in a 65° C. preheated oil bath for 3 d. At the end of the reaction, the mixture is poured into cold methanol (1 l). The precipitated polymer is collected by filtration and yielded 688 mg (1.4 mmol; 69% of theory). It is named reference molecule 1, abbreviated as Ref. 1 as shown in the following table.

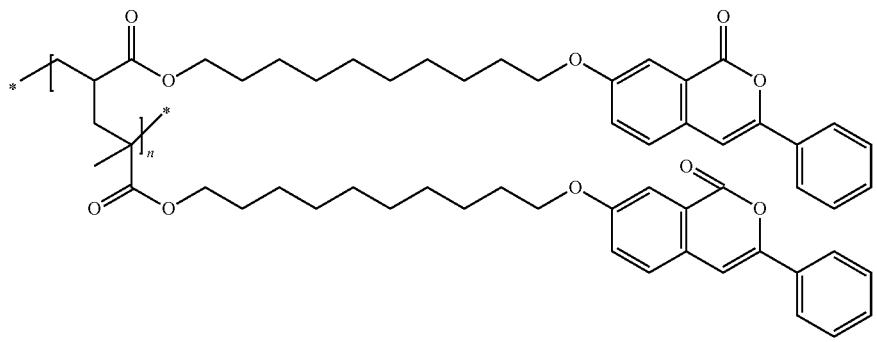

CAS: 1551475-19-4

This polymer has no distinct face-to-face-arrangement.

Examples of Application

Example 13—Investigation of Face-To-Face Arrangement

The synthesis of polymer P-003 is described in example 11a being a dendritic coumarin derivative with face-to-face arrangement of coumarin moieties.

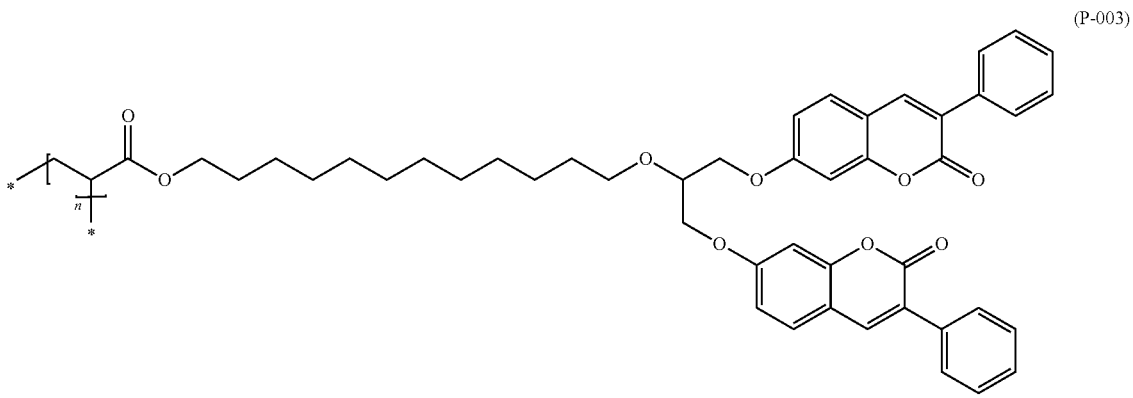

In order to investigate the effect of face-to-face arrangement of coumarin moieties on the photocrosslinking of the compounds, the photodimerization characteristics of the chromophores in Ref. 1 and P-003 are investigated. Polymer films from Ref. 1 and P-003 are prepared by spin coating from 1-8 wt % solutions of the polymers in chloroform onto quartz plates. UV-Vis absorption spectra of the films are recorded with a Perkin Elmer Lambda 9 spectrometer. The typical absorption maximum of the π-π* electronic transition in phenylcoumarin is 340 nm. Both thin polymer films are then irradiated by a high-pressure mercury lamp at a distance of 10 cm. After 5, 10, and 15 minutes of irradiation, UV-Vis absorption spectra of the films are recorded again. As shown in FIG. 2, a continuous decrease in absorbance at 340 nm is expected to be observed, indicating the increasing degree of photodimerization of coumarin moieties.

The dendrimer based polymer P-003 is expected to exhibited a coumarin consumption in the range of 80% to 75% while the reference material Ref. 1 has a coumarin consumption of 70% according to M. Schraub et al., European Polymer Journal 51 (2014) 21-27. In FIG. 2, a consumption of 79% of P-003 is used for the visualization. The expected higher coumarin consumption of the dendrimer based polymer P-003 is believed to be attributed to controlled arrangement and short-distance packing.

Example 14: General Bulk Polymerization Procedure to Produce Blank

A composition of 12-((1,3-Bis((3-(2-(trifluoromethyl)-4-(pentyl)phenyl)coumarin-7-yl)oxy)propan-2-yl)oxy)dodecyl acrylate as described in example 11 d, methyl methacrylate, initiator azobisisobutyronitrile (0.04 eq) and crosslinker ethylene glycol dimethacrylate (0.1-0.4 eq) in different ratios is degassed by three freeze-pump-thaw cycles.

Two glass plates are coated with a polyethylene sheet and a 0.5 mm thick cell is created between the polyethylene sheets using a silicone rubber gasket. The coated faces of the glass sheets are clipped together using spring clips with a syringe needle being placed between the gasket and the polyethylene sheets. The cavity is then filled with the above formulation through the needle using a gastight syringe. Once the cavity is filled the syringe needle is removed, a final clip is used to seal the mould and the assembly is placed in an oven at 60° C. for 24 hours before the oven is ramped to a temperature of 90° C. for a period of 3 hours. The moulds are allowed to cool to room temperature before the film is removed from the mould.

Examples Directed to the Properties of the Compounds

Example 15—Photoinduced Refractive Index Change and Glass Transition Temperature The phase transition temperatures are determined with a TA Instruments Q2000 differential scanning calorimeter during heating in the second heating run with 20 K/min from −100° C. to 200° C. in a hermetic aluminum pans. Irradiations of the blanks are performed with a Coherent Avia 355-7000 UV-Laser. Common photoactive polymers that undergo refractive index change upon irradiation with UV-light exhibit glass transition temperatures as low as 34° C.

Polymer films for refractive index measurements are prepared by spin coating or drop casting from 1-8 wt % solutions of the polymers in chloroform onto silicon wafers or quartz plates. For production of bulk polymer blanks, the monomers are melted under vacuum. Appropriate amounts of a radical initiator and cross-linker are mixed in and quickly filled into a heated polymerization chamber. Crosslinked polymer plates are obtained.

Refractive index change is induced by irradiation at 340-365 nm. The refractive indices (n) of the polymer films and blanks at 590 nm are measured on Schmidt+Haensch AR12 before and after irradiation. The following table shows the refractive indices before and after irradiation as well as the change in refractive index (max. Δn).

Expected values for the cited polymers are given in the following table:

| Polymer No | $T_g$ [° C.] | n | Δn |
|---|---|---|---|
| P-002 | 15.3 | 1.603 | 0.047 |
| P-003 | −4.2 | 1.594 | 0.044 |

Figure 1:
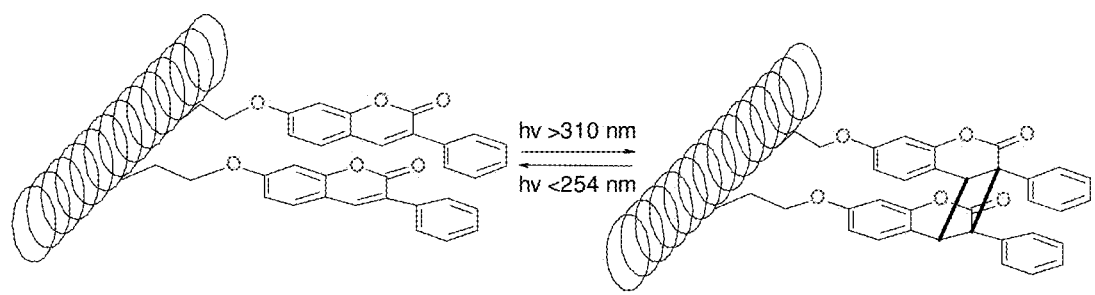
FIG. 1 shows a reversible photodimerization process of coumarin.
Figure 2:
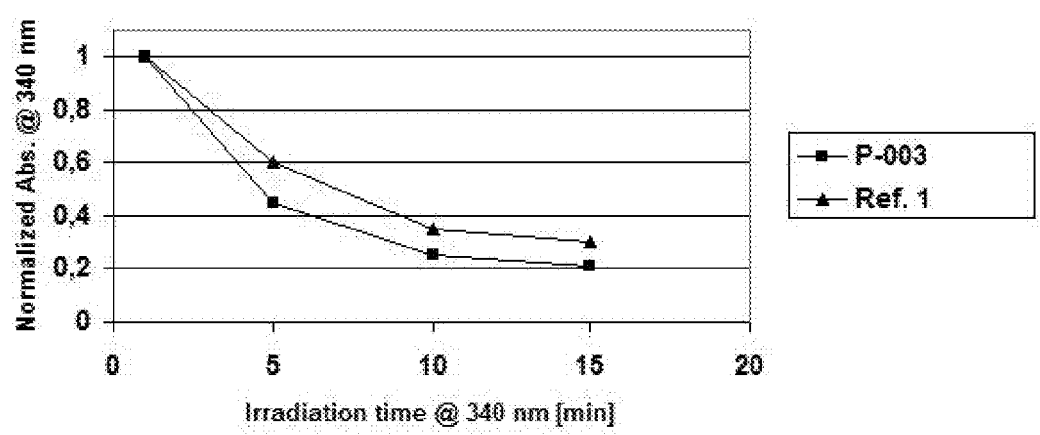
FIG. 2 shows the expected normalized absorbance at 340 nm for the reference material Ref. 1 and P-003 as polymer with optimized short-distance arrangement versus irradiation time. The absorbance at 340 nm correlates to the conversion from monomer to dimer of coumarin groups.

The invention claimed is:

1. A compound of formula (I)

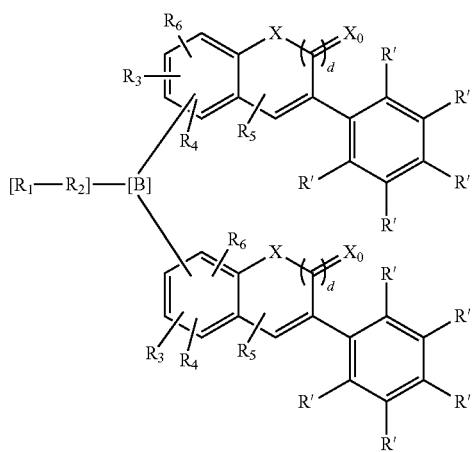

(I)

wherein

X is O, S or $NR_0$, $X_0$ is O or S, d is 0 or 1,

is selected from the group consisting of

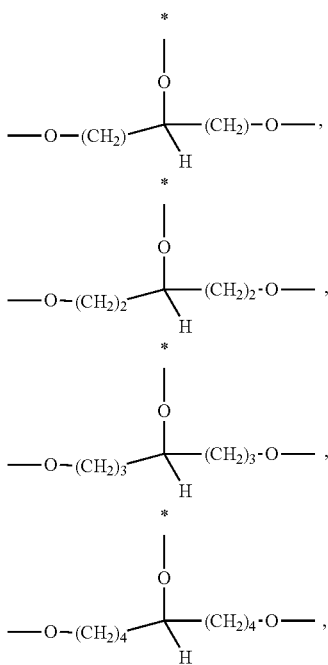

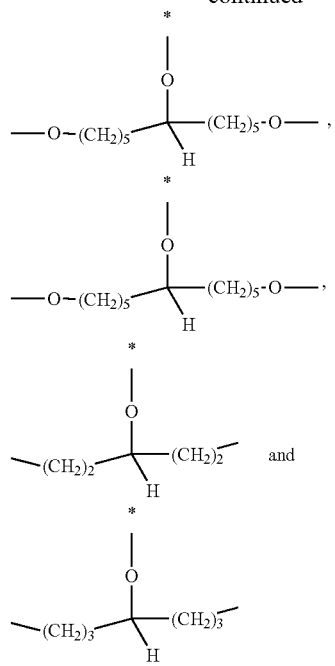

wherein * denotes a linkage to [—$R_2$—$R_1$],

R is at each occurrence independently H, F, OH, a linear or branched alkyl group having 1 to 4 C atoms, a linear or branched hydroxyalkyl group having 1 to 4 C atoms or a linear or branched partially or fully fluorinated alkyl group having 1 to 4 C atoms, R' is at each occurrence independently H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms, $R_0$ is at each occurrence independently a linear or branched alkyl group having 1 to 10 C atoms or a cycloalkyl group having 3 to 6 C atoms, $R_1$ is a polymerizable group selected from the group consisting of alkenyl groups of formula (1), trialkoxysilyl groups, dialkoxyalkylsilyl groups, silyl groups of formula (2), silyl groups of formula (3) and silyl groups of formula (4),

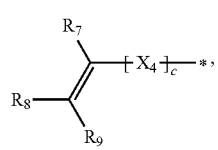

(1)

wherein $X_4$ is O, S, C(=O), or C(=O)O, $R_7$, $R_8$, $R_9$ are at each occurrence independently of each other H, F, a linear or branched, non-fluorinated, partially or completely fluorinated alkyl having 1 to 20 C atoms or aryl with 6 to 14 C atoms,
c is 0 or 1,
* denotes a linkage to [—R$_2$—];
wherein, in the trialkoxysilyl groups and dialkoxyalkylsilyl groups the alkyl and/or alkoxy groups are each independently linear or branched having 1 to 6 C atoms;

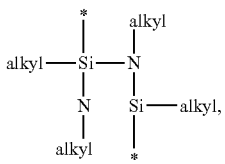

(2)

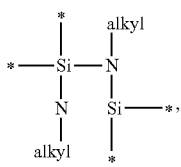

(3)

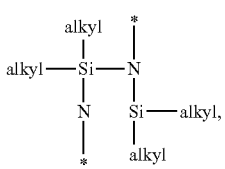

(4)

wherein
alkyl means at each occurrence independently of each other a linear or branched alkyl group having 1 to 6 C atoms, and
* denotes at each occurrence independently of each other a linkage to [—R$_2$—],
—R$_2$— is $(C(R)_2)_o$—, —$(C(R)_2)_p$—X$_1$—$(C(R)_2)_q$—(X$_2$)$_s$—$(C(R)_2)_r$—(X$_3$)$_t$—$(C(R)_2)_u$—, or a cycloalkylene group having 5 or 6 C atoms substituted with at least one R which is different from H,
o is 1 to 20,
X$_1$, X$_2$, X$_3$ are at each occurrence independently O, S or NR$_0$,
s, t are at each occurrence independently is 0 or 1,
p, q are at each occurrence independently 1 to 10,
r, u are at each occurrence independently 0 to 10,
wherein the overall number of atoms for —$(C(R)_2)_p$—X$_1$—$(C(R)_2)_q$—(X$_2$)$_s$—$(C(R)_2)_r$—(X$_3$)$_t$—$(C(R)_2)_u$— is up to 20 atoms,
R$_3$, R$_4$, R$_5$, R$_6$ are at each occurrence independently R'.

2. The compound according to claim 1, wherein

—[B]— is

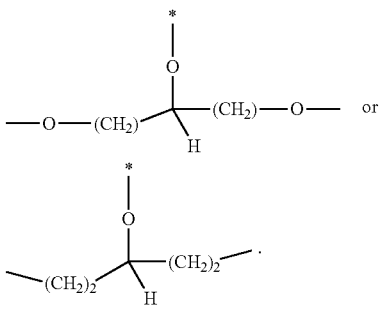

3. The compound according to claim 1, wherein d is 1.

4. The compound according to claim 1, wherein d is 1 and X and X$_0$ are 0.

5. The compound according to claim 1, wherein at least one R' is not H.

6. The compound according to claim 1, wherein at least two R' are not H.

7. The compound according to claim 1, wherein at least four R' are not H.

8. The compound according to claim 1, wherein R$_3$, R$_4$, R$_5$, R$_6$ at each occurrence are identical.

9. The compound according to claim 1, wherein R$_2$ is —(C(R)$_2$)$_o$—.

10. The compound according to claim 1, wherein R$_1$ is an acryl or methacryl radical.

11. An oligomer or polymer comprising a polymerized compound of formula I according to claim 1.

12. A composition comprising at least one compound of formula (I) according to claim 1 and/or an oligomer or polymer comprising a polymerized compound of formula (I).

13. An article comprising at least one compound of formula (I) according to claim 1 or at least one oligomer or polymer comprising a polymerized compound of formula (I).

14. The article according to claim 13, which is a blank which may be transformed into an eye implant or is an eye implant.

15. A process of forming an article of claim 13, comprising
providing a composition comprising at least one compound of formula (I) and/or an oligomer or polymer comprising a polymerized compound of formula (I);
subsequently forming the article of said composition.

16. A process of changing an optical property of an article according to claim 13, comprising exposing said article to irradiation having a wavelength of at least 200 nm and at most 1500 nm.

17. The article according to claim 13, which is an intraocular lens.

* * * * *